United States Patent [19]

Guthrie et al.

[11] Patent Number: 4,975,438

[45] Date of Patent: Dec. 4, 1990

[54] PENTADIENEAMIDE COMPOUNDS WHICH HAVE USEFUL ACTIVITY OF TREATING A DISEASE CHARACTERIZED BY AN EXCESS OF PLATELET ACTIVATING FACTOR

[75] Inventors: Robert W. Guthrie, Saddle Brook; Richard W. Kierstead; Jefferson W. Tilley, both of North Caldwell, all of N.J.

[73] Assignee: Hoffmann-La Roche Inc., Nutley, N.J.

[21] Appl. No.: 241,174

[22] Filed: Sep. 6, 1988

Related U.S. Application Data

[62] Division of Ser. No. 72,389, Jul. 10, 1987, Pat. No. 4,788,206.

[51] Int. Cl.$^5$ .................... A61K 31/47; C07D 217/04
[52] U.S. Cl. .................... 514/307; 514/309; 514/310; 514/308; 546/141; 546/142; 546/143; 546/146; 546/140; 546/144
[58] Field of Search ............... 546/141, 143, 146, 142, 546/140, 144; 514/307, 309, 310, 308

[56] References Cited

U.S. PATENT DOCUMENTS

| Re. 28,034 | 6/1974 | Gray et al. | 546/143 |
| 4,542,145 | 9/1985 | Wright, Jr. et al. | 548/262 |
| 4,568,685 | 2/1986 | Wright, Jr. et al. | 548/262 |
| 4,568,687 | 2/1986 | Wright, Jr. et al. | 548/341 |

FOREIGN PATENT DOCUMENTS

| 61-044870A | 3/1986 | Japan | 548/336 |
| 62-012757A | 1/1987 | Japan | 546/305 |

OTHER PUBLICATIONS

Chemical Abstracts, vol. 105, No. 5, Abstract 42810f.
Chemical Abstracts, vol. 96, No. 21, Abstract 178,218y, p. 444, 1982, Yukigosei Kosyo Co.
Werbel et al., Journal of Med. Chem., vol. 10, pp. 366-370, 1967.
Chemical Abstracts, vol. 105, No. 28, Abstract 226649s, pp. 800-801, 1986, Hotoda et al.
Chemical Abstracts, vol. 104, No. 19, Abstract 168177c.
Chemical Abstracts, vol. 107, No. 25, Abstract 154084v, p. 575, 1987, Makoto et al.
Chemical Abstracts, vol. 97, No. 27, Abstract 6167f, pp. 576-577, 1982, Japan Tobacco and Salt Public Co.

*Primary Examiner*—Robert W. Ramsuer
*Assistant Examiner*—Zinna Northington-Davis
*Attorney, Agent, or Firm*—George M. Gould; Bernard S. Leon; William G. Isgro

[57] ABSTRACT

Compounds of the formula

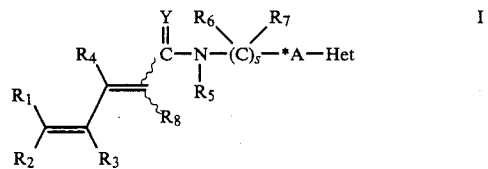

Y is O or S, *A is paraphenylene or *—(CH$_2$)$_n$—(X—)$_m$—(CH$_2$)$_r$—, X is O, S or —CH=CH—, n or r, independently, are integers from 0 to 3, s is an integer from 0 to 1, m is an integer from 0 to 1, provided that when m is 1, n+s must be at least 2, R$_1$ and R$_2$, independently, are hydrogen, lower alkyl, cycloalkyl, lower alkenyl, Het, Aryl, R$_3$, R$_4$ and R$_8$, independently, are hydrogen, lower alkyl, aryl, R$_5$ and R$_6$, independently, are hydrogen or lower alkyl, R$_7$ is hydrogen, lower alkyl, cycloalkyl, Het-lower alkyl or aryl, Het is a monocyclic 5- or 6-membered hetero aromatic or a bicyclic heteroaromatic radical containing one or two hetero atoms selected from nitrogen, oxygen and sulfur, which radical may be substituted by lower alkyl, halogen or aryl, and the asterisk denotes the point of attachment, and when R$_6$ and R$_7$ are different, their enantiomers and racemic mixtures thereof, when R$_1$ and R$_2$ are different, their geometric isomers, and pharmaceutically acceptable acid addition salts thereof, are described.

The compounds of formula I exhibit activity as platelet activating factor (PAF) antagonists and are, therefore, in disease states characterized by excess platelet activating factor or for the prevention and treatment of cardiovascular diseases, pulmonary diseases, immunological disorders, inflammatory diseases, dermatological disorders, shock or transplant rejection.

14 Claims, No Drawings

PENTADIENEAMIDE COMPOUNDS WHICH HAVE USEFUL ACTIVITY OF TREATING A DISEASE CHARACTERIZED BY AN EXCESS OF PLATELET ACTIVATING FACTOR

This is a division of application Ser. No. 72,389 filed July 10, 1987, now U.S. Pat. No. 4,788,206.

BRIEF SUMMARY OF THE INVENTION

The invention relates to compounds of the formula

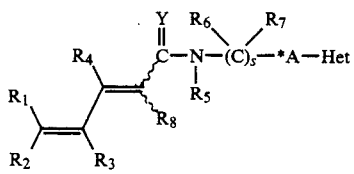

y is O or S, *A is paraphenylene or *—$(CH_2)_n$—$(X)_m$—$(CH_2)_r$—, X is O, S or —CH=CH—, n or r, independently, are integers from 0 to 3, s is an integer from 0 to 1, m is an integer from 0 to 1, provided that when m is 1, n+s must be at least 2. $R_1$ and $R_2$ independently, are hydrogen, lower alkyl, cycloalkyl, lower alkenyl, Het, aryl, $R_3$, $R_4$ and $R_8$ are independently hydrogen, lower alkyl, aryl, $R_5$ and $R_6$, independently are hydrogen or lower alkyl, $R_7$ is hydrogen, lower alkyl, cycloalkyl, Het-lower alkyl or aryl, Het is a monocyclic 5- or 6-membered hetero aromatic or a bicyclic heteroaromatic radical containing one or two hetero atoms selected from nitrogen, oxygen and sulfur, which radical may be substituted by lower alkyl, halogen or aryl, and the asterisk denotes the point of attachment,
and when $R_6$ and $R_7$ are different, their enantiomers and racemic mixtures thereof, when $R_1$ and $R_2$ are different, their geometric isomers, and pharmaceutically acceptable acid addition salts thereof.

The compounds of formula I exhibit activity as platelet activating factor (PAF) antagonists and are, therefore, useful in disease states characterized by excess platelet activating factor or for the prevention and treatment of cardiovascular diseases, pulmonary diseases, immunological disorders, inflammatory diseases, dermatological disorders, shock or transplant rejection.

DETAILED DESCRIPTION OF THE INVENTION

The invention relates to compounds of the formula

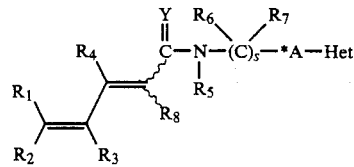

y is O or S, *A is paraphenylene or *—$(CH_2)_n$—$(X)_m$—$(CH_2)_r$—, X is O, S or —CH=CH—, n or r, independently, are integers from 0 to 3, s is an integer from 0 to 1, m is an integer from 0 to 1, provided that when m is 1, n+s must be at least 2, $R_1$ and $R_2$ independently, are hydrogen, lower alkyl, cycloalkyl, lower alkenyl, Het, aryl, $R_3$, $R_4$ and $R_8$ are independently hydrogen, lower alkyl, aryl, $R_5$ and $R_6$, independently are hydrogen or lower alkyl, $R_7$ is hydrogen, lower alkyl, cycloalkyl, Het-lower alkyl or aryl, Het is a monocyclic 5- or 6-membered heteroaromatic radical containing one or two hetero atoms selected from nitrogen, oxygen and sulfur, which radical may be substituted by lower alkyl, halogen or aryl, and the asterisk denotes the point of attachment, and, when $R_6$ and $R_7$ are different. Their enantiomers and racemic mixtures thereof when $R_1$ and $R_2$ are different, their geometric isomers, and pharmaceutically acceptable acid addition salts thereof.

As used herein, the term "alkyl" preferably denotes "lower alkyl", which denotes a straight or branched chain saturated hydrocarbon containing 1 to 7 carbon atoms, for example, methyl, ethyl, propyl, isopropyl, butyl, t-butyl, neopentyl, pentyl, heptyl, and the like. The term "cycloalkyl" denotes a cyclic alkyl group of 3 to 6 carbon atoms, for example, cyclopropyl, cyclohexyl, and the like. The term "lower alkoxy" denotes an alkyl ether group which the alkyl group is as described above, for example, methoxy, ethoxy, propoxy, pentoxy and the like. The term "lower alkenyl" denotes a straight or branched chain unsaturated hydrocarbon containing 3 to 7 carbon atoms, for example, propenyl, butenyl and the like.

The term "halogen" denotes all the halogens, i.e., bromine, chlorine, fluorine, and iodine. The term "aryl" preferably denotes naphthalenyl, phenyl or phenyl or naphthalenyl mono-, di- or trisubstituted by halogen, trifluoromethyl, lower alkyl, phenyl, lower alkoxy or nitro.

The term "Het" denotes a monocyclic 5- or 6-membered heteroaromatic or a bicyclic heteroaromatic radical containing one or two hetero atoms, selected from nitrogen, oxygen and sulfur, which radical may be substituted by lower alkyl, halogen or phenyl, for example, pyridinyl, quinolinyl, isoquinolyl, imidazolinyl, indolyl, benzimidazolinyl, thienyl, furyl, pyrimidinyl, oxazolinyl and the like.

The compounds of formula I exist as the (E) or trans and the (Z) or cis geometric isomers, or mixtures thereof. More specifically, the geometric isomers be characterized by the following formulas

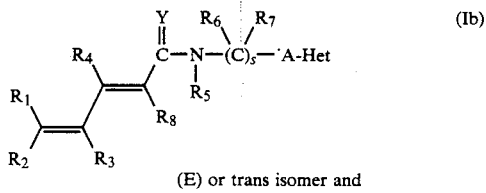

(E) or trans isomer and

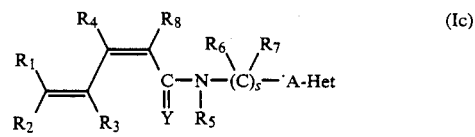

(Z) or cis isomer.

Furthermore, the (E) and (Z) isomers, when $R_6$ and $R_2$ are different, comprise enantiomers which can be characterized by the following formulas:

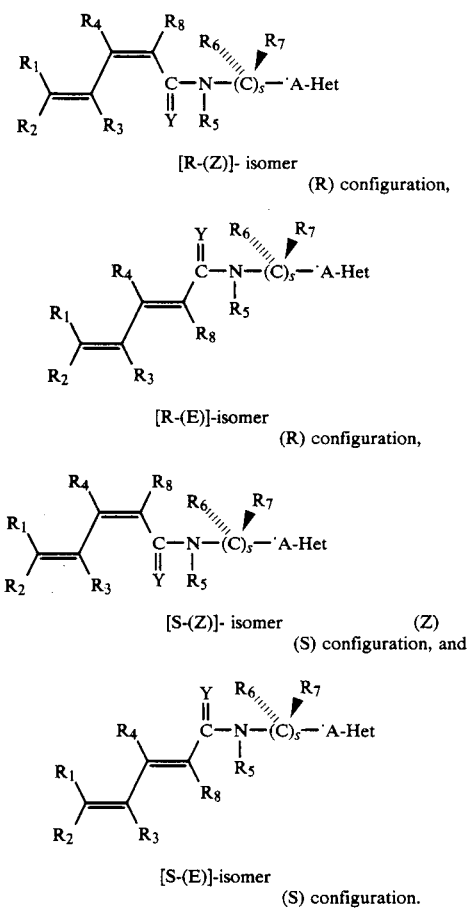

[R-(Z)]- isomer
(R) configuration,

[R-(E)]-isomer
(R) configuration,

[S-(Z)]- isomer (Z)
(S) configuration, and

[S-(E)]-isomer
(S) configuration.

The invention encompasses all the isomers and mixtures thereof.

A preferred group of compounds of formula I are those wherein $R_1$ and $R_2$ are lower alkyl or aryl, $R_3$, $R_4$ and $R_8$ independently are hydrogen or lower alkyl, $R_5$ and $R_7$ are hydrogen, $R_6$ is hydrogen, lower alkyl or cycloalkyl, *A is *—$(CH_2)_n$—$(X)_m$—$(CH_2)_r$ wherein n+r=2 to 6, m=O, Het is a monocyclic 5 or 6 membered heteroaromatic ring containing one or two heteroatoms selected from nitrogen, oxygen and sulfur, y is oxygen or sulfur, s is 1.

A more preferred group of formula I are those wherein $R_1$ is lower alkyl or aryl, $R_2$ is aryl, $R_3$, $R_4$ and $R_8$ are independently hydrogen or lower alkyl, *A is *—$(CH_2)_n$—$(X)_m$—$(CH_2)_r$ wherein n+r=3, m=0, Het is pyridinyl, or pyrimidinyl substituted with lower alkyl, $R_5$ and $R_7$ are hydrogen, $R_6$ is hydrogen, lower alkyl or cyclopropyl, y is oxygen, s is 1.

A most preferred group of compounds of formula I are those where $R_1$ is butyl, pentyl or hexyl or phenyl with up to 3-substituents selected from halogen, or lower alkoxy, $R_2$ is phenyl with up to 3-substituents selected from halogen or lower alkoxy, $R_3$, $R_4$, $R_5$, $R_7$ and $R_8$ are hydrogen, Het is 3-pyridinyl or 2-methyl-3-pyridinyl.

Preferred compounds of the invention are:
[R-(E,E)]-5-(4-methoxyphenyl)-N-[1-methyl-4-(3-pyridinyl)butyl]-2,4-decadienamide;
[R,S-(E,E)]-5-(4-methoxyphenyl)-N-[1-methyl-4-(2-methyl-3-pyridinyl)butyl]-2,4-decadienamide;
(E)-5,5-bis(3-methoxyphenyl)-N-[4-(3-pyridinyl)butyl]-2,4-pentadienamide;
(E)-5,5-bis(3-fluorophenyl)-N-[4-(3-pyridinyl)butyl]-2,4-pentadienamide;
[R-(E,E)]-5-(4-methoxyphenyl)-N-[1-methyl-4-(3-pyridinyl)butyl]-2,4-monodienamide; and
[R-(E)]-N-[1-ethyl-4-(3-pyridinyl)butyl]-5,5-bis(4-methoxyphenyl)-2,4-pentadienamide.

Exemplary compounds of formula I of the invention are:
(E)-5,5-bis(Methoxyphenyl)-N-[4-(2,6-dimethyl-3-pyridinyl)butyl]-2,4-pentadienamide;
[R-(E,E)]-N-[4-(2,6-Dimethyl-3-pyridinyl)butyl]-5-(4-methoxyphenyl)-2,4-decadienamide;
[R-(E,E)]-5-(4-Methoxyphenyl)-N-[1-methyl-4-(4-methyl-3-pyridinyl)butyl]-2,4-decadienamide;
[R-(E)]-5,5-bis(4-Methoxyphenyl)-N-[1-methyl-4-(4-methyl-3-pyridinyl)butyl]-2,4-pentadienamide;
[R-(E,E)]-5-(4-Methoxyphenyl)-N-[1-methyl-4-(4-methyl-3-pyridinyl)butyl]-2,4-nonadienamide;
[R-(E,E)]-5-(4-Methoxyphenyl)-N-[1-methyl-4-[6-(1-methylethyl)-3-pyridinyl]butyl]-2,4-undecadienamide;
[R-(E,E)]-5-(4-Methoxyphenyl)-N-[1-methyl-4-[6-(1-methylethyl)-3-pyridinyl]butyl]-2,4-decadienamide;
[R-(E)]-5,5-bis(4-Methoxyphenyl)-N-[1-methyl-4-[6-(1-methylethyl)-3-pyridinyl]butyl]-2,4-pentadienamide;
[R-(E,E)]-5-(4-Methoxyphenyl)-N-[1-methyl-4-(5-methyl-3-pyridinyl)butyl]-5-(3-pyridinyl)-2,4-pentadienamide;
[R-(E,E)]-5-(4-Methoxyphenyl)-N-[1-methyl-4-(5-methyl-3pyridinyl)butyl]-2,4-decadienamide;
[R-(E,E)]-5-(4-Methoxyphenyl)-N-[1-methyl-4-(5-methyl-3-pyridinyl)butyl]-2,4-nonadienamide;
(E,E)-5-(4-Methoxyphenyl)-N-[4-(3-pyridinyl)phenyl]-2,4-undecadienamide;
(E,E)-5-(4-Methoxyphenyl)-N-[4-(3-pyridinyl)phenyl]-2,4-nonadienamide;
(E,E)-5-(4-Methoxyphenyl)-N-[4-(3-pyridinyl)phenyl]-2,4-decadienamide;
(E)-5,5-bis(3,4-Dimethoxyphenyl)-2,4-dimethyl-N-[4-(3-pyridinyl)butyl]-2,4-pentadienamide;
[R-(E,E)]-5-(4-Methoxyphenyl)-3-methyl-N-[1-methyl-4-(3-pyridinyl)butyl]-2,4-decadienamide;
[R-(E,E)]-5-(4-Methoxyphenyl)-4-methyl-N-[1-methyl-4-(3-pyridinyl)butyl]-2,4-decadienamide;
(E)-5,5-bis(3,4-Dimethoxyphenyl)-3-methyl-N-[4-(3-pyridinyl)butyl]-2,4-pentadienamide;
[R-(E,E)]-5-(4-Methoxyphenyl)-2,4-dimethyl-N-[1-methyl-4-(3-pyridinyl)butyl]-2,4-undecadienamide;
[R-(E,E)]-5-(4-Methoxyphenyl)-4-methyl-N-[1-methyl-4-(3-pyridinyl)butyl]-2,4-nonadienamide;
(E)-5,5-bis(3,4-Dimethoxyphenyl)-4-methyl-N-[4-(3-pyridinyl)butyl]-2,4-pentadienamide;
[R-(E,E)]-5-(4-Methoxyphenyl)-2,4-dimethyl-N-[1-methyl-4-(3-pyridinyl)butyl]-2,4-decadienamide;
[R-(E,E)]-5-(3-Methoxyphenyl)-4-methyl-N-[1-methyl-4-(3-pyridinyl)butyl]-2,4-undecadienamide;
[R-(E,E)]-5-(4-Methoxyphenyl)-4-phenyl-N-[1-methyl-4-(3-pyridinyl)butyl]-2,4-decadienamide;
[R-(E,E)]-N-[1-Methyl-4-(3-pyridinyl)butyl]-5,5-bis(2,3,4-trimethoxyphenyl)-2,4-pentadienamide;
[R-(E,E)]-N-[1-Methyl-4-(3-pyridinyl)butyl]-5-(3-thienyl)-5-(2,3,4-trimethoxyphenyl)-2,4-pentadienamide;
[R-(E,E)]-N-[1-Methyl-4-(3-pyridinyl)butyl]-5-(2,3,4-trimethoxyphenyl)-2,4-nonadienamide;

[R-(E,E)]-N-[1-Methyl-4-(3-pyridinyl)butyl]-5-(2,3,4-trimethoxyphenyl)-2,4-decadienamide;
[R-(E)]-N-[1-Methyl-4-(3-pyridinyl)butyl]-5,5-bis(3,4,5-trimethoxyphenyl)-2,4-pentadienamide;
[R-(E,E)]-N-[1-Methyl-4-(3-pyridinyl)butyl]-5-(3-pyridinyl)-5-(3,4,5-trimethoxyphenyl)-2,4-pentadienamide;
[R-(E,E)]-N-[1-Methyl-4-(3-pyridinyl)butyl]-5-(3,4,5-trimethoxyphenyl)-2,4-decadienamide;
[R-(E)]-5,5-bis(3,5-Dimethoxyphenyl)-N-[1-methyl-4-(3-pyridinyl)butyl]-2,4-pentadienamide:
[R-(E,E)]-5-(3,5-Dimethoxyphenyl)-N-[1-methyl-4-(3-pyridinyl)butyl]-2,4-nonadienamide:
[R-(E,E)]-5-(3,5-Dimethoxyphenyl)-N-[1-methyl-4-(3-pyridinyl)butyl]-2,4-decadienamide;
[R-(E)]-5,5-bis(2,3-Dimethoxyphenyl)-N-[1-methyl-4-(3-pyridinyl)butyl]-2,4-pentadienamide;
[R-(E,E)]-5-(2,3-Dimethoxyphenyl)-N-[1-methyl-4-(3-pyridinyl)butyl]-2,4-undecadienamide;
[R-(E)]-5,5-bis(2,6-Dimethoxyphenyl)-N-[1-methyl-4-(3-pyridinyl)butyl]-2,4-pentadienamide;
[R-(E,E)]-5-(2,6-Dimethoxyphenyl)-N-[1-methyl-4-(3-pyridinyl)butyl]-2,4-nonadienamide;
[R-(E,E)]-5-(2,6-Dimethoxyphenyl)-N-[1-methyl-4-(3-pyridinyl)butyl]-2,4-decadienamide;
[R-(E,E)]-5-(2,6-Dimethoxyphenyl)-N-[1-methyl-4-(3-pyridinyl)butyl]-2,4-undecadienamide:
[R-(E)]-5,5-bis(2,4-Dimethoxyphenyl)-N-[1-methyl-4-(3-pyridinyl)butyl]-2,4-pentadienamide;
[R-(E,E)]-5-(2,4-Dimethoxyphenyl)-N-[1-methyl-4-(3-pyridinyl)butyl]-2,4-nonadienamide;
[R-(E,E)-5-(2,4-Dimethoxyphenyl)-N-[1-methyl-4-(3-pyridinyl)butyl]-2,4-decadienamide;
[R-(E,E)-5-(2,4-Dimethoxyphenyl)-N-[1-methyl-4-(3-pyridinyl)butyl]-5-(2-thienyl)-2,4-pentadienamide;
[R-(E,E)]-5-(4-Methoxynaphthalen-2-yl)-N-[1-methyl-4-(3-pyridinyl)butyl]-2,4-nonadienamide;
[R-(E,E)]-5-(4-Methoxynaphthalen-2-yl)-5-(4-methoxyphenyl)-N-[1-methyl-4-(3-pyridinyl)butyl]-2,4-pentadienamide;
[R-(E,E)]-5-(6-Methoxynaphthalen-2-yl)-N-[1-methyl-4-(3-pyridinyl)butyl]-5-(3-pyridinyl)-2,4-pentadienamide;
[R-(E,E)]-5-(6-Methoxynaphthalen-2-yl)-N-[1-methyl-4-(3-pyridinyl)butyl]-2,4-nonadienamide;
[R-(E,E)]-5-(6-Methoxynaphthalen-2-yl)-N-[1-methyl-4-(3-pyridinyl)butyl]-2,4-decadienamide;
[R-(E,E)]-5-(7-Methoxynaphthalen-2-yl)-N-[1-methyl-4-(3-pyridinyl)butyl]-5-phenyl-2,4-pentadienamide;
[R-(E,E)]-5-(7-Methoxynaphthalen-1-yl)-N-[1-methyl-4-(3-pyridinyl)butyl]-2,4-nonadienamide;
[R-(E,E)]-5-(4,7-Dimethoxynaphthalen-2-yl)-N-[1-methyl-4-(3-pyridinyl)butyl]-5-(2-thienyl)-2,4-pentadienamide;
[R-(E,E)]-5-(7-Methoxynaphthalen-2-yl)-N-[1-methyl-4-(3-pyridinyl)butyl]-2,4-decadienamide;
[R-(E,E)]-5-(7-Methoxynaphthalen-1-yl)-N-[1-methyl-4-(3-pyridinyl)butyl]-2,4-undecadienamide;
[R-(E,E)]-5-(4,7-Dimethoxynaphthalen-2-yl)-N-[1-methyl-4-(3-pyridinyl)butyl]-2,4-decadienamide;
[R-(E,E)]-5-(7-Methoxynaphthalen-2-yl)-N-[1-methyl-4-(3-pyridinyl)butyl]-2,4-undecadienamide;
[R-(E,E)]-5-(7-Methoxynaphthalen-1-yl)-N-[1-methyl-4-(3-pyridinyl)butyl]-2,4-decadienamide;
[R-(E,E)]-5-(4,7-Dimethoxynaphthalen-2-yl)-N-[1-methyl-4-(3-pyridinyl)butyl]-2,4-nonadienamide
[R-(E)]-5,5-bis(3,4-Dimethoxyphenyl)-N-[4-(3-furyl)-1-methylbutyl]-2,4-pentadienamide;
R-(E,E)]-5-(3,4-Dimethoxyphenyl)-N-[4-(3-furyl)-1-methylbutyl]-5-phenyl-2,4-pentadienamide;
R-(E,E)]-5-(3,4-Dimethoxyphenyl)-N-[4-(3-furyl)-1-methylbutyl]-2,4-decadienamide;
R-(E,E)]-5-(3,4-Dimethoxyphenyl)-N-[4-(3-furyl)-1-methylbutyl]-2,4-nonadienamide;
[R-(E,E)]-5-(4-Methoxyphenyl)-N-[1-methyl-4-(3thienyl)butyl]-2,4-decadienamide;
[R-(E]-5,5-bis(4-Methoxyphenyl)-N-[1-methyl-4-(3thienyl)butyl]-2,4-pentadienamide;
[R-(E,E)]-5-(4-Methoxyphenyl)-N-[1-methyl-4-(3thienyl)butyl]-2,4-undecadienamide;
[R-(E]-5,5-bis(3-Methoxyphenyl)-N-[1-methyl-4-(3thienyl)butyl]-2,4-pentadienamide:
[R-(E)]-5,5-(3,4-Dimethoxyphenyl)-N-[1-methyl-4-(1,3-thiazol-2-yl)butyl]-2,4-pentadienamide:
[R-(E,E)]-5-(3,4-Dimethoxyphenyl)-N-[1-methyl-4-(1,3-thiazol-2-yl)butyl]-2,4-nonadienamide;
[R-(E,E)]-5-(3,4-Dimethoxyphenyl)-N-[1-methyl-4-(1,3-thiazol-2-yl)butyl]-2,4-decadienamide;
[R-(E,E)]-5-(4-Methoxyphenyl)-N-[1-methyl-4-(5-pyrimidinyl)butyl]-5-phenyl-2,4-pentadienamide
[R-(E)]-5,5-bis(3-Methoxyphenyl)-N-[1-methyl-4-(5pyrimidinyl)butyl]-2,4-pentadienamide;
[R-(E,E)]-5-(4-Methoxyphenyl)-N-[1-methyl-4-(5pyrimidinyl)butyl]-2,4-decadienamide;
[R-(E,E)]-5-(4-Methoxyphenyl)-N-[1-methyl-4-(2imidazolyl)butyl]-5-phenyl-2,4-pentadienamide;
[R-(E)]-5,5-bis(4-Methoxyphenyl)-N-[1-methyl-4-(2-imidazolyl)butyl]-2,4-pentadienamide;
[R-(E,E)]-5-(4-Methoxyphenyl)-N-[1-methyl-4-(2-imidazolyl)butyl]-2,4-decadienamide;
[R-(E)]-5,5-bis(4-Methoxyphenyl)-N-[1-methyl-4-(2H-pyrrol-3-yl)butyl]-2,4-pentadienamide;
[R-(E)]-5,5-bis(3-Methoxyphenyl)-N-[1-methyl-4-(2H-pyrrol-3-yl)butyl]-2,4-pentadienamide;
[R-(E,E)]-5-(3,4-Dimethoxyphenyl)-N-[1-methyl-4-(2H-pyrrol-3-yl)butyl]-2,4-decadienamide;
[R-(E,E)]-5-(4-Methoxyphenyl)-N-[1-methyl-4-(2H-pyrrol-3-yl)butyl]-2,4-nonadienamide;
[R-(E,E)]-5-(4-Methoxyphenyl)-N-[1-methyl-4-(2H-pyrrol-3-yl)butyl]-2,4-undecadienamide;
[R-(E,E)]-5-(4-Methoxyphenyl)-N-[1-methyl-4-(3-pyridazinyl)butyl]-2,4-nonadienamide;
[R-(E,E)]-5-(4-Methoxyphenyl)-N-[1-methyl-4-(3-pyridazinyl)butyl]-2,4-decadienamide;
[R-(E,E)]-5-(4-Methoxyphenyl)-N-[1-methyl-4-(3-pyridazinyl)butyl]-2-(thienyl)-2,4pentadienamide;
[R-(E,E)]-5-(4-Methoxyphenyl)-N-[1-methyl-4-(2H-chromen-3-yl)butyl]-2,4undecadienamide;
[R-(E,E)]-5-(3-Chlorophenyl)-N-[1-methyl-4-(3-pyridinyl)butyl]-5-phenyl-2,4-pentadienamide;
[R-(E,E)]-5-(3-Chlorophenyl)-N-[1-methyl-4-(3-pyridinyl)butyl]-2,4-decadienamide;
R-(E,E)]-5-(3-Chlorophenyl)-N-[1-methyl-4-(3-pyridinyl)butyl]-5-phenyl-2,4-pentadienamide;
[R-(E,E)]-5-(4-Chlorophenyl)-N-[1-methyl-4-(3-pyridinyl)butyl]-2,4-nonadienamide;
[R-(E)]-5,5-bis[4-(Trifluoromethyl)phenyl]-N-[1-methyl-4-(3-pyridinyl)butyl]-2,4-pentadienamide;
[R-(E,E)]-5-§4-(Trifluoromethyl)phenyl]-N-[1-methyl-4-(3-pyridinyl)butyl]-2,4-decadienamide:
[R-(E,E)]-5-(4-Nitrophenyl)-N-[1-methyl-4-(3-pyridinyl)butyl]-2,4-undecadienamide;
[R-(E,E)]-5-(4-Nitrophenyl)-N-[1-methyl-4-(3-pyridinyl)butyl]-2,4-nonadienamide;
[R-(E,E)]-5-[4-(1-Methylethyl)phenyl]-N-[1-methyl-4-(3-pyridinyl)butyl]-2,4-decadienamide;

[R-(E,E)]-5-[4-(1-Methylethyl)phenyl]-N-[1-methyl-4-(3-pyridinyl)butyl]-2,4-nonadienamide;

[R-(E)]-5,5-bis[4-(Methylthio)phenyl]-N-[1-methyl-4-(3-pyridinyl)butyl]-2,4-pentadienamide;

[R-(E,E)]-5-[4-(Methylthio)phenyl]-N-[1-methyl-4-(3-pyridinyl)butyl]-2,4-nonadienamide;

[R-(E,E)]-5-[4-(Methylsulfinyl)phenyl]-N-[1-methyl-4-(3-pyridinyl)butyl]-5-phenyl-2,4-pentadienamide;

[R-(E,E)]-5-[4-(Methylsulfinyl)phenyl]-N-[1-methyl-4-(3-pyridinyl)butyl]-2,4-undecadienamide;

[R-(E)]-5,5-bis[4-(Dimethylamino)phenyl]-N-[1-methyl-4-(3-pyridinyl)butyl]-2,4-pentadienamide;

[R-(E,E)]-5-[4-(Dimethylamino)phenyl]-N-[1-methyl-4-(3-pyridinyl)butyl]-2,4-decadienamide;

[R-(E)-5,5-bis(3,4-Methylenedioxyphenyl)-N-[1-methyl-4-(3-pyridinyl)butyl]-2,4-pentadienamide;

[R-(E,E)-5-(3,4-Methylenedioxyphenyl)-N-[1-methyl-4-(3-pyridinyl)butyl]-2,4-nonadienamide;

[R-(E,E)]-N-[1-Ethyl-4-(3-pyridinyl)butyl]-5-(4-methoxyphenyl)-2,4-nonadienamide;

[R-(E,E)]-N-[1-Ethyl-4-(3-pyridinyl)butyl]-5-(4-methoxyphenyl)-2,4-decadienamide;

[R-(E,E)]-N-[1-Ethyl-4-(3-pyridinyl)butyl]-5-(4-methoxyphenyl)-2,4-undecadienamide;

[S-(E,E)]-N-[1-Ethyl-4-(3-pyridinyl)butyl]-5-(4-methoxyphenyl)-2,4-decadienamide;

[R-(E,E)]-5-(4-Methoxyphenyl)-N-[1-propyl-4-(3-pyridinyl)butyl]-2,4-nonadienamide;

[R-(E,E)]-5-(4-Methoxyphenyl)-N-[1-propyl-4-(3-pyridinyl)butyl]-2,4-decadienamide;

[R-(E,E)]-5-(4-Methoxyphenyl)-N-[1-propyl-4-(3-pyridinyl)butyl]-5-phenyl-2,4-pentadienamide;

[R-(E,E)]-N-[1-Cyclopropyl-4-(3-pyridinyl)butyl]-5-(4-methoxyphenyl)-2,4-decadienamide;

[R-(E,E)]-N-[1-Cyclopropyl-4-(3-pyridinyl)butyl]-5-(4-methoxyphenyl)-2,4- nonadienamide;

[S-(E,E)]-N-[1-Cyclopropyl-4-(3-pyridinyl)butyl]-5-(4-methoxyphenyl)-2,4decadienamide;

[R,S-(E,E)]-5-(4-Methoxyphenyl)-N-[1-(1-methylethyl)-4-(3-pyridinyl)butyl]-2,4-undecadienamide;

[R,S-(E,E)]-5-(4-Methoxyphenyl)-N-[1-(1-methylethyl)-4-(3-pyridinyl)butyl]-2,4-nonadienamide;

[R-(E,E)]-5-(4-Methoxyphenyl)-N-[1-methyl-2-(3-pyridinyl)ethyl]-2,4-nonadienamide;

[R-(E,E)]-5-(4-Methoxyphenyl)-N-[1-methyl-2-(3-pyridinyl)ethyl]-2,4-decadienamide;

[R-(E,E)]-5-(4-Methoxyphenyl)-N-[1-methyl-3-(3-pyridinyl)propyl]-2,4-undecadienamide;

[R-(E)]-5,5-bis(4-Methoxyphenyl)-N-[1-methyl-3-(3-pyridinyl)propyl]-2,4-pentadienamide;

[R-(E,E)]-5-(4-Methoxyphenyl)-N-[1-methyl-5-(3-pyridinyl)pentyl]-2,4-decadienamide;

[R-(E,E)]-5-(4-Methoxyphenyl)-N-[1-methyl-5-(3-pyridinyl)pentyl]-2,4-undecadienamide;

[R-(E,E)]-5-(4-Methoxyphenyl)-N-[1-methyl-6-(3-pyridinyl)hexyl]-2,4-undecadienamide;

[R-(E,E)]-5-(4-Methoxyphenyl)-N-[1-methyl-7-(3-pyridinyl)heptyl]-2,4-decadienamide;

[R-(E,E)]-5-(4-Methoxyphenyl)-N-[1-methyl-6-(3-pyridinyl)hexyl]-2,4-nonadienamide;

[R-(E,E)]-5-(4-Methoxyphenyl)-N-[1-methyl-7-(3-pyridinyl)heptyl]-2,4-undecadienamide;

[R-(E,E)]-5-(4-Methoxyphenyl)-N-[1-methyl-8-(3-pyridinyl)octyl]-2,4-decadienamide;

[R-(E,E)]-5-(4-Methoxyphenyl)-N-[1-methyl-8-(3-pyridinyl)octyl]-2,4-nonadienamide;

[R-(E,E)]-N-[1-Methyl-4-(3-pyridinyl)butyl]-5-(3-pyridinyl)-2,4-undecadienamide;

[R-(2E,4Z)]-N-[1-Methyl-4-(3-pyridinyl)butyl]-5-(3-pyridinyl)-2,4-decadienamide;

[R-(E,E)]-N-[1-Methyl-4-(3-pyridinyl)butyl]-5-(3-pyridinyl)-2,4-undecadienamide;

[R-(2E,4Z)]-N-[1-Methyl-4-(3-pyridinyl)butyl]-5-(3-pyridinyl)-2,4-decadienamide;

[R-(E,E)]-N-[1-Methyl-4-(3-pyridinyl)butyl]-5-(4-pyridinyl)-2,4-nonadienamide;

[R-(2E,4Z)]-N-[1-Methyl-4-(3-pyridinyl)butyl]-5-(4-pyridinyl)-2,4-nonadienamide;

[R-(E,E)]-N-[1-Methyl-4-(3-pyridinyl)butyl]-5-(2-thienyl)-2,4-undecadienamide;

[R-(2E,4Z)]-N-[1-Methyl-4-(3-pyridinyl)butyl]-5-(2-thienyl)-2,4-undecadienamide;

[R-(E,E)]-N-[1-Methyl-4-(3-pyridinyl)butyl]-5-(3-thienyl)-2,4-nonadienamide;

[R-(2E,4Z)]-N-[1-Methyl-4-(3-pyridinyl)butyl]-5-(3-thienyl)-2,4-nonadienamide;

(E,E)-5-(4-Methoxyphenyl)-N-[3-(3-pyridinyloxy)propyl]-2,4-decadienamide;

(E,E)-5-(4-Methoxyphenyl)-N-[3-(3-pyridinyloxy)propyl]-2,4-nonadienamide;

(E,E)-5-(4-Methoxyphenyl)-N-[3-(3-pyridinyloxy)propyl]-2,4-undecadienamide;

(E,E)-5-(4-Methoxyphenyl)-N-[3-(3-pyridinylamino)propyl]-2,4-undecadienamide;

(E,E)-5-(4-Methoxyphenyl)-N-[3-(3-pyridinylamino)propyl]-2,4-nonadienamide;

(E,E)-5-(4-Methoxyphenyl)-N-[3-(3-pyridinylamino)propyl]-2,4-decadienamide;

(E,E)-5-(4-Methoxyphenyl)-N-[3-[(3-pyridinyl)thio]propyl]-2,4-nonadienamide;

(E,E)-5-(4-Methoxyphenyl)-N-[3-[(3-pyridinyl)thio]propyl]2,4-decadienamide;

(E,E)-5-(4-Methoxyphenyl)-N-[3-[(3-pyridinyl)thio]propyl]-2,4-undecadienamide;

(E,E)-N-[3-(3-pyridinyloxy)propyl]-5-(3-thienyl)-2,4decadienamide;

(E,E)-5-(4-Methoxyphenyl)-N-[2-[3-pyridinylmethoxy]ethyl]-2,4-undecadienamide;

(E,E)-5-(4-Methoxyphenyl)-N-[2-[3-pyridinylmethoxy]ethyl]-2,4-nonaadienamide;

(E,E)-5-(4-Methoxyphenyl)-N-[2-[3-pyridinylmethoxy]ethyl]-2,4-decadienamide;

(E,E)-5-(4-Methoxyphenyl)-N-[2-[(3-pyridinylmethyl)-thio]-ethyl]-2,4-undecadienamide;

(E,E)-5-(4-Methoxyphenyl)-N-[2-[(3-pyridinylmethyl)-thio]-ethyl]-2,4-nonadienamide;

(E,E)-5-(4-Methoxyphenyl)-N-[2-[(3-pyridinylmethyl)-thio]-ethyl]-2,4-decadienamide;

(E,E)-5-(4-Methoxyphenyl)-N-[2-[(3-pyridinylmethyl)amino]-ethyl]-2,4-decadienamide;

(E,E)-5-(4-Methoxyphenyl)-5-(3-pyridinyl)-N-[2-[(3-pyridinylmethyl)amino]ethyl]-2,4-pentadienamide;

(E,E)-5-(4-Methoxyphenyl)-N-[2-[(3-pyridinylmethyl)amino]ethyl]-2,4-undecadienamide;

(E,E)-5-(4-Methoxyphenyl)-N-[2-[(3-pyridinylmethyl)amino]-ethyl]-2,4-nonadienamide;

(E,E)-5-(4-Methoxyphenyl)-N-[2-[methyl-(3-pyridinylmethyl)amino]ethyl]-2,4-undecadienamide;

(E,E)-5-(4-Methoxyphenyl)-N-[2-[methyl-(3-pyridinylmethyl)amino]ethyl]-2,4-decadienamide;

(E,E)-5-(4-Methoxyphenyl)-N-[2-[methyl-(3-pyridinylmethyl)amino]ethyl]-2,4-nonadienamide;

[R-(E,E)]-5-(4-Methoxyphenyl)-9-methyl-N-[1-methyl-4-(3-pyridinyl)butyl]-2,4.8-decatrienamide;

[R-(E,E)]-8-Methoxy-5-(4-methoxyphenyl)-N-[1-methyl-4-[(3-pyridinyl)butyl]-2,4-octadienamide;

[R-(E,E)]-7-Ethoxy-5-(4-methoxyphenyl)-N-[1-methyl-4-[(3-pyridinyl)butyl]-2,4-heptadienamide; and the like.

The compounds of formula I can be prepared as hereinafter described in Reaction Schemes I–XIII.

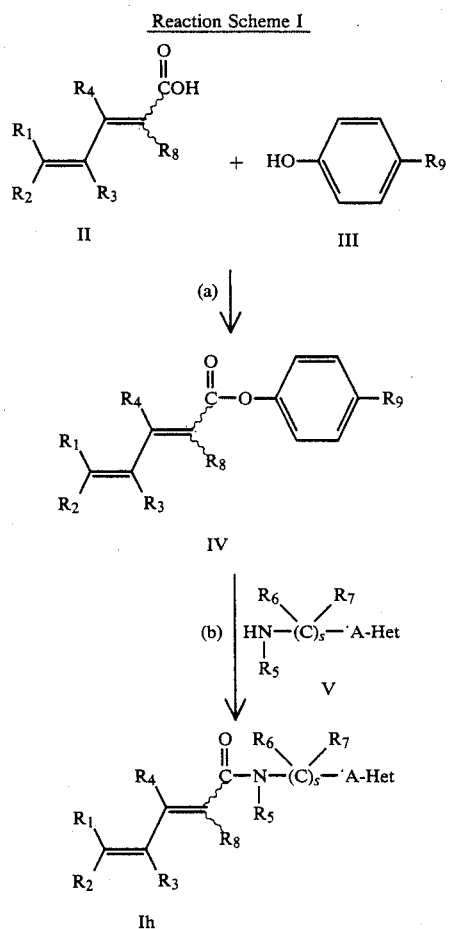

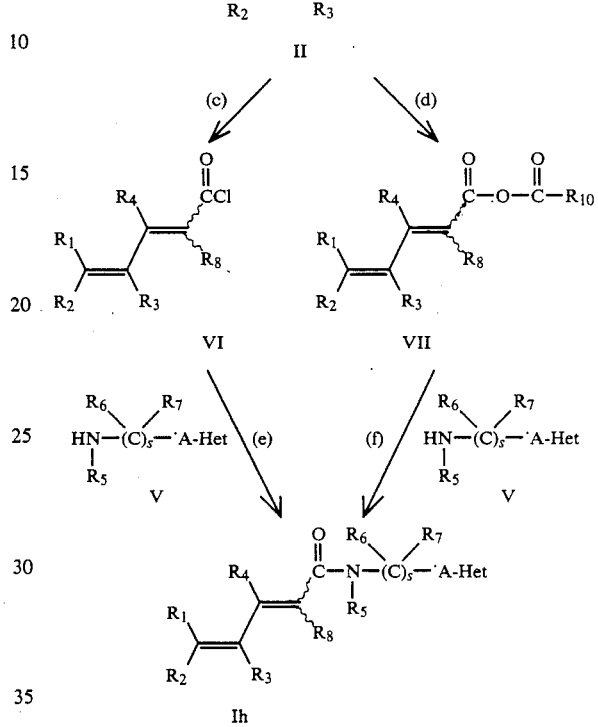

wherein $R_1$, $R_2$, $R_3$, $R_4$, $R_5$, $R_6$, $R_7$, $R_8$, *A, Het and s are as previously described and $R_9$ is hydrogen, halogen, lower alkyloxy, lower alkyl, trihaloalkyl or nitro.

In Reaction Scheme I, step (a), a pentadienoic acid of formula II which includes the (E) and (Z) isomers and mixtures thereof is reacted with a phenol of formula III in the presence of a condensing agent preferably dicyclohexylcarbodiimide, in an inert solvent such as dichloromethane. diethyl ether, dimethylformamide at a temperature of from −80° C. to room temperature. The resulting compounds of formula IV can be isolated utilizing conventional methods, for example, crystallization, chromatography or the like.

In step (b), an "activated" ester of formula IV is reacted with an amine of formula V, which includes the (R)- and (S)- enantiomers and racemic mixtures thereof, in an inert solvent, preferably tetrahydrofuran and diethyl ether, at a temperature of from −80° C. to 100° C. The process is advantageously carried out wherein $R_9$ is nitro. The resulting compound of formula Ih can be isolated utilizing conventional means, for example, crystallization, chromatography or the like.

wherein $R_1$, $R_2$, $R_3$, $R_4$, $R_5$, $R_6$, $R_7$, $R_8$, *A, Het and s are as previously described and $R_{10}$ is lower alkyl.

In Reaction Scheme II, step (c), a pentadienoic acid of formula II which includes the (E)- and (Z)-isomers and mixture thereof, is treated with an acyl halide forming reagent, preferably oxalyl chloride or thionyl chloride, in an inert solvent, preferably dichloromethane or toluene at a temperature of from −80° C. to room temperature. The resulting corresponding compound of formula VI can be isolated by evaporation of the reaction solvent and then, as in step (e), are treated with an amine of structure V which includes the (R)- and (S)-enantiomers and racemic mixtures thereof, in the presence of a tertiary amine, preferably triethylamine, in an inert solvent such as dichloromethane or toluene at a temperature of from −80° C. to room temperature. The resulting compound of formula Ih can be isolated utilizing conventional methods such as crystallization or chromatography or the like.

In step (d), a pentadienoic acid of formula II, which includes the (E)- and (Z)-isomers and mixtures thereof, is treated with an alkyl chloroformate in the presence of a tertiary amine, preferably triethylamine, in an inert solvent, preferably diethyl ether or tetrahydrofurane at a temperature of from −20° C. to 10° C. The resulting mixed anhydride of formula VII is treated in situ as in step (f) with an amine of formula V which includes the (R)- and (S)-enantiomers and racemic mixtures thereof at a temperature of from −20° C. to room temperature. The resulting compound of formula Ih can be isolated utilizing conventional methods such as crystallization and chromatography or the like.

Reaction Scheme III

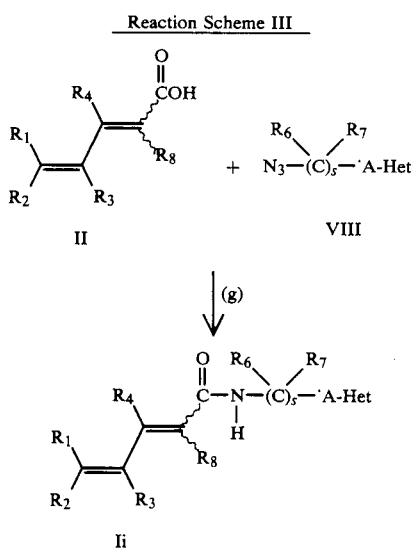

wherein $R_1$, $R_2$, $R_3$, $R_4$, $R_6$, $R_7$, $R_8$, *A, Het and s are as previously described.

In Reaction Scheme III, step (g). a pentadienoic acid of formula II which includes the (E)- and (Z)-isomers and mixtures thereof, is reacted with an azide of formula VIII in the presence of a trialkyl or triarylphosphine in an inert solvent, preferably toluene at a temperature of from room temperature to 100° C. The resulting desired compound of formula Ii can be isolated utilizing conventional methods such as crystallization, chromatography or the like.

Reaction Scheme IV

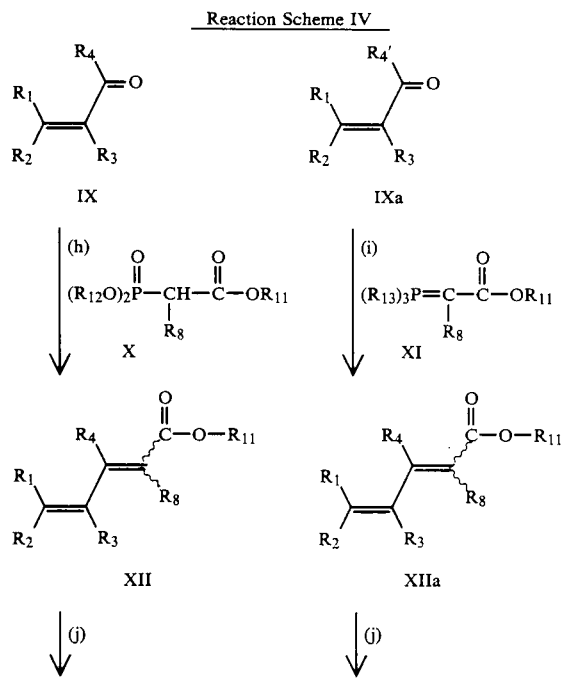

-continued
Reaction Scheme IV

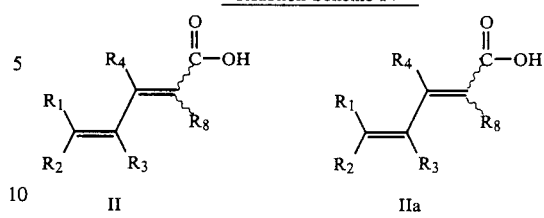

wherein $R_1$, $R_2$, $R_3$, $R_4$ and $R_8$ are as previously described, $R_4'$ is hydrogen, $R_{11}$, $R_{12}$ and $R_{13}$ are independently lower alkyl or aryl.

In Reaction Scheme IV, step (h), a phosphonoacetate triester of formula X is converted to its corresponding carbanion utilizing a strong base, preferably sodium hydride or sodium amide, in an inert solvent, preferably dimethylsulfoxide. dimethylformamide or tetrahydrofurane at temperatures of from 0° C. to 80° C., and then is reacted in situ with a carbonyl derivative of formula IX. The resulting compound of formula XII, may be a mixture of isomers, can be separated, if necessary, utilizing conventional methods such as crystallization, chromatography or the like.

In step (i), a carboxaldehyde of formula IXa is reacted with (carboxalkoxyalkylidene)triarylphosphorane in an appropriate solvent at a temperature of from −20° C. to −50° C. Use of an aprotic solvent, preferably dichloromethane, carbon tetrachloride or dimethylformamide leads to an isomer ratio of >10:1 in favor of the (E)-isomer around the newly formed double bond. When a protic solvent is used as reaction solvent, preferably methanol or ethanol, a higher proportion of the (Z)-isomer is formed (E:Z; ~3:2). The resulting compound of formula XIIa may be separated, if necessary, into the (E)- and (Z)-isomers by conventional methods such as crystallization, chromatography or the like.

In step (j), the pentadienoic acid esters of formula XII or XIIa are reacted with an excess of an alkali metal hydroxide in a solvent mixture preferably methanol-water or ethanol-water at a temperature of from room temperature to 85° C. The resulting compound of formula II or IIa is isolated by conventional methods such as chromatography or the like.

Reaction Scheme V

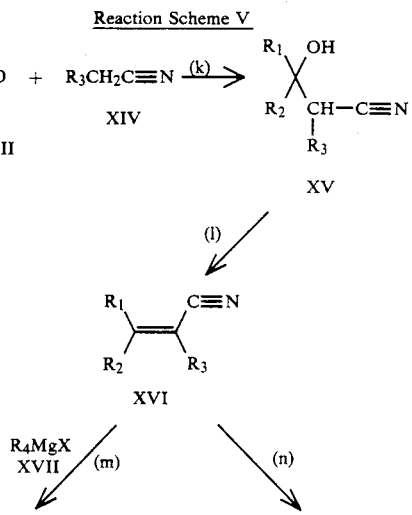

Reaction Scheme V -continued

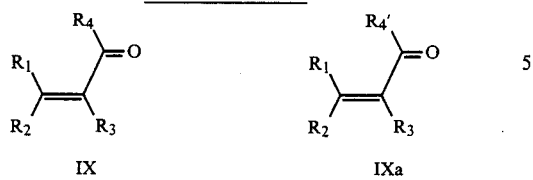

wherein $R_1$, $R_2$, $R_3$, $R_4$ and $R_4'$ are as previously described.

In Reaction Scheme V, step (k), the acetonitrile of formula XIV is converted to its carbanion by treatment with a strong base, preferably sodium hydride, sodamide or lithium diisopropylamide (LDA) in an inert solvent, preferably ether or tetrahydrofuran at temperature of $-80°$ C. to room temperature, and then is reacted in situ with a carbonyl compound of formula XIII. The resulting compound of formula XV is isolated by conventional methods such as chromatography, crystallization or the like.

In step (l), the carbinol of formula XV is reacted with an acid, preferably trifluoroacetic acid or methanesulfonic acid or sulfuric acid, with or without added inert solvents, preferably dichloromethane or chloroform, at a temperature of from $-10°$ C. to 45° C., or reacted with methanesulfonyl chloride in the presence of a tertiary amine, preferably triethylamine in an inert solvent, preferably dichloromethane at a temperature of from $-80°$ C. to room temperature. If $R_1 \neq R_2$ then the resulting compounds of formula XVI may be a mixture of (E)- and (Z)-isomers, which can, if necessary, be separated by conventional methods such as distillation, crystallization chromatography or the like.

In step (m), a compound of formula XVI is reacted with an alkyl or aryl magnesium halide of formula XVII, in an inert solvent, preferably diethyl ether or tetrahydrofurane at a temperature of from $-80°$ C. to reflux temperature. After acid hydrolysis of the intermediate imine, utilizing an aqueous solution of an acid, preferably oxalic acid or sulforic acid, a resulting compound of formula IX can be isolated utilizing conventional methods such as distillation, crystallization, chromatography or the like.

In step (n), a compound of formula XVI is reacted with a reducing agent, preferably diisobutylaluminium hydride, in an inert solvent, preferably toluene at a temperature of from $-80°$ C. to room temperature. After acid hydrolysis of the intermediate imine utilizing an aqueous solution of an acid, preferably oxalic acid or sulfuric acid, a resulting compound of formula IXa can be isolated by conventional methods such as distillation, chromatography. crystallization or the like.

Reaction Scheme VI

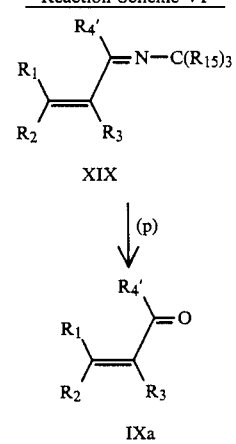

wherein $R_1$, $R_2$, $R_3$, $R_4'$ are as previously described, $R_{14}$ is lower alkyl or aryl and $R_{15}$ is lower alkyl.

In Reaction Scheme VI, step (o), a lithioenamino phosphonate of formula XVIII, prepared in situ by reaction of a carboxaldehyde N-tert-butylimine with a dialkyl chlorophosphonate in the presence of excess lithium diisopropylamide (LDA) is reacted with a carbonyl derivative of formula XIII in an inert solvent, preferably tetrahydrofuran or diethyl ether at a temperature of from $-80°$ C. to 50° C. In step (p), the resulting imine of formula XIX is most often hydrolyzed without isolation, utilizing an aqueous solution of an acid, preferably oxalic acid, hydrochloric acid or sulfuric acid. If $R_1 \neq R_2$ the resulting compound of formula IXa may be mixtures of (E)- and (Z)-isomers, which can, if necessary, be separated by conventional methods such as chromatography, crystallization and the like.

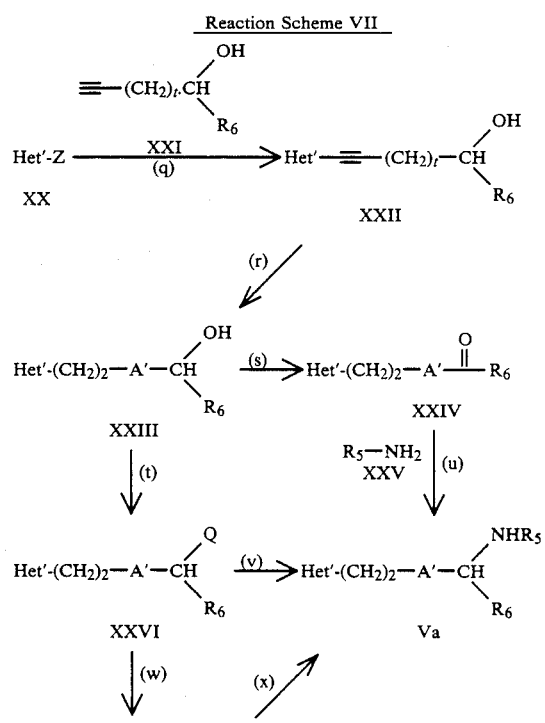

-continued
Reaction Scheme VII

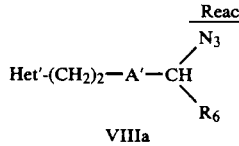

VIIIa

Het'-Z is a monocyclic 5- or 6-membered heteroaromatic or a bicyclic heteroaromatic compound containing one or two heteroatoms selected from nitrogen, oxygen, and sulfur, which compound may be substituted by halogen, lower alkyl or aryl wherein Z is iodide, bromide, or a perfluoroalkylsulfonate and is substituted in a position on the heteroaromatic ring such that it is active in transition metal catalyzed aryl-alkynyl coupling reactions. The compound of formula XXI becomes attached to Het' at the position of the leaving Z group. Examples of Het' are: 3-pyridinyl, 5-pyrimidinyl, 2-thienyl, 3-thienyl, 2-pyridinyl, 6-methyl-2-pyridinyl, 2-methyl-3-pyridinyl, 3-quinolinyl, 4-isoquinolinyl and the like. t is an integer of 0 to 4, A' is alkylene of 1 to 4 carbon atoms, Q is bromo, chloro, or an alkyl- or arylsulfonyloxy radical, and $R_5$ and $R_6$ are as previously described.

In Reaction Scheme VII, step (q), a compound of formula XX is reacted with an acetylene of formula XXI in the presence of an excess of a proton acceptor, for example, triethylamine, and a suitable palladium catalyst, for example, bis(triphenylphosphine)palladium dichloride, optionally in the presence of an inert solvent, for example, dichloromethane or dimethylformamide, at a temperature of from room temperature to 100° C., depending on the particular choice of Z-, solvent, and heteroaromatic ring, to give a compound of formula XXII. The resulting compound of formula XXII can be isolated utilizing conventional methods, for example, distillation, chromatography or the like, or may be used directly in the next step of the synthesis.

In step (r), an acetylene of formula XXII is dissolved in an inert solvent, for example, a lower alkanol, and hydrogenated over a suitable catalyst, for example, palladium on carbon, platinum oxide or the like, at a hydrogen pressure of from one to five atmospheres, preferably at room temperature, until reduction is complete. The resulting compound of formula XXIII can be isolated utilizing conventional methods, for example, distillation, chromatography or the like. Compounds of formula XXIII in which $R_6$ is other than hydrogen may be resolved into their enantiomers using standard methodology, for example, conversion to esters of chiral acids and chromatographic separation followed by ester hydrolysis.

In step (t), an alcohol of formula XXIII is reacted with an alkyl or aryl sulfonyl halide, for example, methanesulfonyl chloride or toluenesulfonyl chloride in the presence of a proton acceptor, for example, pyridine or triethylamine to give a compound of formula XXVI wherein Q is an alkyl- or arylsulfonyloxy radical of the same absolute chirality as the starting alcohol XXIII. Alternatively, a compound of formula XXIII can be reacted with a reagent useful for the conversion of alcohols into halides, for example, thionyl chloride, in the presence of a proton acceptor, for example, pyridine, until conversion to a compound of formula XXVI, Q=Cl, or Br is complete. The resulting compound of formula XXVI generally is not isolated, but utilized directly in the next step.

In step (w), a compound of formula XXVI, is reacted with an alkali metal azide, for example, sodium azide, in the presence of a polar inert solvent, for example, dimethylformamide, N-methylpyrrolidinone, dimethylsulfoxide or the like at a temperature of from about room temperature to 100° C. until azide formation is complete. The resulting compound of formula VIIIa can be isolated utilizing conventional methods, for example, chromatography or the like. This transformation generally proceeds with inversion of chirality at the carbon atom of XXVI bearing Q.

In step (v), a compound of formula XXVI is reacted with an amine anion equivalent to give an intermediate which can be deprotected to give an amine of formula Va. For example, a compound of formula XXVI can be reacted with an alkali metal phthalimide, for example, potassium phthalimide, in a polar aprotic solvent, for example dimethylformamide, dimethyl sulfoxide, N-methylpyrrolidinone, or the like at a temperature of from about 60° C. to 120° C. until reaction is complete to give an intermediate of formula XXVI, Q=phthalimido which can be converted to a compound of formula Va, by conventional means, for example by treatment with hydrazine in a lower alkanol solvent or with methylamine in a polar aprotic solvent such as dimethylformamide. Alternatively, a compound of formula XXVI can be reacted with a perfluoroalkylsulfonamide derived from a primary amine, for example N-alkyltrifluoromethanesulfonamide, in a polar aprotic solvent, for example, acetone, dimethylformamide, dimethylsulfoxide or the like in the presence of a base, for example, an alkali metal hydroxide or as appropriate, an alkali metal hydride, for example sodium hydride at a temperature of from room temperature to 100° C. The resulting compounds of formula Va can be isolated utilizing conventional methods, for example, distillation, crystallization of their acid addition salts, chromatography or the like. When a compound of formula XXVI is chiral, this transformation will generally proceed with inversion of configuration at the carbon atom bearing Q in a compound of formula XXVI.

In step (s), an alcohol of formula XXIII is oxidized to a carbonyl derivative of formula XXIV. Reagents which are useful for this transformation include chrominum based oxidizing reagents, for example, pyridinium chlorochromate. A preferable procedure is described in K. Omura and D. Swern, Tetrahedron 1978, 34, 1651, which involves dissolution of a slight excess of an acid halide, for example, oxalyl chloride in an inert halocarbon solvent, for example dichloromethane, cooling to a reaction temperature of from $-50°$ C. to $-80°$ C., addition of excess dimethyl sulfoxide, stirring for 0.25 to 0.5 hours, addition of one equivalent of an alcohol of formula XXIII, after an additional 0.25 to 0.5 hours, addition of excess triethylamine while maintaining the reaction temperature at from $-50°$ C. to $-80°$ C., and allowing the reaction mixture to warm for 0.5 to 1 hour before quenching with water and excess inorganic base to produce a carbonyl derivative of formula XXIV.

In step (u), a carbonyl derivative of formula XXIV is reacted with an amine of formula XXV to form a Schiff's base which is reduced in the presence of an appropriate reducing agent to produce an amine of formula Va in either a one step or two step process. For example, a compound of formula XXIV is treated with a large excess of an amine of formula XXV and an equivalent amount of a weak organic acid, for example acetic acid, in the presence of a reducing agent such as sodium cyanoborohydride in a suitable solvent, preferably a lower alkanol, for example methanol, at room temperature until the starting material is consumed. Alternatively, an amine of formula XXV and a carbonyl derivative of formula XXIV heated together in an aromatic solvent in an apparatus fitted with a water separator until water formation is complete. The resulting Schiff's base can be hydrogenated over a suitable catalyst, preferably Raney nickel, at a hydrogen pressure of from one to five atmospheres to give a compound of formula Va. When $R_6$ is not hydrogen and $R_5$ is chiral, the resulting amine Va may be enriched in one diastereomer over the other. For example, when $R_5$ is a chiral benzyl group, for example, R-alpha-methylbenzyl, and $R_6$ is lower alkyl, for example, methyl, the compound of formula Va may be diastereomerically enriched, and the chiral benzyl moiety may be removed, for example by hydrogenation over palladium on carbon to give an enantiomerically enriched amine of formula Va, $R_5=$ hydrogen and $R_6=$ lower alkyl. The compounds of formula Va can be isolated utilizing conventional methods, for example, extraction followed by distillation, crystallization of their acid addition salts, chromatography or the like.

In Reaction Scheme VII, step (x), an azide of formula VIIIa is dissolved in a solvent, preferably a lower alkanol, and hydrogenated at a hydrogen pressure of from one to five atmospheres over a nobel metal catalyst, for example, palladium on carbon or platinum oxide.

The resulting compounds of formula Va can be isolated utilizing conventional methods, for example, distillation, crystallization of their acid addition salts, chromatography or the like. This transformation proceeds without alteration of the chirality of the carbon atom bearing the azido group in a compound of formula VIIIa.

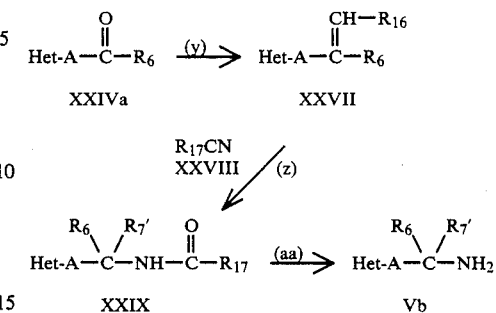

Reaction Scheme VIII wherein Het, A and $R_6$ are as previously described, $R_7$, is alkyl, $R_{16}$ is hydrogen or lower alkyl, and $R_{17}$ is alkyl or aryl.

In Reaction Scheme VIII, step (y), a carbonyl derivative of formula XXIVa is treated with an alkylidene triarylphosphorane in an inert solvent, preferably tetrahydrofuran, dimethylsulfoxide or diethyl ether, at a temperature of from $-80°$ C. to room temperature. The resulting compounds of formula XXVII can be isolated utilizing conventional methods, for example, distillation, chromatography or the like.

In step (z), a nitrile of formula XXVIII is reacted with a compound of formula XXVII in the presence of a strong mineral acid, preferably sulfuric acid and a small amount of water. The resulting compounds of formula XXIX can be isolated utilizing conventional methods, for example, distillation, crystallization, chromatography or the like.

In step (aa), a compound of formula XXIX is hydrolyzed to an amine of formula Vb. This process is advantageously carried out where $R_{17}$ is 2-nitrobenzyl by catalytic reduction of the nitro group for example over palladium on carbon at one atmosphere hydrogen pressure, and heating of the residue in the absence of solvent or in the presence of a solvent, for example acetic acid. The resulting compounds of formula Vb can be isolated utilizing conventional methods, for example, distillation, crystallization of their acid addition salts, chromatography or the like.

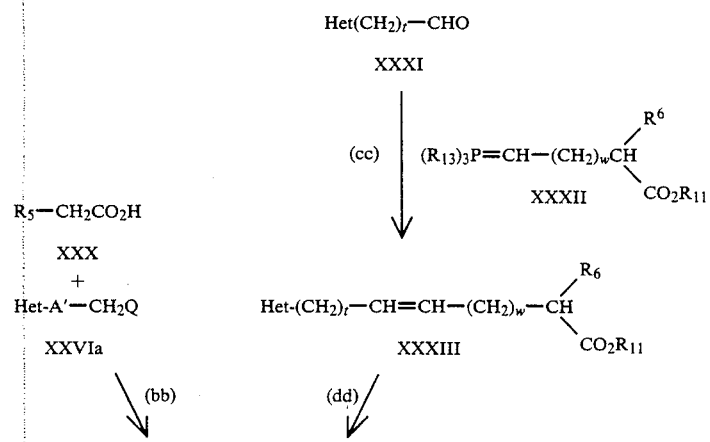

Reaction Scheme IX

Reaction Scheme IX

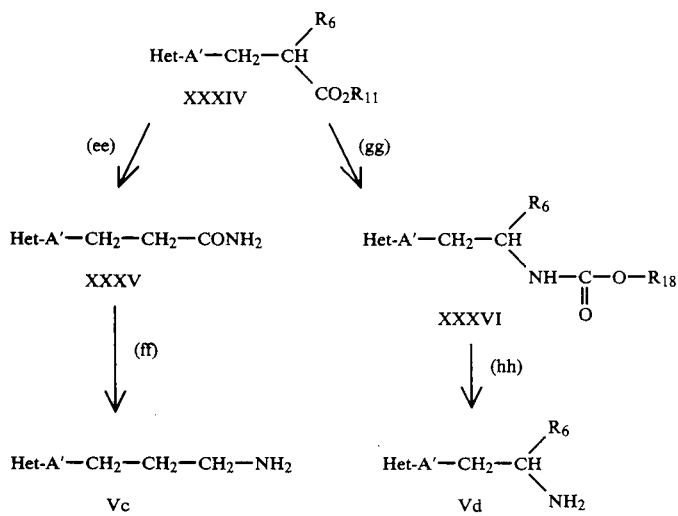

wherein Het, $R_6$, $R_{13}$, $A'$, $Q$ and $t$ are as previously described, and $R_{11}$ is hydrogen or lower alkyl, $R_{18}$ is alkyl or aryl, and w is an integer of 0 to 3.

In Reaction Scheme IX, step (bb), the dilithium salt derived from a compound of formula XXX, for example by treatment with lithium diisopropylamide, is reacted with a compound of formula XXVIa in a suitable inert solvent, for example tetrahydrofuran, to give a compound of formula XXXIV, $R_{11}$=hydrogen. The resulting compounds of formula XXXIV can be isolated utilizing conventional methods, for example, crystallization, chromatography or the like.

Compounds of formula XXXIV in which $R_6$ is non-hydrogen, and $R_{11}$ is hydrogen, may be resolved into their enantiomers by conversion to salts of chiral, enantiomertically pure amines, for example cinchonine, brucine, alpha-methylbenzylamine or the like. The pure diasteromeric salts are obtained by fractional crystallization from an appropriate solvent, for example a lower alkanol. The chiral, enantiomerically pure acids of formula XXXIV, $R_{11}$=hydrogen may be recovered from their salts by conventional means, for example extraction from an aqueous, acidic solution.

In step (cc), a heteroaromatic carboxaldehyde of formula XXXI, is reacted with a (carboxyalkylidene)-triarylphosphorane of formula XXXII in a suitable solvent, for example tetrahydrofuran, dichloromethane, methanol or dimethylsulfoxide, to give a compound of formula XXXIII. The resulting compounds of formula XXXIII can be isolated utilizing conventional methods, for example, crystallization, distillation, chromatography or the like.

In step (dd), a compound of formula XXXIII is hydrogenated over a suitable catalyst, for example, palladium on carbon or platinum oxide, in a suitable solvent, for example, a lower alkanol, at a hydrogen pressure of from one to five atmospheres until the theoretical amount of hydrogen is taken up to give a compound of formula XXXIV.

In step (ee), a compound of formula XXXIV is converted into an amide of formula XXXV using conventional techniques for the conversion of carboxylic acids and esters into the corresponding primary amide. For example, a compound of formula XXXIV, $R_{11}$=hydrogen may be converted to the corresponding acid chloride by treatment with thionyl chloride and then treated with an excess of ammonia to give a compound of formula XXXV. Alternatively, a compound of formula XXXIV, R=lower alkyl, may be converted into a compound of formula XXXV by treatment with excess ammonia, optionally in the presence of co-solvent, for example, a lower alkanol, at a temperature of from −33° C. to room temperature. The reaction may be run in a pressure vessel when appropriate.

In step (ff), a compound of formula XXXV is treated with a reducing agent, for example borane in tetrahydrofuran at a temperature of from room temperature to the reflux temperature of the solvent for 4 to 24 hours or until reduction is complete to give a compound of formula Vc. The resulting compounds of formula Vc can be isolated utilizing conventional methods, for example, by destruction of the excess reagent with a lower alkanol, followed by treatment with a mineral acid, for example, hydrochloric acid, basification, evaporation of the solvent and extraction of the product into a suitable organic solvent, for example, dichloromethane and purified by distillation, chromatography or the like.

In step (gg), an acid of formula XXXIV, $R_{11}$=hydrogen, which may be obtained from the corresponding ester by hydrolysis, is subjected to conditions leading to a Curtius rearrangement in the presence of a lower alkanol. In a preferred procedure, an acid of formula XXXIV (R=hydrogen), is treated with one equivalent of diphenylphosphoryl azide in the presence of a proton acceptor, for example triethylamine or the like, and an excess of a lower alkanol or a phenol to give a compound of formula XXXVI. The resulting compounds of formula XXXVI can be isolated utilizing conventional methods, for example, crystallization, chromatography or the like.

In step (hh), a compound of formula XXXVI is treated with an excess of a mineral acid in water and optionally an addition co-solvent, for example a lower alkanol, at a temperature of from room temperature to 100° C. or with a strong base in water, optionally in the presence of a co-solvent, for example a lower alkanol at a temperature of between 60° C. and 100° C. to form a compound of formula Vd. The resulting compounds of formula Vd can be isolated utilizing conventional methods, for example, crystallization of their acid addition salts, distillation, chromatography or the like.

Reaction Scheme X

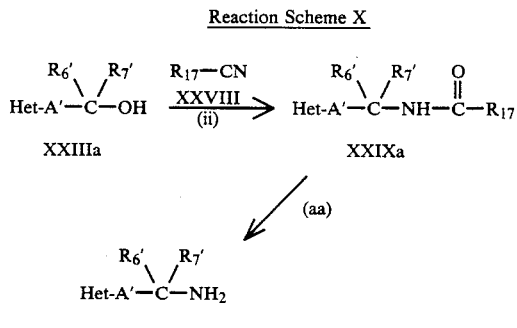

wherein Het, A', $R_7$, and $R_{17}$, are as previously described, and $R_6'$ is lower alkyl.

In Reaction Scheme X, step (ii), an alcohol of formula XXIIIa is reacted with a nitrile of formula XXVIII in the presence of a mineral acid, for example sulfuric acid, and water at a temperature of from $-20°$ C. to room temperature to give a compound of formula XXIXa. The compound of formula XXIXa can be isolated by conventional means, for example chromatography, crystallization or the like.

In this Reaction Scheme, step (aa), is the same as step (aa) in Reaction Scheme VIII to give a compound of formula Vd. The compound of formula Vd can be isolated by conventional means, for example, chromatography, crystallization or its acid addition salts, distillation or the like.

Reaction Scheme XI

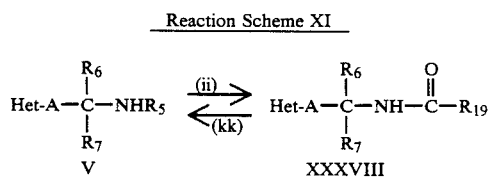

wherein Het, A, $R_5$, $R_6$ and $R_7$ are as previously described, $R_{19}$ is a chiral moiety, for example, a bonded chain lower alkyl or lower alkyl substituted with one or two groups selected from hydroxy, lower alkoxy, lower alkylcarbonyloxy, perfluoroalkyl, or aryl.

In Reaction Scheme XI, step (jj), those compounds of formula V which are chiral may be resolved into their enantiomers by conversion to amides of chiral, enantiomerically pure acids using common techniques of peptide coupling. For example, a chiral amine of formula V may be coupled with a chiral, enantiomerically pure acid, for example (R)-mandelic acid, in the presence of a suitable coupling reagent, for example, dicyclohexylcarbodiimide optionally in the presence of a promoter, for example 1-hydroxybenzotriazole in a polar, aprotic solvent, for example dimethylformamide to give an amide of formula XXXVIII. Amides of formula XXXVIII may be separated into pure diastereomers by fractional crystallization, chromatography or the like.

In step (kk), enantiomerically pure compounds of formula V may be recovered by hydrolysis of diastereomerically pure amides of formula XXXVIII, for example with an aqueous mineral acid at a temperature of from 60° C. to 120° C.

Reaction Scheme XII

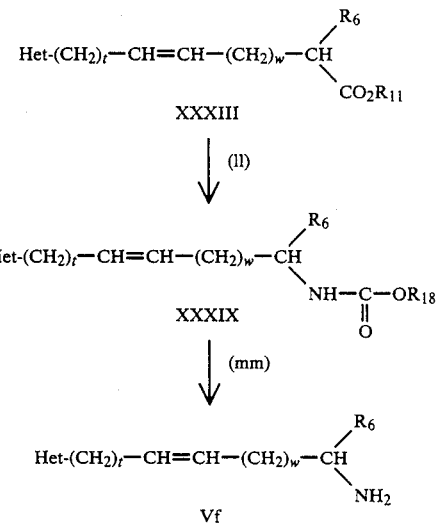

wherein $R_6$, $R_{11}$, $R_{18}$, t, w and Het are as previously described.

In Reaction Scheme XII, step (11), an acid of formula XXXIII, R=hydrogen, which can be obtained from the corresponding ester by hydrolysis, is treated with one equivalent of diphenylphosphoryl azide in the presence of a proton acceptor, for example triethylamine, and an excess of a lower alkanol or phenol to give a compound of formula XXXIX. Compounds of formula XXXIX can be isolated by utilizing conventional methods, for example distillation, crystallization, chromatography or the like.

In Reaction Scheme XII, step (mm), a compound of formula XXXIX is treated with an excess of a mineral acid in water and optionally an additional co-solvent, for example a lower alkanol at a temperature of from room temperature to 100° C. to form a compound of formula Vf. The resulting compounds of formula Vf may be isolated utilizing conventional methods such as chromatography, distillation or the like.

Reaction Scheme XIII

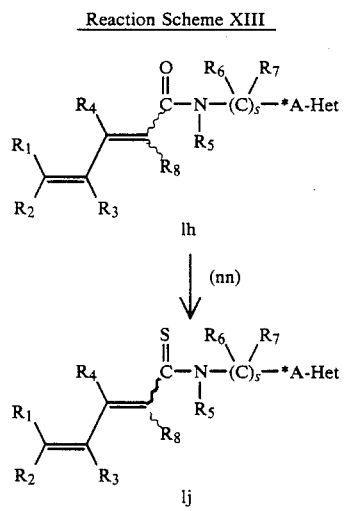

wherein $R_1$, $R_2$, $R_3$, $R_4$, $R_5$, $R_6$, $R_7$, $R_8$, *A, Het and s are as previously described.

In Reaction Scheme XIII, step (nn), a carboxamide of formula 1h is treated with phosphorous pentasulfide, in a suitable solvent, for example dichloromethane or tetrahydrofuran, optionally in the presence of a proton acceptor, for example triethylamine, at a temperature of from room temperature to the reflux temperature of the solvent. The resulting compounds of formula 1j may be isolated utilizing conventional methods, such as chromatography, crystallization or the like.

The compounds of formula I can form acid addition salts with inorganic or organic acids. Thus, they form pharmaceutically acceptable acid addition salts with both pharmaceutically acceptable organic and inorganic acids, for example, with hydrohalic acids, such as, hydrochloric acid, hydrobromic acid, hydroiodic acid, other mineral acid salts, such as, sulfuric acid, nitric acid, phosphoric acid, perchloric acid or the like, alkyl and mono-aryl sulfonic acids such as, ethanesulfonic acid, toluenesulfonic acid, benzenesulfonic acid, or the like, other organic acids such as tartaric acid, maleic acid, citric acid, salicylic acid, ascorbic acid and the like. Non-pharmaceutically acceptable acid addition salts of compounds of formula I can be converted into pharmaceutically acceptable acid addition salts via conventional metathetic reactions whereby the non-pharmaceutically acceptable anion is replaced by a pharmaceutically acceptable anion; or alternatively, by neutralizing the non-pharmaceutically acceptable acid addition salt and then reacting the so-obtained free base with a reagent yielding a pharmaceutically acceptable acid addition salt.

The compounds of formula I exhibit activity as platelet activating factor (PAF) antagonists and are, therefore, useful in disease states characterized by excess platelet activating factor or for the prevention and treatment of cardiovascular diseases, pulmonary diseases, immunological disorders, inflammatory diseases, dermatological disorders, shock or transplant rejection.

The useful activity of the compounds of formula I can be demonstrated by the following procedures:

Binding Assay (a) Assay

The binding assay was done in 400 μl polyethylene microcentrifuge tubes (Beckman) containing 50 μl of an oil mixture of 2 parts Siliconol AR200 (Serva): 1 part Silicone Fluid (Arthur H. Thomas). Buffer, standards, or analogs (150 μl total volume) were added to the tubes. Radiolabelled $^3$H-PAF (50 μl) was then added to the tubes. The reaction was started by the addition of 50 μl of dog platelets ($2 \times 10^7$ platelets). The tubes were capped, inverted several times to mix, and incubated for 10 minutes at room temperature. The platelets were separated from the incubation mixture by centrifuging 1 minute in a Beckman Microfuge B centrifuge. The tip of the microfuge tube was cut off, and the platelets were washed out of the tip with 200 μl of 50% methanol (Burdick and Jackson). Aquasol (NEN, 10 ml) was added and the radioactivity in the samples was determined using an LS 8100 Beckman liquid scintillation counter linked to a Techtran tape recorder. Data was processed through an in-house computer system. Alternatively, radioactivity was determined using a Searle Mark III liquid scintillation counter linked to a Iso-Data microprocessor. Results are set forth in Table I.

(b) Preparation of Platelets

Blood was collected from anesthesized or unanesthesized dogs into 50ml plastic centrifuge tubes containing 3.8% sodium citrate as the anticoaqulant (1 volume of citrate/9 volumes of blood). The red cells were removed by centrifugation for 15 minutes at 600 rpm (100–125 g) at room temperature. An aliquot of the supernatant platelet rich plasma (PRP) was saved for cell counting and the remainder was acidified to PH 6.5 with 0.15M citric acid. The platelet pellet was obtained after a 10 minute centrifugation at 2000 rpm (1000 g) at room temperature. Washed platelets were prepared by resuspending the platelet pellet once with PBS containing 1 mM EDTA, centrifuging as noted, and then resuspending the platelets in 0.1% BSA-PBS. An aliquot of the washed platelets was counted. Platelets used for binding assays were diluted to $2 \times 10^7$ platelets/assay tube ($4 \times 10^8$ platelets/ml). Platelet counting was done using a Royco Cell-Crit 921.

PAF Induced Bronchoconstriction Assay

Male animals (Hartlet Strain, 400–500 g) were anesthetized with urethane (2 g/kg, i.p.). Each animal's trachea was cannulated and the guinea pigs were repirated using a Harvard small animal rodent respirator (3.0 cc stroke volume, 40 breaths per min.). Tracheal pressure was recorded from a cannula inserted in the trachea and connected to a Statham Pressure Transducer.

The jugular vein was cannulated for administering compounds. Spontaneous breathing was arrested with succinylcholine (1.2 mg/kg, i.v.) administered 2 minutes prior to intravenous injection of platelet activating factor (PAF). Since propranolol has been shown to enhance bronchoconstrictor responses, all animals were pretreated five minutes prior to challenge with propranolol (0.1 mg/kg. i.v.).

For, the intravenous testing, the guinea pig is given a 5-minute pretreatment with propranolol at a dose of 1 mg/kg intravenously. The test compound is administered with a 1 minute pretreatment prior to intravenous challenge with PAF The animal is than challenged with a 1.0 μg/kg intravenous dose of PAF and the change is tracheal pressure is measured.

For the oral testing, the procedure includes a 2-hour pretreatment period with the test compound administered through an oral gavage tube. Propranolol or succinylcholine and PAF are administered intravenously, and the change in tracheal pressure measured.

The change is tracheal pressure is determined by subtracting the steady state baseline achieved after administration of succinylcholine from the peak bronchoconstriction seen after challenge with PAF. The mean is calculated for each test compound and compared to the mean of the control animals to give the percent inhibition of bronchoconstriction. The standard error is calcuated as the standard error of the mean.

PAF Induced Platelet Count Decrease

Male Hartley guinea pigs weighing between 500 and 900 grams were fed standard guinea pig chow and tap water ad libitum. PAF was solubilized in ethanol and stored as a 2mM stock solution at $-70°$ C. The stock solution of PAF was diluted to 1 pM in Tris buffer pH 7.4 and 0.1% BSA for all experiments.

(a) Intravenous Procedure

Guinea pigs were anesthetized with urethane (1.6 g/kg, i.p.) A catheter (PE50) was introduced into the right carotid artery for withdrawing blood. A second catheter PE10) was introduced into the jugular vein for injecting drugs and for administering the PAF challenge (75 ng/kg, i.v.). A control blood sample was obtained and platelets were counted in a whole blood platelet analyzer. PAF was then given and blood samples were taken 15, 30, and 60 seconds after the challenge for platelet counts. Fifteen minutes later, selected concentrations of the test compound were solubilized in DMSO and injected intravenously into a group of 4–6 animals. Only one concentration of antagonist was used in each animal group. Fifteen minutes after drug injection, blood samples were taken before and 15, 30, and 60 sec after the PAF challenge, and analyzed for platelet number.

(b) Oral Procedure

Animals were anesthetized with sodium pentobarbital (35 mg/kg, i.p.) and the caritoid artery and jugular vein were cannulated as described above. The cannulae were exteriorized at the base of the neck and the animals were allowed to recover. At least 18 hours after surgery, conscious unrestrained guinea pigs were used in the experiment. The animals were challenged two time with PAF (120 ng/kg, i.v.); the first to establish a consistent response to PAF and the second to serve as a control for the PAF challenge. Blood samples were taken before and 15, 30, and 45 seconds after PAF challenge and platelets were counted. Thirty minutes after the control PAF challenge, the animal were orally dosed with either gum acacia or the test compound. Animals were then challenged with PAF at 1, 3, 5, and 24 hours after the administration of the drug.

Data Analysis and Statistics

The % change, i.e., the difference in platelet number before and after PAF challenge was calculated by:

$$\% \text{ change} = \frac{\# \text{ control platelets (0 Time)} - \text{lowest } \# \text{ of platelets after } PAF}{\# \text{ of control platelets (0 Time)}}$$

the % activity of drug was then determined by % activity =

$$\frac{\% \text{ change (control)} - \% \text{ change (drug)}}{\% \text{ change (control)}}$$

Statistical significance ($p < 0.05$) of the difference between the mean PAF control and mean drug treated activity was determined with paried Students's t-test.

The compounds of formula I also have Thromboxane Synthase ($TXA_2Syn.$) Inhibitory Activity, which can be demonstrated as follows.

$TXA_2$ Synthesis Inhibition

Thromboxane Synthase inhibitory $TAX_2$ syn. activity is measured by following the conversion of $^{14}C$-thromboxane $A_2$ ($TXA_2$) using microsomal fractions from human platelets as enzyme source. In the aqueous incubation medium the $TA\ X_2$ decomposes rapidly into $TXB_2$. The amount of $TXA_2$ syn. is adjusted so that under the conditions of the assay approximately 80–90% of the substrate, $PGH_2$, is converted to product in control tubes. To prepare $^{14}C$-$PGH_2$, $^{14}C$-AA(50–60-mCi/mmole; Rose Chem.) is incubated with sheep seminal vesicular gland microsomes for 1.5 min. at 37° C. and then the $^{14}C$-$PGH_2$ is extracted with diethylether, purified on columns of Sephadax LH-20 or silicic acid, and stored in acetone at $-70°$ C. Incubations are done as follows. Sufficient $^{14}C$-PGH to yield a final substrate concentration of 10 $\mu$M ($\sim 30,000$ cpm) is added to the incubation tubes and then the acetone is removed under nitrogen. The tubes are placed in an ice bath and then 215 $\mu$l of ice cold phosphate buffered saline, 10 $\mu$l of ethanol (control) or of test drug in ethanol, and 25 $\mu$l of the microsomal suspension are added with mixing in that order as rapidly as possible. The tubes are incubated at 22° C. for 2 minutes, the reaction is stopped and then the radioactive produces and the unconverted $PGH_2$ are extracted and analyzed by thin layer chromatography. The amount of $^{14}C$-$PGH_2$ converted to products is analyzed by thin layer chromatography. The amount of $^{14}C$-$PGH_2$ converted to products was used as a measure of $TXA_2$ synthase activity. Inhibitors were tested initially at a concentration of 100 $\mu$M. $IC_{50}$ values were calculated by linear regression analysis of successive 10 fold dilutions of the test compound concentration.

Test results obtained with compounds of formula I in the described tests are set forth in Table I which follows:

| Compound | Inhib of PAF Binding $IC_{50}$ (nM) | Percent Inhib. of PAF-Induced Bronchoconstriction | | Percent Inhib. of PAF-Induced Platelet Count Decrease | |
|---|---|---|---|---|---|
| | | 1 mg/Kg i.v. | 50 mg/Kg p.o. | 3 mg/Kg i.v. | 30 mg/Kg p.o. |
| (E)-5,5-Diphenyl-N-[4-(3-pyridinyl)butyl]-2,4-pentadienamide | 55 | 35 ± 15 | 12 ± 1 | 14 | |
| (Z)-5,5-Diphenyl-N-[4-(3-pyridinyl)butyl]-2,4-pentadienamide | 400 | | | | |
| [R,S-(E)]-5,5-Diphenyl-N-[1-methyl-4-(3-pyridinyl)butyl]-2,4-pentadienamide | 100 | | | | |
| (E)-5,5-Diphenyl-2-methyl-N-[4-(3-pyridinyl)butyl]-2,4-pentadienamide | 100 | | | | |
| (E)-5,5-bis(3-Fluorophenyl)-N-[4-(3-pyridinyl)butyl]-2,4-pentadienamide | 20 | 72 ± 16 | 37 ± 11 | 61 | 58 |
| [R,S-(E)]-5,5-bis(3-Fluorophenyl)-N-[1-methyl-4-(3-pyridinyl)butyl]-2,4-pentadienamide | 30 | | | | |
| [R-(E)]-5,5-bis(3-Fluorophenyl)-N-[1-methyl-4-(3-pyridinyl)butyl]-2,4-pentadienamide | 170 | 73 ± 6 | 91 ± 5 | 17 | |
| [S-(E)]-5,5-bis(3-Fluorophenyl)-N-[1-methyl-4-(3-pyridinyl)butyl]-2,4-pentadienamide | 250 | 34 ± 7 | 46 ± 8 | 19 | |
| (E)-5,5-bis(3-Fluorophenyl)-N-[1,1-dimethyl-4-(3-pyridinyl)butyl]-2,4-pentadienamide | | | 11 ± 10 | | |
| (E)-5,5-bis(4-Fluorophenyl)-N-[4-(3-pyridinyl)butyl]-2,4-pentadienamide | 40 | 91 ± 3 | 97 ± 1 | 18 | |
| [R-(E)]-5,5-bis(4-Fluorophenyl)-N-[1-methyl- | 250 | 70 ± 9 | 53 ± 11 | 11 | |

-continued

| Compound | Inhib of PAF Binding IC$_{50}$ (nM) | Percent Inhib. of PAF-Induced Bronchoconstriction | | Percent Inhib. of PAF-Induced Platelet Count Decrease | |
|---|---|---|---|---|---|
| | | 1 mg/Kg i.v. | 50 mg/Kg p.o. | 3 mg/Kg i.v. | 30 mg/Kg p.o. |
| 4-(3-pyridinyl)butyl]-2,4-pentadienamide | | | | | |
| [S-(E)]-5,5-bis(4-Fluorophenyl)-N-[1-methyl-4-(3-pyridinyl)butyl]-2,4-pentadienamide | 275 | | 44 ± 10 | | |
| (E)-5,5-bis(4-Fluorophenyl)-N-[1,1-dimethyl-4-(3-pyridinyl)butyl]-2,4-pentadienamide | | | 20 ± 14 | | |
| (E)-5,5-bis(3-Methoxyphenyl)-N-[4-(3-pyridinyl)butyl]-2,4-pentadienamide | 2 | 69 ± 7 | 31 ± 11 | 75 | 48 |
| (Z)-5,5-bis(3-Methoxyphenyl)-N-[4-(3-pyridinyl)butyl]-2,4-pentadienamide | | | | | |
| (E)-5,5-bis(3-Methoxyphenyl)-N-[6-(3-pyridinyl)hexyl]-2,4-pentadienamide | 450 | | | | |
| [R,S-(E)]-5,5-bis(3-Methoxyphenyl)-N-[1-methyl-4-(3-pyridinyl)butyl]-2,4-pentadienamide | 20 | | | | |
| [R-(E)]-5,5-bis(3-Methoxyphenyl)-N-[1-methyl-4-(3-pyridinyl)butyl]-2,4-pentadienamide | 35 | 87 ± 4 | 87 ± 8 | 31 | |
| [S-(E)]-5,5-bis(3-Methoxyphenyl)-N-[1-methyl-4-(3-pyridinyl)butyl]-2,4-pentadienamide | 300 | 36 ± 4 | 10 ± 5 | 10 | |
| (E)-5,5-bis(3-Methoxyphenyl)-N-[1,1-dimethyl-4-(3-pyridinyl)butyl]-2,4-pentadienamide | | | 22 ± 10 | | |
| (E)-5,5-bis(4-Methoxyphenyl)-N-[4-(3-pyridinyl)butyl]-2,4-pentadienamide | 25 | 92 ± 3 | 82 ± 12 | 40 | 45 |
| [R,S-(E)]-5,5-bis(4-Methoxyphenyl)-N-[1-methyl-4-(3-pyridinyl)butyl]-2,4-pentadienamide | | | | | |
| [R-(E)]-5,5-bis(4-Methoxyphenyl)-N-[1-methyl-4-(3-pyridinyl)butyl]-2,4-pentadienamide | 65 | 87 ± 4 | 97 ± 2 | 85 | 8 |
| [S-(E)]-5,5-bis(4-Methoxyphenyl)-N-[1-methyl-4-(3-pyridinyl)butyl]-2,4-pentadienamide | 200 | 42 ± 13 | 90 ± 6 | 42 | |
| (E)-5,5-bis(4-Methoxyphenyl)-N-[1,1-dimethyl-4-(3-pyridinyl)butyl]-2,4-pentadienamide | | | 54 ± 9 | | |
| (E)-5,5-bis(3,4-Dimethoxyphenyl)-N-[4-(3-pyridinyl)butyl]-2,4-pentadienamide | 55 | 78 ± 6 | 71 ± 2 | | |
| [R-(E)]-5,5-bis(3,4-Dimethoxyphenyl)-N-[1-methyl-4-(3-pyridinyl)butyl]-2,4-pentadienamide | 50 | 99 ± 1 | 66 ± 19 | | |
| (E)-5,5-bis(3-Chlorophenyl)-N-[4-(3-pyridinyl)=butyl]-2,4-pentadienamide | 25 | 76 ± 14 | 35 ± 7 | 21 | |
| (E)-5,5-bis(4-Chlorophenyl)-N-[4-(3-pyridinyl)=butyl]-2,4-pentadienamide | 60 | 95 ± 2 | 63 ± 10 | 0 | |
| (E)-5,5-bis[2-(Trifluoromethyl)phenyl]-N-[4-(3-pyridinyl)butyl]-2,4-pentadienamide | 80 | 6 ± 10 | — | 0 | |
| (E)-5,5-bis[3-(Trifluoromethyl)phenyl]-N-[4-(3-pyridinyl)butyl]-2,4-pentadienamide | 150 | inactive | — | 83 | |
| (E)-5,5-bis(3-Nitrophenyl)-N-[4-(3-pyridinyl)=butyl]-2,4-pentadienamide | 115 | 18 ± 2 | | | |
| (E,E)-5-(3-Methoxyphenyl)-5-phenyl-N-[4-(3-pyridinyl)butyl]-2,4-pentadienamide | 20 | | 13 ± 18 | 40 | |
| (2E,4Z)-5-(3-Methoxyphenyl)-5-phenyl-N-[4-(3-pyridinyl)butyl]-2,4-pentadienamide | 35 | | 10 ± 10 | inactive | |
| (2E,4Z)-5-(3-Fluorophenyl)-5-(3-methoxyphenyl)-N-[4-(3-pyridinyl)butyl]-2,4-pentadienamide | 40 | 90 ± 5 | 1 ± 8 | 67 (1 min) | |
| (E,E)-5-(3-Fluorophenyl)-5-(3-methoxyphenyl)-N-[4-(3-pyridinyl)butyl]-2,4-pentadienamide | 25 | 88 ± 4 | 25 ± 14 | inactive | |
| (E)-5,5-bis[1,1'-Biphenyl]-4-yl]-N-[4-(3-pyridinyl)butyl]-2,4-pentadienamide | | | | | |
| (E)-5,5-bis(4-Methoxyphenyl)-N-[5-(2-pyridinyl)=pentyl]-2,4-pentadienamide | 1000 | 27 ± 6 | | | |
| (E)-5,5-bis(4-Methoxyphenyl)-N-[3-(4-pyridinyl)=propyl]-2,4-pentadienamide | 100 | 8 ± 12 | | | |
| (E)-5,5-bis(4-Methoxyphenyl)-N-[4-(3-pyridinyl=methyl)ethoxy]-2,4-pentadienamide | 25 | 48 ± 7 | | | |
| (E)-5,5-bis(4-Methoxyphenyl)-N-[3-[(3-pyridinyl)=oxy]propyl]-2,4-pentadienamide | 300 | | | | |
| (E)-N-[4-(4-Isoquinolinyl)butyl]-5,5-bis=(4-methoxyphenyl)-2,4-pentadienamide | >1000 | | | | |
| (E)-N-[3-(8-Isoquinolinyl)propyl]-5,5-bis=(4-methoxyphenyl)2,4-pentadienamide | >1000 | | | | |
| (E)-N-(5-Isoquinolinyl)-5,5-bis(4-methoxyphenyl)-2,4-pentadienamide | 600 | | | | |
| (E)-5,5-bis(4-Methoxyphenyl)-N-[4-(3-pyridinyl)=phenyl]2,4-pentadienamide | 10 | 97 ± 1 | 84 ± 8 | | |
| (E)-5,5-bis(4-Methoxyphenyl)-N-[4-(3-pyridinyl=methyl)phenyl]-2,4-pentadienamide | 250 | 3 ± 7 | | | |
| [R,S-(E)]-5,5-bis(4-Methoxyphenyl)-N-[1-methyl-4-(6-methyl-3-pyridinyl)butyl]-2,4-pentadienamide | 700 | | | | |
| [R,S-(E)]-5,5-bis(4-Methoxyphenyl)-N-[1-methyl-4-(2-methyl-3-pyridinyl)butyl]-2,4-pentadienamide | 30 | 47 ± 10 | | | |
| [R,S-(E)]-5,5-bis(4-Methoxyphenyl)-N-[1-methyl-4- | 900 | | | | |

-continued

| Compound | Inhib of PAF Binding IC$_{50}$ (nM) | Percent Inhib. of PAF-Induced Bronchoconstriction | | Percent Inhib. of PAF-Induced Platelet Count Decrease | |
|---|---|---|---|---|---|
| | | 1 mg/Kg i.v. | 50 mg/Kg p.o. | 3 mg/Kg i.v. | 30 mg/Kg p.o. |
| (6-ethyl-3-pyridinyl)butyl]-2,4-pentadienamide | | | | | |
| [R,S-(E)]-N-[1-Ethyl-4-(3-pyridinyl)butyl]-5,5-bis= (4-methoxyphenyl)-2,4-pentadienamide | 90 | 86 ± 8 | 99 ± 1 | | |
| [R-(E)]-N-[1-Ethyl-4-(3-pyridinyl)butyl]-5,5-bis= (4-methoxyphenyl)-2,4-pentadienamide | 120 | 99 ± 0.4 | 99 ± 1 85 ± 12 (8 hr) | | |
| [S-(E)]-N-[1-Ethyl-4-(3-pyridinyl)butyl]-5,5-bis= (4-methoxyphenyl)-2,4-pentadienamide | 400 | 44 ± 8 | | | |
| [R,S-(E)]-5,5-bis(4-Methoxyphenyl)-N-[1-propyl-4-(3-pyridinyl)butyl]-2,4-pentadienamide | >1000 | 24 ± 13 | | | |
| [R,S-(E)]-5,5-bis(4-Methoxyphenyl)-N-[1-(1-methyl= ethyl)-3-pyridinyl)butyl]-2,4-pentadienamide | 800 | 87 ± 7 | 57 ± 19 | | |
| [R,S-(E)]-N-[1-Butyl-4-(3-pyridinyl)butyl]-5,5-bis= (4-methoxyphenyl)-2,4-pentadienamide | >1000 | 42 ± 7 | | | |
| [R,S-(E)]-N-[1-Cyclopropyl-4-(3-pyridinyl)butyl]-5,5-bis(4-methoxyphenyl)-2,4-pentadienamide | 60 | 98 ± 1 | 99 ± 0.3 | | |
| [R,S-(E)]-N-[1-Cyclopentyl-4-(3-pyridinyl)butyl]-5,5-bis(4-methoxyphenyl)-2,4-pentadienamide | >1000 | 19 ± 14 | | | |
| [R,S-(E)]-N-[1-Cyclohexyl-4-(3-pyridinyl)butyl]-5,5-bis(4-methoxyphenyl)-2,4-pentadienamide | >1000 | 11 ± 15 | | | |
| [R,S-(E)]-N-[1-(4-Bromophenyl)-4-(3-pyridinyl)butyl]-5,5-bis(4-methoxyphenyl)-2,4-pentadienamide | >1000 | 6 ± 13 | | | |
| (E)-5,5-bis(4-Methoxyphenyl)-N-[1-[3-(3-pyridinyl)= propyl]-4-(3-pyridinyl)butyl]-2,4-pentadienamide | 500 | 50 ± 15 | | | |
| (E)-5,5-bis(2-Methoxyphenyl)-N-[4-(3-pyridinyl)= butyl]-2,4-pentadienamide | 40 | 40 ± 2 | | | |
| (E)-5,5-bis(4-Methylphenyl)-N-[4-(3-pyridinyl)= butyl]-2,4-pentadienamide | 60 | 95 ± 1 | 67 ± 15 11 ± 6 (8 hr) | | |
| [R-(E)]-5,5-bis(4-Methylphenyl)-N-[1-methyl-4-(3-pyridinyl)butyl]-2,4-pentadienamide | 250 | 97 ± 3 | 91 ± 7 14 ± 16 (8 hr) | | |
| [R-(E,E)]-5-(4-Methoxyphenyl)-N-[1-methyl-4-(3-pyridinyl)butyl]-5-phenyl-2,4-pentadienamide | | 89 ± 4 | 95 ± 1 | | |
| [R-(2E,4Z)]-5-(4-Methoxyphenyl)-N-[1-methyl-4-(3-pyridinyl)butyl]-5-phenyl-2,4-pentadienamide | | 74 ± 11 | 0 ± 2 | | |
| [R-(2E,4Z)]-5-(4-Methoxyphenyl)-6-methyl-N-[1-methyl-4-(3-pyridinyl)butyl]-2,4-heptadienamide | 40 | 89 ± 3 | 71 ± 14 | | |
| [R-(E,E)]-5-(4-Methoxyphenyl)-N-[1-methyl-4-(3-pyridinyl)butyl]-2,4-octadienamide | 50 | 86 ± 7 | 9 ± 13 | | |
| [R-(E,E)]-5-(4-Methoxyphenyl)-N-[1-methyl-4-(3-pyridinyl)butyl]-2,4-nonadienamide | 14 | 99 ± 1 | 98 ± 1 | | |
| [R,S-(E,E)]-5-(4-Methoxyphenyl)-N-[1-methyl-4-(3-pyridinyl)butyl]-2,4-nonadienamide | | | | | |
| [R-(E,E)]-5-(3-Methoxyphenyl)-N-[1-methyl-4-(3-pyridinyl)butyl]-2,4-nonadienamide | 15 | 91 ± 5 | | | |
| [R-(2E,4Z)]-5-(3-Methoxyphenyl)-N-[1-methyl-4-(3-pyridinyl)butyl]-2,4-nonadienamide | | | | | |
| (E,E)-5-(4-Methoxyphenyl)-N-[4-(3-pyridinyl)= butyl]-2,4-decadienamide | 15 | 99 ± 1 | 26 ± 2 | | |
| (2E,4Z)-5-(4-Methoxyphenyl)-N-[4-(3-pyridinyl)= butyl]-2,4-decadienamide | 40 | 68 ± 11 | | | |
| [R-(E,E)]-5-(4-Methoxyphenyl)-N-[1-methyl-4-(3-pyridinyl)butyl]-2,4-decadienamide | 40 | 99 ± 1 | 100 ± 0.5 71 ± 14 (8 hr) | | |
| [S-(E,E)]-5-(4-Methoxyphenyl)-N-[1-methyl-4-(3-pyridinyl)butyl]-2,4-decadienamide | 120 | 46 ± 16 | 25 ± 13 | | |
| [R-(2E,4Z)]-5-(4-Methoxyphenyl)-N-[1-methyl-4-(3-pyridinyl)butyl]-2,4-decadienamide | | 57 ± 12 | | | |
| [R-(E,E)]-5-(3-Fluorophenyl)-N-[1-methyl-4-(3-pyridinyl)butyl]-2,4-decadienamide | 30 | 93 ± 0.9 | | | |
| [R-(2E,4Z)]-5-(3-Fluorophenyl)-N-[1-methyl-4-(3-pyridinyl)butyl]-2,4-decadienamide | 105 | 93 ± 1 | | | |
| [R(E,E)]-5-(4-Flourophenyl)-N-[1-methyl-4-(3-pyridinyl)butyl]-2,4-decadienamide | 40 | 95 ± 1 | | | |
| [R-(E,E)]-5-(3,4-Dimethoxyphenyl)-N-[1-methyl-4-(3-pyridinyl)butyl]-2,4-decadienamide | 6 | 99 ± 0.4 | | | |
| [R,S-(E,E)]-5-(4-Methoxyphenyl)-N-[1-methyl-4-(2-methyl-3-pyridinyl)butyl]-2,4-decadienamide | 5 | 77 ± 5 | | | |
| [R,S(E,E)]-5-(4-Methoxyphenyl)-N-[(Z)-1-methyl-4-(3-pyridinyl)-3-butenyl]-2,4-decadienamide | | | | | |
| [R-(E,E)]-5-(4-Methoxyphenyl)-N-[1-methyl-4-(3-pyridinyl)butyl]-2,4-undecadienamide | 9 | 100 ± 1 | 96 ± 1 | | |
| [R-(E,E)]-5-(4-Methoxyphenyl)-N-[1-methyl-4-(3-pyridinyl)butyl]-2,4-tridecadienamide | 5 | 98 ± 1 | 84 ± 8 | | |
| [R-(E,E)]-5-(4-Methoxyphenyl)-N-[1-methyl-4-(3-pyridinyl)butyl]-2,4-heptadecadienamide | 45 | 28 ± 2 | | | |
| [R-(E)]-N-[1-Methyl-4-(3-pyridinyl)butyl]-5-pentyl-2,4-decadienamide | 100 | 78 ± 7 | 4 ± 4 | | |

A compound of formula I, an enantiomer thereof or a salt thereof or a composition containing a therapeutically effective amount of a compound of formula I, an enantiomer thereof or a salt thereof can be administered by methods well known in the art. Thus, a compound of formula I an enantiomer thereof or a salt thereof can be administered either singly or with other pharmaceutical agents, for example, antihistamines, mediator release inhibitors, methyl xanthines, beta agonists or antiasthmatic steroids such as prednisone and prednisolone, orally, parenterally, rectally, or by inhalation, for example, in the form of an aerosol, micropulverized powder or nebulized solution. For oral administration they can be administered in the form of tablets, capsules, for example, in admixture with talc, starch, milk sugar or other inert ingredients, that is, pharmaceutically acceptable carriers, or in the form of aqueous solutions, suspensions, elixirs or aqueous alcoholic solutions, for example, in admixture with sugar or other sweetening agents, flavoring agents, colorants, thickeners and other conventional pharmaceutical excipients. For parenteral administration, they can be administered in solutions or suspension, for example, as an aqueous or peanut oil solution or suspension using excipients and carriers conventional for this mode of administration. For administration as aerosols, they can be dissolved in a suitable pharmaceutically acceptable solvent, for example, ethyl alcohol or combinations of miscible solvents, and mixed with a pharmaceutically acceptable propellant. Such aerosol compositions are packaged for use in a pressurized container fitted with an aerosol valve suitable for release of the pressurized composition. Preferably, the aerosol valve is a metered valve, that is one which on activation releases a predetermined effective dose of the aerosol composition.

In the practice of the invention, the dose of a compound of formula I or a salt thereof to be administered and the frequency of administration will be dependent on the potency and duration of activity of the particular compound of formula I or salt to be administered and on the route of administration, as well as the severity of the condition, age of the mammal to be treated and the like. Oral doses of a compound of formula I or a salt thereof contemplated for use in practicing the invention are in the range of from about 25 to about 1000 mg per day, preferably about 25 to about 250 mg either as a single dose or in divided doses.

The geometric isomers encompassed by formula I can be separated by conventional means, for example, chromatography. crystallization and the like. It is noted, however, that the separation in most instances is done at a earlier stage in the synthesis of the compounds of formula I.

Furthermore, since compounds of formula I of the invention, when $R_6$ and $R_7$ are different. Possess an asymmetric carbon atom, they are ordinarily obtained as racemic mixtures. The resolution of such racemates into the optically active isomers can be carried out by known procedures. Some racemic mixtures can be precipitated as eutectics and can thereafter be separated. Chemical resolution is, however, preferred. By this method, diastereomers are formed from the racemic mixture of a compound of formula I, with an optically active resolving agent, for example, an optically active base, such as di-(+)-α-methylbenzylamine, which can be reacted with a carboxyl group. The formed diastereomers are separated by selective crystallization and converted to the corresponding optical isomer. Thus, the invention covers the racemates of the compounds of formula I as well as their optically active isomers (enantiomers).

The examples which follow also further describe the invention. All temperatures given are in degree centigrade unless otherwise stated.

EXAMPLE 1

(R,S)-alpha-Methyl-4-(3-pyridinyl)-3-butyn-1-ol

In an inert atmosphere, 26g of bis(triphenylphosphine) palladium dichloride and 2.28g of cuprous iodide were added to a stirred solution of 311.2g of (R,S)-4-pentyn-2-ol 556.8g of 3-bromopyridine and 665 mL of triethylamine in 1.8L of dichloromethane at ambient temperature. After stirring for 75 minutes, the mildly exothermic reaction reached reflux temperature, and when the gentle boiling had subsided (40 minutes). external heat was applied to maintain reflux for 5 additional hours. The cooled reaction was stirred overnight at room temperature, then 1L of water and 500g of ice were added, followed by 420 mL of conc. hydrochloric acid (HCl) and the stirring was continued for several minutes. After the phases were separated, the aqueous layer was extracted with dichloromethane (4×1L) and then the organic layers were backwashed with 1L of 1N HCl before being discarded. The original aqueous phase was treated with 500 mL of 10N sodium hydroxide (NaOH) and the second aqueous layer was basified with 200 mL of 10N NaOH before each was extracted in turn with dichloromethane (1×2 L; 3×1 L). The combined organic extracts were dried over potassium carbonate ($K_2CO_3$) and evaporated to constant weight under reduced pressure to yield 477.3g of crude (R,S)-alpha-methyl-4-(3-pyridinyl)-3-butyn-1-ol as an amber oil.

EXAMPLE 2

Preparation of (R,S)-alpha-methyl-4-pyridinebutanol

The crude (R,S)-alpha-methyl-4-(3-pyridinyl)-3-butyn-1-ol (477.3g) obtained in the previous Example was hydrogenated over 20g of platinum oxide in 3.5L of ethanol at room temperature and atmospheric pressure. After the uptake of hydrogen had stopped, the catalyst was filtered and the solvent was removed under reduced pressure. The residual oil was distilled on a Kugelrohr apparatus (115°-120° C./ 0.1mm) to yield 420.5g of (R,S)-alpha-methyl-3-pyridinebutanol.

EXAMPLE 3

Preparation of 5-(3-pyridinyl)-2-pentanone

A stirred solution of 218.6g of oxalyl chloride in 1.5L of dry dichloromethane was cooled to −75° C. under argon then a mixture of 141g of dry dimethylsulfoxide in 200 mL of dichloromethane was added dropwise over 75 minutes such that the reaction temperature did not exceed −72° C. The mixture was stirred at −75° C. for 10 minutes, then a solution of 271.5g of (R,S)-alpha-methyl-3-pyridinebutanol in 125 mL of dichloromethane was added dropwise over 55 minutes, while the reaction temperature was maintained below −70° C. After the addition of substrate was completed, the mixture was stirred at −75° C. for another 30 minutes, then 520 mL of triethylamine was added over 65 minutes while the reaction temperature was maintained between −65° and −70° C. The cooling bath was removed, and after the reaction was allowed to equilibrate to room temperature over 1 hour, 1 L of water was added and the phases separated. The aqueous layer was extracted with dichloromethane (2×800 mL) and then the organic phase and extracts were washed in turn with 800 mL of 1.5N NaOH and with 800 mL of 10% sodium chloride (NaCl). The combined organic layers were dried (K$_2$CO$_3$) and evaporated to yield 266 g of crude ketone. The product was distilled to yield 248.6 g of 5-(3-pyridinyl)-2-pentanone (bp 100°-102° C./0.2mm).

EXAMPLE 4

Preparation of (R,S)-melhanesulfonic acid 5-(3-pyridinyl)-2-pentyl ester

In an inert atmosphere, a solution of 2.42 mL of methanesulfonyl chloride in 10 mL of dichloromethane was added over 10 minutes to a stirred mixture of 5.0 g of (R,S)-alpha-methyl-3-pyridinebutanol and 6.2mL of triethylamine in 50 mL of dry dichloromethane maintained at −40° C. After 30 minutes the reaction was warmed to 0° C., then a small piece of ice was added and the mixture was stirred in a an ice bath for another 15 minutes. The solution was then washed in turn with water (3×15 mL), 1N NaOH (2×15 mL) and brine (10 mL). The dried (K$_2$CO$_3$) organic layer was evaporated to furnish 7.2 g of (R,S)-methanesulfonic acid 5-(3-pyridinyl)-2-pentyl ester.

EXAMPLE 5

Preparation of (R,S)-3-(4-azidopentyl)pyridine.

A mixture of 2.5g of (R,S)-methanesulfonic acid 5-(3-pyridinyl)-2-pentyl ester, 0.832g of sodium azide, 1.5 mL of water and 15 mL of dimethylformamide was stirred at 50° C. under argon for 150 minutes. The cooled solution was diluted with 40 mL of water and extracted with dichloromethane (3×30 mL). The extracts were washed in turn with water (2×20 mL) and then were combined, dried (K$_2$CO$_3$) and evaporated to furnish 1.76 g of (R,S)-3-(4-azidopentyl)pyridine as an oil.

EXAMPLE 6

Preparation of (R,S)-3-(ethoxycarbonyl)butyltriohenylphosphonium bromide.

A solution of 86.3g of (R,S)-4-bromo-2-methylbutanoic acid ethyl ester and 104.9 g of triphenylphosphine in 600 mL of toluene was stirred at reflux for 4 days. As the reaction proceeded, the phosphonium bromide separated from solution as an oil. After the reaction was cooled, the toluene supernatant was decanted and replaced with 500 mL of fresh toluene. The mixture was stirred at reflux for 30 minutes, then was cooled and the toluene layer was again decanted. After this process was repeated a second time, the residual oil was dried in vacuo to give 187 g. of (R,S)-3-(ethoxycarbonyl)butyltriphenylphosphonium bromide as a viscous oil.

EXAMPLE 7

Preparation of [(R,S)-Z]-2-methyl-5-(3-pyridinyl)-4-pentenoic acid ethyl ester

A stirred solution of 10.56 g of sodium hydride (60% dispersion in oil) in 1000 mL of dry dimethylsulfoxide was heated at 70° C. until the evolution of hydrogen stopped (30 minutes). then the solution was cooled to 0° C. and a solution of 103.7 g of (R,S)-3-(ethoxycarbonyl)butyltriphenylphosphonium bromide in 200 mL dimethylsulfoxide was added. After the mixture had stirred at room temperature for 30 minutes, a solution of 20.8 mL of 3-pyridinecarboxaldehyde in 100 mL of tetrahydrofuran was added and the reaction was stirred at room temperature overnight. The mixture was diluted with ice-water and extracted with dichloromethane (6×150 mL). The combined organic layers were then extracted with 4×400 mL of 0.5N HCl. The acidic layers were made basic with 125 mL triethylamine and extracted with dichloromethane (5×150 mL), and the dried (K$_2$CO$_3$) extracts were evaporated to furnish 34 g of crude reaction product. An initial purification of the material by high pressure liquid chromatography (HPLC) (ether-hexane; 3:2) yielded 11.9 g of a mixture of (Z)- and (E)-isomers (4:1). A subsequent separation of the mixture by HPLC with recycle gave 6.77 g of [(R,S)-Z]-2-methyl-5- (3-pyridinyl)-4-pentenoic acid ethyl ester and 3 g of a mixture of [(R,S)-Z]-2-methyl-5-(3-pyridinyl)-4-pentenoic acid ethyl ester and its (E)-isomer.

EXAMPLE 8

Preparation of (R,S)-alpha-methyl-3-pyridinepentanoic acid ethyl ester

A solution of 5.5 g of a mixture (1:1) of [(R,S)-E]- and [(R,S)-Z]-2-methyl-5-(3-pyridinyl)-4-pentenoic acid ethyl ester in 100 mL was ethanol was hydrogenated over 0.4 g of 10% palladium on carbon (Pd/C). After the uptake of hydrogen had stopped, the catalyst was removed by filtration and the solvent evaporated to give 5.33 g of (R,S)-alpha-methyl-3- pyridinepentanoic acid ethyl ester.

EXAMPLE 9

Preparation of (R,S)-alpha-methyl-3-pyridinepentanoic acid

A mixture of 5.3 g of (R,S)-alpha-methyl-3-pyridinepentanoic acid 35 mL of 1N NaOH and 35 mL of methanol was stirred at reflux for 3 hours, then most of the methanol was removed under reduced pressure. The solution was diluted to 100 mL with water and extracted with dichloromethane (3×35 mL). The aqueous layer was then neutralized with 35 ml of 1N HCl and extracted with dichloromethane (3×30 mL), then dried over sodium sulfate (Na$_2$SO$_4$). Extracts were evaporated to yield 3.47 g of (R,S)-alpha-methyl-3-pyridinepentanoic acid.

EXAMPLE 10

Preparation of (R,S)-[1-methyl-4-(3-pyridinyl)butyl]carbamic acid 1-dimethylethyl ester.

As in Example 36, 1.93 g of (R,S)-alpha-methyl-3-pyridinepentanoic acid when treated with 2.21 mL of diphenylphosphorylazide in 10 mL of t-butanol containing 1.4 mL of triethylamine furnished 2.45 g of crude product. Purification of the material by HPLC (ethyl acetate) yielded 2.2 g of (R,S)-[1-methyl-4-(3-pyridinyl)butyl]carbamic acid 1,1-dimethylethyl ester as a colorless oil.

EXAMPLE 11

Preparation of (R,S)-N-[1-methyl-4-(3-pyridinyl)butyl]acetamide

To a mixture of 10.6 g of (R,S)-alpha-methyl-3-pyridinebutanol in 30 mL of acetonitrile was added 20 mL of sulfuric acid. After the reaction was stirred at 50° C. for 2 hours, it was poured over a mixture of 500 g of ice and 400 mL of 4N NaOH and extracted with dichloromethane (2×150 mL). Evaporation of the dried (K$_2$CO$_3$) extracts gave 6 g of crude product which was purified by HPLC (methanol-ethyl acetate; 1:49) and triturated with ether to yield 2.9 g of (R,S)-N-[1-methyl-4-(3-pyridinyl)butyl]acetamide, mp 70°–71.5° C.

EXAMPLE 12

Preparation of
(R,S)-alpha-methyl-3-pyridinebutanamine

From 5-(3-pyridinyl)-2-pentanone

A mixture of 248.5 g of 5-(3-pyridinyl)-2-pentanone, 95.85 g of sodium cyanoborohydride and 1170 g of ammonium acetate in 5.3L of dry methanol was stirred at room temperature for 8 days, then 3L of methanol was removed by distillation under reduced pressure (internal temp ~30° C.). The reaction was cooled in an ice bath as 3.8L of 6N HCL was added dropwise over 2 hours. After the mixture was stirred at room temperature overnight, it was made strongly basic by the addition of 2L of 12.5N NaOH and extracted with dichloromethane (1×2L; 2×1L). The combined extracts were dried (K$_2$CO$_3$) and evaporated to yield 244 g of a light brown oil, which was distilled to give 205 g of (R,S)-alpha-methyl-3-pyridinebutanamine (bp 95°–100° C./0.15 mm).

EXAMPLE 13

Preparation of
(R,S)-alpha-methyl-3-pyridinebutanamine (a) From 3-(4-azidopentyl)pyridine A solution of 0.9 g of (R,S)-3-(4-azidopentyl)pyridine in 25 mL ethanol was hydrogenated over 0.05 g 10% Pd/C at 50 psi. After 105 minutes, the catalyst was removed by filtration and the solvent was removed under reduced pressure to yield 0.69 g of a colorless oil. Evaporative distillation of the crude product furnished 0.57 g of (R,S)-alpha-methyl-3-pyridinebutanamine.

(b) From (R,S)-[1-methyl-4-(3-pyridinyl)butyl]carbamic acid 1,1-dimethylethyl ester As in Example 37, hydrolysis of 2.1 g of (R,S)-[1-methyl-4-(3-pyridinyl)butyl]carbamic acid 1,1-dimethylethyl ester in 25 mL of 1N HCl yielded, after the usual work up and evaporative distillation of the product (95°–100° C./0.2 mm). 1.25 g of (R,S)-alpha-methyl-3-pyridinebutanamine.

(c) From (R,S)-N-[1-methyl-4-(3-pyridinyl)butyl]acetamide

A solution of 2.06 g of (R,S)-N-[1-methyl-4-(3-pyridinyl)butyl]acetamide in 50 mL of 6N HCl was stirred at reflux for 22 hours. In an argon atmosphere, the cooled mixture was made basic with the careful addition of 30 mL of 10N NaOH and was extracted with dichloromethane (2×75 mL). The extracts were washed with brine, then were combined, dried (K$_2$CO$_3$) and evaporated to give 1.43 g of (R,S)-alpha-methyl-3-pyridinebutanamine.

EXAMPLE 14

Preparation of
[R-(R*,R*)]-alpha-hydroxy-N-[1-methyl-4-(3-pyridinyl)butyl]benzeneacetamide (a) From (R,S)-alpha-methyl-3-pyridinebutanamine A solution of 281.5 g of 1,3-dicyclohexylcarbodiimide in 400 ml of dimethylformamide was added to a stirred solution of 204 g of (R,S)-alpha-methyl-3-pyridinebutanamine, 198.4 g of (R)-mandelic acid and 209.75 g of 1-hydroxybenzotriazole in 1400 mL of dimethylformamide, maintained at −10° C. during the addition by intermittent cooling with a dry ice-acetone bath. After stirring at −5° for 4 hours, then at room temperature overnight the mixture was recooled to 0° C. for 2 hours. The precipitated solids were filtered and washed in turn with cold dimethylformamide (2×150 mL) and ethyl acetate (2×300 mL). This material, a mixture of 1,3-dicyclohexylurea (DCU) and the less soluble (R*,R)-mandelamide, was dispersed in 2L of 1N HCl and stirred at room temperature for 3 hours. The undissolved solids (DCU) were removed by filtration and were washed with 200 mL of dilute HCl and with water. The filtrate was basified and the resulting material was collected by filtration, washed with water and dried in vacuo to give 64.4 g of [R-(R*.R*)]-alpha-hydroxy-N-[1-methyl-4-(3-pyridinyl)butyl]benzeneacetamide, the (R*,R)-mandelamide, mp 144°–146° C.; $[\alpha]_D^{25}$ −27.8° (c, 1.0, MeOH).

The original mother liquors and washings were concentrated to dryness under reduced pressure and the residue was dispersed in 2L of 1.5N NaOH and extracted with dichloromethane (1×2L; 2×1L). The organic extracts were washed with in turn with 1N NaOH (2×800 mL) and then in turn with 1N HCl (1×1.5L; 2×750 mL). The combined acidic aqueous layers were basified with 350 mL of 10N NaoH and extracted with dichloromethane (1×2L; 2×1L). The extracts were dried (K$_2$CO$_3$) and evaporated to give 280 g of mandelamide, rich (~3:2) in the (S*,R)-diastereomer. The residue was crystallized three times from 2-propanol to yield 74.1 g of the less soluble R*,R)-mandelamide, mp 144°–146° C.

The mother liquors from the final two crystallizations were combined, evaporated and the residue crystallized twice from 2-propanol to give an additional 7.2 g of the (R*,R)-diastereomer, mp 143°–145° C. The total yield of [R-(R*,R*)]-alpha-hydroxy-N-[1-methyl-4-(3-pyridinyl)butyl]benzeneacetamide, obtained in three crops, was 145.6 g (78.5%).

All remaining mother liquors were combined, evaporated and dried to give 198 g of mandelamide rich in the (S*,R)-diastereoisomer. This material was reserved for further processing, particularly to serve as a potential source of (S)-alpha-methyl-4-pyridinebutanamine.

(b) Via an enatioselective process from 5-(3-pyridinyl)-2-pentanone

A solution of 70.5 g of 5-(3-pyridinyl)-2-pentanone and 53.5 g of (R)-(+)-alpha-methylbenzylamine in 700 mL of toluene containing 1.8 g of p-toluenesulfonic acid was heated at reflux for 17 hours. Water was removed from the reaction as it was formed using a Dean-Stark trap. The cooled solution was hydrogenated over 70 g of Raney Nickel at room temperature and 50 psi. When approximately 50% of the theoretical amount of hydrogen had been taken up, the reaction essentially stopped. The spent catalyst was removed and replaced with 70 g of fresh Raney Nickel and the hydrogenation was continued until the absorption of hydrogen ceased. After the catalyst was removed by filtration the filtrate was washed with 250 mL of 1N sodium hydroxide solution, then was dried and evaporated to give 106 g of an oil. HPLC analysis of the product showed that the main component (~68%) was [R-(R*,R)]-N-[1-methyl-(3- pyridinyl) butyl]-alpha-methylbenzylamine along with 13% of the related (S*,R)-diastereomer.

The above mixture (105 g) in 1L of ethanol was hydrogenolysed over 21 g of 20% Pd(OH)$_2$ on charcoal (50° C.; 25 psi) for a total of 51 hours. After the catalyst was removed by filtration, the solvent was evaporated and the residue distilled to provide 33.6 g of alpha-methyl-3-pyridinebutanamine enriched in the (R)-enantiomer.

To a cooled (−5° C.) solution of 32 g of the above enriched amine, 33 g of 1-hydroxybenzotriazole and 31.22 g of (R)-mandelic acid in 350 mL of dimethylformamide, was added a solution of 44.26 g of 1,3-dicyclohexylcarbodiimide in 150 mL of dimethylformamide and the mixture was stirred at −5° C. for 18 hours. After the precipitated dicyclohexylurea was removed by filtration, the filtrate was evaporated and the residue dispersed in 300 mL of cold 2N sodium hydroxide. The resulting solids were removed by filtration, washed with dilute sodium hydroxide solution and with water and then dissolved in 500 mL of 2N hydrochloric acid. The acidic solution was extracted with dichloromethane (3×150 mL) to remove neutral impurities, then was basified with 10N sodium hydroxide and extracted with dichloromethane (6×300 mL). The dried extracts were evaporated to give 55 g of residual solid. Crystallization of the product from ethanol gave 25.6 g of [R-(R*,R)]-alpha-hydroxy-N-[1-methyl-4-(3-pyridinyl)butyl]benzeneacetamide, mp 141°-143° C. An additional 1.3 g of product, mp 141°-143° C., was obtained from the mother liquors.

EXAMPLE 15

Preparation of [S-(S*,S*)]-alpha-hydroxy-N-[1-methyl-4-(3-pyridinyl)-butyl]benzeneacetamide (a) From (R,S)-alpha-methyl-3-pyridinebutanamine To an ice cold solution of 2.0 g of (S)-(+)-mandelic acid and 1.82 mL of triethylamine in 20 mL of dry dimethylformamide was added 2.82 mL of diphenylphosphoryl azide. The mixture was stirred at 0° C. for 30 minutes before 2.15 g of (R,S)-alpha-methyl-3-pyridinebutanamine was added. After the reaction was stirred at room temperature overnight, it was diluted with 130 mL of ethyl acetate, washed with water (4×50 mL), dried (K$_2$CO$_3$) and evaporated. The residue was crystallized from ethyl acetate (3×) to give 0.45 g of [S-(S*,S)]-alpha-hydroxy-N-[1-methyl-4-(3-pyridinyl)-butyl]benzeneacetamide, mp 142°-145° C.

The absolute configuration of [S-(S*,S*)]-alpha-hydroxy-N-[1-methyl-4-(3-pyridinyl)butyl]benzeneacetamide, was established by X-ray crystallographic analysis.

(b) From enriched (S)-alpha-methyl-pyridinebutanamine

A solution of 160 g of crude [S-(R*,R)]-alpha-hydroxy-N-[1-methyl-4-(3-pyridinyl)butyl]benzeneacetamide in 800 mL of 6N HCl was treated with 85 mL conc. HCl and then was heated at reflux overnight as described in Example 16. The crude amine (~85 g), isolated in the normal manner, was distilled to furnish 76.4 g of (S)-alpha-methyl-3-pyridinebutanamine. (60% ee; bp 89°-91°/0.15 mm).

Under the conditions outlined in Example 14a, 76.2 g of the amine was reacted with 74.2 g of (S)-mandelic acid in the presence of 105.2 g of 1,3-dicyclohexylcarbodiimide and 78.4 g of 1-hydroxybenzotriazole in 1L of dimethylformamide. A similar workup furnished 109 g of [S-(S*,S*)]-alpha-hydroxy-N-[1-methyl-4-(3-pyridinyl)butyl]benzeneacetamide, mp 143°-145° C., $[\alpha]_D^{25}$ +27.8° (c, 1.0, MeOH).

EXAMPLE 16

Preparation of (R)-alpha-methyl-3-pyridinebutanamine

A solution of 145 g of [R-(R.,R*)]-alpha-hydroxy-N-[1-methyl-4-(3-pyridinyl)butyl]benzeneacetamide in 900 mL of 6N HCl was treated with 80 mL of conc. HCl and then was heated at reflux for 2 days. After most of the solvent was removed under reduced pressure. The residue was made decidedly basic with 10N NaOH in an argon atmosphere and extracted with dichloromethane (1×1.2L; 2×600 mL). The dried (K$_2$CO$_3$) extracts were evaporated and the crude product was distilled to give 78.5 g of (R)-alpha-methyl-3-pyridinebutanamine, (bp 95° C./0.2 mm).

EXAMPLE 17

Preparation of (S)-alpha-methyl-3-pyridinebutanamine

As in Example 16, a solution of 16.3 g of [S-(S*,S*)]-alpha-hydroxy-N-[1-methyl-4-(3-pyridinyl)butyl]benzeneacetamide in 160 mL of 6N HCl was heated at reflux for 22 hours. The crude product, obtained by the usual work up was distilled to yield 8.3 g of (S)-alpha-methyl-3-pyridinebutanamine, (bp 85°-87° C./0.1 mm).

EXAMPLE 18

Preparation of (R,S)-alpha-ethyl-4-(3-pyridinyl)-3-butyn-1-ol

Under the conditions described in Example 1, 395 g of 3-bromopyridine and 259.3 g of (R,S)-5-hexyne-3-ol were reacted together in 1.5L of dichloromethane in the presence of 418 mL of triethylamine, 17.56 g of bis(triphenylphosphine)palladium dichloride and 1.7 g of cuprous iodide. The usual work-up furnished 361.5 g of crude (R,S)-alpha-ethyl-4-(3-pyridinyl)-3-butyn-1-ol as a brown oil.

EXAMPLE 19

Preparation of (R,S)-alpha-ethyl-3-pyridinebutanol

As in Example 2, hydrogenation of 361.5 g of crude (R,S)-alpha-ethyl-4-(3-pyridinyl)-3-butyn-1-ol over 15 g of platinum oxide in 3L of ethanol at room temperature and atmospheric pressure and distillation of the product furnished 357 g of (R,S)-alpha-ethyl-3-pyridinebutanol (bp 120°-130°/0.1 mm) as a colorless oil.

EXAMPLE 20

Preparation of 6-(3-pyridinyl)-3-hexanone

As in Example 3,356.6 g of (R,S)-alpha-ethyl-3-pyridinebutanol was added to a mixture prepared in the prescribed manner from 211.7 g of oxalyl chloride and 170 g of dimethylsulfoxide in 1.75L of dichloromethane. After the addition of 630 mL of triethylamine, the reaction was worked up in the usual way to yield 347.6 g of crude product which was distilled to give 327.9 g of 5-(3-pyridinyl)-3-hexanone (bp 110°-115° C./0.1 mm).

EXAMPLE 21

Preparation of (R,S)-alpha-ethyl-3-pyridinebutanamine

In the manner described in Example 12, 372.9 g of 6-(3-pyridinyl)-3-hexanone was reacted with 116.5 g of sodium cyanoborohydride and 1426 g of ammonium acetate in 6.5L of dry methanol for 3 days at room temperature, and then 4.5L of 6N HCl was added and the mixture stirred overnight. Distillation of the crude product gave 289.4 g of (R,S)-alpha-ethyl-3-pyridinebutanamine (bp 95°–100° C./0.1 mm).

EXAMPLE 22

Preparation of
[R-(R*,R*)1-alpha-hydroxy-N-[1-ethyl-4-(3-pyridinyl)-butyl]benzeneacetamide and
[S-(R*,R*)]-alpha-hydroxy-N-[1-ethyl-4-(3-pyridinyl)-butyl benzeneacetamide.

As in Example 14a, a solution of 367.4 g of 1,3-dicyclohexylcarbodiimide in 500 mL of dimethylformamide was added to a stirred solution of 289 g of (R,S)-alpha-ethyl-3-pyridinebutanamine. 259 g of (R)-mandelic acid and 274 g of 1-hydroxybenzotriazole in 1.7L of dimethylformamide maintained at −10° C. during the addition. After stirring at −-5° C. for 3 hours. Then at room temperature overnight, the mixture was recooled to 0° C. for 2 hours. The precipitated solids were filtered and washed in turn with cold dimethylformamide (3×150 mL) and ethyl acetate (3×200 mL). The solids, a mixture of 1,3-dicyclohexylurea (DCU) and the less soluble (R*,R)-mandelamide, was dispersed in 1N HCl (2L) and stirred at room temperature for 4 hours. The undissolved solids (DCU) were removed by filtration and were washed with 200 mL dilute HCl and with water. The filtrate was basified and the resulting crystalline material was collected by filtration washed with water and dried in vacuo to give 195.4 g of [R-(R*,R*)]-alpha-hydroxy-N-[1-ethyl-4-(3-pyridinyl)butyl]benzeneacetamide, mp 161.5°–163°; $[\alpha]_D^{25} -14.9°$ (c, 1.0 MeOH).

The original mother liquors and washings were concentrated to dryness and were worked up as in Example 14a. The crude residue was triturated with hot hexane (1L), and the solids filtered to give 265 g of mandelamide rich (>7:1) in the more soluble (S*,R)-diastereomer. Fractional crystallization of the residue from 2-propanol furnished 147 g of [S-(R*,R*)]-alpha-hydroxy-N-[1-ethyl-4-(3-pyridinyl)butyl]benzeneacetamide, mp 122°–124° C.; $[\alpha]_D^{25} -41.2°$ (c, 1.0 MeOH).

EXAMPLE 23

Preparation of (R)-alpha-ethyl-3-pyridinebutanamine

As in Example 16, a solution of 195 g of [R-(R*,R*)]-alpha-hydroxy-N-[1-ethyl-4-(3-pyridinyl)butyl]benzeneacetamide in 1.1L of 6N HCl was treated with 104 mL of conc. HCl and then was heated at reflux for 2 days. The crude amine, obtained by the normal work up was distilled to give 109 g of (R)-alpha-ethyl-3-pyridinebutanamine, (bp 105° C./0.2 mm): $[\alpha]_D^{25}$ −11.9° (c, 1.0, MeOH).

EXAMPLE 24

Preparation of (S)-alpha-ethyl-pyridinebutanamine

As in Example 16, a solution of 31.2 g of [S-(R*,R*)]-alpha-hydroxy-N-[1-ethyl-4-(3-pyridinyl)butyl]benzeneacetamide in 175 ml of 6N HCl was treated with 16 mL of conc. HCl and then was heated at reflux for 42 hours. The normal work up furnished 16.4 g of (S)-alpha-ethyl-3-pyridinebutanamine, (bp 95°–98° C./0.1 mm; $[\alpha]_D^{25} +11.75°$ (c, 1.0, MeOH).

EXAMPLE 25

Preparation of trifluoromethanesulfonic acid 6-methyl-3-pyridinyl ester

A suspension of 7.48 g of 5-hydroxy-2-methylpyridine and 24.4 g of bis(trifluoromethanesulphonyl)-phenylimide in 25 mL of dichloromethane was cooled in an ice bath as 10 mL of dry triethylamine was added. After 1 hour at 0° C., the mixture was allowed to stir at room temperature for 18 hours, then was washed in turn with 1N NaOH (2×50 mL) and with half saturated $K_2CO_3$ solution. Concentration of the dried ($K_2CO_3$) solution gave a yellow oil which was evaporatively distilled to yield 14.48 g of trifluoromethanesulfonic acid 6-methyl-3-pyridinyl ester, (bp 65°–70° C.0.1 mm.)

EXAMPLE 26

Preparation of (R,S)-5-(6-methyl-3-pyridinyl)-4-pentyn-2-ol.

A solution of 28 g trifluoromethanesulfonic acid 6-methyl-3-pyridinyl ester and 14.4 g of (R,S)-4-pentyn-2-ol and 110 mL triethylamine in 350 mL of dry dimethylformamide was deoxygenated with argon and 2.4 g of bis(triphenylphosphine) palladium dichloride was added. After the mixture was stirred at 90° C. for 3 hours. It was cooled then acidified with 300 mL of 6N HCl and extracted with ether. The aqueous phase was made basic with sodium hydroxide solution and extracted with ethyl acetate. The organic extract was washed with brine, then dried ($K_2CO_3$) and evaporated to furnish an oil which was evaporatively distilled to yield 10.8 g of (R,S)-5-(6-methyl-3-pyridinyl)-4-pentyn-2-ol, bp 123°–130° C./0.02 mm.

EXAMPLE 27

Preparation of (R,S)-alpha-6-dimethyl-3-pyridinebutanol

As in Example 2,10.3 g of (R,S)-5-(6-methyl-3-pyridinyl)-4-pentyn-2-ol was hydrogenated over 1.1 g of 10% Pd/C in 135 mL of ethanol at room temperature and atmospheric pressure. After the usual workup, the resulting yellow oil was purified by HPLC (ethyl acetate) to give 10.45 g of (R,S)-alpha-6-dimethyl-3-pyridinebutanol. A portion was evaporatively distilled at 105°–110° C./0.1 mm to furnish the analytical sample.

EXAMPLE 28

Preparation of 5-(6-methyl-3-pyridinyl)-2-pentanone

Under conditions similar to that describe in Example 3, 10.25 g of (R,S)-alpha-6-dimethyl-3-pyridinebutanol in 50 mL of dichloromethane was added to an mixture prepared from 8.58 g of oxalyl chloride and 9.27 g of dimethylsulfoxide in 225 mL of dichloromethane. After the addition of 36.8 mL of triethylamine, the reaction was worked up in the usual manner and the crude product was purified by HPLC (ethyl acetate-hexane; 1:1). The resulting material was distilled to give 7.4 g of 5-(6-methyl-3-pyridinyl)-2-pentanone (bp 88°–92° C./0.05 mm).

EXAMPLE 29

Preparation of (R,S)-6-alpha-dimethyl-3-pyridinebutanamine

As in Example 12, 7.27 g of 5-(6-methyl-3-pyridinyl)-2-pentanone was reacted with 2.71 g of sodium cyanoborohydride and 31.1 g of ammonium acetate in 115 mL of dry methanol for 3 days at room temperature. After the chilled reaction was quenched by the addition of 110 mL of 6N HCl, the mixture heated at reflux for 90 minutes then was cooled and worked up in the usual manner. Distillation of the crude product gave 4.31 g of (R,S)-6-alpha-dimethyl-3-pyridinebutanamine (bp 98°-101° C./0.1 mm).

EXAMPLE 30

Preparation of 5-bromo-2-[(2-trimethylsilyl)ethynyl]pyridine

A degassed solution of 15.0 g of 2,5-dibromopyridine, 9.0 mL of trimethylsilylacetylene and 0.27 g of cuprous iodide in 200 mL of triethylamine was treated with 1.0 g of bis(triphenylphosphine)palladium dichloride. After an ice bath was used to control the initial exotherm, the reaction was stirred at room temperature overnight, then was diluted with 400 mL ether. The mixture was washed in turn with water (4×75 mL) and with brine (75 mL). then was dried (K₂CO₃) and evaporated. The residual dark oil was passed through a plug of silica gel (ether) and then was purified by HPLC (ether-hexane; 1:49). Crystallization of the resulting material from hexane gave 11.86 g of 5-bromo-2-[(2-trimethylsilyl)ethynyl]pyridine, mp 56°-59° C.

EXAMPLE 31

Preparation of (R,S)-5-[6-[2-trimethylsilyl)ethyny]-3-pyridinyl]-4-pentyne-2-ol.

A solution of 9.78 g of 5-bromo-2-[(2-trimethylsilyl)ethynyl]pyridine and 0.19 g of cuprous iodide in 150 mL of triethylamine and 50 mL dichloromethane were deoxygenated with argon and 3.4 g of (R,S)-4-pentyn-2-ol and 0.7 g of bis(triphenylphosphine)palladium dichloride were added. After the dark mixture was stirred overnight at room temperature. The solvents were removed under reduced pressure and the residue was dissolved in ether. The solution was washed with water and brine, then was dried (K₂CO₃) and evaporated. The crude product was filtered through a plug of silica gel (ethyl acetate-hexane; 1:10) and then was purified by HPLC (ethyl acetate) to give (R,S)-5-[6-[2-trimethylsilyl)ethynyl]-3-pyridinyl]-4-pentyne-2-ol, mp 79°-80° C.

EXAMPLE 32

Preparation of (R,S)-6-ethyl-3-pyridine-alpha-methylbutanol

A solution of 8.51 g of (R,S)-5-[6-[2-(trimethylsilyl) ethynyl]-3-pyridinyl]-4-pentyn-2-ol in 60 mL of methanol and 15 mL of 2.5N NaOH was stirred for 1 hour and diluted to 300 mL with ethyl acetate. The separated organic layer was washed in turn with water and brine, then was dried (K₂CO₃) and evaporated. The residue was hydrogenated over 0.7 g of 10% Pd/C in 150 mL of ethanol at atmospheric pressure and room temperature. After the normal work up, the crude hydrogenation product was evaporatively distilled to afford 5.61 g of (R,S)-6-ethyl-3-pyridine-alpha-methylbutanol (bp 110°-115° C./0.1 mm).

EXAMPLE 33

Preparation of 5-(6-ethyl-3-pyridinyl)-2-pentanone.

5-(6-Ethyl-3-pyridinyl)-2-pentanone was prepared by the method described in Example 3. Starting with 4.4 g of (R,S)-6-ethyl-3-pyridine-alpha-methylbutanol, there was obtained 4.9 g of 5-(6-ethyl-3-pyridinyl)-2-pentanone (bp 107°-110° C./0.1 mm).

EXAMPLE 34

Preparation of (R,S)-6-ethyl-alpha-methyl-3-pyridinebutanamine.

(R,S)-6-ethyl-alpha-methyl-3-pyridinebutanamine was made by the method outlined in Example 12. Starting from 4.75 g of 5-(6-ethyl-3-pyridinyl)-2-pentanone there was obtained 2.44 g of (R,S)-6-ethyl-alpha-methyl-3-pyridinebutanamine, bp 101°-104° C./0.15 mm.

EXAMPLE 35

Preparation of (R,S)-alpha-cyclopropyl-3-pyridinepentanoic acid.

In an inert atmosphere, 33 mL of 1.6M butyl lithium in hexane was added to a stirred solution of 7.4 mL diisopropylamine in 20 mL dry tetrahydrofuran previously cooled to −78° C. for 30 minutes, then a solution of 2.5 g cyclopropaneacetic acid in 10 mL dry tetrahydrofuran was added over 3 minutes. The reaction was allowed to equilibrate to ambient temperature and then was heated at 50° C. for 1 hour to complete the formation of the dianion. The mixture was recooled to −78° C. and a solution of 7.67 g 3-(3-bromopropyl) pyridine (freshly liberated from its HBr salt) in 20 mL tetrahydrofuran was added. The reaction was allowed to warm to room temperature and then was heated at 50° C. for 7 hours. The solvents were removed in vacuo and the residue was dissolved in 100 mL 1N HCl and extracted with dichloromethane (3×50 ml). The organic layers were backwashed in turn with 2×25 mL portions of 1N HCl, then the aqueous layers were basified with 17 mL 10N NaOH solution and extracted with dichloromethane (3×100 mL) to remove the starting bromide. The aqueous phase was then acidified by the addition of 3 mL acetic acid and extracted with dichloromethane (1×150 mL; 2×100 mL). The extracts were washed with brine, then were combined, dried (Na₂SO₄) and evaporated to give 4.6 g of (R,S)-alpha- cyclopropyl-3-pyridinepentanoic acid as a colorless solid. A portion was crystallized from ether-hexane to yield the analytical sample mp 82°-84° C.

EXAMPLE 36

Preparation of (R,S)-[1-cyclopropyl-4-(3-pyridinyl)butyl]carbamic acid 1,1-dimethylethyl ester.

A solution of 4.2 g of (R,S)-alpha-cyclopropyl-3-pyridinepentanoic acid 5.8 g of diphenylphosphorylazide and 3 mL of triethylamine in 40 mL of t-butanol was stirred at reflux under argon overnight. After the solvents were removed under reduce pressure, the residue was dissolved in 100 mL of dichloromethane and washed with 2×50 mL portions of 1N NaOH. The aqueous layers were washed in turn with 50 mL of dichloromethane. Then the combined organic extracts were dried (K₂CO₃) and evaporated to yield 5.6 g of an oil. The crude carbamate was purified by HPLC (ethyl acetate) to furnish 4.8 g of (R,S)-[1-cyclopropyl-4-(3-pyridinyl)butyl]carbamic acid 1,1-dimethylethyl ester as a colorless oil.

EXAMPLE 37

Preparation of (R,S)-alpha-cyclopropyl-3-pyridinebutanamine.

A solution of 4.4 g of (R,S)-[1-cyclopropyl-4-(3-pyridinyl)butyl]-carbamic acid 1,1-dimethylethyl ester in 50 mL of 1N HCl was heated on a steam bath for 75 minutes then was cooled and extracted with 50 mL of ether. In an atmosphere of argon, the aqueous layer was treated with 6 mL of 10N NaOH and extracted with 2×50 mL portions of dichloromethane. Evaporation of the dried (K$_2$CO$_3$) extracts gave 2.8 g of (R,S)-alpha-cyclopropyl-3-pyridinebutanamine as a colorless oil.

EXAMPLE 38

Preparation of (R,S)-alpha-propyl-3-pyridinepentanoic acid.

As in Example 35, 2.04 g of pentanoic acid was treated with two equivalents of lithium diisopropylamide (LDA) and then reacted with 4.0 g of 3-(3-bromopropyl)pyridine. After workup, the crude product (3.5 g) was crystallized from ether-hexane to afford 2.7 g of (R,S)-alpha-propyl-3-pyridinepentanoic acid, mp 55°–57° C.

EXAMPLE 39

Preparation of (R,S)-[1-propyl-4-(3-pyridinyl)butyl]carbamic acid 1,1-dimethylethyl ester.

As in Example 36, 2.5 g of (R,S)-alpha-propyl-3-pyridinepentanoic acid when reacted with 2.45 mL of diphenylphosphorylazide in 25 mL of t-butanol containing 1.6 mL of triethylamine furnished 3.1 g of crude carbamate. Purification of the material by HPLC (ethyl acetate) yielded 2.75 g (R,S)-[1-propyl-4-(3-pyridinyl)butyl]carbamic acid 1,1-dimethylethyl ester as an oil.

EXAMPLE 40

Preparation of (R,S)-alpha-propyl-3-pyridinebutanamine

As in Example 37, hydrolysis of 1.8 g of (R,S)-[1-propyl-4-(3-pyridinyl)butyl]carbamic acid 1,1-dimethylethyl ester in 25 mL of 1N HCl, after the usual workup, gave 1.15 g of (R,S)-alpha-propyl-3-pyridinebutanamine. A portion was distilled on a Kugelrohr apparatus (110° C./0.1 mm) to yield the analytical sample.

EXAMPLE 41

Preparation of (R,S)-alpha-(1-methylethyl)-3-pyridinepentanoic acid.

As in Example 35, 2.04 g of isovaleric acid was treated with two equivalents of LDA and then reacted with 4.0 g of 3-(3-bromopropyl)pyridine. The crude product was crystallized from ether-hexane to yield 2.8 g of (R,S)-alpha-(1-methylethyl)-3-pyridinepentanoic acid. mp 52°–55° C. Recrystallization of a sample from the same solvents gave the analytical specimen, mp 54°–56° C.

EXAMPLE 42

Preparation of (R,S)-[1-(1-methylethyl)-4-(3-pyridinyl)butyl]carbamic acid 1,1-dimethylethyl ester.

As in Example 36, 2.3 g of (R,S)-alpha-(1-methylethyl)-3-pyridine-pentanoic acid, when reacted with 2.3 mL of diphenylphosphorylazide in 25 mL of t-butanol containing 1.5 mL of triethylamine gave 2.8 g of product. Purification of the crude ester by HPLC (ethyl acetate) gave 2.5 g of (R,S)-[1-(1-methylethyl)-4-(3-pyridinyl)butyl]carbamic acid 1,1-dimethylethyl ester as an oil.

EXAMPLE 43

Preparation of (R,S)-alpha-(1-methylethyl)-3-pyridinebutanamine.

As in Example 37, hydrolysis of 1.7 g of (R,S)-[1-(1-methylethyl)-4-(3-pyridinyl)butyl]carbamic acid 1,1-dimethylethyl ester in 25 mL of 1N HCl yielded 1.1 g of (R,S)-alpha-(1-methylethyl)-3-pyridinebutanamine. A small sample was distilled on a Kugelrohr (110°–115° C./0.1 mm) to furnish the analytical specimen.

EXAMPLE 44

Preparation of (R,S)-alpha-butyl-3-pyridinepentanoic acid.

As in Example 35, 2.32 g of hexanoic acid was treated with two equivalents of LDA and then reacted with 4.0 g of 3-(3-bromopropyl)pyridine. The usual workup yielded 4 g of (R,S)-alpha-butyl-3-pyridinepentanoic acid, as an oil.

EXAMPLE 45

Preparation of (R,S)-1-[1-butyl-4-(3-pyridinyl)butyl]carbamic acid 1,1-dimethylethyl ester.

As in Example 36, 3.7 g of (R,S)-alpha-butyl-3-pyridinepentanoic acid, when reacted with 3.4 mL of diphenylphosphorylazide in 25 mL of t-butanol containing 2.2 mL of trierhylamine yielded 4.4 g of crude carbamate. Purification of the product by HPLC (ethyl acetate) gave 3.6 g of (R,S)-[1-butyl-4-(3-pyridinyl)butyl]carbamic acid 1,1-dimethylethyl ester as an oil.

EXAMPLE 46

Preparation of (R,S)-alpha-butyl-3-pyridinebutanamine.

As in Example 37, hydrolysis of 2.2 g of (R,S)-[1-butyl-4-(3-pyridinyl)butyl]carbamic acid 1,1-dimethylethyl ester in 25 mL 1N HCl, after the usual workup, yielded 1.35 g of (R,S)-alpha-butyl-3-pyridinebutanamine. A portion was distilled on a Kugelrohr (115° C./0.1 mm) to yield the analytical sample.

EXAMPLE 47

Preparation of (R,S)-alpha-cyclopentyl-3-pyridineoentanoic acid.

As in Example 35, 2.56 g of cyclopentaneacetic acid was treated with two equivalents of LDA and then reacted with 4.0 g of 3-(3-bromopropyl)pyridine. The crude product (4 g) was crystallized from ether-hexane to yield 3.1 g of (R,S)-alpha-cyclopentyl-3-pyridinepentanoic acid, mp 95°–97° C.

EXAMPLE 48

Preparation of (R,S)-[1-cyclopentyl-4-(3-pyridinyl)butyl]carbamic acid 1,1-dimethylethyl ester.

As in Example 36, 2.8 g of (R,S)-alpha-cyclopentyl-3-pyridinepentanoic acid, when treated with 2.5 mL of diphenylphosphorylazide in 25 mL of t-butanol containing 1.58 mL of triethylamine yielded 3.4 g of product. Purification of the crude by HPLC (ethyl acetate) yielded 2.5 g of (R,S)-[1-cyclopentyl-4-(3-pyridinyl)-butyl]carbamic acid 1,1-dimethylethyl ester as an oil.

EXAMPLE 49

Preparation of (R,S)-alpha-(1-cyclopentyl)-3-pyridinebutanamine.

As in Example 37, hydrolysis of 1.6 g of (R,S)-[1-cyclopentyl)-4-(3-pyridinyl)butyl]carbamic acid 1,1-dimethylethyl ester in 25 mL of 1N HCl yielded 1.05 g of (R,S)-alpha-(1-cyclopentyl)-3-pyridinebutanamine. A sample was distilled (125°–130° C./0.1 mm) to yield the analytical specimen.

EXAMPLE 50

Preparation of (R,S)-alpha-cyclohexyl-3-pyridinepentanoic acid.

As in Example 35, 2.84 g of cyclohexaneacetic acid was treated with two equivalents of LDA and then reacted with 4.0 g of 3-(3-bromopropyl)pyridine. The crude product (3.8 g) was crystallized from ether-hexane to give 2.7 g of (R,S)-alpha-cyclohexyl-3-pyridinepentanoic acid, mp 92°–93° C.

EXAMPLE 51

Preparation of (R,S)-[1-cyclohexyl-4-(3-pyridinyl)butyl]carbamic acid 1,1-dimethylethyl ester.

As in Example 36, 2.5 g of (R,S)-alpha-cyclohexyl-3-pyridinepentanoic acid, when reacted with 2.68 g of diphenylphosphorylazide in 25 mL of t-butanol containing 0.97 g of triethylamine yielded 3.1 g of crude product. Purification by HPLC (ethyl acetate) furnished 2.8 g of (R,S)-[1-cyclohexyl-4-(3-pyridinyl)butyl]carbamic acid 1,1-dimethylethyl ester. The material was crystallized from ether-hexane to yield the analytical sample, mp 64°–66° C.

EXAMPLE 52

Preparation of (R,S)-alpha-(1-cyclohexyl)-3-pyridinebutanamine.

As in Example 37, hydrolysis of 1.9 g of (R,S)-1-[1-cyclohexyl-4-(3-pyridinyl)butyl]carbamic acid 1,1-dimethylethyl ester in 25 mL of 1N HCl yielded 1.25 g of (R,S)-alpha-(1-cyclohexyl)-3-pyridinebutanamine. Distillation of a portion of the material on a Kugelrohr apparatus (140°–145° C./0.1 mm) yielded the analytical sample.

EXAMPLE 53

Preparation of alpha-[3-(3-pyridinyl)propyl]-3-pyridinepentanoic acid.

As in Example 35, 7.16 g of 3-pyridinepentanoic acid was treated with two equivalents of LDA and then reacted with 8.8 g of 3-(3-bromopropyl)pyridine. The usual work-up yielded 8.9 g of an orange colored oil, consisting mainly of alpha-[3-(3-pyridinyl)propyl]-3-pyridinepentanoic acid contaminated by a small amount of starting 3-pyridinepentanoic acid.

EXAMPLE 54

Preparation of [1-[3-(3-pyridinyl)propyl]-4-(3-pyridinyl)butyl]carbamic acid 1,1-dimethylethyl ester.

As in Example 36, 8.8 g of alpha-[3-(3-pyridinyl)-propyl]-3-pyridinepentanoic acid, when reacted with 9.1 g of diphenylphosphorylazide in 75 mL of t-butanol containing 4.1 mL of triethylamine furnished 11.1 g of product. Purification of the crude by HPLC (ethyl acetate-methanol; 13:1) yielded 5.5 g of [1-[3-(3-pyridinyl)propyl]-4-(3-pyridinyl)butyl]carbamic acid 1,1-dimethylethyl ester as an oil.

EXAMPLE 55

Preparation of alpha-[3-(3-pyridinyl)propyl-3-pyridinebutanamine.

As in Example 37, hydrolysis of 5.4 g of [1-[3-(3-pyridinyl)-propyl]-4-(3-pyridinyl)butyl]carbamic acid 1,1-dimethylethyl ester in 55 mL of 1N HCl yielded 3.15 g of alpha-[3-(3-pyridinyl)propyl]-3-pyridinebutanamine.

EXAMPLE 56

Preparation of (R,S)-alpha-(4-bromophenyl)-3-pyridinepentanoic acid.

As in Example 35, 2.15 g of p-bromophenylacetic acid was treated with two equivalents of LDA and then reacted with 2.0 g of 3-(3-bromopropyl)pyridine. The crude product was crystallized from ether-hexane to yield 1.46 g of (R,S)-alpha-(4-bromophenyl)-3-pyridinepentanoic acid, mp 123°–126° C.

EXAMPLE 57

Preparation of (R,S)-[1-(4-bromophenyl)-4-(3-pyridinyl)butyl]carbamic acid 1,1-dimethylethyl ester.

As in Example 36, 1.45 g of (R,S)-alpha-(4-bromophenyl)-3-pyridinepentanoic acid, when treated with 0.94 mL of diphenylphosphorylazide in 10 mL of t-butanol containing 0.44 g of triethylamine yielded 1.7 g of crude (R,S)-[1-(4-bromophenyl)-4-(3-pyridinyl)-butyl]carbamic acid 1,1-dimethylethyl ester as an oil.

EXAMPLE 58

Preparation of (R,S)-alpha-(4-bromophenyl)-3-pyridinebutanamine.

As in Example 37, hydrolysis of 1.7 g of (R,S)-[1-(4-bromophenyl)-4-(3-pyridinyl)butyl]carbamic acid 1,1-dimethylethyl ester in 15 mL of 1N HCl yielded 1.1 g of (R,S)-alpha-(4-bromophenyl)-3-pyridinebutanamine.

EXAMPLE 59

Preparation of [(R,S)-Z]-2-methyl-5-(3-pyridinyl)-4-pentenoic acid.

A solution of 9.95 g of [(R,S)-Z]-2-methyl-5-(3-pyridinyl)-4-pentenoic acid ethyl ester in 75 mL of 1N NaOH and 75 mL of methanol were stirred at reflux for 3 hours, then most of the methanol was removed under reduced pressure. After the solution was extracted with dichloromethane (3×50 mL). the aqueous layer was neutralized with 75 ml of 1N HCl and extracted with dichloromethane (4×40 mL). The dried (Na₂SO₄) extracts were evaporated to give 7.28 g of a solid which was crystallized from ether-hexane to yield 6.12 g of

[(R,S)-Z]-2-methyl-5-(3-pyridinyl)-4-pentenoic acid, mp 79°-82° C.

EXAMPLE 60

[(R,S)-Z]-[1-methyl-4-(3-pyridinyl)-3-butenyl]carbamic acid 1,1-dimethylethyl ester.

As in Example 36, 2.87 g of [(R,S)-Z]-2-methyl-5-(3-pyridinyl)-4-pentenoic acid was reacted with 3.31 mL of diphenylphosphoryl azide in 30 mL of t-butanol containing 2.1 mL of triethylamine. The product was isolated in the usual manner to yield 3.88 g of [(R,S)-Z]-1-[1-methyl-4-(3-pyridinyl)-3-butenyl]carbamic acid 1,1-dimethylethyl ester as an oil.

EXAMPLE 61

[(R,S)-Z]-1-methyl-4-(3-pyridinyl)-3-butenamine

As in Example 37, hydrolysis of 3.88 g of [(R,S)-Z]-[1-methyl-4-(3-pyridinyl)-3-butenyl]carbamic acid 1,1-dimethylethyl ester in 50 mL of 1N HCl yielded, after the usual work-up and evaporative distillation of the Product (100°-120° C./0.1 mm), 1.7 g of [(R,S)-Z]-1-methyl-4-(3-pyridinyl)-3-butenamine as an oil.

EXAMPLE 62

Preparation of 3-(4-methyl-4-pentenyl)pyridine.

A suspension of 7.0 g of sodium hydride (60% dispersion in oil) in 75 mL of dry dimethylsulfoxide was stirred at 75° C. under argon for 45 minutes, at which time the evolution of hydrogen had ceased. After the solution was cooled, 61 g of methyltriphenylphosphonium bromide was added and the mixture was stirred at room temperature for 30 minutes before the addition of 25 g of 5-(3-pyridinyl)-2-pentanone in 125 mL of dimethylsulfoxide. The reaction was then stirred at room temperature overnight. After the addition of 1L of 1N hydrochloric acid solution, the precipitated triphenylphosphine oxide was removed by filtration, and the filtrate was basified with 110 mL of 10N sodium hydroxide. The product was extracted with dichloromethane (4×300 ml) and the extracts were washed with brine, then were combined, dried ($K_2CO_3$) and evaporated to give 25 g of crude product. The material was purified by HPLC (ethyl acetate:hexane: 1:1) to yield 17.5 g of 3-(4-methyl-4-pentenyl)pyridine as a colorless oil.

EXAMPLE 63

Preparation of N-[1,1-dimethyl-4-(3-pyridyl)butyl]-2-nitrobenzeneacetamide

A mixture of 22.7 g of 3-(4-methyl-pentenyl)pyridine and 22.8 g of 2-nitrobenzeneacetonitrile in 80 mL of acetic acid was cooled to 12°-13° C. and then 16 mL of sulfuric acid was added dropwise over 6 minutes. The reaction was stirred for 2 hours at ambient temperature, then after the acetic acid was removed in vacuo, 1L of water was added and the mixture was extracted with dichloromethane to remove neutral impurities. The aqueous layer was basified with 10N sodium hydroxide, and extracted with dichloromethane (4×200 mL). The dried ($K_2CO_3$) extracts were evaporated to give 35.6 g of N-[1,1-dimethyl-(3-pyridyl)butyl]-2-nitrobenzeneacetamide. A portion was crystallized from ethyl acetate-hexane to yield the analytical sample, mp 117°-118.5° C.

EXAMPLE 64

Preparation of alpha, alpha-dimethyl-3-pyridinebutanamine.

A solution of 35.2 g of N-[1,1-dimethyl-4-(3-pyridyl)butyl]-2-nitrobenzeneacetamide in 250 mL of acetic acid was hydrogenated over 3.5 g of 10% Pd/C at atmospheric pressure and ambient temperature. The reaction was exothermic and stopped abruptly after the uptake of the theoretical amount of hydrogen (7.5 L). The catalyst was removed by filtration and the filtrate was heated at reflux for 90 minutes. After the solution gas cooled, 10 mL of conc. HCl was added and the solvent was removed under reduced pressure. The residue was taken up in 1L of water and extracted with ethyl acetate (4×200 mL) to remove the byproduct, oxindole. The aqueous layer was basified with 10N NaOH and extracted with dichloromethane to give, after evaporation of the dried ($K_2CO_3$) extracts 15 g of product. The material was distilled on a Kugelrohr apparatus (95° C.: 0.1 mm) to yield 14.3 g of alpha-dimethy -3-pyridinebutanamine.

EXAMPLE 65

Preparation of 4-pyridinepropanamide.

In an inert atmosphere 10.7 g of 4-pyridinecarboxaldehyde was added to a stirred solution of 35.1 g of (carbomethoxy)methylenetriphenylphosphorane in 250 mL of methanol. After 90 minutes, the solvent was removed under reduced pressure and the residue was triturated with etherhexane. The resulting solid (triphenylphosphine oxide) was removed by filtration, and the filtrate was evaporated to yield 18 g of a mixture of (E)- and (Z)-3-(4-pyridinyl)-2-propenoic acid methyl ester contaminated with a small amount of residual triphenylphosphine oxide.

The crude mixture (18 g) was hydrogenated over 1.6 g of 10% Pd/C in 200 mL of methanol at atmospheric pressure and room temperature. After the uptake of hydrogen had stopped, the catalyst was removed by filtration and the solvent was removed in vacuo to furnish 16 g of crude 4-pyridinepropanoic acid methyl ester.

The crude ester was dissolved in 250 mL of 7.1M methanolic ammonia solution and was stirred at room temperature for 65 hours. After the solvent and excess ammonia were removed by distillation under reduced pressure. The residue was dissolved in 150 mL of 1N HCl and extracted with dichloromethane to remove residual triphenylphosphine oxide. The aqueous phase was basified with 40 mL of 4N NaOH and then was extracted with ethyl acetate (5×300 mL). The dried ($Na_2SO_4$) extracts were evaporated to furnish 6 g of the amide. The aqueous layer was concentrated to dryness and triturated with tetrahydrofuran (4×100 mL) and evaporation of the tetrahydrofuran extracts yielded an additional 5% of amide. The combined crude products were dried, triturated with ether and the solids were filtered to yield 10.7 g of 4-pyridinepropanamide, mp 164°-166° C.

EXAMPLE 66

Preparation of 4-pyridinepropanamine.

A 1M solution of $BH_3$ in tetrahydrofuran (192 mL) was added over 10 minutes to a stirred suspension of 7.2 g of 4-pyridinepropanamide in 50 mL of tetrahydrofuran at 0°–5° C. After the cooling bath was removed, the reaction was stirred at reflux for 17 hours and then the solvent was removed in vacuo. The residue was dissolved in 160 mL of 3.5N HCl and after the solution was heated on a steam bath overnight, it was cooled, basified with excess 10N NaOH and then extracted with dichloromethane. The dried ($K_2CO_3$) extract was evaporated to furnish 6.98 g of an amber oil, which was distilled in vacuo to give 4.3 g of 4-pyridinepropanamine (bp 100°–110° C./0.2 mm).

EXAMPLE 67

Preparation of 5-(2-pyridinyl)-4-pentyn-1-ol.

As in Example 1,15.8 g of 2-bromopyridine and 8.4 g of 4-pentyn-1-ol were reacted together in 125 mL of dichloromethane in the presence of 4.2 mL of triethylamine, 2.1 g of bis(triphenylphosphine)Palladium dichloride and 0.135 g of cuprous iodide. After 48 hours at reflux, the reaction was worked up in the usual manner. Distillation of the crude product yielded 8.8 g of 5-(2-pyridinyl)-4-pentyn-1-ol (bp 115°–120° C./0.25 mm).

EXAMPLE 68

Preparation of 2-pyridinepentanol.

5-(2-pyridinyl)-4-pentyn-1-ol (8.8 g) was hydrogenated over 1.0 g of 10% Pd/C in 125 mL of ethanol at room temperature and atmospheric pressure. After the uptake of hydrogen had stopped, the catalyst was removed by filtration and the solvent was removed under reduced pressure. The residual oil was distilled on a Kugelrohr apparatus (115°–120° C./0.1 mm) to yield 8.4 g of 2-pyridinepentanol.

EXAMPLE 69

Preparation of 2-(5-chloropentyl)pyridine.

A solution of 4.1 mL of thionyl chloride in 30 mL of dichloromethane was added over 10 minutes to a stirred solution of 6.65 g of 2-pyridinepentanol in 60 mL of dichloromethane maintained at -5° C. After the addition was complete, the mixture was stirred at room temperature for 17 hours, then was rechilled to 5° C. as 150 ml of 1N NaOH was added dropwise over 10 minutes. The layers were separated and the aqueous layer was extracted with 75 mL of dichloromethane. The organic layers were washed with brine, then were combined, dried ($K_2CO_3$) and evaporated to yield 7.4 g of 2-(5-chloropentyl)pyridine as an oil.

EXAMPLE 70

Preparation of 1-[5-(2-pyridinyl)pentyl]-1H-isoindole-1,3-(2H)-dione.

A mixture of 6.35 g of 2-(5-chloropentyl)pyridine, 7.7 g potassium phthalimide, 5.2 g of sodium iodide and 3.7 g of sodium carbonate in 50 mL of dimethylformamide was stirred at 50° C. for 20 hours. After the solvent was removed under reduced pressure, the residue was taken up in 100 mL of water and extracted with dichloromethane (1×250 mL; 1×150 mL). The organic extracts were washed with brine, then were combined, dried ($K_2CO_3$) and concentrated in vacuo to give 10.1 g of an orange colored oil. Purification of the crude material by HPLC (ethyl acetate-hexane) yielded 6.7 g of 1-[5-(2-pyridinyl) pentyl]-1H-isoindole-1,3-(2H)-dione.

EXAMPLE 71

Preparation of 2-pyridinepentanamine.

A solution of 6.5 g of 1-[5-(2-pyridinyl)pentyl]-1H-isoindole-1,3-(2H)-dione and 1.15 mL of hydrazine hydrate in 35 mL of ethanol was heated at reflux for 90 minutes. The cooled reaction mixture was treated with 10 ml of 6N HCl, and the solids were removed by filtration and washed With 20 mL of 0.5N HCl. After the filtrate was concentrated to remove ethanol, it was basified with 10N NaOH and extracted with dichloromethane. The organic extract was washed with brine, then was dried ($K_2CO_3$) and evaporated to give 3.4 g of a yellow oil. The crude reaction product was evaporatively distilled (105°–110° C./0.01 mm) to yield 2.4 g of 2-pyridinepentanamine.

EXAMPLE 72

Preparation of 3-(8-isoquinolinyl)-2-propyn-1-ol.

In an inert atmosphere, 0.068 g of bis(triphenylphosphine)palladium dichloride and 0.013 g of cuprous iodide was added with stirring to a deoxygenated solution of 1 g of 8-bromoisoquinoline, 0.56 mL of propargyl alcohol and 2 mL of triethylamine in 25 mL of dichloromethane. The mixture was stirred at room temperature for 2 hours and then at reflux for 20 hours. The cooled reaction was filtered and the filtrate was concentrated in vacuo. The residual oil was purified by HPLC (ethyl acetate-toluene; 2:3) to yield 0.4 g of 3-(8-isoquinolinyl)-2-propyn-1-ol, mp 138°–139° C.

EXAMPLE 73

Preparation of 8-isoquinolinepropanol.

A solution of 0.4 g of 3-(8-isoquinolinyl)-2-propyn-1-ol in a mixture of 10 mL of ethanol and 5 mL of methanol was hydrogenated over 0.06 g 10% Pd/C at room temperature and atmospheric pressure for 22 hours and then at 50 Psi for 20 hours. After the catalyst was removed by filtration and the filtrate was concentrated, the residual oil was purified by HPLC (methanol-chloroform; 1:19) and crystallized from ethyl acetate-hexane to yield 0.136 g of 8-isoquinolinepropanol, mp 66°–69° C.

EXAMPLE 74

Preparation of [3-(8-isoquinolinyl)propyl]-1H-isoindole-1.3-(2H)-dione.

A solution of 0.142 g of 8-isoquinolinepropanol in 3 mL of chloroform was added to a solution of 0.085 mL of thionyl chloride in 1 mL of chloroform and the reaction was stirred at reflux for 3 hours. The cooled mixture was washed with $NaHCO_3$ solution and with brine, then was dried ($Na_2SO_4$) and evaporated. The residual oil was stirred with 0.281 g of potassium phthalimide and 0.126 potassium iodide in 3 mL of dry dimethylformamide at 130° C. for 90 minutes. After evaporation of the solvent. The residue was partitioned between dichloromethane and water. The dried ($Na_2SO_4$) organic layer was concentrated and the crude product was purified by HPLC (ethyl acetate-toluene; 1:4) and then crystallized from ether to give 0.177 g of [3-(8-isoquinolinyl)propyl]-1H-isoindole-1,3-(2H)-dione, mp 135°–140° C.

EXAMPLE 75

Preparation of 8-isoquinolineorooanamine.

To a refluxing solution of 0.174 g of [3-(8-isoquinolinyl) propyl]-1H-isoindole-1,3-(2H)-dione in 8 mL of ethanol was added 0.12 mL of hydrazine hydrate and the reaction was stirred at reflux for 5.5 hours. The solvent was removed under reduced pressure and the residue was triturated with chloroform. The chloroform extract was concentrated to an oil which was passed through a short column of silica gel (chloroform-methanoltriethylamine; 1:4:15) to yield 0.103 g of 8-isoquinolinepropanamine as an oil.

EXAMPLE 76

Preparation of 4-(4-isoquinolinyl)-3-butyn-1-ol.

In an inert atmosphere, 0.268 g of bis(triphenylphosphine) palladium dichloride and 0.072 g of cuprous iodide was added with stirring to a deoxygenated solution of 5 g of 4-bromoisoquinoline. 3.02 g of 3-butyn-1-ol and 10 mL of triethylamine in 20 mL of dichloromethane. The reaction was stirred at room temperature for 1 hour and then at reflux for 18 hours. The cooled mixture was filtered and the filtrate was washed with water. The dried ($Na_2SO_4$) organic phase was concentrated in vacuo and the residual oil was purified by HPLC (ethyl acetate-toluene; 2:3) to yield 3.4 g of 4-(4-isoquinolinyl)-3-butyn-1-ol as an oil.

EXAMPLE 77

Preparation of (E)-4-(4-isoquinolinyl)-3-buten-1-ol.

A solution of 3.4 g of 4-(4-isoquinolinyl)-3-butyn-1-ol in 35 mL of ethanol was hydrogenated over 0.35 g of 10% Pd/C at room temperature and atmospheric pressure for 5 hours. The catalyst was removed by filtration and the filtrate was evaporated to yield 3.3 g of (E)-4-(4-isoquinolinyl)-3- buten-1-ol as an oil.

EXAMPLE 78

Preparation of (E)-4-(4-chloro-1-butenyl)isoouinoline.

A solution of 3.3 g of (E)-4-(4-isoquinolinyl)-3-buten-1-ol in 15 mL of dry chloroform was added to a cold solution of 1.8 mL of thionyl chloride in 5 mL of dry chloroform. After 15 minutes, the cooling bath was removed and the reaction was stirred at room temperature for 1 hour and then at reflux for 3 hours. The cooled mixture was washed with $NaHCO_3$ solution and with brine, then was dried ($Na_2SO_4$) and evaporated. The residue was purified by chromatography over silica gel (ethyl acetate-toluene; 3:17) to yield 2.2 g of (E)-4-(4-chloro-1-butenyl)isoquinoline as an oil.

EXAMPLE 79

Preparation of (E)-1-[4-(4-isoquinolinyl)-3-butenyl]-1H-isoindole-1,3-(2H)-dione.

A mixture of 2.2 g of (E)-4-(4-chloro-1-butenyl) isoquinoline, 3.8 g of potassium phthalimide and 1.7 g of potassium iodide in 20 mL of dry dimethylformamide was maintained at 130° C. for 5 hours. After evaporation of the solvent, the residue was partitioned between dichloromethane and water. The dried ($Na_2SO_4$) organic layer was concentrated and the crude product was purified by chromatography over silica gel (ethyl acetate-toluene; 3:7) to yield 1.75 g of (E)-1-[4-(4-isoquinolinyl)-3-butenyl]-1H-isoindole-1,3-(2H)-dione. mp 135°-140°.

EXAMPLE 80

Preparation of (E)-4-(4-isoquinolinyl)-3-buten-1-amine.

To a refluxing solution of 1.75 g of (E)-1-[4-(4-isoquinolinyl)-3-butenyl]-1H-isoindole-1,3-(2H)-dione in 80 mL of ethanol was added 1.1 mL of hydrazine hydrate and the reaction was stirred at reflux for 17 hours. The solvent was removed in vacuo and the residue was triturated with chloroform. The extract was concentrated to yield 1 g of (E)-4-(4-isoquinolinyl)-3-buten-1-amine as an oil.

EXAMPLE 81

Preparation of 4-isocuinolinebutanamine.

A solution of 1 g of (E)-4-(4-isoquinolinyl)-3-buten-1-amine in 20 mL of ethanol was hydrogenated over 0.12 g of 10% Pd/C at room temperature and atmospheric pressure. After 8 hours, the catalyst was removed by filtration and the filtrate was concentrated to yield 0.893 g of 4-isoquinolinebutanamine.

EXAMPLE 82

3,3'-bis(Trifluoromethyl)benzophenone

To a stirred solution of n-butyl lithium in hexane (1.6M: 100 mL) at −78° C. under argon was added dropwise a solution of 3-bromobenzotrifluoride (36 g) in dry ether (75 mL) over 15 minutes. After the addition was complete, the solution was stirred at −78° C. for 45 minutes. Then a solution of alpha, alpha, alpha-trifluoro-m-toluonitrile (25.7 g) in dry ether was added over 20 minutes. The deep red mixture was allowed to react at −78° C. for 30 minutes. Then immediately after the cooling bath was removed 6N hydrochloric acid (100 mL) was added in a rapid stream. The reaction mixture decolorized and a dense precipitate formed as the reaction temperature rose rapidly to 0°-5° C. Water (200 mL) and ether (200 mL) were added, and the reaction was warmed to 35° C. and was stirred at that temperature until the precipitate dissolved (2 hours). After the reaction was cooled, the layers were separated and the aqueous phase was washed with ether (200 mL). The organic extracts were washed in turn with saturated sodium bicarbonate, then were combined, dried ($MgSO_4$) and evaporated. The solid residue was dissolved in hot hexane (200 mL) and the mixture was left at 0°-5° C. overnight. The resulting colorless crystalline material was filtered, washed with hexane and dried to give 43.9 g of 3,3'-bis(trifluoromethyl)benzophenone mp 98.5°-99.5° C.

EXAMPLE 83

3-Fluoro-3'-methoxybenzophenone

A solution of 3-methoxybenzoyl chloride (301 g) in dry tetrahydrofurane (600 mL) was added with stirring to a chilled solution of 2-mercaptopyridine (200.5 g) and triethylamine (345 mL) in dry tetrahydrofurane (1.2 L) under argon. The reaction temperature was maintained at 0°-5° C. by using an ice-water bath. The cooling bath was removed and after 45 minutes at room temperature. The reaction was filtered to remove triethylamine hydrochloride. The filtrate and washes were evaporated to dryness and the residue was partitioned between 1N sodium hydroxide solution (250 mL) and ether (2 L). The organic phase was separated washed with 1N sodium hydroxide (2×250 mL) and with brine, then was evaporated. The residual oil (428.8 g) was distilled on a Kugelrohr (180°–200° C.; 0.05 mm) to afford 417.3 g of S-(2-pyridyl)-3-methoxybenzenethionate (3). Anal. Calculated for : C. 63.65; H. 4.52; N, 5.71; S, 13.07 Found: C, 63.85; H. 4.56; N, 5.68; S, 13.33.

A solution of 3-fluorophenylmagnesium bromide, prepared from magnesium (3.2 g) and 3-bromofluorobenzene (22.25 g) in tetrahydrofurane (55 mL), was added dropwise to a cooled (−5° C.) solution of the above S-(2-pyridyl)-3-methoxybenzenethionate (30.66 g) in tetrahydrofurane at such a rate that the reaction temperature did not exceed 5° C. The mixture was stirred at 0° C. for 15 minutes, then at room temperature for 30 minutes. After water (5 mL) had been added to the reaction. The solvent was removed under reduced pressure and the residue was taken up in a mixture of 1N hydrochloric acid solution (300 mL) and ether (300 mL). The separated organic layer was washed with 1N hydrochloric acid (2×100 mL), 1N sodium hydroxide solution (3×150 mL) and with brine. The aqueous layers were backwashed in turn with ether (2×200 mL), then the combined ether layers were dried (MgSO$_4$) and evaporated to give 30 g of a pale yellow solid. The crude material was crystallized from hexane to yield 22.1 g of 3-fluoro-3'-methoxybenzophenone mp 56°–67° C. Concentration of the mother liquors gave an additional 3.4 g of the product. mp 55°–57° C. Anal. Calculated for C$_{14}$H$_{11}$FO$_2$: C, 73.03; H, 4.82; F, 8.25 Found: C, 72.79; H. 5.03; F, 8.05.

EXAMPLE 84

3,3-Diphenyl-2-propenal

A solution of freshly distilled diisopropylamine (193.2 mL) in dry tetrahydrofurane (1 L) under argon was cooled to −5° C. with an acetone-dry ice bath. Anhydrous conditions were maintained throughout the reaction. A 1.6M solution of n-butyl lithium in hexane (862 mL) was added at such a rate that the reaction temperature did not exceed −5° C. After the addition was complete, the solution was stirred at 5° C. for 15 minutes. Then it was cooled to −78° C. and acetaldehyde N-tert-butylimine (88.5 mL) was added dropwise over 10 minutes. After stirring at −78° C. for 30 minutes. diethyl chlorophosphonate (101.2 mL) was added slowly while maintaining the reaction temperature below −65° C. and the yellow solution was stirred at −78° C. for 1 hour. The cooling bath was then removed and the mixture was allowed to warm to −10° C. over 45 minutes. Benzophenone (109.3 g) was added via a Gooch tube, and the mixture was then stirred at ambient temperature overnight. After the solvents were removed in vacuo. The residue was taken up in a solution of oxalic acid dihydrate (175 g) in water (1.5 L) and toluene (1.5 L) was added. The mixture was stirred vigorously under argon overnight. The layers were separated and the organic phase was washed in turn with 5% oxalic acid, brine, saturated sodium bicarbonate and brine. The aqueous layers were backwashed with toluene (500 mL), and the combined organic extracts were dried (MgSO$_4$), charcoaled and concentrated to ~250 mL. The concentrate was passed through a short column of silica gel (500 g) made up in dichloromethane, and the product was eluted with the same solvent (7×400 mL fractions). The appropriate fractions were combined and evaporated and the residue was dissolved in warm hexane (1.2 L). The gently stirred solution was cooled slowly to 5° C. and the resulting crystalline solid was recovered by filtration to yield 109.3 g of 3,3-diphenyl-2-propenal, mp 45°–46.5° C. Concentration of the mother liquors furnished a second crop of impure 3,3-diphenyl-2-propenal which after two recrystallizations from hexane gave an additional 10.1 g of product. mp 44.5°–46° C.

EXAMPLE 85

3,3-bis(2-Fluorophenyl)-2-propenal

The compound was prepared according to the procedure described in Example 84. The following reagents were used: 2,2'-difluorobenzophenone (6.0 g) diisopropylamine (28.8 mL) 1.6M n-butyl lithium in hexane (129 mL), acetaldehyde N-tert-butylimine (13.2 mL). diethyl chlorophosphonate (14.85 mL) and tetrahydrofurane (100 mL). The reaction was worked up in the usual manner, with the exception that the oxalic acid catalyzed hydrolysis was slow and it was necessary to heat the mixture to 85° C. for one hour to complete the conversion. The crude product (5.8 g), obtained as an orange oil, was crystallized from hexane to give 4.6 g of 3,3-bis(2-fluorophenyl)-2-propenal mp 75°–77.° C. Anal. Calculated for : C$_{15}$H$_{10}$F$_2$O: C. 73.76; H, 4.13; F, 15.56 Found: C, 73.32; H, 4.27; F, 15.74.

EXAMPLE 86

3,3-bis(3-Fluorophenyl)-2-propenal

The compound was prepared according to the procedure described in Example 84. The following reagents were used: 3'-difluorobenzophenone (19.8 g), diisopropylamine (32.2 mL), 1.55M n-butyl lithium in hexane (148 mL), acetaldehyde N-tert-butylimine (14.75 mL), diethyl chlorophosphonate (16.6 mL) and tetrahydrofurane (200 mL). The usual work up gave 23 g of material which was crystallized from hexane to give 17.4 g of 3,3-bis(3-fluorophenyl)-2-propenal, mp 51°–53° C. A small portion was recrystallized from the same solvent to provide the analytical sample, mp 52°–54° C. Anal. Calculated for C$_{15}$H$_{10}$F$_2$O; C, 73.76; H. 4.13; F, 15.56 Found: C, 73.90; H, 4.03: F, 15.61.

EXAMPLE 87

3,3-bis(4-Fluorophenyl)-2-propenal

The compound was prepared according to the procedure described in Example 84. The following reagents were used: 4.4'-difluorobenzophenone (22.4 g), diisopropylamine (32.2 mL), 1.55M n-butyl lithium in hexane (148 mL), acetaldehyde N-tert-butylimine (14.75 mL), diethyl chlorophosphonate (16.6 mL) and tetrahydrofurane (200 mL). The usual work up furnished 26 g of an orange oil which was crystallized from 2-propanol to give 19.3 g of 3,3-bis(4-fluorophenyl)-2-propenal, mp 56°–58° C. A small portion was recrystallized from pentane to yield the analytical sample, mp 58°–59.5° C. Anal. Calculated for C$_{15}$H$_{10}$F$_2$O; C, 73.76; H. 4.13; F. 15.56 Found: C, 3.52; H, 4.43; F, 15.59.

EXAMPLE 88

3,3-bis(3-Methoxyphenyl)-2-propenal

The compound was prepared according to the procedure described in Example 84 except that the reaction was worked up after 30 hours. The following reagents were used: 3,3-dimethoxybenzophenone (48.5 g), diisopropylamine (64.4 mL). 1.55M n-butyl lithium in hexane (286 mL), acetaldehyde N-tertbutylimine (29.5 mL), diethyl chlorophosphonate (33.2 mL) and tetrahydrofurane (400 mL). The work up varied only in that the oxalic acid catalyzed hydrolysis was done at 85° C. over two hours, furnished 53 g of essentially pure 3,3-bis(3-methoxyphenyl)-2-propenal as a pale yellow oil.

EXAMPLE 89

3,3-bis(4-Methoxyphenyl)-2-propenal

The compound was prepared according to the procedure described in Example 84 except that the reaction time was extended to 68 hours. The following reagents were used: 4,4'-dimethoxybenzophenone (24.2 g), diisopropylamine (32.2 mL) 1.55M n-butyl lithium in hexane (148 mL). acetaldehyde N-tert-butylimine (14.75 mL), diethyl chlorophosphonate (16.6 mL) and tetrahydrofurane (200 mL). The usual work up furnished 25.6 g of an orange oil which was crystallized from ether-hexane to give 22.7 g of 3,3-bis(4-dimethoxyphenyl)-2-propenal, as a yellow solid, mp 55°-57° C. The analytical specimen, mp 56°-57° C., crystallized from the same solvent system had been prepared in a previous experiment. Anal. Calculated for $C_{17}H_{16}O_3$: C, 76.10; H. 6.01 Found: C, 76.29: H, 6.29.

EXAMPLE 90

3,3-bis(3,4-Dimethoxyphenyl)-2-propenal

The compound was prepared according to the procedure described in Example 84. The following reagents were used: 3,3',4,4'-tetramethoxybenzophenone (32.2 g). diisopropylamine (32.2 mL), 1.6M n-butyl lithium in hexane (144 mL), acetaldehyde N-tert-butylimine (14.75 mL) diethyl chlorophosphonate (16.6 mL) and tetrahydrofurane (300 mL). At the end of the reaction, some insolubles (8 g) that were later identified as the starting benzophenone were filtered off. The usual work up furnished 22 g of a yellow-orange solid which was crystallized from ether to give 19.6 g of 3,3-bis(3,4-dimethoxyphenyl)-2-propenal mp 129°-130° C. Anal. Calculated for $C_{19}H_{20}O_5$: 69.50; H, 6.14 Found: C, 69.32; H, 6.29.

EXAMPLE 91

3,3-bis(3-Chlorophenyl)-2-propenal

The compound was prepared according to the procedure described in Example 84. The following reagents were used: 3,3'-dichlorobenzophenone (25.1 g), diisopropylamine (32.2 mL), 1.6M n-butyl lithium in hexane (144 mL), acetaldehye N-tert-butylimine (14.75 mL), diethyl chlorophosphonate (16.6 mL) and tetrahydrofurane (200 mL). The usual work up furnished 24.0 g of essentially pure 3,3-bis(3-chlorophenyl)-2-propenal as an orange oil.

EXAMPLE 92

3,3-bis(4-Chlprophenyl)-2-propenal

The compound was prepared according to the procedure described in Example 84. The following reagents were used: 4,4'-dichlorobenzophenone (25.1 g), diisopropylamine (32.2 mL), 1.6M n-butyl lithium in hexane (144 mL), acetaldehyde N-tert-butylimine (14.75 mL), diethyl chlorophosphonate (16.6 mL) and tetrahydrofurane (200 mL). The usual work up furnished 23.8 g of essentially pure 3,3-bis(4-chlorophenyl)-2-propenal as an orange oil.

EXAMPLE 93

3,3-bis[3-(Trifluoromethyl)phenyl]-2-propenal

The compound was prepared according to the procedure described in Example 84. The following reagents were used: 3,3'-bis(trifluorpmethyl)benzophenone (31.8 g), diisopropylamine (32.2 mL), 1.6M n-butyl lithium in hexane (144 mL), acetaldehyde N-tert-butylimine (14.75 mL) diethyl chlorophosphonate (16.6 mL) and tetrahydrofurane (200 mL). After the usual work up, the product was purified by HPLC to give 30,8 g of 3,3-bis[3-(trifluoromethyl)phenyl]-2-propenal as an oil.

EXAMPLE 94

3,3-bis(3-Nitrophenyl)-2-propenal

The compound was prepared as in Example 84. The following reagents were used: 3,3'-dinitrobenzophenone (27.3 g) diisopropylamine (32.2 mL), 1.55M n-buryl lithium in hexane (148 mL), acetaldehyde N-tert-butylimine (14.75 mL), diethyl chlorophosphonate (16.6 mL) and tetrahydrofurane (200 mL). The usual work up furnished a tan solid that was crystallized from 2-propanol to give 23 g of slightly impure aldehyde. The material was recrystallized from dichloromethane-hexane to yield 20.6 g of 3,3-bis(3-nitrophenyl)-2-propenal, mp 131°-136° C. A small portion was recrystallized from the same solvents to give the analytical sample, mp 134°-136° C. Anal. Calculated for $C_{15}H_{10}N_2O_5$: C. 60.41; H. 3.38; N, 9.39 Found: C. 60.66; H. 3.47: N, 9.31.

EXAMPLE 95

(E)-and (Z)-3-(3-Methoxyphenyl)-3-phenyl-2-propenal

The mixture of (E)- and (Z)-isomers was prepared according to the procedure described in Example 84. The following reagents were used: 3-methoxybenzophenone (17.0 g), diisopropylamine (32.2 mL) 1.55M n-butyl lithium in hexane (148 mL), acetaldehyde-tert-butylimine (14.75 mL), diethyl chlorophosphonate (16.6 mL) and tetrahydrofurane (200 mL). The usual work up followed by purification of the crude product through HPLC furnished 13.0 g of a mixture (5:4) of the (E)- and (Z)-isomers of 3-(3-methoxyphenyl)-3-phenyl-2-propenal as an oil. The attempted separation of the isomers by HPLC was unsuccessful.

EXAMPLE 96

(E)- and (Z)-(3-Fluorophenyl)-3-(3-methoxyphenyl)-2-propenal

The isomeric mixture was prepared according to the procedure described in Example 84. The following reagents were used: 3-fluoro-3'methoxybenzophenone (23 g). diisopropylamine (32.2 mL). 1.55M n-butyl lithium in hexane (148 mL). acetaldehyde N-tert-butylimine (14.75 mL), diethyl chlorophosphonate (16.6 mL) and tetrahydrofurane (200 mL). The usual work up yielded 30 g of an oil which was purified by HPLC (dichloromethanehexane; 8:3) to give 25.2 g of 3-(4-fluorophenyl)-3-(3-methoxyphenyl)-2-propenal as a mixture (1:1) of its (E)- and (Z)-isomers. The compounds could not be efficiently separated by HPLC.

EXAMPLE 97

3,3-bis[2-(Trifluoromethyl)phenyl]-2-propenal

A stirred solution of diisopropylamine (4.02 mL) in dry tetrahydrofurane (30 mL) under argon was treated dropwise with 1.6M n-butyl lithium in hexane (18 mL). The reaction was kept at −5° C. during the addition and for 15 minutes thereafter, then it was cooled to −78° C. and a solution of 2,2'-bis(trifluoromethyl)benzophenone (8.0 g) in tetrahydrofurane was added at such a rate that the reaction temperature did not exceed −65° C. The mixture was stirred at −78° C. for 10 minutes, then it was allowed to slowly equilibrate to room temperature over 30 minutes. After the solvents were removed under reduced pressure, the residue was treated with water (100 mL) and the resulting solid was filtered off, washed with water and dried. Crystallization of the solid from dichloromethanehexane furnished 7.72 g of 3-hydroxy-3,3-bis[2-(trifluoromethyl)phenyl]-propanenitrile, mp 168°–170° C. A sample was recrystallized from the same solvent system to give the analytical specimen, mp 171°–172° C. Anal. Calculated for $C_{17}H_{11}F_6NO$: 56.83: H, 3.08: F, 31.73: N, 3.80. Found: C. 56.87; H, 2.81: F, 31.88: N, 4.14.

Sulfuric acid (25 mL) was cooled to −5° C. during the portionwise addition of the above carbinol 3-hydroxy-3. 3-bis[2-(trifluoromethyl)phenyl]-propanenetrile (7.2 g). When the addition was complete, the cooling bath was withdrawn and the suspension was stirred until all the solids had dissolved (30 min). The reaction was Poured over ice (300 g) and the resulting oily mixture was extracted with toluene (2×100 mL). The organic extracts were washed with water (2×100 mL). then were combined, dried (MgSO4) and evaporated to give 6.6 g of an oil. The material was crystallized from 2-propanol to afford 5.8 g of 3,3-bis[2-(trifluoromethyl)-phenyl]-2-propenenitrile mp 65°–68° C. Recrystallization of a portion from 2-propanol furnished analytically pure nitrile, mp 67°–68° C. Anal. Calculated for $C_{17}H_9F_6N$: C, 59.83; H. 2.66; N, 4.10. Found: C, 59.71; H, 2.71; N. 4.36.

A solution of the above nitrile (5.6 g) in dry toluene, cooled to −40° C. under argon was treated with a 1.5M solution of diisobutylaluminum hydride in toluene (12 mL) added with over 15 minutes and then the mixture was allowed to warm to room temperature. After 30 minutes, the solution was rechilled in an ice bath and 2N sulfuric acid solution (50 mL) was added dropwise. The acidified mixture was stirred at 25° C. for 2 hours. Then the separated aqueous phase was extracted with toluene (50 mL). The organic layers were washed with water then were combined, dried (MgSO4) and evaporated to give 5.2 g of essentially pure 3,3-bis[2-(trifluoromethyl)-phenyl]-2-propenal as an oil.

EXAMPLE 98

3,3-bis[(1,1′biphenyl)-4-yl]-2-propenal

To a stirred suspension of 4,4′-diphenylbenzophenone (15.5 g) and acetonitrile in dry benzene (200 mL), was added at a rapid dropwise rate a suspension of sodamide (2.3 g) in dry benzene (20 mL). The resulting mixture was stirred at reflux for 60 minutes, then the reaction was cooled and treated carefully with ice (50 g). The layers were separated, and the aqueous Phase was extracted with toluene. The organic extracts were washed with water, then were combined, dried (MgSO4) and evaporated to furnish 13.5 g of 3,3-bis[(1,1′-biphenyl)-4-yl]-3-hydroxypropanenitrile as an oil. The material was contained a minor impurity that was presumed to be the starting ketone.

The crude carbinol 3,3-bis[(1.1-biphenyl)-4-yl]-3-hydroxypropanenitrile (13.5 g; 0.036 mol) was dissolved in trifluoroacetic acid (30 mL) and the solution was heated at 65° C. for 10 min. After the solvent was removed in vacuo the residue was triturated with water and the resulting solids were dissolved in dichloromethane. The dried (MgSO4) solution was evaporated to provide 12.2 g of 3,3-bis[(1,1′-biphenyl)-4-yl]-2-propenenitrile as an oil that was contaminated with a small amount of starting ketone.

A stirred solution of the above nitrile (12.2 g) in dry toluene (75 mL) was cooled to −40° C. and was maintained at that temperature during the dropwise addition of a 1.5M solution of diisobutylaluminum hydride in toluene (25 mL). The reaction was allowed to equilibrate to room temperature, then after 30 min it was cooled to 10° C. before the dropwise addition of 2N sulfuric acid (100 mL) with vigorous agitation. The mixture was stirred for 30 minutes at ambient temperature then the phases were separated and the aqueous layer was extracted with toluene (50 mL). The combined organic extracts were washed, dried (MgSO4) and concentrated to yield 12 g of crude aldehyde. The material was purified by HPLC (toluene) to give 3.8 g of 3,3-bis[(1,1′-biphenyl)-4-yl]-2-propenal. A sample was crystallized from dichloromethane-ethyl acetate to afford the analytically pure aldehyde, mp 163°–164° C. Anal. Calculated for $C_{27}H_{20}O$: C, 89.97; H, 5.59 Found: C. 89.77; H. 5.72.

EXAMPLE 99

(E)-5,5-Diphenyl-2,4-pentadienoic acid and (Z)-5,5-diphenyl-2,4-pentadienoic acid A solution of 3,3-diphenyl-2-propenal (18.73 g) and (carbethoxymethylene)triphenylphosphine (33.1 g) in ethanol (100 mL) was stirred at room temperature for 1 hour. The solvent was removed in vacuo and the residual solid was refluxed in a mixture of ether (125 mL) and hexane (250 mL) for 10 minutes. The mixture was cooled to room temperature and the precipitated triphenylphosphine oxide (25 g) was removed by filtration and was washed with ether-hexane (1:2; 2×50 mL). The filtrates were evaporated and the residue was passed through a short column of silica gel (200 g) made up in dichloromethane to remove residual triphenylphosphine oxide and starting yield. After evaporation of the appropriate eluates, the resulting mixture of esters was separated by using HPLC (dichloromethane-hexane; 1:1). The fractions containing the less polar material were combined and evaporated to yield 4.2 g of (Z)-5,5-diphenyl-2,4-pentadlenoic acid ethyl ester as an oil which crystallized on standing, mp 36°–37° C. Anal. Calculated for : $C_{19}H_{18}O_2$: C, 81.98; H. 6.51 Found: C. 81.78; H. 6.67.

Evaporation of the fractions containing the more Polar ester furnished 20.2 g of (E)-5,5-diphenyl-2,4-pentadieneoic acid ethyl ester. Crystallization of a portion from pentane afforded the analytical specimen, mp 34°–35° C. Anal. Calculated for $C_{19}H_{18}O_2$ C, 81.98: H, 6.51 Found: C. 82.10; H, 6 70.

A solution of (Z)-5,5-diphenyl-2,4-pentadieneoic acid ethyl ester (3.5 g) in methanol (20 mL) was treated with a 4N potassium hydroxide solution (5 mL) and the mixture was stirred at reflux for 30 minutes. Most of the methanol was removed under reduced pressure. Then the residual solution was poured over ice containing 3N hydrochloric acid (10 mL). The resulting solid was collected by filtration washed with water, dried and crystallized from dichloromethane-hexane to furnish 3.05 g of (Z)-5,5-diphenyl-2,4-pentadienoic acid mp 175°–176.5° C. Anal. Calculated for $C_{17}H_{14}O_2$: C, 81.57; H, 5.63 Found: C, 81.51; H. 5.77.

A solution of (E)-5,5-diphenyl-2,4-pentadieneoic acid ethyl ester (15 g) in methanol (80 mL) was treated with a 4N Potassium hydroxide solution (20 mL) and the mixture was stirred at reflux for 45 minutes. Most of the methanol was removed under reduced pressure, then the residual solution was poured over ice containing 3N hydrochloric acid (30 mL). The resulting solid was collected by filtration washed with water and dried. Crystallization of the crude material from 2-propanol furnished 11.7 g of (E)-5,5-diphenyl-2,4-pentadienoic acid mp 193°-194° C. Recrystallization from the same solvent did not affect the melting Point. Anal. Calculated for $C_{17}H_{14}O_2$: C, 81.57: H, 5.63 Found: C, 81.43; H. 5.81.

EXAMPLE 100

(E)-5,5-Diphenyl-2-methyl-2,4-pentadienoic acid

As in the Example 99, a solution of 3,3-diphenyl-2-propenal (2.08 g) in ethanol (25 mL) was reacted with (carbethoxyethylidene)triphenylphosphine (4.0 g) for 30 minutes at room temperature. The reaction was worked up in the usual manner to give 2.8 g of (E)-5,5-diphenyl-2-methyl-2,4-pentadienoic acid ethyl ester as the sole product. The crude ester (2.89) in methanol (25 mL) was treated with 2N potassium hydroxide (10 mL) and the mixture was heated at reflux until the oil dissolved. Then it was cooled and left at ambient temperature overnight. The reaction was diluted with water (20 mL) and most of the methanol was removed under reduced pressure. The solution was acidified with 2N hydrochloric acid (12 mL) and the resulting solid was recovered by filtration washed with water and dried. The crude acid was triturated with hot hexane to furnish 2.08 g of (E)-5,5-diphenyl-2-methyl-2,4-pentadienoic acid. mp 184°-186° C. A sample was crystallized from 2-propanol to afford the analytical specimen. mp 185°-186.5° C. Anal. Calculated for $C_{18}H_{16}O_2$: C, 81.79; H. 6.10 Found: C, 81.73; H. 6.17.

EXAMPLE 101

(E)-5,5-bis(2-Fluorophenyl)-2,4-pentadienoic acid and (Z)-5,5-bis(2-fluorophenyl)-2,4-pentadienoic acid As described in Example 99, 3,3-bis(2-fluorophenyl)-2-propenal (1.85 g) was reacted with (carbethoxymethylene)triphenylphosphine (2.8 g) in methanol. The mixture of esters obtained from the usual work up was separated by HPLC (dichloro- methane-hexane; 1:2) to yield 0.4 g of (Z)-5,5-bis(2-fluoro- phenyl)-2,4-pentadienoic acid ethyl ester as an oil and 1.7 g of (E)-5,5-bis(2-fluorophenyl)-2,4-pentadienoic acid ethyl ester as an oil.

Hydrolysis of (Z)-5,5-bis(2-fluorophenyl)-2,4-pentadienoic acid ethyl ester (0.4 g) in methanol (5 mL) was carried out as before using 4N sodium hydroxide (0.6 mL). After acidification, the product was extracted into dichloromethane (2×30 mL). The combined dried extracts were evaporated and the residue crystallized from ether-hexane to yield 0.35 g of (Z)-5,5-bis(2-fluorophenyl)-2,4-pentadienoic acid mp 147°-148° C. Anal. Calculated for $C_{17}H_{12}F_2O_2$: C, 71.32; H. 4.22; F, 13.27 Found: C, 71.36; H, 4.31; F. 13.52.

As before. (E)-5.5-bis(2-fluorophenyl)-2,4-pentadienoic acid ethyl ester (1.7 g) in methanol (15 mL) was carried out using 4N sodium hydroxide (2.5 mL). After acidification, the product was extracted into dichloromethane (2×50 mL). The combined extracts were dried and evaporated and the residue crystallized from ether-hexane to provide 1.45 g of (E)-5,5-bis(2-fluorophenyl)-2,4-pentadienoic acid, mp 159°-160° C. Anal. Calculated for $C_{17}H_{12}F_2O_2$: C, 71.32; H, 4.22; F, 13.27 Found: C, 71.09; H, 4.42; F, 13.26.

EXAMPLE 102

(E)-5,5-bis(3-Fluorophenyl)-2,4-pentadienoic acid and (Z)-5,5-bis(3-fluorophenyl)-2,4-pentadienoic acid In the manner described in Example 99, 3,3-bis(3-fluorophenyl)-2-propen al (17.8 g) was reacted with (carbethoxymethylene)triphenylphosphine (26.2 g) in carbon tetrachloride (200 mL) at room temperature overnight. The crude product (23 g) obtained from the usual work up was Predominantly (E)-5,5-bis(3-fluorophenyl)-2,4-pentadienoic acid ethyl ester. A stirred solution of the above material (23 g) in hot methanol (200 mL) was treated in one portion with 2N sodium hydroxide solution (75 mL). After 10 minutes at reflux, the reaction had become homogeneous and most of the methanol was distilled off. The cooled solution was diluted with water (300 mL), then was extracted with dichloromethane (3×200 mL). The organic extracts were discarded and the aqueous phase was added in a fine stream to a stirred mixture of 2N hydrochloric : acid (20mL) and ice (300 g). The resulting precipitate was filtered off then washed with water and dried. Triturating of the crude acid with hot hexane (150 mL) furnished 18.2 g of (E)-5,5-bis(3-fluorophenyl)-2,4-pentadienoic acid mp 162°-164° C. The analytical sample was obtained from 2-propanol. mp 163.5°-165° C.- Anal Calculated for $C_{17}H_{12}F_2O_2$: C, 71.32; H, 4.22; F. 13.27 Found: C, 71.17; H. 4.23; F, 13.37.

The mother liquors from the triturating of the crude (E)-acid were evaporated to give 1.2 g of a solid rich in the (Z)-isomer. This material was crystallized three times from ether-hexane to provide 0.62 g of (Z)-5,5-bis-(3-fluorophenyl)-2,4-pentadienoic acid mp 141.5-143° C. Anal. Calculated for $C_{17}H_{12}F_2O_2$: C, 71.32; H, 4.22; F. 13.27 Found: C, 71.38; H. 4.31; F, 13.27.

EXAMPLE 103

(E)-5,5-bis(4-Fluorophenyl)-2,4-pentadienoic acid

As described in Example 99, 3.3-bis(4-fluorophenyl)-2-propenal (9.8 g) was reacted with (carbethoxymethylene)triphenylphosphorane (14.3 g) in ethanol (20 mL) for 30 minutes at ambient temperature. The mixture of esters obtained from the usual work up was purified by HPLC (dichloromethane-hexane; 1:1) to give 2.0 g of the less polar (Z)-5,5-bis(4-fluorophenyl)-2,4-pentadienoic acid ethyl ester as an oil, and 9.3 g of (E)-5,5-bis(4-fluorophenyl)-2,4-pentadienoic acid ethyl ester. A sample of the (E)-isomer was crystallized from hexane to give the pure ester, mp 71°-72.5° C. Anal. Calculated for $C_{19}H_{16}F_2O_2$: C, 72.60; H, 5.13; F, 12.09 Found: C, 72.56; H, 5.17; F, 12.36.

A solution of (E)-5,5-bis(4-fluorophenyl)-2,4-pentadienoic acid ethyl ester (8.8 g) in methanol (30 mL) was treated with 2N sodium hydroxide solution (20 mL) and the mixture was heated at reflux for 15 minutes. The crude solid obtained from the usual work up, was crystallized from dichloromethane-hexane to yield 7.5 g of (E)-5,5-bis(4-fluorophenyl)-2,4-pentadienoic acid mp 186°-188° C. A portion was recrystallized from ether-hexane to furnish the analytical specimen, mp 187°-188° C. Anal. Calculated for $C_{17}H_{12}F_2O_2$: C, 71.32: H, 4.22; F, 13.27 Found: C, 71.48; H, 4.22; F, 13.53.

EXAMPLE 104

(E)-5,5-bis(3-Methoxyphenyl)-2,4-pentadienoic acid and (Z)-5,5-bis(3-methoxyphenyl)-2,4-pentadienoic acid In the manner described in Example 99, 3,3-bis(3-methoxyphenyl)-2-propenal (24.8 g) was reacted with (carbethoxymethylene)triphenylphosphorane (33 g) in ethanol (100 ml) for 30 minutes at 50° C. The mixture of esters obtained from the usual work up was purified by HPLC (hexane-ether; 9:1) to give 2.3 g of the less polar (Z)-5,5-bis(3-methoxyphenyl)-2,4-pentadienoic acid ethyl ester as an oil, and 19.8 g of (E)-5,5-bis(3-methoxyphenyl)-2,4-pentadienoic acid ethyl ester.

A mixture of (E)-5,5-bis(3-methoxyphenyl)-2,4-pentadienoic acid ethyl ester (19.8 g) methanol (200 mL) and 2N sodium hydroxide solution (40 mL) was heated at reflux for 30 minutes. After most of the methanol was distilled off in vacuo, the solution was diluted with water (300 ml), acidified with 2N hydrochloric acid (50 mL) and the resulting solid filtered. The dried material (17.8 g) was crystallized from dichloromethane-hexane to afford 15.9 g of (E)-5,5-bis (3-methoxyphenyl)-2,4-pentadienoic acid, mp 179°–180.5° C. Anal. Calculated for $C_{19}H_{18}O_4$: C, 73.53; H, 5.85 Found: C, 73.80; H, 5.94

In a similar fashion, (Z)-5,5-bis(3-methoxyphenyl)-2,4-pentadienoic acid ethyl ester (2.2 g) in methanol (15 mL) was hydrolyzed using 2N sodium hydroxide solution (5 mL). The usual work up furnished 2.0 g of (Z)-5,5-bis(3-methoxyphenyl)-2,4-pentadienoic acid. Crystallization of a portion from ether furnished the analytically pure acid, mp 178°–180° C. Anal. Calculated for $C_{19}H_{18}O_4$C: 73.53; H, 5.85 Found: C, 73.29; H, 5.91.

EXAMPLE 105

(E)-5,5-bis(4-Methoxyphenyl)-2,4-pentadienoic acid

A mixture of 3,3-bis(4-methoxyphenyl)-2-propenal (22.7 g) and (carbethoxymethylene)triphenylphosphorane (30 g) in carbon tetrachloride (200 mL) was stirred overnight at room temperature and then at reflux for 5 hours to complete the reaction. The crude product (28.4 g) obtained from the usual work up consisted mainly of (E)-5,5-bis(4-methoxyphenyl)-2,4-pentadienoic acid ethyl ester. The crude ester (28.4 g) in a mixture of methanol (200 mL) and 2N sodium hydroxide solution (100 mL) was heated at reflux for 30 minutes, then most of the methanol was distilled from the reaction. The base mixture was cooled, diluted with water (300 mL), extracted with dichloromethane (3×400 mL) and then was poured into a stirred mixture of concentrated hydrochloric acid (50 mL), water (200 mL) and ice (200 mL). The yellow precipitate was filtered off, washed with water and dried. The material was triturated with ether (3×100 ml) to provide 21.5 g of (E)-5,5-bis(4-methoxyphenyl)-2,4-pentadienoic acid, mp 187°–189° C. Crystallization from dichloromethane-hexane furnished the pure acid, mp 189.5°–190.5° C. Anal. Calculated for $C_{19}H_{18}O_4$C: 73.53; H, 5.85 Found: C, 73.34; H, 5.92.

EXAMPLE 106

(E)-5,5-bis(3,4-Dimethoxyphenyl)-2,4-pentadienoic acid

A mixture of 3,3-bis(3,4-dimethoxyphenyl)-2-propenal (19.6 g) and (carbomethoxymethylene)triphenylphosphorane (22 g) in benzene (150 mL) was stirred overnight at 55° C. The solvent was removed under reduced pressure and the residue (45 g), consisting of mainly triphenylphosphine oxide and (E)-5,5-bis(3,4-dimethoxyphenyl)-2,4-pentadienoic acid methyl ester, was taken up a mixture of methanol (100 mL) and 2N sodium hydroxide solution (50 mL) and heated at reflux for 30 minutes. After the methanol was removed in vacuo, the concentrate was diluted water (100 mL) and the precipitated triphenylphosphine oxide was filtered off. The basic filtrate was first extracted with ether to remove neutral impurities, then was poured into 1N hydrochloric acid (300 mL) and extracted with dichloromethane (3×150 mL). The dried ($MgSO_4$) extracts were evaporated and the residue triturated with ether to give 18.7 g of (E)-5,5-bis(3,4-dimethoxyphenyl)-2,4-pentadienoic acid mp 174°–175,5° C. Crystallization from dichloromethane-2-propanol furnished the analytical sample, mp 174°–175,5° C. Anal. Calculated for $C_{21}H_{22}O_6$: C, 68.10; H, 5.99 Found: C, 68.32; H, 6.16.

EXAMPLE 107

(E)-5,5-bis(3-Chlorophenyl)-2,4-pentadienoic acid and (Z)-5,5-bis(3-chlorophenyl)-2,4-pentadienoic acid In the manner described in Example 99, 3,3-bis(3-chlorophenyl)-2-propenal (14.6 g) was reacted with (carbethoxymethylene)triphenylphosphorane (19.15 g) in ethanol (50 ml) for 30 minutes at ambient temperature. The mixture of esters obtained from the usual work up was purified by HPLC (dichloromethanehexane; 1:2) to provide 3.2 g of the less polar (Z)-5,5-bis(3-chlorophenyl)-2,4-pentadienoic acid ethyl ester as an oil, and 11.2 g of (E)-5,5-bis(3-chlorophenyl)-2,4-pentadienoic acid ethyl ester. A portion of the (E)-isomer (E)-5,5-bis(3-chlorophenyl)-2,4-pentadienoic acid ethyl ester was crystallized from 2-propanol to give the ester, mp 68°–69° C. Anal. Calculated for $C_{19}H_{16}Cl_2O_2$:C, 65.72; H, 4.64; Cl, 20.42 Found: C, 65.26; H, 5.09; Cl, 20.00.

(E)-5,5-bis(3-chlorophenyl)-2,4-pentadienoic acid ethyl ester (10.5 g) in methanol (30 mL) was treated with 2N sodium hydroxide solution (20 mL) and the mixture was heated at reflux for 15 minutes. The crude solid, obtained from the usual work up, was crystallized from dichloromethane-hexane to furnish 8.95 g of (E)-5,5-bis(3-chlorophenyl)-2,4-pentadienoic acid, mp 167°–168° C. Recrystallization from ether-hexane gave the analytical specimen, mp 167°–168° C. Anal. Calculated for $C_{17}H_{12}Cl_2O_2$: C, 63.97; H, 3.79; Cl, 22.21 Found: C, 63.93; H, 3.77; Cl, 22.25.

Hydrolysis of the isomeric (Z)-5,5-bis(3-chlorophenyl)-2,4-pentadienoic acid ethyl ester (3.2 g) under the same conditions provided 2.5 g of crude (Z)-5,5-bis(3-chlorophenyl)-2,4-pentadienoic acid, mp 142°–145° C. A portion of the material was crystallized from ether-hexane to afford the analytical specimen, mP 145°–146° C. Anal. Calculated for $C_{17}H_{12}Cl_2O_2$ C. 63.97; H, 3.79; Cl, 22.21 Found: C, 63.49; H, 3.86; Cl, 22.25.

EXAMPLE 108

(E)-5,5-bis(4-Chlorophenyl)-2,4-pentadienoic acid and (Z)-5,5-bis(4-chlorophenyl)-2,4-pentadienoic acid As in Example 99, 3,3-bis(4-chlorophenyl)-2-propenal (11.08) Was reacted with (carbethoxymethylene)triphenylphosphorane (14.3 g) in ethanol (30 ml) for 30 minutes at ambient temperature. The mixture of esters obtained from the usual work up was purified by crystallization from ether-hexane to give 8.1 g of (E)-5,5-bis(4-chlorophenyl)-2,4-pentadienoic acid ethyl ester, mp 98°–100° C. A portion of the (E)-isomer was crystallized from hexane to yield the pure ester (E)-5,5-bis(4-chlorophenyl)-2,4-pentadienoic acid ethyl ester mp 98.5°–100° C. Anal. Calculated from $C_{19}H_{16}Cl_2O_2$: C, 65.72; H, 4.64; Cl. 20.42 Found: C, 65.75; H, 4.67; Cl, 20.16.

A mixture of (E)-5,5-bis(4-chlorophenyl)-2,4-pentadienoic acid ethyl ester (7.5 g) in methanol (30 mL) and 2N sodium hydroxide solution (15 mL) was heated at reflux for 30 minutes. The crude solid obtained from the usual work up, was crystallized from ether-hexane to yield 6.55 g of (E)-5,5-bis(4-chlorophenyl)-2,4-pentadienoic acid, mp 213°–215° C. Recrystallization of a portion from 2-propanol furnished the analytical sample, mp 214°–215° C. Anal. Calculated for $C_{17}H_{12}Cl_2O_2$: C, 63.97; H, 3.79; Cl. 22.21 Found: C, 63.80; H, 3.90; Cl, 21.99.

The mother liquors from the isolation of the (E)-dienoic acid ester were evaporated and purified by HPLC dichloromethane-hexane; 1:2) to provide 0.9 g of the isomeric (Z)-5,5-bis(4-chlororophenyl)-2,4-pentadienoic acid ethyl ester as an oil. Saponification of the (Z)-ester (0.9 g) under the usual conditions gave 0.76 g of crude (Z)-5,5-bis(4-chlorophenyl)-2,4-pentadienoic acid. Two crystallizations of the material from dichloromethane-hexane afforded the purified acid. mp 215°–217° C. Anal. Calculated for $C_{17}H_{12}Cl_2O_2$: C, 63.97; H, 3.79; Cl, 22.21 Found: C, 63.59; H, 3.91; Cl, 21.97.

EXAMPLE 109

(E)-5,5-bis[2-(Trifluoromethyl)phenyl]-2,4-pentadienoic acid

A solution of 3,3-bis[2-(trifluoromethyl)phenyl]-2-propenal (1.76 g) and (carbethoxymethylene)triphenylphosphorane (2.5 g) in dichloromethane (30 mL) was stirred under reflux for 1 hour. The usual work up furnished 2.4 g of crude product which was purified by HPLC (hexane-dichloromethane; 2:1) to give 1.6 g of (E)-5,5-bis[2-(trifluoromethyl)phenyl]-2,4-pentadienoic acid ethyl ester as well as a minor amount (0.2 g) of the (Z)-isomer.

A solution of the major isomer (1.6 g; 0.00386 mol) in methanol (10 mL) was treated with 10N sodium hydroxide solution (0.5 mL) and the mixture was stirred at reflux for 20 min. After the methanol was removed in vacuo the residue was partitioned between 1N hydrochloric acid (20 mL) and dichloromethane (40 mL). The organic phase was washed with brine, then was dried (MgSO$_4$) and evaporated to give 1.4 g of acid. Crystallization from dichloromethane-hexane furnished 1.14 g of (E)-5,5-bis[2-(trifluoromethyl)phenyl]-2,4-pentadienoic acid mp 162°–164° C. The analytical sample, mp 164°–165° C. was obtained from the same solvent system. Anal. Calculated for $C_{19}H_{12}F_6O_2$: C, 59.08; H, 3.13; F, 29.51 Found: C, 58.77; H, 3.27; F, 29.22.

EXAMPLE 110

(E)-5,5-bis[3-(Trifluoromethyl)phenyl]-2,4-pentadienoic acid and
(Z)-5,5-bis[3-(trifluoromethyl)phenyl]-2,4-pentadienoic acid A solution of 3,3-bis[3-(trifluoromethyl)phenyl]-2-propenal (18.5 g) and (carbethoxymethylene)triphenylphosphorane (19.15 g) in methanol (100 mL) was stirred at room temperature for 1 hour. The usual work up furnished a mixture of isomeric esters that was separated by HPLC (hexane-dichloromethane; 2:1) to give 2.8 g of the less polar (Z)-5,5-bis[3-(trifluoromethyl)phenyl]-2,4-pentadienoic acid ethyl ester and 16.8 g of (E)-5,5-bis[3-(trifluoromethyl)phenyl]-2,4-pentadienoic acid ethyl ester. A portion of the (E)-isomer (E)-5,5-bis[3-(trifluoromethyl)phenyl]-2,4-pentadienoic acid ethyl ester was crystallized from hexane to provide the analytical sample, mp 53°–55° C. Anal. Calculated for $C_{21}H_{16}F_6O_2$: C, 60.87; H, 3.89; F, 27.51 Found: C, 61.15; H, 4.04; F, 27.31.

A mixture of the major isomer (E)-5,5-bis[3-trifluoromethyl)phenyl]-2,4-pentadienoic acid ethyl ester (16.2 g) in methanol (100 ml) and 1N sodium hydroxide solution (50 mL) was stirred at reflux for 30 minutes. After the methanol was removed in vacuo, the concentrate was poured into a stirred mixture of ice and 6N hydrochloric acid (20 mL). The solids were recovered by filtration, washed with water, dried and crystallized from dichloromethane-hexane to furnish 12.1 g of (E)-5,5-bis [3-(trifluoromethyl)phenyl]-2,4-pentadienoic acid, mp 153°–155° C. The analytical sample, mp 154°–155° C., was obtained by recrystallization from the same solvents. Anal. Calculated for $C_{19}H_{12}F_6O_2$: C, 59.08; H, 3.13; F, 29.51 Found: C, 59.28; H, 3.16; F, 29.36.

The minor (Z)-isomer (2.8 g) was saponified in the same manner. The resulting crude acid was purified by HPLC (ether-dichloromethane; 1:4) to yield 1.3 g of (Z)-5,5-bis[3-(trifluoromethyl)phenyl]-2,4-pentadienoic acid. The material was crystallized twice from ether-hexane to afford the pure acid, mp 110°–112° C. Anal. Calculated for $C_{19}H_{12}F_6O_2$: C, 59:08; H, 3.13; F, 29.51 Found: C, 58.91; H, 3.25; F, 29.72.

EXAMPLE 111

(E)-5,5-bis(3-Nitrophenyl)-2,4-pentadienoic acid

As in Example 99, a solution of 3,3-bis(3-nitrophenyl)-2-propenal (7.9 g) and (carboethoxymethylene)triphenylphosphorane (9.75 g) in ethanol was stirred at room temperature for 1 hour. The usual work up gave a mixture of esters which was crystallized from dichloromethane-hexane to furnish 6.7 g of (E)-5,5-bis(3-nitrophenyl)-2,4-pentadienoic acid ethyl ester, mp 121°–123° C. Recrystallization from the same solvent gave the analytical sample, mp 122°–123° C. Anal. Calculated for $C_{19}H_{16}N_2O_6$: C, 61.96; H, 4.38; N, 7.60 Found: C, 62.63; H, 4.60; N, 7.79.

The material recovered from the combined mother liquors was separated by HPLC (dichloromethane-hexane; 2:1) to provide an additional 0.9 g of the (E)-ester (E)-5,5-bis(3-nitrophenyl)-2,4-pentadienoic acid ethyl ester and 1.6 g of the isomeric (Z)-5,5-bis(3-nitrophenyl)-2,4-pentadienoic acid ethyl ester. The latter was crystallized from dichloromethane-hexane to yield 1.35 g of (Z)-5,5-bis(3-nitrophenyl)-2,4-pentadienoic acid ethyl ester mp 105°–106° C. Anal. Calculated for $C_{19}H_{16}N_2O_6$: C, 61.95; H, 4.38; N, 7.60 Found: C, 61.68; H, 4.33; N, 7.72.

A mixture of (E)-5,5-bis(3-nitrophenyl)-2,4-pentadienoic acid ethyl ester (6.1 g) methanol (25 mL) and 2N sodium hydroxide solution (12.5 mL) was stirred at reflux for 15 minutes, then was diluted with water (50 mL) and concentrated in vacuo to remove the methanol. The basic solution was poured into a mixture of ice and 2N hydrochloric acid (20 mL), and the resulting buff-colored solids were filtered and dried to afford 5,5 g of (E)-5,5-bis(3-nitrophenyl)-2,4-pentadienoic acid mp 234°–237° C. Recrystallization of a portion from chloroform-ethanol furnished the acid as its 0.25 molar hydrate, mp 237°–238° C. Anal. Calculated for $C_{17}H_{12}N_2O_6.0.25H_2O$: C, 59.22; H, 3.65; N, 8.12 Found: C, 59.27; H, 3.63; N, 8.13.

EXAMPLE 112

(2E,4E)-5-(3-Methoxyphenyl)-5-phenyl-2,4-pentadienoic acid and
(2E,4Z)-5-(3-methoxyphenyl-5-phenyl-2,4-pentadienoic acid A solution of the isomeric mixture of (E)- and (Z)-3-(3-methoxyphenyl)-3-phenyl-2-propenals and (carbethoxymethylene)triphenylphosphorane (19.1 g) in ethanol (150 mL) was stirred at 25° C. for 2 hours. The usual work up gave 16 g of a mixture of the four possible isomeric 5-(3-methoxyphenyl)-5-phenyl-2,4-pentadienoic acid ethyl esters. Two isomers, the (2Z,4Z)- and (2Z,4E)-esters were present in minor amounts, while the (2E,4E)- and (2E,4Z)-esters, were major components in the mixture. purification of the mixture by using HPLC [(dichloromethanehexane; 4:1) and then (ether-hexane; 1:12; two recycles)] gave 2.1 g of the mixed minor isomers, and 5.2 g of (2E,4E)-5-(3-methoxyphenyl)-5-phenyl-2,4-pentadienoic acid ethyl ester as an oil and 5.1 g of (2E,4Z)-5-(3-methoxyphenyl)-5-phenyl-2,4-pentadienoic acid ethyl ester.

Saponification of the (2E,4Z)-ester (4.6 g) was carried out in methanol (30 mL) containing 2N sodium hydroxide (10 mL) under the usual conditions. The crude (2E,4Z)-5-(3-methoxyphenyl)-5-phenyl-2,4-pentadienoic acid obtained through the usual work up, was crystallized from dichloromethane-hexane to give 3.7 g of acid, mp 150°–151° C. Anal. Calculated for $C_{18}H_{16}O_3$: C, 77.12; H, 5.75 Found: C, 76.83; H, 5.96.

In the same way, the second major isomer (2E,4E)-5-(3-methoxyphenyl)-5-phenyl-2,4-pentadienoic acid ethyl ester (5.2 g) was converted into (2E,4E)-5-(3-methoxyphenyl)-5-phenyl-2,4-pentadienoic acid. Crystallization from 2-propanol-hexane provided the purified acid, mp 134°–136° C. Anal. Calculated for $C_{18}H_{16}O_3$:C, 77.12; H, 5.75 Found: C, 77.26; H, 5.99.

EXAMPLE 113

(2E,4Z)-5-(3-fluorophenyl)-5-(3-methoxyphenyl)-2,4-pentadienoic acid and
(2E,4E)-5-(3-fluorophenyl)-5-(3-methoxyphenyl)-2,4-pentadienoic acid A solution of the isomeric mixture of (E)- and (Z)-3-(3-fluorophenyl)-3-(3-methoxyphenyl)-2-propenals (25 g) and (carbomethoxymethylene)triphenylphosphorane (35 g) in carbon terachloride was stirred at room temperature for 16 hours. The usual work up gave 28.4 g of a mixture of the four possible 5-(3-fluorophenyl)-5-(3-methoxyphenyl)-2,4-pentadienoic acid methyl esters. A preliminary gross separation of the two faster moving minor products, the (2Z,4Z)- and (2Z,4E)-esters (2.8 g), from the two major components, the (2E,4E)- and (2E,4Z)-esters, (23.5 g), was achieved by using HPLC (ether-hexane: 1:9).

A portion (12 g) of the major products mixture was further purified by HPLC (ether-hexane; 1:8; 3 recycles), gave 3.6 g of (2E,4Z)-5-(3-fluorophenyl)-5-(3-methoxyphenyl)-2,4-pentadienoic acid methyl ester, 5,5 g of mixed cuts and 2.4 g of (2E,4E)-5-(3-fluorophenyl)-5-(3-methoxyphenyl)-2,4-pentadienoic acid methyl ester.

The (2E,4Z)-ester (2E,4Z)-5-(3-fluorophenyl)-5-(3-methoxyphenyl)-2,4-pentadienoic acid methyl ester (3.6 g) was saponified in methanol (25 mL) containing 1N sodium hydroxide (25 mL) under the usual conditions. Crystallization of the crude acid from ether-hexane gave 2.9 g of (2E,4Z)-5-(3-fluorophenyl)-5-(3-methoxyphenyl)-2,4-pentadienoic acid mp 151°–153° C. A sample was recrystallized from ethyl acetate-hexane to afford the analytical specimen, mp 152.5°–153.5° C. Anal. Calculated for $C_{18}H_{15}FO_3$: C, 72.47; H, 5.07; F, 6.37 Found: C, 72.29; H, 5.28; F, 6.07.

Under the same conditions, the (2E,4E)-ester (2.4 g) was saponified to provide 2.0 g of crude (2E,4E)-5-(3-fluorophenyl)-5-(3-methoxyphenyl)-2,4-pentadienoic acid. Crystallization of the crude from ether-hexane yielded 1.75 g of the pure acid (2E,4E)-5-(3-fluorophenyl)-5-(3-methoxyphenyl)-2,4-pentadienoic acid mp 156°–157° C. Anal. Calculated for $C_{18}H_{15}FO_3$: C, 72.47; H, 5.07; F, 6.37 Found: C, 72.07; H, 5.18; F, 6.65.

EXAMPLE 114

(E)-5,5-Bis[(1,1'-biphenyl)-4-yl]-2,4-pentadienoic acid

In the manner described in Example 99, 3,3-bis[(1,1'-biphenyl)-4-yl]-2-propenal (2 g) was reacted with (carbethoxymethylene)triphenylphosphorane (2 g) in methanol (30 ml) for 60 minutes at ambient temperature. The mixture of esters obtained from the usual work up was purified by HPLC (dichloromethane-hexane; 1:1) to afford 0.3 g of the less polar (Z)-ester and 1.8 g of (E)-5,5-bis[(1,1'-biphenyl)-4-yl]-2,4-pentadienoic acid ethyl ester. The (E)-isomer was crystallized from 2-propanol to provide 1.5 g of material, mp 143°–145° C., which was hydrolysed in the normal manner to furnish 1.3 g of (E)-5,5-bis[(1,1'-biphenyl)-4-yl]-2,4-pentadienoic acid. The acid was crystallized from 2-propanol to give 1.1 g of (E)-5,5-bis[(1,1'-biphenyl)-4-yl]-2,4-pentadienoic acid as its 0.2 molar hydrate, mp 253°–255° C. Anal. Calculated for $C_{29}H_{22}O_2.0.2H_2O$: C, 85.77; H, 5,56 Found: C. 85.70; H, 5.85.

EXAMPLE 115

(E)-5,5-Diphenyl-2-methyl-2,4-pentadienoic acid 4-nitrpohenyl ester

A solution of (E)-5,5-diphenyl-2-methyl-2,4-pentadienoic acid (1.85 g) and 4-nitrophenol (1.12 g) in dichloromethane (25 mL), stirred at 0°–5° C. in an icewater bath, was treated with 1,3-dicyclohexylcarbodiimide (1.44 g). The mixture was stirred at 0°–5° C. for 30 minutes, then at room temperature for 1 hour. After the precipitated dicyclohexylurea was filtered off, the concentrated filtrate was passed through a short column of silica gel (~25 g) made up in dichloromethane-hexane (3:2). The appropriate fractions were combined and evaporated to give 2.4 g of (E)-5,5-diphenyl-2-methyl-2,4-pentadienoic acid 4-nitrophenyl ester. Crystallization of the material from 2-propanol furnished 1.64 g of (E)-5,5-diphenyl-2-methyl-2,4-pentadienoic acid 4-nitrophenyl ester mp 139°–141° C. Anal. Calculated for $C_{24}H_{19}NO_4$: C, 74.79; H, 4.97; N, 3.63 Found: C, 74.83; H, 5.05; N, 3.68.

EXAMPLE 116

(E)-5,5-Diphenyl-2,4-pentadienoic acid 4-nitrophenyl ester as in Example 115, (E)-5,5-diphenyl-2,4-pentadienoic acid (1 g) and 4-nitrophenol (0.7 g) in dichloromethane (10 mL) was treated with 1,3-dicyclohexylcarbodiimide (0.824 g). The mixture was stirred at 0°–5° C. for 10 minutes, then at room temperature for 45 minutes. After the usual work up, the ester was crystallized from 2-propanol to yield 1.1 g of (E)-5,5-diphenyl-2,4-pentadienoic acid 4-nitrophenyl ester mP 113°–115° C.

EXAMPLE 117

(E)-5,5-bis(3-Fluorophenyl)-2,4-pentadienoic acid 4-nitrophenyl ester

As in Example 115, (E)-5,5-bis(3-fluorophenyl)-2,4-pentadienoic acid (20 g) and 4-nitrophenol (11.2 g) in dichloromethane (250 mL) was treated with 1,3-dicyclohexylcarbodiimide (14.7 g). The mixture was stirred at 0°–5° C. for 60 minutes, then at room temperature for 3 hours. After the usual work up, the ester was crystallized from dichloromethane-hexane to yield 26.1 g of (E)-5,5-bis (3-fluorophenyl)-2,4-pentadienoic acid 4-nitrophenyl ester mp 129°–130° C. Recrystallization of a portion from the same solvents afforded the analytical sample, mp 129.5°–130.5° C. Anal. Calculated for $C_{23}H_{15}F_2NO_4$: C, 67.81; H, 3.71; N, 3.44; F, 9.33 Found: C, 67.81; H, 3.74; N, 3.41; F, 9.37.

EXAMPLE 118

(E)-5,5-bis(4-Fluorophenyl)-2,4-pentadienoic acid 4-nitrophenyl ester

As in Example 115, (E)-5,5-bis(4-fluorophenyl)-2,4-pentadienoic acid (23.75 g) and 4-nitrophenol (12.7 g) in dichloromethane (250 mL) was treated with 1,3-dicyclohexylcarbodiimide (17.12 g). The mixture was stirred at 0°–5° C. for 60 minutes and then at room temperature for 1 hour. After the usual work up, the crude product was crystallized from 2-propanol to give 26.5 g of (E)-5,5-bis (4-fluorophenyl)-2,4-pentadienoic acid 4-nitrophenyl ester mp 112°–114° C. Recrystallization of a portion from the same solvent yielded the analytical sample, mp 112.5°–114° C. Anal. Calculated for $C_{23}H_{15}F_2NO_4$:C, 67.81; H, 3.71; N, 3.44; F, 9.33 Found: C, 67.76; H, 3.77; N, 3.48; F, 9.11.

EXAMPLE 119

(E)-5,5-bis(3-Methoxyphenyl)-2,4-pentadienoic acid 4-nitrophenyl ester

As in Example 115, (E)-5,5-bis(3-methoxyphenyl)-2,4-pentadienoic acid (49.6 g) and 4-nitrophenol (25 g) in dichloromethane (600 mL) was treated with 1,3-dicyclohexylcarbodiimide (33 g). The mixture was stirred at 0°–5° C. for 1 hour, then at room temperature for 2 hours. After the usual work up, the crude product (67 g) was crystallized from 2-propanol-ether-hexane to give 61.0 g of (E)-5,5-bis (3-methoxyphenyl)-2,4-pentadienoic acid 4-nitrophenyl ester mp 95°–97° C. Recrystallization of a portion from dichloromethane-hexane yielded the analytical sample, mp 99°–100° C. Anal. Calculated for $C_{25}H_{21}NO_6$: C, 69.60; H, 4.91; N, 3.23 Found: C, 69.62; H, 5.04; N, 3.23.

EXAMPLE 120

(E)-5,5-bis(4-Methoxyphenyl)-2,4-pentadienoic acid 4-nitrophenyl ester

As in Example 115, (E)-5,5-bis(4-methoxyphenyl)-2,4-pentadienoic acid (21.0 g) and 4-nitrophenol (11.2 g) in dichloromethane (300 mL) was treated with 1,3-dicyclohexylcarbodiimide (14 g). The mixture was stirred at 0°–5° C. for 1 hour, then at room temperature overnight. After the usual work up, the crude product was crystallized from ether-hexane to give 24.7 g of (E)-5,5-bis(4-methoxyphenyl)-2,4-pentadienoic acid 4-nitrophenyl ester mp 121°–123° C. Recrystallization of the material from 2-propanol afforded the purified ester, mp 125°–126° C. Anal. Calculated for $C_{25}H_{21}NO_6$: C, 69.60; H, 4.91; N, 3.23 Found: C, 69.19; H, 4.94; N, 3.25.

EXAMPLE 121

(E)-5,5-bis(3,4-Dimethoxyphenyl)-2,4-pentadienoic acid 4-nitrophenyl ester

As in Example 115, (E)-5,5-bis(3,4-dimethoxyphenyl)-2,4-pentadienoic acid (16 g) and 4-nitrophenol (6.6 g) in dichloromethane (160 mL) was treated with 1,3-dicyclohexylcarbodiimide (9.3 g). The mixture was stirred at 0.5° C. for 1 hour, then at room temperature for 18 hours. After the usual work up, the crude product was triturated with ether to give 13.2 g of (E)-5,5-bis(3,4-dimethoxyphenyl)-2,4-pentadienoic acid 4-nitrophenyl ester. Crystallization of a portion from ether afforded the analytical sample, mp 140°–142° C. Anal. Calculated for $C_{27}H_{25}NO_8$: C, 69.60; H, 4.91; N, 3.23 Found: C, 69.19; H, 4.94; N, 3.25.

EXAMPLE 122

(E)-5,5-bis(3-Chlorophenyl)-2,4-pentadienoic acid 4-nitrophenyl ester

As in Example 115, (E)-5,5-bis(3-chlorophenyl)-2,4-pentadienoic acid (4.79 g) and 4-nitrophenol (2.5 g) in dichloromethane (50 mL) was treated with 1,3-dicyclohexylcarbodiimide (3.1 g). The mixture was stirred at 0°–5° C. for 1 hour, then at room temperature for 1 hour. The usual work up furnished 7.2 g of (E)-5,5-bis(3-chlorophenyl)-2,4-pentadienoic acid 4-nitrophenyl ester as an oil essentially homogeneous by tlc. This material was used without further purification in subsequent reactions.

EXAMPLE 123

(E)-5,5-bis(4-Chlorophenyl)-2,4-pentadienoic acid 4-nitrophenyl ester

As in Example 115, (E)-5,5-bis(4-chlorophenyl)-2,4-pentadienoic acid (4.79 g) and 4-nitrophenol (2.5 g) in dichloromethane (50 mL) was treated with 1,3-dicyclohexylcarbodiimide (3.1 g). The mixture was stirred at 0°–5° C. for 1 hour, then at room temperature for 1 hour. The usual work up furnished 6.9 g of (E)-5,5-bis(4-chlorophenyl)-2,4-pentadienoic acid 4-nitrophenyl ester as a pale yellow oil homogeneous by tlc. This material was used without further purification in subsequent reactions.

EXAMPLE 124

(E)-5,5-bis[2-(Trifluoromethyl)phenyl]-2,4-pentadienoic acid 4-nitrophenyl ester As in Example 115, (E)-5,5-bis[2-(trifluoromethyl)phenyl]-2,4-pentadienoic acid (1.135 g) and 4-nitrophenol (0.450 g) in dichloromethane (15 mL) was treated with 1,3-dicyclohexylcarbodiimide (0.607 g). The mixture was stirred at 0°-5° C. for 1 hour, then at room temperature for 30 minutes. The usual work up furnished 1.45 g of (E)-5,5-bis[2-(trifluoromethyl)-phenyl]2,4-pentadienoic acid 4-nitrophenyl ester as an oil essentially homogeneous by tlc. This material was used without further purification in subsequent reactions.

EXAMPLE 125

(E)-5,5-bis[3-(Trifluoromethyl)phenyl]-2,4-pentadienoic acid 4-nitrophenyl ester As in Example 115, (E)-5,5-bis[3-(trifluoromethyl)-phenyl]-2,4-pentadienoic acid (5.8 g) and 4-nitrophenol (2.5 g) in dichloromethane (50 mL) was treated with 1,3-dicyclohexylcarbodiimide (3.1 g). The mixture was stirred at 0°-5° C. for 1 hour, then at room temperature for 2 hours. The usual work up furnished 8 g of (E)-5,5-bis[3-(trifluoromethyl)phenyl]-2,4-pentadienoic acid 4-nitrophenyl ester as an oil essentially homogeneous by tlc. This material was used without further purification in subsequent reactions.

EXAMPLE 126

(E)-5,5-bis(3-Nitrophenyl)-2,4-pentadienoic acid 4-nitrophenyl ester

As in Example 115, (E)-5,5-bis(3-nitrophenyl)-2,4-pentadienoic acid (0.78 g) and 4-nitrophenol (0.35 g) in dichloromethane (10 mL) was treated with 1,3-dicyclohexylcarbodiimide (0.47 g). The mixture was stirred at 0°-5° C. for 1 hour, then at room temperature for 1 hour. The usual work up furnished 1.01 g of crude (E)-5,5-bis(3-nitrophenyl)-2.4-pentadienoic acid 4-nitrophenyl ester. This intermediate was used without further purification.

EXAMPLE 127

(2E,4E)-5-(3-Methoxyphenyl)-5-phenyl-2,4-pentadienoic acid 4-nitrophenyl ester

As in Example 115, (2E,4E)-5-(3 methoxyphenyl)-5-phenyl-2,4-pentadienoic acid (3.2 g) and 4-nitrophenol (1.73 g) in dichloromethane (50 mL) was treated with 1,3-dicyclohexylcarbodiimide (2.35 g) and the mixture was stirred at room temperature for 1.5 hours. The usual work up furnished 4.2 g of crude product which was crystallized from 2-propanol to give 3.5 g of (2E,-4E)-5-(3-methoxyphenyl)-5-phenyl-2,4-pentadienoic acid 4-nitrophenyl ester mp 101°-103° C. Anal. Calculated for $C_{24}H_{19}NO_5$: C, 71.81; H, 4.77; N, 3.49 Found: C, 72.12; H, 5.02; N, 3.42.

EXAMPLE 128

(2E,4Z)-5-(3-Methoxyphenyl)-5-phenyl-2,4-pentadienoic acid 4-nitrophenol ester

As in Example 115, (2E,4Z)-5-(3-methoxyphenyl)-5-phenyl-2,4-pentadienoic acid (2.85 g) and 4-nitrophenol (1.56 g) in dichloromethane (35 mL) was treated with 1,3-dicyclohexylcarbodiimide (2.1 g) and the mixture was stirred at room temperature for 75 minutes. The usual work up furnished 3.5 g of crude product which was crystallized from 2-propanol to give 3.0 g of (2E,4Z)-5-(3-methoxyphenyl)-5-phenyl-2,4-pentadienoic acid 4-nitrophenyl ester mp 155°-157° C. Anal. Calculated for $C_{24}H_{19}NO_5$: C, 71.81; H, 4.77; N, 3.49 Found: C, 72.09; H, 5.03; N, 3.55.

EXAMPLE 129

(2E,4Z)-5-(3-Fluorophenyl)-5-(3-methoxyphenyl)-2,4-pentadienoic acid 4-nitrophenyl ester As in Example 115, (2E,4Z)-5-(3-fluorophenyl)-5-(3-methoxyphenyl)-2,4-pentadienoic acid (2.65 g) and 4-nitrophenol (1.42 g) in dichloromethane (45 mL) was treated with 1,3-dicyclohexylcarbodiimide (1.88 g) and the mixture was stirred at 0°-5° C. for 15 minutes then at room temperature overnight. The usual work up provided 3.65 g of (2E,4Z)-5-(3-fluorophenyl)-5-(methoxyphenyl)-2,4-pentadienoic acid 4-nitrophenyl ester, a portion of which was crystallized from 2-propanol to give the analytical sample, mp 134°-135° C. Anal. Calculated for $C_{24}H_{18}FNO_5$: C, 68.73; H, 4.33; F, 4.53; N, 3.34 Found: C, 68.98; H, 4.46; F, 4.55; N, 3.45.

EXAMPLE 130

(2E,4E)-5-(3-Fluorophenyl)-5-(3-methoxyphenyl)-2,4-pentadienoic acid 4-nitrophenyl ester As in Example 115, (2E,4E)-5-(3-fluorophenyl)-5-(3-methoxyphenyl)-2,4-pentadienoic acid (1.5 g) and 4-nitrophenol (0.804 g) in dichloromethane (35 mL) was treated with 1,3-dicyclohexylcarbodiimide (1.067 g) and the mixture was stirred at 0.5° C. for 15 minutes then at room temperature overnight. The usual work up afforded 2.01 g of (2E,4E)-5-(3-fluorophenyl)-5-(methoxyphenyl)-2,4-pentadienoic acid 4-nitrophenyl ester. A portion was crystallized from 2-propanol to give the analytical sample, mp 146.5°-147.5° C. Anal. Calculated for $C_{24}H_{18}FNO_5$: C, 68.73; H, 4.33; F, 4;53; N, 3.34 Found: C, 68.97; H, 4.50; F, 4.67; N, 3.40.

The structure of this material was confirmed by X-ray crystallography.

EXAMPLE 131

(E)-5,5-bis(1,1'-Biphenyl)-4-yl]-2,4-pentadienoic acid 4-nitrophenyl ester

As in Example 115, a solution of (E)-5,5-bis[(1,1'-biphenyl)-4-yl]-2,4-pentadienoic acid (0.673 g) and 4-nitrophenol (0.256 g) in dichloromethane (7 mL) was treated with 1,3-dicyclohexylcarbodiimide (0.345 g). The mixture was stirred at room temperature for 1.5 hours. The usual work up furnished 0.88 g of (E)-5,5-bis[(1,1'-biphenyl)-4-yl]-2,4-pentadienoic acid 4-nitrophenyl ester.

EXAMPLE 132

(Z)-5,5-bis(3-Methoxyphenyl)-2,4-pentadienoic acid 4-nitrophenyl ester

A solution of (Z)-5,5-bis(3-methoxyphenyl)-2,4-pentadienoic acid (1.85 g) and 4-nitrophenol (0.912 g) in dichloromethane (25 mL) was treated with 1,3-dicyclohexylcarbodiimide (1.23 g). The mixture was stirred at 0°-5° C. for 1 hour, then at room temperature for 1 hour. The usual work up furnished 2.2 g of crude (Z)-5,5-bis(3-methoxyphenyl)-2,4-pentadienoic acid 4-nitrophenyl ester contaminated with the corresponding (E)-isomer, purification of the product by HPLC (dichloromethane-hexane; 3:1) yielded 1.2 g of the (Z)-isomer (Z)-5,5-bis(3-methoxyphenyl)-2,4-pentadienoic acid 4-nitrophenyl ester as an oil.

EXAMPLE 133

(E)-5,5-Diphenyl-N-[4-(3-pyridinyl)butyl]-2,4-pentadienamide

To a stirred solution of 5,5-diphenyl-2,4-pentadienenoic acid (6.00 g) and triethylamine (3.7 mL) in dry tetrahydrofurane (40 mL) at 0° C. was added a solution of ethyl chloroformate (2.37 mL) in tetrahydrofurane (15 mL) dropwise such that the reaction temperature was maintained at 0° C. After the addition was complete, the reaction was stirred at 0° C. for 15 minutes, then a solution of 3-pyridinebutanamine (3.78 g) in tetrahydrofurane (20 mL) was added dropwise while keeping the reaction at 0° C. The mixture was stirred at 0° C. for 1 hour and then at room temperature for 2 hours before the precipitated triethylamine hydrochloride was removed by filtration. The evaporated filtrate was partitioned between 1N hydrochloric acid solution (80 mL) and ether (80 mL). After the ethereal extract was discarded, the aqueous layer was basified with 4N sodium hydroxide (30 mL) and extracted with ether (4×100 mL). Evaporation of the dried ($K_2CO_3$) organic extracts afforded the crude amide which was purified by HPLC (hexane-ethyl acetate-triethylamine; 25:75:2) to provide 3.55 g of (E)-5,5-diphenyl-N-[4-(3-pyridinyl)butyl]-2,4-pentadienamide 0.2 molar hydrate as an oil. Anal. Calculated for $C_{26}H_{26}N_2O$. $0.2H_2O$: C, 80.88; H, 6.29; N, 7.25 Found: C, 80.81; H, 6.91; N, 7.30.

EXAMPLE 134

[R,S-(E)]-5,5-Diphenyl-N-(1-methyl-4-(3-pyridinyl)-2,4-pentadienamide

A solution of (E)-5,5-diphenyl-2,4-pentadienoic acid 4-nitrophenyl ester (1.11 g) and (R,S)-alpha-methyl-3-pyridinebutanamine (0.6 g) in tetrahydrofurane (10 mL) was stirred for 16 hours at room temperature. After the solvent was removed under reduced pressure, a solution of the residue in dichloromethane (25 mL) was washed with 0.5N sodium hydroxide solution (4×25 mL). The aqueous layers were backwashed with dichloromethane (2×25 mL), then the dried ($K_2CO_3$) organic extracts were evaporated. The resulting crude amide was purified by HPLC (ethyl acetate) to give 1.2 g [R,S-(E)]-5,5-diphenyl-N-[1-methyl-4-(3-pyridinyl)-2,4-pentadienamide. The material was crystallized from ethyl acetate-hexane to furnish 0.98 g of the amide, mp 124.5°–125,5° C. Anal. Calculated for $C_{27}H_{28}N_2O$: C, 81.78; H, 7.12; N, 7.06 Found: C, 81.84; H, 7.18; N, 7.08.

EXAMPLE 135

(E)-5,5-Diphenyl-2-methyl-N-[4-(3-pyridinyl)butyl]-2,4-pentadienamide

As in Example 134, (E)-5,5-diphenyl-2-methyl-2,4-pentadienoic acid 4-nitrophenyl ester (1.6 g) was reacted with 3-pyridinebutanamine (0.63 g) for 18 hours at 25° C. The crude amide obtained from the usual work up was purified by HPLC (ethyl acetate) and then crystallized from ether to provide 1.42 g of (E)-5,5-diphenyl-2-methyl-N-[4-(3-pyridinyl)butyl]2,4-pentadienamide mp 93°–94° C. Anal. Calculated for $C_{27}H_{28}N_2O$: C, 81.78; H, 7.12; N, 7.06 Found: C, 81.74; H, 7.02; N, 7.01.

EXAMPLE 136

(E)-5,5-bis(3-Fluorophenyl)-N-[4-(3-pyridinyl)butyl]-2,4-pentadienamide

As in Example 134, a solution of (E)-5,5-bis-(3-fluorophenyl)-2,4-pentadienoic acid 4-nitrophenyl ester (25.85 g) and 3-pyridinebutanamine (10 g) in tetrahydrofuran (100 mL) was stirred for 18 hours at room temperature and was worked up in the usual manner. The crude product was purified by HPLC (ethyl acetate) and then crystallized from ethyl acetate-hexane to afford 23.9 g of (E)-5,5-bis(3-fluorophenyl)-N-[4-(3-pyridinyl)butyl]-2,4-pentadienamide mp 103°–104° C. Anal. Calculated for $C_{26}H_{24}F_2N_2O$: C, 74.62; H, 5.78; F, 9.08; N, 6.69 Found: C, 74.35; H, 5.99; F, 8.93; N. 6.59.

EXAMPLE 137

[R,S-(E)]-5,5-bis(3-fluorophenyl)-N-[1-methyl-4-(3-pyridinyl)butyl]-2,4-pentadienamide As in Example 134, a solution of (E)-5,5-bis(3-fluorophenyl)-2,4-pentadienoic acid 4-nitrophenyl ester (6.34 g) and (R,S)-alpha-methyl-3-pyridinebutanamine (2.8 g) in tetrahydrofuran (100 mL) was stirred for 18 hours at room temperature and was then worked up in the usual manner. The crude amide was purified by HPLC (ethyl acetate) and then crystallized from ethyl acetate-hexane to give 3.35 g of [R,S-(E)]-5,5-bis(3-fluorophenyl)-N-[1-methyl-4-(3-pyridinyl)butyl]-2,4-pentadienamide mp 103°–106° C. Anal. Calculated for $C_{27}H_{26}F_2N_2O$: C, 74.98; H, 6.06; F, 8.79; N. 6.48 Found: C, 74.50; H, 5.99; F, 8.66; N, 6.15.

EXAMPLE 138

[R-(E)]1,5,5-bis(3-Fluorophenyl)-N-(1-methyl-4-(3-pyridinyl)butyl]-2,4-pentadienamide As in Example 134, a solution of (E)-5,5-bis(3-fluorophenyl)-2,4-pentadienoic acid 4-nitrophenyl ester (2.04 g) and (R)-alpha-methyl-3-pyridinebutanamine (0.82 g) in tetrahydrofuran (15 mL) was stirred for 18 hours at room temperature and was then worked up in the usual manner. The crude amide was purified by HPLC (ethyl acetate) and then crystallized from ethyl acetate-hexane to yield 1.8 g of [R-(E)]-5,5-bis(3-fluorophenyl)-N-[1-methyl-4-(3-pyridinyl)butyl]-2,4-pentadienamide mp 137°–139° C.; $[\alpha]_D^{25}$ +30.64° (c, 1.0, MeOH). Anal. Calculated for $C_{27}H_{26}F_2N_2O$: C, 74.98: H, 6.06; F, 8.79; N, 6.48 Found: C, 74.96; H, 6.17; F, 8.48; N, 6.44.

EXAMPLE 139

[S-(E)]-5,5-bis(3-Fluorophenyl)-N-[1-methyl-4-(3-pyridinyl)butyl]-2,4-pentadienamide As in Example 134, a solution of (E)-5,5-bis(3-fluorophenyl)-2,4-pentadienoic acid 4-nitrophenyl ester (0.815 g) and (S)-alpha-methyl-3-pyridinebutanamine (0.33 g) in tetrahydrofuran (10 mL) was stirred for 18 hours at room temperature and was then worked up in the usual manner. The crude amide was purified by HPLC (ethyl acetate) and then crystallized from ethyl acetate-hexane to afford 0.8 g of [S-(E)]-5,5-bis(3-fluorophenyl)-N-[1-methyl-4-(3-pyridinyl) butyl]-2,4-pentadienamide mp 135°–136° C.; $[\alpha]_D^{25}$ −29.5° (c. 1.0, MeOH). Anal. Calculated for $C_{27}H_{26}F_2N_2O$: C, 74.98; H, 6.06; F, 8.79; N, 6.48 Found: C,. 75.06; H, 6.03; F. 8.46; N, 6.49.

EXAMPLE 140

(E)-5,5-bis(3-Fluorophenyl)-N-[1,1-dimethyl-4-(3-pyridinyl)butyl]-2,4-pentadienamide As in Example 134, a solution of (E)-5,5-bis(3-fluorophenyl)-2,4-pentadienoic acid 4-nitrophenyl ester (1.63 g) and alpha,alpha-dimethyl-3-pyridinebutanamine (0.9 mL) in tetrahydrofuran (20 mL) was stirred for 29 hours at reflux and was then worked up in the usual manner. The crude amide was crystallized from ethyl acetate-hexane to furnish 1.6 g of (E)-5,5-bis(3-fluorophenyl)-N-[1,1-dimethyl-4-(3-pyridinyl)butyl]-2,4-pentadienamide mp 135°–136° C. Anal. Calculated for $C_{28}H_{28}F_2N_2O$ : C, 75.32: H, 6.32; F, 8.51; N, 6.27 Found: C, 75.30; H, 6.49; F, 8.21; N, 6.30.

EXAMPLE 141

(E)-5,5-bis(4-Fluorophenyl)-N-[4-(3-pyridinyl)butyl-2,4-pentadienamide

As in Example 134, a solution of (E)-5,5-bis(4-fluorophenyl)-2,4-pentadienoic acid 4-nitrophenyl ester (15 g) and 3-pyridinebutanamine (5,53 g) in tetrahydrofuran (60 mL) was stirred for 1.5 hours at room temperature and was worked up in the usual manner. The crude amide was crystallized from ethyl acetate-hexane (2×) to give 14.45 g of (E)-5,5-bis(4-fluorophenyl)-N-[4-(3-pyridinyl) butyl]-2,4-pentadienamide mp 155°–156° C. Anal. Calculated for $C_{26}H_{24}F_2N_2O$: C, 74.62; H, 5.78; F, 9.08; N, 6.69 Found: C, 74.55; H, 5.87; F, 9.33; N, 6.60.

EXAMPLE 142

[R-(E)]-5,5-bis(4-Fluorophenyl)-N-[1-methyl-4-(3-pyridinyl)butyl]-2,4-pentadienamide As in Example 134, a solution of (E)-5,5-bis (4-fluorophenyl)-2,4-pentadienoic acid 4-nitrophenyl ester (2.04 g) and (R)-alpha-methyl-3-pyridinebutanamine (0.82 g) in tetrahydrofuran (15 mL) was stirred for 18 hours at room temperature and was then worked up in the usual manner. The crude amide was purified by HPLC (ethyl acetate) and then crystallized from ether-hexane to yield 1.8 g of [R-(E)]-5,5-bis (4-fluorophenyl)-N-[1-methyl-4-(3-pyridinyl)butyl]-2,4-pentadienamide, mp 160°–162° C. A portion was recrystallized from ethyl acetate-hexane to give the analytical sample, mp 160.5°–161.5° C. $[\alpha]_D^{25}$ +32.15° (c, 1.0 MeOH). Anal. Calculated for $C_{27}H_{26}F_2N_2O$: C, 74.98; H, 6.06; F, 8.79; N, 6.48 Found: C, 74.87; H, 6.08; F, 8.49; N, 6.46.

EXAMPLE 143

[S-(E)]-5,5-bis(4-fluorophenyl)-N-[1-methyl-4-(3-pyridinyl)butyl]-2,4-pentadienamide As in Example 134, a solution of (E)-5,5-bis(4-fluorophenyl)-2,4-pentadienoic acid 4-nitrophenyl ester (0.815 g) and (S)-alpha-methyl-3-pyridinebutanamine (0.33 g) in tetrahydrofuran (10 mL) was stirred for 18 hours at room temperature and was worked up in the usual manner. The crude amide was purified by HPLC (ethyl acetate) and then crystallized from ethyl acetate-hexane to provide 0.8 g of [S-(E)]-5,5-bis(4-fluorophenyl)-N-[1-methyl-4-(3-pyridinyl)butyl]-2,4-pentadienamide, mp 155°–156° C.: $[\alpha]_D^{25}$ −30.2° (c. 1.0, MeOH). Anal. Calculated for $C_{27}H_{26}F_2N_2O$: C, 74.98; H, 6.06; F, 8.79; N, 6.48 Found: C, 75.06; H, 6.03; F, 8.46; N, 6.49.

EXAMPLE 144

(E)-5.5-bis(4-Fluorophenyl)-N-[1,1-dimethyl-4-(3-pyridinyl)butyl]-2,4-pentadienamide As in Example 134, a solution of (E)-5,5-bis(4-fluorophenyl)-2,4-pentadienoic acid 4-nitrophenyl ester (1.63 g) and alpha,alpha-dimethyl-3-pyridinebutanamine (0.9 mL) in tetrahydrofuran (20 mL) was stirred at reflux for 24 hours. The crude product, isolated in the usual manner, was crystallized from ethyl acetate to yield 1.6 g of (E)-5,5-bis(4-fluorophenyl)-N-[1,1-dimethyl-4-(3-pyridinyl)butyl]-2,4-pentadienamide, mp 163.5°–164.5° C. Anal. Calculated for $C_{28}H_{28}F_2N_2O$: C, 75.32; H, 6.32; F, 8.51; N, 6.27 Found: C, 75.23; H, 6.48; F, 8.39; N, 6.22.

EXAMPLE 145

(E)-5,5-bis(3-Methoxyphenyl)-N-[4-(3-pyridinyl)butyl]-2,4-pentadienamide

As in Example 134, a solution of (E)-5,5-bis(3-methoxyphenyl)-2,4-pentadienoic acid 4-nitrophenyl ester (32.36 g) and 3-pyridinebutanamine (11.4 g) in tetrahydrofuran (120 mL) Was stirred for 18 hours at room temperature and was worked up in the usual manner. The crude material was purified by HPLC (ethyl acetate) and then triturated with ether-hexane to furnish 29.6 g of (E)-5,5-bis (3-methoxyphenyl)-N-[4-(3-pyridinyl)butyl]-2,4-pentadienamide mp 84°–86° C. Crystallization of the product from ethyl acetate-ether provided 29.0 g of amide, mp 86°–88° C. Anal. Calculated for $C_{28}H_3N_2O_3$: C, 75.99; H, 6.83; N, 6.33 Found: C, 75.85; H, 6.84; N, 6.27.

EXAMPLE 146

(E)-5,5-bis(3-Methoxyphenyl)-N-[6-(3-pyridinyl)hexyl]-2,4-pentadienamide

As in Example 134. a solution of (E)-5,5-bis(3-methoxyphenyl)-2,4-pentadienoic acid 4-nitrophenyl ester (3.0 g) and 3-pyridinehexanamine (1.25 g) in tetrahydrofuran (20 mL) was stirred for 1.5 hours at room temperature and was then worked up in the usual manner. The product was purified by HPLC (ethyl acetate) and triturated with ether to give 2.5 g of (E)-5,5-bis(3-methoxyphenyl)-N-[6-(3-pyridinyl)hexyl]-2,4-pentadienamide mp 66°–70° C. Crystallization of a portion from ethyl acetate-hexane afforded of the pure amide, mp 71°–72° C. Anal. Calculated for $C_{30}H_{34}N_2O_3$: C, 76.57; H, 7.28; N, 5.98 Found: C, 76.39; H, 7.28; N, 5.90.

EXAMPLE 147

[R,S-(E)]-5,5-bis(3-Methoxyphenyl)-N-[1-methyl-4-(3-pyridinyl)butyl]-2,4-pentadienamide As in Example 134, a solution of (E)-5,5-bis(3-methoxyphenyl)-2,4-pentadienoic acid 4-nitrophenyl ester (3.1 g) and (R,S)-alpha-methyl-3-pyridinebutanamine (1.4 g) in tetrahydrofuran (25 mL) was stirred for 18 hours at room temperature and was worked up in the usual fashion. The crude product was purified by HPLC (ethyl acetate) and then crystallized from ether-hexane to give 2.6 g of [R,S-(E)]-5,5-bis(3-methoxyphenyl)-N-[1-methyl-4-(3-pyridinyl)butyl]-2,4-pentadienamide, mp 95°–97° C. Recrystallization from the same solvents did not alter the melting point. Anal. Calculated for $C_{29}H_{32}N_2O_3$: C, 76.29; H, 7.06; N, 6.13 Found: C, 75.99; H, 6.98; N, 5.87.

EXAMPLE 148

[R-(E)]-5,5-bis(3-Methoxyphenyl)-N-[1-methyl-4-(3-pyridinyl)-butyl-2,4-pentadienamide As in Example 134, a solution of (E)-5,5-bis (3-methoxyphenyl)-2,4-pentadienoic acid 4-nitrophenyl ester (2.16 g) and (R)-alpha-methyl-3-pyridinebutanamine (0.82 g) in tetrahydrofuran (15 mL) was stirred for 67 hours at room temperature. The crude amide, isolated in the usual way, was purified by HPLC (ethyl acetate) and then crystallized from ethyl acetate-hexane to provide 1.9 g of [R-(E)]-5,5-bis (3-methoxyphenyl)-N-[1-methyl-4-(3-pyridinyl)butyl]-2,4-pentadienamide mp 109°–110° C.; $[\alpha]_D^{25}+27.2°$ (c, 1.0, MeOH). Anal. Calcd for $C_{29}H_{32}N_2O_3$: C, 76.29; H, 7.07; N, 6.13 Found: C, 76.41; H, 6.86; N, 6.11.

EXAMPLE 149

[S-(E)]-5,5-bis(3-methoxyohenyl)-N-[1-methyl-4-(3-pyridinyl)butyl]2,,4-pentadienamide (1 g)

As in Example 134, a solution of (E)-5,5-bis(3-methoxyphenyl)-2,4-pentadienoic acid 4-nitrophenyl ester 0.863 g; and (S)-alpha-methyl-3-pyridinebutanamine (0.33 g) in tetrahydrofuran (10 mL) was stirred for 18 hours at room temperature and was worked up in the usual fashion. The crude amid was purified by HPLC (ethyl acetate) and then crystallized from ethyl acetate-hexane to furnish 0.8 g of [S-(E)]-5,5bis(3-methoxyphenyl)-N-[1-methyl-4-(3-pyridinyl)butyl]-2,4-pentadienamide mp 105°–108° C.; $[\alpha]_D^{25}-26.2°$ (c,1.0, MeOH). Anal. Calculated for $C_{29}H_{32}N_2O_3$: C, 76.29; H, 7.06; N, 6.14 Found: C, 76.33; H, 7.08; N, 612.

EXAMPLE 150

(E)-5,5-bis(3-Methoxyphenyl)-N-[1,1-dimethyl-4-(3-pyridinyl)butyl]2,4-pentadienamide As in Example 134, a solution of (E)-5,5-bis-(3-methoxyphenyl)-2,4-pentadienoic acid 4-nitrophenyl ester 1.73 and alpha,alpha-dimethyl-3-pyridinebutanamine (0.9 mL) in tetrahydrofuran (20 mL) was stirred for 30 hours at reflux and, after the usual work up, the product was crystallized from ethyl acetate-hexane to afford 1.6 g of (E)-5,5-bis(3-methoxyphenyl)-N-[1,1-dimethyl-4-(3-pyridinyl)butyl]-2,4-pentadienamide mp 120°–121° C. Anal. Calculated for $C_{30}H_{34}N_2O_3$: C, 76.57; H, 7.28; N, 5.95 Found: C, 76.67; H, 7.44; N, 5.88.

EXAMPLE 151

(E)-5,5-bis(4-Methoxyphenyl)-N-[4-(3-pyridinyl)butyl]-2,4-pentadienamide

As in Example 134, a solution of (E)-5,5-bis(4-methoxyphenyl)-2,4-pentadienoic acid 4-nitrophenyl ester (4.3 g) and 3-pyridinebutanamine (1.51 g) in tetrahydrofuran (20 mL) was stirred for 1.5 hours at room temperature and was worked up in the usual fashion. The crude product was crystallized from ethyl acetate-hexane to provide 3.6 g of (E)-5,5-bis(4-methoxyphenyl)-N-[4-(3-pyridinyl) butyl]-2,4-pentadienamide mp 76°–77° C. Anal. Calculated for $C_{28}H_{30}N_2O_3$: C, 75.99; H, 6.83; N, 6.33 Found: C, 76.36; H, 6.97; N, 6.35.

EXAMPLE 152

[R,S-(E)]-5,5-bis(4-Methoxyphenyl)-N-[1-methyl-4-(3-pvridinyl)butyl]-2,4-pentadienamide 0.25 molar hydrate As in Example 134, a solution of (E)-5,5-bis(4-methoxyphenyl)-2,4-pentadienoic acid 4-nitrophenyl ester (2.16 g) and (R,S)-alpha-methyl-3-pyridinebutanamine (0.82 g) in tetrahydrofuran (15 mL) was stirred overnight at room temperature and was worked up in the usual manner. The crude amide was purified by HPLC (ethyl acetate) and then lyophilized from benzene to yield 2.3 g of [R,S-(E)]-5,5-bis(4-methoxyphenyl)-N-[1-methyl-4-(3-pyridinyl)butyl]-2,4-pentadienamide 0.25 molar hydrate as an amorphous solid. Anal. Calculated for $C_{29}H_{32}N_2O_3.0.25 H_2O$: C, 75,54; H, 7.10; N, 6.07 Found: C, 75,51; H, 6.94; N, 6.04.

EXAMPLE 153

[R-(E)]-5,5-bis(4-Methoxyphenyl)-N-[1-methyl-4-(3-pyridinyl)butyl]-2,4-pentadienamide 0.4 molar hydrate As before in Example 134, a solution of (E)-5,5-bis(4-methoxyphenyl)-2,4-pentadienoic acid 4-nitrophenyl ester (2.16 g) and (R)-alpha-methyl-3-pyridinebutanamine (0.82 g) in tetrahydrofuran (15 mL) was stirred for 18 hours at room temperature and was then worked up in the usual manner. The crude product was purified by HPLC (ethyl acetate) and then lyophilized from benzene to give 2.3 g of [R-(E)]-5,5-bis(4- methoxyphenyl)-N-[1-methyl-4-(3-pyridinyl)butyl]-2,4-pentadienamide 0.4 molar hydrate as an amorphous solid, mp 50°–60° C.; $[\alpha]_D^{25}+27.7°$ (c, 1.0, MeOH). Anal. Calculated for $C_{29}H_{32}N_2O_3.0.4 H_2O$: C, 75.10; H, 7.13; N, 6.04 Found: C, 75.03; H, 7.10; N, 5.89.

EXAMPLE 154

[S-(E)]-5,5-bis(4-Methoxyphenyl)-N-[1-methyl-4-(3-pyridinyl)butyl]-2,4-pentadienamide As in Example 134, a solution of (E)-5,5-bis(4-methoxyphenyl)-2,4-pentadienoic acid 4-nitrophenyl ester (0.863 g) and (S)-alpha-methyl-3-pyridinebutanamine (0.33 g) in tetrahydrofuran (10 mL) was stirred for 18 hours at room temperature and was then worked up in the usual fashion. The crude amide was purified by HPLC (ethyl acetate) and then lyophilized from benzene to afford 0.9 g of [S-(E)]-5,5-bis(4-methoxyphenyl)-N-[1-methyl-4-(3-pyridinyl) butyl]-2,4-pentadienamide as anamorphous solid, mp 60°–70° C.; $[\alpha]_D^{25}+27.7°$ (c, 1.0, MeOH). Anal. Calculated for $C_{29}H_{32}N_2O_3$: C, 76.29; H, 7.06; N, 6.14 Found: C, 76.00; H, 7.20; N, 6.03.

EXAMPLE 155

(E)-5,5-bis(4-Methoxyphenyl)-N-[1,1-dimethyl-4-(3-pyridinyl)-butyl]-2,4-pentadienamide As in Example 134, a solution of (E)-5,5-bis(4-methoxyphenyl)-2,4-pentadienoic acid 4-nitrophenyl ester (1.73 g) and alpha,alpha-dimethyl-3-pyridinebutanamine (0.9 mL) in tetrahydrofuran (20 mL) was stirred for 20 hours at room temperature and then at reflux for an additional 24 hours to complete the reaction. After the usual work up, the crude amide was crystallized from ethyl acetate-hexane (2x) to furnish 1.55 g of (E)-5,5-bis(4-methoxyphenyl)-N-[1,1-dimethyl-4-(3-pyridinyl)butyl]-2,4-pentadienamide mp 144°–145° C. Anal. Calculated for $C_{30}H_{34}N_2O_3$: C, 76.57; H, 7.28; N, 5.95 Found: C, 76.70; H, 7.48; N, 6.20.

EXAMPLE 156

(E)-5,5-bis(3.4-Dimethoxyphenyl)-N-[4-(3-Pyridinyl)-butyl]-2,4-pentadienamide

As in Example 134, a solution of (E)-5,5-bis(3,4-dimethoxyphenyl)-2,4-pentadienoic acid 4-nitrophenyl ester (4.9 g) and 3-pyridinebutanamine (1.5 g) in tetrahydrofuran (25 mL) was stirred for 17 hours at room temperature and was then worked up in the usual manner. The crude amide was crystallized from ethyl acetate-hexane to provide 3.6 g of (E)-5,5-bis(3,4-dimethoxyphenyl)-N-[4-(3-pyridinyl)butyl]-2,4-pentadienamide mp 145°–146° C. Anal. Calculated for $C_{30}H_{34}N_2O_5$: C, 71.69; H, 6.82; N, 5,57 Found: C, 71.33; H, 6.93; N, 5.72.

EXAMPLE 157

[R-(E)]-5,5-bis(3,4-Dimethoxyphenyl)-N-[1-methyl-4-(3-pyridinyl)-butyl]-2,4-pentadienamide As in Example 134, a solution of (E)-5,5-bis (3,4-dimethoxyphenyl)-2,4-pentadienoic acid 4-nitrophenyl ester (2,46 g) and (R)-alpha-methyl-3-pyridinebutanamine (0.82 g) in tetrahydrofuran (15 mL) was stirred overnight at room temperature and was worked up in the usual manner. The crude amide was purified by HPLC (ethyl acetate) and then crystallized from ether to provide 2.3 g of [R-(E)]-5,5-bis(3,4- dimethoxyphenyl)-N-[1-methyl-4-(3-pyridinyl)butyl]-2,4-pentadienamide mp 140°–141° C. A portion was recrystallized from ethyl acetate to afford the analytical sample, 140.5°–141.5° C.; $[\alpha]_D^{25}+26.01°$ (c, 1.0, MeOH). Anal. Calculated for $C_{31}H_{36}N_2O_5$: C, 72.07; H, 7.02; N, 5.42 Found: C. 71.88; H, 7.19; N, 5.36.

EXAMPLE 158

(E)-5,5-bis(3-Chlorophenyl)-N-[4-(3-pyridinyl)butyl]-2,4-pentadienamide

As in Example 134, a solution of (E)-5,5-bis(3-chlorophenyl)-2,4-pentadienoic acid 4-nitrophenyl ester (6.4 g) and 3-pyridinebutanamine (2.7 g) in tetrahydrofuran (75 mL) was stirred for 40 minutes at 40° C. and was worked up in the usual manner. The crude amide was purified by HPLC (ethyl acetate) and then crystallized from ethyl acetate-hexane to yield 5.1 g of (E)-5,5-bis(3-chlorophenyl)-N-[4-(3-pyridinyl)butyl]-4-pentadienamide, mp 100°–102° C. Anal. Calculated for $C_{26}H_{24}Cl_2N_2O$: C, 69.18; H, 5.36; Cl. 15.71; N, 6.21 Found: C, 69.20; H, 5,50; Cl, 15.61; N, 6.19.

EXAMPLE 159

(E)-5,5-bis(4-Chlorophenyl)-N-[4-(3-pyridinyl)butyl]-2,4-pentadienamide

As in Example 134, a solution of (E)-5,5-bis(4-chlorophenyl)-2,4-pentadienoic acid 4-nitrophenyl ester (6.35 g) and 3-pyridinebutanamine (2.7 g) in tetrahydrofuran (75 mL) was stirred for 2 hours at 25° C. and was worked up in the usual fashion. The crude material was purified by HPLC (ethyl acetate) and then crystallized from ethyl acetate-hexane to give 5.3 g of (E)-5,5-bis(4-chlorophenyl)-N-[4-(3-pyridinyl)butyl]-2,4-pentadienamide mp 146°–147° C. Anal. Calculated for $C_{26}H_{24}Cl_2N_2O$: C, 69.18; H, 5.36; Cl, 15.71; N, 6.21 Found: C, 69.00; H, 5,57; Cl, 15.71; N, 6.21.

EXAMPLE 160

(E)-5,5-bis[2-(Trifluoromethyl)phenyl]-N-[4-(3-pyridinyl)butyl]-2,4-pentadienamide As in Example 134, a solution of (E)-5,5-bis[2-(trifluoromethyl)phenyl]-2,4-pentadienoic acid 4-nitrophenyl ester (1.45 g) and 3-pyridinebutanamine (0.44 g) in tetrahydrofuran (10 mL) was stirred for 1 hour at 25° C. and was worked up in the usual fashion. The crude product was passed through a column of silica gel (12 g) made up in dichloromethane and the amide was eluted with ethyl acetate. The material was crystalized from ethyl acetate-hexane to give 1.01 g of (E)-5,5-bis[2-(trifluoromethyl)phenyl]-N-[4-(3-pyridinyl)butyl]-2,4-pentadienamide mp 110°–112° C. Anal. Calculated for $C_{28}H_{24}F_6N_2O$: C, 64.86; H, 4.67; F. 21.98; N, 5.40 Found: C, 64.74; H, 4.94; F, 21.82; N, 5.37.

EXAMPLE 161

(E)-5,5-bis[3-(Trifluoromethyl)phenyl]-N-[4-(3-pyridinyl)butyl]-2,4-pentadienamide As in Example 134, a solution of (E)-5,5-bis[3-(trifluoromethyl)phenyl]-2,4-pentadienoic acid 4-nitrophenyl ester (4.8 g) and 3-pyridinebutanamine (1.5 g) in tetrahydrofuran (20 mL) was stirred for 2 hours at room temperature and was then worked up in the usual manner. The crude product was purified by HPLC (ethyl acetate) and then crystallized from ether-hexane to afford 3.2 g of (E)-5,5-bis[3-(trifluoromethyl)phenyl]-N-[4-(3-pyridinyl)butyl]-2,4-pentadienamide mp 89°–90° C. Anal Calculated for $C_{28}H_{24}F_6N_2O$ : C, 64.86; H, 4.67; F, 21.98; N, 5.40 Found: C, 64.82; H, 4.72; F, 22.19; N, 5.38.

EXAMPLE 162

(E)-5,5-bis(3-Nitrophenyl)-N-[4-(3-pyridinyl)butyl]-2,4-pentadienamide

As in Example 134, a solution of (E)-5,5-bis(3-nitrophenyl)-2,4-pentadienoic acid 4-nitrophenyl ester (0.950 g) and 3-pyridinebutanamine (0.34 g) in tetrahydrofuran (10 mL) was stirred at room temperature for 1 hour. The crude amide that had been isolated in the usual way, was crystallized from ethyl acetate-hexane to yield 0.82 g of (E)-5,5-bis(3-nitrophenyl)-N-[4-(3-pyridinyl)butyl]-2,4-pentadienamide mp 158°–159° C. Anal. Calculated for : $C_{26}H_{24}N_4O_5$: C, 66.09; H, 5.12; N, 11.86 Found: C, 65.91; H, 5.34; N, 11.82.

EXAMPLE 163

(2E,4E)-5-(3-Methoxyphenyl)-5-phenyl-N-[4-(3-pyridinyl)butyl]-2,4-pentadienamide As in Example 134, a solution of (2E,4E)-5-(3-methoxyphenyl)-5-phenyl-2,4-pentadienoic acid 4-nitrophenyl ester (2.96 g) and 3-pyridinebutanamine (1.107 g) in tetrahydrofuran (15 mL) was stirred for 1 hour at room temperature. After the usual work up, the crude amide was purified by HPLC (ethyl acetate) and then crystallized from ethyl acetate-hexane to provide 2.5 g of (2E,4E)-5-(methoxyphenyl)-5-phenyl-N-[4-(3-pyridinyl)butyl]-2,4-pentadienamide mp 66°–68° C. Anal. Calculated for $C_{28}H_{28}N_2O_2$: C, 78.61; H, 6.84; N. 6.79 Found: C, 78.42; H, 6.88; N, 6.79.

EXAMPLE 164

(2E,4E)-5-(3-Fluorophenyl)-5-(methoxyphenyl)-N-[4-(3-pyridinyl)butyl]-2,4-pentadienamide As in Example 134, a solution of (2E,4E)-5-(3-fluorophenyl)-5-(3-methoxyphenyl)-2,4-pentadienoic acid 4-nitrophenyl ester (1.8 g) and 3-pyridinebutanamine (0.650 g) in tetrahydrofuran (20 mL) was stirred for 17 hours at room temperature. The crude amide, isolated in the usual fashion, was purified by HPLC (ethyl acetate) and then crystallized from ether-hexane to furnish 1.6 g of (2E,4E)-5-(3-fluorophenyl)-5-(3-methoxyphenyl)-N-[4-(3-pyridinyl)butyl]-2,4-pentadienamide mp 55°–60° C. A sample was recrystallized from ethyl acetate-hexane to yield the analytical specimen, mp 58°-60° C. Anal. Calculated for $C_{27}H_{27}FN_2O_2$: C, 75.33; H, 6.32; F, 4.41; N, 6.51 Found: C, 75.31; H, 6.34; F, 4.38; N, 6.47.

EXAMPLE 165

(E)-5,5-bis[(1,1'-Biphenyl)-4-yl]-N-4-(3-pyridinyl)-butyl]-2,4-pentadienamide 0.15 molar hydrate As in Example 134, a solution of (E)-5,5-bis[(1,1'-biphenyl)-4-yl]-2,4-pentadienoic acid 4-nitrophenyl ester (0.880 g) and 3-pyridinebutanamine (0.251 g) in tetrahydrofuran (5 mL) was stirred for 1 hour at room temperature and was worked up in the usual way. The crude product was chromatographed over silica gel (7 g) and eluted with ethyl acetate to furnish 0.65 g of an oil. Lyophilization of the material from benzene gave (E)-5,5-bis[(1,1'-biphenyl)-4-yl]-N-[4-(3-pyridinyl)-butyl]-2,4-pentadienamide 0.15 molar hydrate as an amorphous powder. Anal. Calculated for $C_{38}H_{34}N_2O.0.15H_2O$: C, 84.93; H, 6.43; N, 5.21 Found: C, 84.68; H, 6.38; N, 5.28.

EXAMPLE 166

(Z)-5,5-Diphenyl-N-[4-(3-pyridinyl)butyl]-2,4-pentadienamide

As in Example 133, the mixed anhydride formed from (Z)-5,5-diphenyl-2,4-pentadienoic acid (2.75 g) triethylamine (1.68 mL) and ethyl chloroformate (1.08 mL) in tetrahydrofuran (35 mL) was treated with 3-pyridinebutanamine (1.73 g). After the usual work up, the crude amide was purified by HPLC (hexane-ethyl acetate-triethylamine; 25:75:2) to provide 2.5 g of (Z)-5,5-diphenyl-N-[4-(3-pyridinyl)butyl]-2,4-pentadienamide. The material was crystallized from ether to give 2.07 g of the amide, mp 87°-89° C. Anal. Calculated for $C_{26}H_{26}N_2O$: C, 81.64; H, 6.85; N, 7.32 Found: C, 81.59; H, 6..99; N, 7.36.

EXAMPLE 167

(Z)-5,5-bis(3-Methoxyphenyl)-N-[4-(3-pyridinyl)butyl]-2,4-pentadienamide

As in Example 134, a solution of (Z)-5,5-bis(3-methoxyphenyl)-2,4-pentadienoic acid 4-nitrophenyl ester (1.2 g) and 3-pyridinebutanamine (0.42 g) in tetrahydrofuran (7 mL) was stirred at room temperature for 1 hour. The crude amide that had been isolated in the usual way, was contaminated with a minor amount of the (E)-isomer. The mixture was separated by HPLC (ethyl acetate) and the desired product was crystallized from ether (2x) to yield 0.48 g of (Z)-5,5-bis(3-methoxyphenyl)- N-[4-(3-pyridinyl)-butyl]-2,4-pentadienamide mp 69°-73° C. Anal. Calculated for $C_{28}H_{30}N_2O_3$: C, 75.99; H, 6.83; N, 6.33 Found: C, 75.79; H, 6.70; N, 6.39.

EXAMPLE 168

Preparation of 3,3-bis(4-methylphenyl)-2-propenal.

The compound was prepared according to the procedure described in Example 84 except that the reaction was worked up after 30 hours. The following reagents were used: 4,4'-dimethylbenzophenone (21 g), diisopropylamine (32.2 mL), 1.55M n-butyl lithium in hexane (143 mL), acetaldehyde N-tert-butylimine (14.75 mL), diethyl chlorophosphonate (17.6 mL) and tetrahydrofuran (200 ml). The work up, varied only in that the oxalic acid catalyzed hydrolysis was done overnight at room temperature, furnished 23 g of crude product which was crystallized from hexane to give 18.1 g of 3,3-bis(4-methylphenyl)-2-propenal, mp 92°-93.5° C. Anal Calcd for $C_{17}H_{16}O$: C, 86.40; H, 6.82 Found: C, 86.48; H, 6.75.

EXAMPLE 169

Preparation of
(E)-3-(2-methoxyphenyl)-3-(4-methoxyphenyl)-2-propenal and
(Z)-3-(2-methoxyphenyl)-3-(4-methoxyphenyl)-2-propenal.

The compounds were prepared according to the procedure described in Example 84 except that the reaction was worked up after 17 hours. The following reagents were used: 2,4'-dimethoxybenzophenone (21.8 g), diisopropylamine (32.2 mL). 1.55M n-butyl lithium in hexane (143 mL), acetaldehyde N-tert-butylimine (14.75 mL) diethyl chlorophosphonate (16.6 mL) and tetrahydrofuran (200 mL). The work up, varied only in that the oxalic acid catalyzed hydrolysis was done overnight at room temperature, furnished 24 g of crude product containing (E)-3-(2-methoxyphenyl)-3-(4-methoxyphenyl)-2-propenal and (Z)-3-(2-methoxyphenyl)-3-(4-methoxyphenyl)-2-propenal in an E/Z ratio of ~7:3. Crystallization of the material three times from ether-hexane gave 10 g of (E)-3-(2-methoxyphenyl)-3(4-methoxyphenyl)-2-propenal, mp 92°-94° C. A sample was recrystallized from ether-hexane to afford the analytical specimen, mp 93°-94° C.

Anal. Calcd for $C_{17}H_{16}O_3$: C, 76.10; H, 6.01 Found: C, 76.16; H, 6.18.

The mother liquor from the intial crystallization was evaporated and was separated by HPLC (ether-hexane; 1:3; 3 recycles). Evaporation of fractions containing the less polar aldehyde gave 3 g of an oil which was crystallized from ether-hexane to furnish 2.2 g of (Z)-3-(2-methoxyphenyl)-3-(4-methoxyphenyl)-2-propenal. Recrystallization of a portion from the same solvents provided the analytical sample, mp 110° C. (softens ~78° C.).

Anal Calcd for $C_{17}H_{16}O_3$: C, 76.10; H, 6.01 Found: C, 76.12; H, 6.28.

EXAMPLE 170

Preparation of
(E)-3-(4-methoxyphenyl)-3-phenyl-2-propenal and
(Z)-3-(4-methoxyphenyl)-3-phenyl-2-propenal.

The compounds were prepared according to the procedure described in Example 84 except that the reaction was worked up after 40 hours. The following reagents were used: 4-methoxybenzophenone (21.2 g), diisopropylamine (32.2 mL), 1.55M n-butyl lithium in hexane (143 mL), acetaldehyde N-tert-butylimine (14.75 mL), diethyl chlorophosphonate (16.6 mL) and tetrahydrofuran (200 mL). The work up, varied only in that the oxalic acid hydrolysis was done overnight at room temperature, furnished 24.2 g of crude product containing (E)-3-(4-methoxyphenyl)-3-phenyl-2-propenal and (Z)-3-(4-methoxyphenyl)-3-phenyl-2-propenal in an E/Z ratio of ~1:1. Separation of the products by HPLC (ether-hexane; 1:7; 3 recycles) gave 7.3 g of the less polar component (Z)-3-(4-methoxyphenyl)-3-phenyl-2-propenal as an oil, as well as 8.7 g of the more polar isomer (E)-3-(4-methoxyphenyl)-3-phenyl-2-propenal as an oil.

EXAMPLE 171

Preparation of (E)-3-(4-methoxyphenyl)-3-(2-thienyl)-2-propenal and
(Z)-3-(4-methoxyphenyl)-3-(2-thienyl)-2-propenal The compounds were prepared according to the procedure described in Example 84 except that the reaction was worked up after 3 days. The following reagents were used: 2-(4-methoxybenzoyl)thiophene (21.8 g), diisopropylamine (32.2 mL), 1.6M n-butyl lithium in hexane (144 mL), acetaldehyde N-tert-butylimine (14.75 mL), diethyl chlorophosphonate (16.6 mL) and tetrahydrofuran (200 mL). The work up, varied only in that the hydrolysis of the imine was done overnight at room temperature, furnished 22 g of crude material made up mainly of a mixture (~1:1) of (E)-3-(4-methoxyphenyl)-3-(2-thienyl)-2-propenal and (Z)-3-(4-methoxyphenyl)-3-(2-thienyl)-2-propenal.

EXAMPLE 172

Preparation of
(E)-3-(4-methoxyphenyl)-3-(3-pyridinyl)-2-propenal
and
(Z)-3-(4-methoxyphenyl)-3-(3-pyridinyl)-2-propenal.

The compounds were prepared according to the procedure described in Example 84 except that the reaction was worked up after 17 hours. The following reagents were used: 3-(4-methoxybenzoyl)pyridine (22 g), diisopropylamine (32.2 mL), 1.55M n-butyl lithium in hexane (148 mL), acetaldehyde N-tert-butylimine (14.75 mL), diethylchlorophosphonate (16.6 mL) and tetrahydrofuran (200 mL). The work up, varied only in that the hydrolysis step was done by treating the intermediate imine with 2N HCl (300 ml) for 9 hours at 70° C. furnished, after basification and extraction, 24 g of crude material made up of a mixture of (E)-3-(4-methoxyphenyl)-3-(3-pyrdinyl)-2-propenal and (Z)-3-(4-methoxyphenyl)-3-(3-pyridinyl)-2-propenal. Purification of the crude by HPLC (ether; 3 recycles) provided 5.45 g of the less polar aldehyde, (E)-3-(4-methoxyphenyl)-3-(3-pyridinyl)-2-propenal along with 11 g of the isomer (Z)-3-(4-methoxyphenyl)-3-(3-pyridinyl)-2-propenal as oils.

EXAMPLE 173

Preparation of (E)-3-(4-methoxyphenyl)-2-propenal.

The compound was prepared according to the procedure described in Example 84 except that the reaction was worked up after 3 days. The following reagents were used: 4-methoxybenzaldehyde (13.5 g). diisopropylamine (32.2 mL), 1.6M n-butyl lithium in hexane (143 mL), acetaldehyde N-tert-butylimine (14.75 mL), diethyl chlorophosphonate (16.6 mL) and tetrahydrofuran (200 mL). The work up, varied only in that the oxalic acid catalyzed hydrolysis was done overnight at room temperature and then at 85° C. for 2 hours, furnished 12.5 g of crude product which was crystallized from ether-hexane to yield 10 g of (E)-3-(4-methoxyphenyl)-2-propenal, mp 58.5°–60° C.

Anal. Calcd for $C_{10}H_{10}O_2$: C, 74.06; H, 6.21 Found: C, 74.14; H, 6.26.

EXAMPLE 174

Preparation of (E)-3-(4-methoxyphenyl)-2-butenal and (Z)-3-(4-methoxyphenyl)-2-butenal.

The compounds were prepared according to the procedure described in Example 84 except that the reaction was worked up after 3 days. The followinq reaqents were used: 4'-methoxyacetophenone (15 g), diisopropylamine (32.2 mL), 1.6M n-butyl lithium in hexane (143 mL), acetaldehyde N-tert-butlyimine (14.75 mL), diethyl chlorophosphonate (16.6 mL) and tetrahydrofuran (200 mL). The work up, varied only in that the oxalic acid hydrolysis was done overnight at room temperature, furnished 16.3 g of crude product containing (E)-3-(4-methoxyphenyl)-2-butenal and (Z)-3-(4-methoxyphenyl)-2-butenal in an E/Z ratio of ~3:2. The material was dissolved in dichloromethane (400 mL) containing trifluoroacetic acid (20 mL) and the solution was stirred at room temperature overnight before it was washed in turn with water (3×250 mL), 2N NaOH (100 mL) and brine. The dried ($MgSO_4$) organic layer was evaporated and the residue was passed through a short column of silica gel (150 g) made up in dichloromethane to give a mixture of (E)-3-(4-methoxyphenyl)-2-butenal and (Z)-3-(4-methoxyphenyl)-2-butenal with an E/Z ratio that was now ~3:1. The mixture was separated by HPLC (ether-hexane; 1:3) to provide 2.85 g of the less polar (Z)-3-(4-methoxyphenyl)-2-butenal as an oil and 8.6 g of the crystalline (E)-3-(4-methoxyphenyl)-2-butenal. A sample of the (E)-isomer was crystallized from ether-hexane to afford the analytical specimen, mp 42.5°–45° C.

Anal. Calcd for $C_{11}H_{12}O_2$: C, 74.98; H, 6.86 Found: C, 74.80; H, 6.77.

EXAMPLE 175

Preparation of (E)-3-(4-methoxyphenyl)-2-pentenal and
(Z)-3-(4-methoxyphenyl)-2-pentenal The compounds were prepared according to the procedure described in Example 84 except that the reaction was worked up after 3 days. The following reagents were used: 4'-methoxypropiophenone (16.4 g), diisopropylamine (32.2 mL). 1.6M n-butyl lithium in hexane (143 mL), acetaldehyde N-tert-butylimine (14.75 mL), diethyl chlorophosphonate (16.6 mL) and tetrahydrofuran (200 mL). The work up, varied only in that the oxalic acid hydrolysis was run for 3 days at room temperature, furnished 21.4 g of crude product containing (E)-3-(4-methoxyphenyl)-2-pentenal and (Z)-3-(4-methoxyphenyl)-2-pentenal in an E/Z ratio of ~1:1. The mixture was separated by HPLC (ether-hexane; 1:7.5) to provide 7 g of the less polar (Z)-3-(4-methoxyphenyl)-2-pentenal as an oil as well as 7.1 g of its isomer, (E)-3-(4-methoxyphenyl)-2-pentenal, as an oil.

EXAMPLE 176

Preparation of
(E)-3-(4-methoxyphenyl)-4-methyl-2-pentenal and
(Z)-3-(4-methoxyphenyl)-4-methyl-2-pentenal.

The compounds were prepared according to the procedure described in Example 84 except that the reaction was worked up after 3 days. The following reagents were used: 1-(4-methoxyphenyl)-2-methylpropanone (17.8 g), diisopropylamine (32.2 mL), 1.6M n-butyl lithium in hexane (143 mL), acetaldehyde N-tert-butylimine (14.75 mL), diethyl chlorophosphonate (16.6 mL) and tetrahydrofuran (200 mL). The work up, varied only in that the oxalic acid hydrolysis was run overnight at room temperature, furnished 21.3 g of crude product containing (E)- and (Z)-3-(4-methoxyphenyl)-4-methyl-2-pentenal in the ratio of ~2:3. An attempt to separate the crude by HPLC (ether-hexane; 3:17; multiple recycles) only resulted in mixtures of (E)-3-(4-methoxphenyl)-4-methyl-2-pentenal and (Z)-3-(4-methoxyphenyl)-4-methyl-2-pentenal with E/Z ratios that varied between 1:4 and 1:1.

EXAMPLE 177

Preparation of (E)-3-(4-methoxyphenyl)-2-hexenal and (Z)-3-(4-methoxyphenyl)-2-hexenal.

The compounds were prepared according to the procedure described in Example 84 except that the reaction was worked up after 3 days. The following reagents were used: 4'-methoxybutyrophenone (17.8 g), diisopropylamine (32.2 mL). 1.6M n-butyl lithium in hexane (143 mL), acetaldehyde N-tert-butylimine (14.75 mL), diethyl chlorophosphonate (16.6 mL) and tetrahydrofuran (200 mL). The work up, varied only in that the oxalic acid hydrolysis was run for 3 days at room temperature, furnished 21.1 g of crude product containing (E)-3-(4-methoxyphenyl)-2-hexenal and (Z)-3-(4-methoxy- phenyl)-2-hexenal in an E/Z ratio of ~3:4. The mixture was separated by HPLC (ether-hexane; 1:7.5) to give 8.2 g of the less polar (Z)-3-(4-methoxyphenyl)-2-hexenal as an oil and 6.0 g of its isomer, (E)-3-(4-methoxyphenyl)-2-hexenal, as an oil.

EXAMPLE 178

Preparation of (E)-3-(4-methoxyphenyl)-2-heptenal and (Z)-3-(4-methoxyphenyl)-2-heptenal.

The compounds were prepared according to the procedure described in Example 84 except that the reaction was worked up after 3 days. The following reagents were used: 4'-methoxyvalerophenone (19.2 g), diisopropylamine (32.2 mL). 1.55M n-butyl lithium in hexane (148 mL). acetaldehyde N-tert-butylimine (14.75 mL), diethyl chlorophosphonate (16.6 mL) and tetrahydrofuran (200 mL). The work up varied only in that the oxalic acid catalyzed hydrolysis was run overnight at room temperature. furnished 22.1 g of crude product containing (E)-3-(4-methoxyphenyl)-2-heptenal and (Z)-3-(4-methoxyphenyl)-2-heptenal in an E/Z ratio of ~4:3. The mixture was separated by HPLC (ether-hexane: 1:7.5; 3 recycles) to give 7.5 g of the less polar (Z)-3-(4-methoxyphenyl)-2-heptenal as an oil and 10 g of the isomer (E)-3-(4-methoxyphenyl)-2-heptenal, as an oil.

EXAMPLE 179

Preparation of (E)-3-(3-methoxyphenyl)-2-heptenal and (Z)-3-(3-methoxyphenyl)-2-heptenal.

The compounds were prepared according to the procedure described in Example 84 except that the reaction was worked up after 3 days. The following reagents were used: 3'-methoxyvalerophenone (20.6 g), diisopropylamine (32.2 mL), 1.6M n-butyl lithium in hexane (144 mL). acetaldehyde N-tert-butylimine (14.75 mL), diethyl chlorophosphonate (16.6 mL) and tetrahydrofuran (200 mL). The work up varied only in that the oxalic acid hydrolysis was run for several days at room temperature, furnished 24.3 g of an oil containing a mixture (4.3) of (E)-3-(3-methoxyphenyl)-2-heptenal and (Z)-3-(3-methoxyphenyl)-2-heptenal. The mixture was used in a subsequent step without further purification.

EXAMPLE 180

Preparation of (E)-3-(4-methoxyphenyl)-2-octenal and (Z)-3-(4-methoxyphenyl)-2-octenal.

The compounds were prepared according to the procedure described in Example 84 except that the reaction was worked up after 5 days. The following reagents were used: 4'-methoxyhexanophenone (20.6 g), diisopropylamine (32.2 mL), 1.55M n-butyl lithium in hexane (148 mL), acetaldehyde N-tert-butylimine (14.75 mL), diethyl chlorophosphonate (16.6 mL) and tetrahydrofuran (200 mL). The work up varied only in that the oxalic acid hydrolysis was run overnight at room temperature, furnished 23.3 g of crude product containing (E)-3-(4-methoxyphenyl)-2-octenal and (Z)-3-(4-methoxyphenyl)-2-octenal in an E/Z ratio of ~3:2. The mixture was separated by HPLC (ether-hexane; 1:7) to yield 8.1 g of the less polar (Z)-3-(4-methoxyphenyl)-2-octenal as an oil and 9 g of the isomer (E)-3-(4-methoxyphenyl)-2-octenal, as an oil.

EXAMPLE 181

Preparation of (E)-3-(4-methoxyphenyl)-2-octenal, (alternative method)

As in Example 97, acetonitrile (30 mL) and a solution of 4'-methoxyhexanophenone (93.2 g) in dry tetrahydrofuran (250 mL) were added in turn to a chilled (−70° C.) solution of lithium diisopropylamide prepared from diisopropylamine (72.5 mL) and 2.5M n-butyl lithium in hexane (207 mL) in tetrahydrofuran (250 mL). After the mixture was stirred at −70° C. for 15 minutes, the cooling bath was removed. and when the temperature had climbed to −40° C. a solution of acetic acid (60 g) in water (60 mL) was added at a rapid dropwise rate. The reaction was then allowed to equilibrate to room temperature and was worked up in the normal manner to proVide 112.8 g of an oil. The crude material was crystallized from ether-hexane to give 107.8 g of 3-hydroxy-3-(4-methoxyphenyl)octanenitrile as a colorless solid. mp 45°-47° C.

A solution of the above carbinol (107.8 g) in dichloromethane (540 mL) containing trifluoroacetic acid (21.6 mL) was heated at reflux for 7 hours and then was left at room temperature overnight. The solution was washed in turn with water (250 mL), 1N NaOH solution (500 mL) and with brine (100 mL). After the aqueous layers were backwashed with dichloromethane (2×100 mL), the combined organic phases were dried (MgSO4) and evaporated to yield 99.2 g of crude (E)-3-(4-methoxypehnyl)-2-octenenitrile as an oil. The crude contained <8% of the (Z)-isomer.

A solution of the crude nitrile (99.2 g) in dry toluene (960 mL) was treated, as in Example 97, with a 1.5M solution of diisobutylaluminum hydride in toluene (385 mL) at −40° C. After stirring 60 minutes at −40° C., the reaction was worked up in the normal manner to furnish 100.2 g of crude (E)-3-(4-methoxyphenyl)-2-octenal as a pale yellow oil. This material, which was contaminated with <8% of the corresponding (Z)-octenal, was used in subsequent reactions without further purification.

EXAMPLE 182

Preparation of (E)-3-(3-fluorophenyl)-2-octenal and (Z)-3-(3-fluorophenyl)-2-octenal The compounds were prepared according to the procedure described in Example 84 except that the reaction was worked up after several days. The following reagents were used: 4'-fluorohexanophenone (19.4 g), diisopropylamine (32.2 mL), 1.6M n-butyl lithium in hexane (143 mL), acetaldehyde N-tert-butylimine (14.75 mL). diethyl chlorophosphonate (16.6 mL) and tetrahydrofuran (200 mL). The work up, varied only in that the oxalic acid hydrolysis was done for 3 days at room temperature, furnished 23.7 g of crude product containing (E)-3-(3-fluorophenyl)-2-octenal and (Z)-3-(3-fluorophenyl) -2-octenal in an E/Z ratio of ~1:1. The mixture was separated by HPLC (ether-hexane; 1:7) to yield 6.5 g of the less polar (Z)-3-(3-fluorophenyl)-2octenal as an oil and 6.0 g of its isomer, (E)-3-(3-fluorophenyl)-2-octenal, as an oil.

EXAMPLE 183

Preparation of (E)-3-(4-fluorophenyl)-2-octenal and (Z)-3-(4-fluorophenyl)-2-octenal.

The compounds were prepared according to the procedure described in Example 84 except that the reaction was worked up after several days. The following reagents were used: 4'-fluorohexanophenone (19.4 g), diisopropylamine (32.2 mL), 1.6M n-butyl lithium in hexane (143 mL), acetaldehyde N-tert-butylimine (14.75 mL), diethyl chlorophosphonate (16.6 mL) and tetrahydrofuran (200 mL). The work up, varied only in that the oxalic acid hydrolysis was for 3 days at room temperature. furnished 21.5 g of crude product containing (E)-3-(4-fluorophenyl-2-octenal and (Z)-3-(4-fluorophenyl) -2-octenal in an E/Z ratio of ~1:1. The mixture was separated by HPLC (ether-hexane; 1:7) to give 8.3 g of the less polar (Z)-3-(4-fluorophenyl)-2-octenal as an oil and 8.7 g of its isomer (E)-3-(4-fluorophenyl)-2-octenal, as an oil.

EXAMPLE 184

Preparation of (E)-3-(3,4-dimethoxyphenyl)-2-octenal and (Z)-3-(3,4-dimethoxyoehenyl)-2-octenal, The compounds were prepared according to the procedure described in Example 84 except that the reaction was worked up after 3 days. The following reagents were used: 3',4'-dimethoxyhexanophenone (23.6 g). diisopropylamine (32.2 mL), 1.6M n-butyl lithium in hexane (144 mL). acetaldehyde N-tert-butylimine (14.75 mL), diethyl chlorophosphonate (16.6 mL) and tetrahydrofuran (200 mL). The work up, varied only in that the oxalic acid hydrolysis was run for several days at room temperature, gave 25,5 g of an orange oil containing a mixture (~4:3) of (E)-3-(3,4-dimethoxyphenyl)-2-octenal and (Z)-3-(3,4-dimethoxyphenyl)-2-octenal. The mixture was used in a subsequent step without further purification.

EXAMPLE 185

Preparation of (E)-3-(4-methoxyphenyl)-2-nonenal and (Z)-3-(4-methoxyphenyl)-2-nonenal.

The compounds were prepared according to the procedure described in Example 84 except that the reaction was worked up after 3 days. The following reagents were used: 4'-methoxyheptanophenone (22 g), diisopropylamine (32.2 mL), 1.6M n-butyl lithium in hexane (143 mL), acetaldehyde N-tert-butylimine (14.75 mL), diethyl chlorophosphonate (16.6 mL) and tetrahydrofuran (200 mL). The work up, varied only in that the oxalic acid hydrolysis was done overnight at room temperature, furnished 27 g of crude product containing (E)-3-(4-methoxyphenyl)-2-nonenal and (Z)-3-(4-methoxyphenyl)-2-nonenal in an E/Z ratio of ~2:3. The material was dissolved in dichloromethane (500 mL) containing trifluoroacetic acid (20 mL) and the solution was stirred at room temperature overnight before it was washed in turn with water (3×200 mL), 1N NaOH (2×200 mL) and brine. The dried (MgSO4) organic layer was evaporated and the residue was passed through a short column of silica gel (150 g) made up in dichloromethane to give 22.3 g of a mixture of (E)-3-(4-methoxyphenyl)-2-nonenal and (Z)-3-(4-methoxyphenyl)-2-nonenal with an E/Z ratio that was now ~11:9. This material was used in subsequent reactions without further purification.

EXAMPLE 186

Preparation of (E)-3-(4-methoxyphenyl)-2-undecenal and (Z)-3-(4-methoxyphenyl)-2-undecenal.

The compounds were prepared according to the procedure described in Example 84 except that the reaction was worked up after 3 days. The following reagents were used: 4'-methoxynonanophenone (24.8 g), diisopropylamine (32.2 mL), 1.6M n-butyl lithium in hexane (143 mL), acetaldehyde N-tert-butlylimine (14.75 mL). diethyl chlorophosphonate (16.6 mL) and tetrahydrofuran (200 mL). The work up, varied only in that the oxalic acid hydrolysis was done overnight at room temperature, furnished 31 g of crude product containing (E)-3-(4-methoxyphenyl)-2-undecenal and (Z)-3-(4-methoxyphenyl)-2-undecenal in an E/Z ratio of 2:3. The material was dissolved in dichloromethane (500 mL) containing trifluoroacetic acid (20 mL) and the solution was stirred at room temperature overnight before it was washed in turn with water (3×200 mL), 1N NaOH (2×200 mL) and brine. The dried (MgSO4) organic layer was evaporated and the residue was passed through a short column of silica gel (150 g) made up in dichloromethane to give 26 g of a mixture of (E)-3-(4-methoxyphenyl)-2-undecenal and (Z)-3-(4-methoxyphenyl)-2-undecenal with an E/Z ratio that was now ~3:2. This material was used in subsequent reactions without further purification.

EXAMPLE 187

Preparation of (E)-3-(4-methoxyphenyl-2-pentadecenal and (Z)-3-(4-methoxyphenyl)-2-pentadecenal.

The compounds were prepared according to the procedure described in Example 84 except that the reaction was worked up after 3 days. The following reagents were used: 4'-methoxytridecanophenone (30.4 g), diisopropylamine (32.2 mL), 1.6M n-butyl lithium in hexane (143 mL), acetaldehyde N-tert-butylimine (14.75 mL), diethyl chlorophosphonate (16.6 mL) and tetrahydrofuran (200 mL). The work up, varied only in that the oxalic acid catalyzed hydrolysis was run for several days at room temperature. furnished 32 g of a mixture (~1:1) of (E)-3-(4-methoxyphenyl)-2-pentadecenal and (Z)-3-(4-methoxyphenyl)-2-pentadecenal. This material was used in a subsequent reaction without further purification.

EXAMPLE 188

Preparation of
(E)-3-cyclopropyl-3-(4-methoxyphenyl)-2-propenal and
(Z)-3-cyclopropyl-3-(4-methoxyphenyl)-2-propenal The compounds were prepared according to the procedure described in Example 84 except that the reaction was worked up after 3 days. The following reagents were used: cyclopropyl 4-methoxyphenyl ketone (17.6 g), diisopropylamine (32.2 mL), 1.6M n-butyl lithium in hexane (143 mL), acetaldehyde N-tert-butylimine (14.75 mL), diethyl chlorophosphonate (16.6 mL) and tetrahydrofuran (200 mL). The work up varied only in that the acid catalyzed hydrolysis was run for 3 days at room temperature, yielded 21.1 g of a mixture (~2:3) of (E)- and (Z)-aldehydes. The material was purified by HPLC (ether-hexane; 1:7.5) to give 7.2 g of the less polar (Z)-3-cyclopropyl-3-(4-methoxyphenyl)-2-propenal and 10.3 g of a mixture of the isomeric aldehydes rich (7:3) in (E)-3-cyclopropyl-3-(4-methoxyphenyl)-2-propenal. The impure (E)-isomer was used in a subsequent reaction without further purification.

EXAMPLE 189

Preparation of
(E)-3-cyclohexyl-3-(4-methoxyphenyl)-2-propenal and
(Z)-3-cyclohexyl-3-(4-methoxyphenyl)-2-propenal.

The compounds were prepared according to the procedure described in Example 84 except that the reaction was worked up after 3 days. The following reagents were used: cyclohexyl 4-methoxyphenyl ketone (21.8 g), diisopropylamine (32.2 mL), 1.6M n-butyl lithium in hexane (143 mL), acetaldehyde N-tert-butylimine (14.75 mL), diethyl chlorophosphonate (16.6 mL) and tetrahydrofuran (200 mL). The work up varied only in that the oxalic acid hydrolysis was run for 3 days at room temperature provided 25 g of a mixture (~9:11) of (E)- and (Z)-aldehydes. The material was purified by HPLC (ether-hexane; 1;7; 3 recycles) to give 5.9 g of the less polar (E)-3-cyclohexyl-3-(4-methoxyphenyl)-2-propenal as an oil as well as 7.3 g of the isomer (Z)-3-cyclohexyl-3-(4-methoxyphenyl) -2-propenal.

EXAMPLE 190

Preparation of 3-pentyl-2-octenal

The compound was prepared according to the procedure described in Example 84 except that the reaction was worked up after 3 days. The following reagents were used: 6-undecanone (17 g). diisopropylamine (32.2 mL), 1.6M n-butyl lithium in hexane (143 mL), acetaldehyde N-tert-butylimine (14.75 mL), diethyl chlorophosphonate (16.6 mL) and tetrahydrofuran (200 mL). The work up, varied only in that the oxalic acid catalyzed hydrolysis was run overnight at room temperature, gave the crude aldehyde which was purified by HPLC (ether-hexane; 1:16.6) to yield 15.5 g of 3-pentyl-2-octenal as an oil.

EXAMPLE 191

Preparation of beta
hydroxy-beta-(2-methoxyphenyl)-2-methoxybenzenepropanenitrile As in Example 97, a solution of 2,2'-dimethoxybenzophenone (24.2 g) and acetonitrile (6 mL) in tetrahydrofuran (120 mL) was added to a chilled (−70° C.) solution of lithium diisopropylamide prepared from diisopropylamine (16 mL) and 1.55M n-butyl lithium in hexane (74 mL) in dry tetrahydrofuran (120 mL). After the reaction was kept at −70° C. for 15 minutes, it was allowed to warm to room temperature and then was worked up in the usual manner to furnish 26.4 g of beta-hydroxy-beta-(2-methoxyphenyl)-2-methoxybenzenepropanenitrile, mp 170°–180° C. A sample was recrystallized from methanol to give the analytical specimen, mp 181°–182° C.

Anal. Calcd for $C_{17}H_{17}NO_3$: C, 72.07, H, 6.05: N, 4.94 Found: C, 71.99: H, 5.94: N, 4.70.

EXAMPLE 192

Preparation of
3,3-bis(2-methoxyphenyl-2-propenenitrile

Thionyl chloride (4.5 mL) was added to a stirred suspension of beta-hydroxy-beta-(2-methoxyphenyl)-2-methoxybenzenepropanenitrile (13.45 g) in dry pyridine (70 mL) maintained at 10° C. during the addition. The reaction was stirred at room temperature for 2 hours, then was diluted with ice-water and extracted with dichloromethane. The organic extract was washed with 3N HCl (1×150 mL; 1×20 mL) and brine and then was dried (MgSO$_4$) and evaporated. The residue was crystallized from isopropanol-hexane to provide 9.0 g of 3,3-bis(2-methoxyphenyl)-2-propenenitrile, mp 99°–100° C. Recrystallization of a portion from the same solvents afforded the analytical sample, mp 100.5°–101.5° C.

Anal. Calcd. for $C_{17}H_{15}NO_2$: C, 76.96: H, 5.70: N, 5.28 Found: C, 77.00; H, 5.86: N, 5.21.

EXAMPLE 193

Preparation of 3,3-bis(2-methoxyphenyl)-2-propenal

As previously described in Example 97, a solution of 3,3-bis(2-methoxyphenyl)-2-propenenitrile (7.3 g) in toluene (70 mL) was treated at −40° C. with a solution of 1.5M diisobutylaluminum hydride in toluene (21 mL). After 15 minutes at −40° C. the reaction was allowed to equilibrate to room temperature then, after 30 minutes, was worked up in the normal manner. Crystallization of the crude product from ether-hexane gave 7.2 g of 3,3-bis(2-methoxyphenyl)-2-propenal, mp 59.5°–61.5° C.

Anal. Calcd. for $C_{17}H_{16}O_3$: C, 76.10: H, 6.10 Found: C, 75.69; H, 6.05.

EXAMPLE 194

Preparation of
(E)-5,5-bis(4-methylphenyl)-2,4-pentadienoic acid

In the manner described in Example 99, 3,3-bis(4-methylphenyl) -2-propenal (9.45 g) was reacted with (carbomethoxymethylene)triphenylphosphorane (15.3 g) in carbon tetrachloride (95 ml) for 3 days at room temperature. The solvent was removed under reduced pressure and the residue was stirred at reflux in mixture of methanol (40 mL) and 2N NaOH for 45 minutes. The cooled solution was diluted with water (300 ml), extracted with dichloromethane (3×100 mL) to remove non-acidic material, and then acidified with 6N HCl (50 ML) and extracted with dichloromethane. The dried (MgSO$_4$) extracts were evaporated and the crude product was crystallized from 2-propanol to afford 7.5 g of (E)-5,5-bis(4-methylphenyl)-2,4-pentadienoic acid, mp 224 5°–226.5° C.

Anal Calcd for $C_{19}H_{18}O_2$: C, 81.99; H, 6.52. Found: C, 81.92; H, 6.69.

EXAMPLE 195

Preparation of
(E)-5,5-bis(2-methoxyphenyl)-2,4-pentadienoic acid methyl ester

In the manner described in Example 99, 3,3-bis(2-methoxyphenyl) -2-propenal (7.1 g) was reacted with (carbomethoxymethylene) triphenylphosphorane (9.7 g) in carbon tetrachloride (60 ml) and dichloromethane (20 mL) for 3 days at room temperature and then overnight at reflux. The crude ester isolated in the normal manner was crystallized from 2-propanol-hexane to yield 6.5 g of (E)-5,5-bis(2-methoxyphenyl)-2,4-pentadienoic acid methyl ester, mp 100°–102° C. A portion was recrystallized from the same solvents to furnish the analytical sample, mp 101°–102° C.

Anal. Calcd for $C_{20}H_{20}O_4$: C, 74.06; H, 6.21. Found: C, 73.83; H, 6.23.

EXAMPLE 196

Preparation of
(E)-5,5-bis(2-methoxyphenyl)-2,4-pentadienoic acid

In the manner described in Example 99, 5,5-bis(2-methoxyphenyl) -2,4-pentadienoic acid methyl ester (6.3 g) was saponified in a refluxing mixture of methanol (50 mL) and 1N NaOH (50 mL). After 45 minutes the crude acid was isolated in the normal manner and the crystallized from 2-propanol to yield 5.1 g of (E)-5,5-bis(2-methoxyphenyl)-2,4-pentadienoic acid, mp 196°–197° C.

Anal. Calcd for $C_{19}H_{18}O_4$: C, 73.53; H, 5.85. Found: C. 73.36; H, 5.85.

EXAMPLE 197

Preparation of
(E,E)-5-(2-methoxyphenyl)-5-(4-methoxyphenyl)-2,4-pentadienoic acid methyl ester As described in Example 99, (E)-3-(2-methoxyphenyl)-3-(4-methoxyphenyl)-2-propenal (5 g) was reacted with (carbomethoxymethylene)triphenylphosphorane (6.83 g) in a mixture of carbon tetrachloride (50 ml) and dichloromethane (25 mL) for 4 days at room temperature. The crude ester was isolated in the usual way and was crystallized from 2-propanol-hexane to provide 4.6 g of (E,E)-5-(2-methoxyphenyl)-5-(4-methoxyphenyl)-2,4-pentadienoic acid methyl ester. Recrystallization of a sample from the same solvents gave the analytical specimen, mp 99.5°–102.5° C.

Anal. Calcd for $C_{20}H_{20}O_4$: C, 74.06; H, 6.21. Found: C, 73.74; H, 6.12.

EXAMPLE 198

Preparation of
(E,E)-5-(2-methoxyphenyl)-5-(4-methoxyphenyl)-2,4-pentadienoic acid In the manner described in Example 99, (E,E)-5-(2-methoxyphenyl)-5-(4-methoxyphenyl)-2,4-pentadienoic acid methyl ester (4.3 g) was saponified in a refluxing mixture of methanol (35 mL) and 1N NaOH (35 mL). After 1 hour the reaction was worked up in the usual fashion and the crude acid was crystallized from 2-propanol to afford 3.6 g of (E,E)-5-(2-methoxyphenyl)-5-(4-methoxyphenyl)-2,4-pentadienoic acid, mp 210.5°–211.5° C.

Anal Calcd for $C_{19}H_{18}O_4$: C, 73.53; H, 5.85. Found: C, 73.33; H, 5.77.

EXAMPLE 199

Preparation of
(2E,4Z)-5-(2-methoxyphenyl)-5-(4-methoxyphenyl)-2,4-pentadienoic acid methyl ester As described in Example 99, (Z)-3-(2-methoxyphenyl)-3-(4-methoxyphenyl)-2-propenal (2 g) was treated with (carbomethoxymethylene)triphenylphosphorene (2.73 g) in dichloromethane (10 mL) for 3 days at room temperature. The crude ester was isolated in the usual way and purified by HPLC (ether-hexane; 1:3) to give 1.8 g of (2E,4Z)-5-(2-methoxyphenyl)-5-(4-methoxyphenyl)-2,4-pentadienoic acid methyl ester as an oil.

EXAMPLE 200

Preparation of
(2E,4Z)-5-(2-methoxyphenyl)-5-(4-methoxyphenyl)-2,4-pentadienoic acid In the manner described in Example 99, (2E,4Z)-5-(2-methoxyphenyl)-5-(4-methoxyphenyl)-2,4-pentadienoic acid methyl ester (1.8 g) was saponified in a refluxing mixture of methanol (15 mL) and 1N NaOH (15 mL). After 1 hour the reaction was worked up in the usual fashion ant the crude acid was crystallized from 2-propanol to afford 1.1 g of (2E,4Z)-5-(2-methoxyphenyl)-5-(4-methoxyphenyl)-2,4-pentadienoic acid. A sample was recrystallized from 2-propanol-hexane to give the analytical specimen, mp 159°–161° C.

Anal. Calcd for $C_{19}H_{18}O_4$: C, 73.53; H, 5.85. Found: C, 73.38; H, 6.22.

EXAMPLE 201

Preparation of
(E,E)-5-(4-methoxyphenyl)-5-(3-pyridlnyl)-2,4-pentadienoic acid methyl ester As described in Example 99, (E)-3-(4-methoxyphenyl)-3-(3-pyridinyl)-2-propenal (5.25 g) was reacted with (carbomethoxymethylene)triphenylphosphorane (7.4 g) in dichloromethane (40 mL) for 17 hours at room temperature. The crude ester was isolated in the usual way and was purified by HPLC to give 4.6 g of the ester. A portion was crystallized twice from ether-hexane to give the analytical sample of (E,E)-5-(4-methoxyphenyl)-5-(3-pyridinyl)-2,4-pentadienoic acid methyl ester, mp 75°–76° C.

Anal. Calcd for $C_{18}H_{17}NO_3$: C, 73.20; H, 5.80;, N, 4.74. Found: C, 73.20; H, 5.77;, N, 4.72.

EXAMPLE 202

Preparation of
(E,E)-5-(4-methoxyphenyl)-5-(3-pyridinyl)-2,4-pentadienoic acid

In the manner described in Example 99, (E,E)-5-(4-methoxyphenyl)-5-(3-pyridinyl)-2,4-pentadienoic acid methyl ester (0.295 g) was saponified in a refluxing mixture of methanol (1.5 mL) and 1N NaOH (1.5 mL). After the cooled reaction was neutralized with 1N HCI (1.5 mL), the crude acid was filtered off and crystallized from methanol to afford 0.235 g of (E,E)-5-(4-methoxyphenyl)-5-(3-pyridinyl)-2,4-pentadienoic acid as its 0.33 molar hydrate, mp 173°–175° C.

Anal. Calcd for $C_{17}H_{15}NO_3 \cdot 0.33\ H_2O$: C, 71.08; H, 5.49; N, 4.88. Found: C, 71.01; H, 5.59; N, 4.85.

EXAMPLE 203

Preparation of
(2E,4Z)-5-(4-methoxyphenyl)-5-(3-pyridinyl)-2,4-pentadienoic acid methyl ester As described in Example 99, (Z)-3-(4-methoxyphenyl)-3-(3-pyridinyl)-2-propenal (9.9 g) was treated with (carbomethoxymethylene)triphenylphoshorane (14.4 mL) in dichloromethane (75 mL) for 3 days at room temperature. The crude ester was isolated in the usual way, purified by HPLC (ether-hexane; 13:7) and crystallized from ether-hexane to give 7.275 g of (2E,4Z)-5-(4-methoxyphenyl)-5-(3-pyridinyl)-2,4-pentadienoic acid methyl ester, mp 99°-100.5° C.

Anal. Calcd for $C_{18}H_{17}NO_3$: C, 73.20; H, 5.80;, N, 4.74. Found: C, 73.40; H, 5.90;, N, 4.65.

EXAMPLE 204

Preparation of
(2E,4Z)-5-(4-methoxyphenyl)-5-(3-pyridinyl)-2,4-pentadienoic acid In the manner described in Example 99, (2E,4Z)-5-(4-methoxyphenyl)-5-(3-pyridinyl)-2,4-pentadienoic acid methyl ester (6.2 g) was saponified a refluxing mixture of methanol (30 mL) and 1N NaOH (30 mL). After 1 hour, the cooled reaction was neutralized with the addition of 1N HCI (30 mL) and the resulting crystalline solid was filtered off and washed well with water to give 5.8 g of (2E,4Z)-5-(4-methoxyphenyl)-5-(3-pyridinyl)-2,4-pentadienoic acid, mp 235°-238° C. A sample was recrystallized from methanol to furnish the analytical specimen, mp 238°-240° C.

Anal. Calcd for $C_{17}H_{15}NO_3$: C, 72.58; H, 5.37; N, 4.98. Found: C, 72.13; H, 5.30;, N, 4.88.

EXAMPLE 205

Preparation of
(2E,4Z)-5-(4-methoxyphenyl)-5-phenyl-2,4-pentadienoic acid methyl ester As described in Example 99(Z)-3-(4-methoxyphenyl)-3-phenyl-2-propenal (7.3 g) was treated with (carbomethoxymethylene)triphenylphosphorane (11.9 g) in carbon tetrachloride (50 mL) and dichloromethane (10 mL) overnight at room temperature. The crude ester was isolated in the usual way and purified by HPLC (ether-hexane; 1:7.5) to furnish 6.4 g of (2E,4Z)-5-(4-methoxyphenyl)-5-phenyl-2,4-pentadienoic acid methyl ester as an oil.

EXAMPLE 206

Preparation of
(2E,4Z)-5-(4-methoxyphenyl)-5-phenyl-2,4-pentadienoic acid

In the manner described in Example 99, (2E,4Z)-5-(4-methoxyphenyl)-5-phenyl-2,4-pentadienoic acid methyl ester (6.4 g) was saponified in a refluxing mixture of methanol (30 mL) and 2N NaOH (23 mL). After 2.5 hours the reaction was worked up in the usual fashion and the crude acid was crystallized from 2-propanol to yield 4.25 g of (2E,4Z)-5-(4-methoxyphenyl)-5-phenyl-2,4-pentadienoic acid. A sample was recrystallized from 2-propanol to give the analytical specimen, mp 184°-185° C.

Anal. Calcd for $C_{18}H_{16}O_3$: C, 77.12; H, 5.75. Found: C, 77.14; H, 5.87.

EXAMPLE 207

Preparation of
(2E,4Z)-5-(4-methoxyphenyl)-5-(2-thienyl)-2,4-pentadienoic acid methyl ester As described in Example 99, a mixture (1:1) of (E)- and (Z)-3-(4-methoxyphenyl)-3-(2-thienyl)-2-propenal (22 g) was reacted with (carbomethoxymethylene)triphenylphosphorane (37 g) in carbon tetrachloride (150 mL) for 3 days at room temperature. The crude mixture of (E,E)- and (2E,4Z)-esters was isolated in the normal fashion was crystallized twice from ether-hexane to furnish 9.5 g of a solid, mp 85°-98° C., enriched in the (2E,4Z)-isomer. The material was recrystallized from 2-propanol to furnish 3.4 g of (2E,4Z)-5-(4-methoxyphenyl)-5-(2-thienyl)-2,4-pentadienoic acid methyl ester, mp 97°-99° C.

EXAMPLE 208

Preparation of
(2E,4Z)-5-(4-methoxyphenyl)-5-(2-thienyl)-2,4-pentadienoic acid

In the manner described in Example 99, (2E,4Z)-5-(4-methoxyphenyl)-5-(2-thienyl)-2,4-pentadienoic acid methyl ester (4.7 g) was saponified in a refluxing mixture of methanol (20 mL) and 2N NaOH (20 mL). After the cooled reaction was worked up in the usual manner, the crude acid was crystallized from 2-propanol to provide 3.4 g of (2E,4Z)-5-(4-methoxyphenyl) -5-(2-thienyl)-2,4-pentadienoic acid, mp 214°-216° C.

Anal Calcd for $C_{16}H_{19}O_3S$: C, 67.11; H, 4.93; S, 11.20. Found: C, 67.05; H, 4.86; S, 10.92.

EXAMPLE 209

Preparation of
(E,E)-5-cyclopropyl-5-(4-methoxyphenyl)-2,4-pentadienoic acid methyl ester and
(2E,4Z)-5-cyclopropyl-5-(4-methoxyphenyl)-2,4-pentadienoic acid methyl ester As described in Example 99, a mixture (7:3) of (E)- and (Z)-3-cyclopropyl-3-(4-methoxyphenyl)-2-propenal (10.3 g) was reacted with (carbomethoxymethylene)triphenylphosphorane (19 g) in carbon tetrachloride (70 mL) and dichloromethane (15 mL) for 4 days at room temperature. The crude mixture of (E,E)- and (2E,4Z)-esters was isolated in the normal fashion was purified by HPLC (ether-hexane; 1:9; 2 recyles) to yield 6.8 g of the less polar isomer, (E,E)-5-cyclopropyl-5-(4-methoxyphenyl)-2,4-pentadienoic acid methyl ester, as an oil as well as 3.1 g of (2E,4Z)-5-cyclopropyl-5-(4-methoxyphenyl)-2,4-pentadienoic acid methyl ester as an oil.

EXAMPLE 210

Preparation of
(E,E)-5-cyclopropyl-5-(4-methoxyphenyl)-2,4-pentadienoic acid

As described in Example 99, (E,E)-5-cyclopropyl-5-(4-methoxyphenyl)-2,4-pentadienoic acid methyl ester (6.8 g) was saponified in a refluxing mixture of methanol (30 mL) and 2N NaOH (30 mL). After 2.5 hours the cooled reaction was worked up in the usual manner, and the crude acid was crystallized from 2-propanol-hexane to give 5.6 g of (E,E)-5-cyclopropyl-5-(4-methoxyphenyl)-2,4-pentadienoic acid, mp 158°-160° C.

Anal. Calcd for $C_{15}H_{16}O_3$: C, 73.75; H, 6.60;. Found: C, 73.61; H, 6.57.

EXAMPLE 211

Preparation of (2E,4Z)-5-cyclopropyl-5-(4-methoxyphenyl)-2,4-pentadienoic acid

As described in Example 99, (2E,4Z)-5-cyclopropyl-5-(4-methoxyphenyl)-2,4-pentadienoic acid methyl ester (3.1 g) was saponified in a refluxing mixture of methanol (15 mL) and 2N NaOH (15 mL). After 3 hours the reaction was worked up in the usual way, and the crude was crystallized from 2-propanolhexane to give 2 g of (2E,4Z)-5-cyclopropyl-5-(4-methoxyphenyl)-2,4-pentadienoic acid, mp 154°–155.5° C.

Anal. Calcd for $C_{15}H_{16}O_3$: C, 73.75; H, 6.60;. Found: C, 73.68; H, 6.55.

EXAMPLE 212

Preparation of (E,E)-5-cyclopropyl-5-(4-methoxyphenyl)-2,4-pentadienoic acid methyl ester As described in Example 99, (E)-3-cyclohexyl-3-(4-methoxyphenyl)-2-propenal (5.6 g) was reacted with (carbomethoxymethylene)triphenylphosphorane (8.5 g) in carbon tetrachloride (35 mL) and dichloromethane (8 mL) overnight at room temperature. The ester was isolated in the normal fashion and purified to yield 6.1 g of (E,E)-5-cyclopropyl-5-(4-methoxyphenyl)-2,4-pentadienoic acid methyl ester, as an oil.

EXAMPLE 213

Preparation of (E,E)-5-cyclohexyl-5-(4-methoxyphenyl)-2,4-pentadienoic acid

As described in Example 99, (E,E)-5-cyclohexyl-5-(4-methoxyphenyl)-2,4-pentadienoic acid methyl ester (5.9) was saponified in a refluxing mixture of methanol (20 mL) and 2N NaOH (20 mL). After 2 hours the reaction was worked up in the normal manner, and the crude was crystallized from cyclohexane-hexane to give 3.37 g of (E,E)-5-cyclohexyl-5-(4-methoxyphenyl)-2,4-pentadienoic acid, mp 130.5°–131.5° C.

Anal. Calcd for $C_{18}H_{22}O_3$: C, 75.50; H, 7.74:. Found: C, 75.70; H, 7.76.

EXAMPLE 214

Preparation of (2E,4Z)-5-cyclohexyl-5-(4-methoxyphenyl)-2,4-pentadienoic acid methyl ester As in Example 99, (Z)-3-cyclohexyl-3-(4-methoxyphenyl)-2-propenal (7.3 g) was reacted with (carbomethoxymethylene)triphenylphosphorane (11 g) in carbon tetrachloride (40 mL) and dichloromethane (4 mL) overnight at room temperature. The crude ester, isolated in the normal fashion, was purified by HPLC (ether-hexane; 1:7) to yield 5.7 g of (2E,4Z)-5-cylcohexyl-5-(4-methoxyphenyl)-2,4-pentadienoic acid methyl ester. A portion was crystallized from hexane to give the analytical specimen, mp 70.5°–72° C.

Anal. Calcd for $C_{19}H_{24}O_3$: C, 75.97; H, 8.05;. Found: C, 75.86; H, 7.93.

EXAMPLE 215

Preparation of (2E,4Z)-5-cyclohexyl-5-(4-methoxyphenyl)-2,4-pentadienoic acid

As described in Example 99, (2E,4Z)-5-cyclohexyl-5-(4-methoxyphenyl)-2,4-pentadienoic acid methyl ester (5.2 g) was saponified in a refluxing mixture of methanol (20 mL) and 2N NaOH (20 mL). After 2.5 hours the crude product was isolated in the usual way crystallized from 2-propanol-hexane to give 3.5 g of (2E,4Z)-5-cyclohexyl-5-(4-methoxyphenyl)-2,4-pentadienoic acid, mp 185°–186° C.

Anal. Calcd for $C_{18}H_{22}O_3$: C, 75.50; H, 7.74;. Found: C, 75.56; H, 7.75.

EXAMPLE 216

Preparation of (E,E)-5-(4-methoxyphenyl)-2,4-pentadienoic acid

In the manner described in Example 99, (E)-3-(4-methoxyphenyl)-2-propenal (9.5 g) was reacted with (carbomethoxymethylene) triphenylphosphorane (21.7 g) in carbon tetrachloride (80 ml) and dichloromethane (15 mL) for 3 days at room temperature. The reaction was worked up in the usual manner, the crude acid was saponified in a mixture of methanol (60 mL) and 1N NaOH (120 mL) for 15 minutes. The cooled solution was diluted with methanol (300 ml), stirred for several minutes and the solid was filtered off to give 9.15 of (E,E)-5-(4-methoxyphenyl)-2,4-pentadienoic acid as its sodium salt. A solution of the salt in refluxing mixture of water (130 mL) and methanol (50 mL) was acidified with 6N HCl (9 mL) and the solid was recovered by filtration to yield 7.0 g of (E,E)-5-(4-methoxyphenyl)-2,4-pentadienoic acid. Crystallization of a portion from 2-propanol gave the analytical sample, mp 133.5°–135° C.

Anal. Calcd for $C_{12}H_{12}O_3$: C, 70.58; H, 5.92. Found: C, 70.54; H, 5.94.

EXAMPLE 217

Preparation of (E,E)-5-(4-methoxyphenyl)-2,4-hexadienoic acid methyl ester

As described in Example 99, (E)-3-(4-methoxyphenyl)-2-butenal (8 g) was treated with (carbomethoxymethylene)triphenylphosphorane (17 g) in carbon tetrachloride (70 mL) and dichloromethane (15 mL) overnight at room temperature. The ester was isolated in the normal fashion and crystallized from hexane to afford 7.2 g of (E,E)-5-(4-methoxyphenyl)-2,4-hexadienoic acid methyl ester, mp 84°–86° C.

Anal. Calcd for $C_{14}H_{16}O_3$: C, 72.39; H, 6.94;. Found: C, 72.39; H, 7.00.

EXAMPLE 218

Preparation of (E,E)-5-(4-methoxyphenyl)-2,4-hexadienoic acid

As described in Example 99, (E,E)-5-(4-methoxyphenyl)-2,4-hexadienoic acid methyl ester (6.8 g) was saponified in a refluxing mixture of methanol (30 mL) and 2N NaOH (30 mL). After 2.5 hours the reaction was worked up in the normal manner to give 6.1 g of (E,E)-5-(4-methoxyphenyl)-2,4-hexadienoic acid. Crystallization of a portion from 2-propanol furnished the analytical sample, mp 174°–177° C.

Anal. Calcd for $C_{13}H_{14}O_3$: C, 71.54; H, 6.47. Found: C, 70.90; H, 6.44.

EXAMPLE 219

Preparation of (E,E)-5-(4-methoxyphenyl)-2,4-heptadienoic acid methyl ester

As described in Example 99, (E)-3-(4-methoxyphenyl)-2-pentenal (7.1 g) was treated with (carbomethoxymethylene)triphenylphosphorane (14 g) in carbon tetrachloride (70 mL) and dichloromethane (15 mL) overnight at room temperature. The ester was isolated in the normal fashion to afford 8 g of (E,E)-5-(4-methoxyphenyl)-2,4-heptadienoic acid methyl ester as an oil.

EXAMPLE 220

Preparation of (E,E)-5-(4-methoxyphenyl)-2,4-heptadienoic acid

As described in Example 99, (E,E)-5-(4-methoxyphenyl)-2,4heptadienoic acid methyl ester (8 g) was saponified in a refluxing mixture of methanol (30 mL) and 2N NaOH (30 mL). After 2.5 hours the reaction was worked up in the usual way and the acid crystallized from 2-propanol-hexane to give 5.4 g of (E,E)-5-(4-methoxyphenyl)-2,4-heptadienoic acid, mp 135.5°–137° C.

Anal Calcd for $C_{14}H_{16}O_3$: C, 72.39; H, 6.94. Found: C, 72.34; H, 6.92.

EXAMPLE 221

Preparation of (E,E)-5-(4-methoxyphenyl)-6-methyl-2,4-heptadienoic acid methyl ester and (2E,4Z)-5-(4-methoxyphenyl)-6-methyl-2,4-heptadienoic acid methyl ester As described in Example 99, a mixture (1:1) of (E)- and (Z)-(4-methoxyphenyl)-4-methyl-2-pentenal (9.85 g) was treated with (carbomethoxymethylene)triphenylphosphorane (18.1 g) in carbon tetrachloride (75 mL) and dichloromethane (15 mL) for 2 days at room temperature. The mixture of esters was isolated in the normal way and separated by HPLC (ether-hexane; 1:9) to yield 4.2 g of the less polar isomer, (E,E)-5-(4-methoxyphenyl)-6-methyl-2,4-heptadienoic acid methyl ester as an oil and 4.4 g of (2E,4Z)-5-(4-methoxyphenyl)-6-methyl-2,4-heptadienoic acid methyl ester as an oil. A sample of the (E)-isomer was crystallized from hexane to give the analytical specimen, mp 65°–66° C.

Anal. Calcd for $C_{16}H_{20}O_3$: C, 73.82; H, 7.74. Found: C, 3.97; H, 7.86.

EXAMPLE 222

Preparation of (E,E)-5-(4-methoxyphenyl)-6-methyl-2,4-heptadienoic acid

As described in Example 99, (E,E)-5-(4-methoxyphenyl)-6-methyl-2,4-heptadienoic acid methyl ester (4 g) was saponified in a refluxing mixture of methanol (15 mL) and 2N NaOH (15 mL). After 2 hours reaction was worked up in the usual way and the crude acid was crystallized from cyclohexane-hexane to provide 2.8 g of (E,E)-5-(4-methoxyphenyl)-6-methyl-2,4-heptadienoic acid, mp 140.5°–141.5° C.

Anal. Calcd for $C_{15}H_{18}O_3$: C, 73.15; H, 7.37. Found: C, 73.45; H, 7.48.

EXAMPLE 223

Preparation of (2E,4Z)-5-(4-methoxyphenyl)-6-methyl-2,4-heptadienoic acid

As described in Example 99, (2E,4Z)-5-(4-methoxyphenyl)-6-methyl-2,4-heptadienoic acid methyl ester (4.2 g) was saponified in a refluxing mixture of methanol (15 mL) and 2N NaOH (15 mL). After 2 hours reaction was worked up in the usual way to afford 3.8 g of (2E,4Z)-5-(4-methoxyphenyl)-6-methyl-2,4-heptadienoic acid. A sample was crystallized from cyclohexane-hexane to give the analytical specimen, mp 131.5°–133° C.

Anal. Calcd for $C_{15}H_{18}O_3$: C, 73.15; H, 7.37. Found: C, 73.09; H, 7.47.

EXAMPLE 224

Preparation of (E,E)-5-(4-methoxyphenyl)-2,4-octadienoic acid methyl ester

As described in Example 99, (E)-3-(4-methoxyphenyl)-2-hexenal (6 g) was treated with (carbomethoxymethylene)triphenylphosphorane (11 g) in carbon tetrachloride (70 mL) and dichloromethane (15 mL) for 4 days at room temperature. The ester was isolated in the normal manner to give 6.7 g of (E,E)-5-(4-methoxyphenyl)-2,4-octadienoic acid methyl ester as an oil.

EXAMPLE 225

Preparation of (E,E)-5-(4-methoxyphenyl)-2,4-octadienoic acid

As described in Example 99, (E,E)-5-(4-methoxyphenyl)-2,4-octadienoic acid methyl ester (6.7 g) was saponified in a refluxing mixture of methanol (30 mL) and 2N NaOH (30 mL). After 3 hours reaction was worked up in the usual way and the crude acid crystallized from 2-propanol-hexane to provide 4.85 g of (E,E)-5-(4-methoxyphenyl)-2,4-octadienoic acid, mp 151°–152.5° C.

Anal. Calcd for $C_{15}H_{18}O_3$: C, 73.15; H, 7.36. Found C, 73.11; H, 7.24.

EXAMPLE 226

Preparation of (E,E)-5-(4-methoxyphenyl)-2,4-nonadienoic acid methyl ester

As described in Example 99, (E)-3-(4-methoxyphenyl)-2-heptenal (10 g) was treated with (carbomethoxymethylene)triphenylphosphorane (17 g) in carbon tetrachloride (70 mL) and dichloromethane (15 mL) for 4 days at room temperature. The ester was isolated in the normal way and purified by HPLC (ether-hexane; 1:9) to furnish 8 g of (E,E)-5-(4-methoxyphenyl)-2,4-nonadienoic acid methyl ester, as an oil.

EXAMPLE 227

Preparation of (E,E)-5-(4-methoxyphenyl)-2,4-nonadienoic acid

As described in Example 99, (E,E)-5-(4-methoxyphenyl)-2,4-nonadienoic acid methyl ester (8g) was saponified in a refluxing mixture of methanol (30 mL) and 2N NaOH (30 mL). After 2.5 hours the reaction was worked up in the normal manner and the crude product crystallized from 2-propanol-hexane to give 6.2 g of (E,E)-5-(4-methoxyphenyl)-2,4-nonadienoic acid, mp 138°–139.5° C.

Anal. Calcd for $C_{16}H_{20}O_3$: C, 73.82; H, 7.74. Found: C, 73.75; H, 7.54.

EXAMPLE 228

Preparation of (E,E)-5-(3-methoxyphenyl)-2,4-nonadienoic acid methyl ester and (2E,4Z)-5-(3-methoxyphenyl)-2,4-nonadienoic acid methyl ester As described in Example 99, a mixture (3:4) of (E)- and (Z)-3-(3-methoxyphenyl)-2-heptenal (24.3 g) was treated with (carbomethoxymethylene)triphenylphosphorane (27 g) in dichloromethane (150 mL) for 2 days at room temperature. The mixture of esters was isolated in the normal manner and separated by HPLC (ether-hexane; 1:7.5) to yield 7.77 g of the less polar ester, (E,E)-5-(3-methoxyphenyl)-2,4-nonadienoic acid methyl ester as an oil and 11.67 g of the isomeric (2E,4Z)-5-(3-methoxyphenyl)-2,4-nonadienoic acid methyl ester as an oil.

EXAMPLE 229

Preparation of (E,E)-5-(3-methoxyphenyl)-2,4-nonadienoic acid

As described in Example 99, (E,E)-5-(3-methoxyphenyl)-2,4-nonadienoic acid methyl ester (6.41 g) was saponified in a refluxing mixture of methanol (30 mL) and 2N NaOH (30 mL). After 3 hours the reaction was worked up in the usual way and the crude acid was crystallized from hexane to furnish 4.86 g of (E,E)-5-(3-methoxyphenyl)-2,4-nonadienoic acid, mp 77.5°–78.5° C.

Anal. Calcd for $C_{16}H_{20}O_3$: C, 73.82; H, 7.53. Found: C, 73.74; H, 7.61.

EXAMPLE 230

Preparation of (2E,4Z)-5-(3-methoxyphenyl)-2,4-nonadienoic acid

As described in Example 99, (2E,4Z)-5-(3-methoxyphenyl)-2,4-nonadienoic acid methyl ester (11 g) was saponified in a refluxing mixture of methanol (30 mL) and 2N NaOH (30 mL). After 2 hours the reaction was worked up in the usual way to yield 7.87 g of (2E,4Z)-5-(3-methoxyphenyl)-2,4-nonadienoic acid. A portion was crystallized from ether-hexane to give the analytical sample, mp 106.5°–107.5° C.

Anal. Calcd for $C_{16}H_{20}O_3$: C, 73.82; H, 7.74. Found: C, 73.63; H, 7.95.

EXAMPLE 231

Preparation of (E,E)-5-(4-methoxyphenyl)-2,4-decadienoic acid methyl ester

As described in Example 99, (E)-3-(4-methoxyphenyl)-2-octenal (6 g) was treated with (carbomethoxymethylene)triphenylphosphorane (9.5 g) in carbon tetrachloride (60 mL) for 4 days at room temperature. The ester was isolated in the normal manner and purified by HPLC (ether-hexane; 1:7.5) to furnish 6.1 g of (E,E)-5-(4-methoxyphenyl)-2,4-decadienoic acid methyl ester as an oil.

EXAMPLE 232

Preparation of (E,E)-5-(4-methoxyphenyl)-2,4-decadienoic acid

As described in Example 99, (E,E)-5-(4-methoxyphenyl)-2,4-decadienoic acid methyl ester (6.1 g) was saponified in a refluxing mixture of methanol (25 mL) and 2N NaOH (25 mL). After 45 minutes the reaction was worked up in the usual way and the crude acid crystallized from 2-propanol to give 4.7 g of (E,E)-5-(4-methoxyphenyl)-2,4-decadienoic acid, mp 126°–127.5° C.

Anal. Calcd for $C_{17}H_{22}O_3$: C, 74.42: H, 8.08. Found: C, 74.42; H, 8.13.

EXAMPLE 233

Preparation of (2E,4Z)-5-(4-methoxyphenyl)-2,4-decadienoic acid methyl ester

As described in Example 99, (Z)-3-(4-methoxyphenyl)-2-octenal (5.5 g) was treated with (carbomethoxymethylene)triphenylphosphorane (8.7 g) in carbon tetrachloride (55 mL) for 4 days at room temperature. The mixture was isolated in the usual way and purified by HPLC (ether-hexane; 3:17) to afford 3.6 g of (2E,4E)-5-(4-methoxyphenyl)-2,4-decadienoic acid methyl ester as an oil.

EXAMPLE 234

Preparation of (2E,4Z)-5-(4-methoxyphenyl)-2,4-decadienoic acid

As described in Example 99, (2E,4Z)-5-(4-methoxyphenyl)-2,4-decadienoic acid methyl ester (3.6 g) was saponified in a refluxing mixture of methanol (40 mL) and 1N NaOH (40 mL). After 45 minutes the acid was isolated in the usual way and crystallized from ether-hexane to give 3.0 g of (2E,4Z)-5-(4-methoxyphenyl)-2,4-decadienoic acid, mp 86.5°–87.5° C.

Anal. Calcd for $C_{17}H_{22}O_3$: C, 74.42; H, 8.08. Found: C, 74.25; H, 8.19.

EXAMPLE 235

Preparation of (E,E)-5-(3-fluorophenyl)-2,4-decadienoic acid methyl ester

As described in Example 99, (E)-3-(3-fluorophenyl)-2-octenal (5.43 g) was treated with (carbomethoxymethylene)triphenylphosphorane (9 g) in dichloromethane (50 mL) for 4 days at room temperature. The ester was isolated in the usual manner and purified by HPLC (ether-hexane; 1:9) to provide 6.04 g of (E,E)-5-(3-fluorophenyl)-2,4-decadienoic acid methyl ester as an oil.

EXAMPLE 236

Preparation of (E,E)-5-(3-fluorophenyl)-2,4-decadienoic acid

As described in Example 99, (E,E)-5-(3-fluorophenyl)-2,4-decadienoic acid methyl ester (5.54 g) was saponified in a refluxing mixture of methanol (30 mL) and 2N NaOH (30 mL). After 45 minutes the reaction was worked up in the usual way and the crude acid crystallized from hexane to yield 3.85 g of (E,E)-5-(3-fluorophenyl)-2,4-decadienoic acid, mp 84°–85.5° C.

Anal. Calcd for $C_{16}H_{19}O_3$: C, 73.26; H, 7.30; F, 7.24. Found: C, 73.36; H, 7.21; F, 7.21.

EXAMPLE 237

Preparation of (2E,4Z)-5-(3-fluorophenyl)-2,4-decadienoic acid methyl ester

As described in Example 99, (Z)-3-(3-fluorophenyl)-2-octenal (6.2 g) was treated with (carbomethoxymethylene)triphenylphosphorane (10.5 g) in dichloromethane (50 mL) for 4 days at room temperature. The ester was isolated in the usual way and furnished 6.6 g of (2E,4Z)-5-(3-fluorophenyl)-2,4-decadienoic acid methyl ester as an oil.

EXAMPLE 238

Preparation of (2E,4Z)-5-(3-fluorophenyl)-2,4-decadienoic acid

As described in Example 99, (2E,4Z)-5-(3-fluorophenyl)-2,4-decadienoic acid methyl ester (6.1 g) was saponified in a refluxing mixture of methanol (40 mL) and 2N NaOH (30 mL). After 1 hour the crude acid was isolated in the usual way and crystallized from ether-hexane to give 4.1 g of (2E,4Z)-5-(3-fluorophenyl)-2,4-decadienoic acid, mp 100.5°-101° C.

Anal. Calcd for $C_{16}H_{19}O_2$: C, 73.26; H, 7.30; F, 7.24. Found: C, 73.15; H, 7.27; F, 7.44.

EXAMPLE 239

Preparation of (E,E)-5-(4-fluorophenyl)-2,4-decadienoic acid methyl ester

As described in Example 99, (E)-3-(4-fluorophenyl)-2-octenal (7.4 g) was treated with (carbomethoxymethylene)triphenylphosphorane (13.5 g) in dichloromethane (60 mL) for 4 days at room temperature. The ester was isolated in the normal manner and purified by HPLC (ether-hexane; 1:9) to yield 7.04 g of (E,E)-5-(4-fluorophenyl)-2,4-decadienoic acid methyl ester as an oil.

EXAMPLE 240

Preparation of (E,E)-5-(4-fluorophenyl)-2,4-decadienoic acid

As described in Example 99, (E,E)-5-(4-fluorophenyl)-2,4-decadienoic acid methyl ester (6.5 g) was saponified in a refluxing mixture of methanol (30 mL) and 2N NaOH (30 mL). After 2 hours the crude acid was isolated in the usual way and crystallized from hexane to yield 4.99 g of (E,E)-5-(4-fluorophenyl)-2,4-decadienoic acid, mp 116.5°-117.5° C.

Anal. Calcd for $C_{16}H_{19}O_2$: C, 73.26; H, 7.30; F, 7.24. Found: C, 73.18; H, 7.28; F, 7.22.

EXAMPLE 241

Preparation of (E,E)-5-(3,4-dimethoxyohenyl)-2,4-decadienoic acid methyl ester and (2E,4Z)-5-(3.4-dimethoxyphenyl)-2,4-decadienoic acid methyl ester As described in Example 99, a mixture (4:3) of (E)- and (Z)-3-(3,4-dimethoxyphenyl)-2-octenal (25.5 g) was treated with (carbomethoxymethylene)triphenylphosphorane (37 g) in dichloromethane (150 mL) for 2 days at room temperature. The normal isolation procedure yielded 29.7 of crude product and a portion of the crude (14.5 g) was separated by HPLC (ether-hexane; 3:17) to give 5.26 g of the less polar ester. (E,E)-5-(3,4-dimethoxyphenyl)-2,4-decadienoic acid methyl ester as an oil and 6.2 g of the isomeric (2E,4Z)-5-(3,4-dimethoxyphenyl)-2,4-decadienoic acid methyl ester as an oil.

EXAMPLE 242

Preparation of (E,E)-5-(3,4-dimethoxyohenyl)-2,4-decadienoic acid

As described in Example 99, (E,E)-5-(3,4-dimethoxyphenyl)-2,4-decadienoic acid methyl ester (4.9 g) was saponified in a refluxing mixture of methanol (30 mL) and 2N NaOH (30 mL). After 3 hours the reaction was worked up in the usual manner and the crude acid was crystallized from ether-hexane to provide 3.27 g of (E,E)-5-(3,4-dimethoxyphenyl)-2,4-decadienoic acid, mp 98°-99.5° C.

Anal. Calcd for $C_{18}H_{24}O_4$: C, 71.03; H, 7.95. Found: C, 70.88; H, 8.01.

EXAMPLE 243

Preparation of (E,E)-5-(4-methoxyphenyl)-2,4-undecadienoic acid methyl ester and (2E,4Z)-5-(4-methoxyphenyl)-2,4-undecadienoic acid methyl ester As described in Example 99, a mixture (11:9) of (E)- and (Z)-3-(4-methoxyphenyl)-2-nonenal (22.3 g) was treated with (carbomethoxymethylene)triphenylphosphorane (37 g) in carbon tetrachloride (150 mL) and dichloromethane (10 mL) for 4 days at room temperature. The crude product, isolated in the usual way, and was separated by HPLC (ether-hexane; 1:7.5; 4 recycles) to provide 11 g of the less polar ester, (E,E)-5-(4-methoxyphenyl)-2,4-undecadienoic acid methyl ester as an oil and 8.6 of the isomeric (2E,4Z)-5-(4-methoxyphenyl)-2,4-undecadienoic acid methyl ester as an oil.

EXAMPLE 244

Preparation of (E,E)-5-(4-methoxyphenyl)-2,4-undecadienoic acid

As described in Example 99, (E,E)-5-(4-methoxyphenyl)-2,4-undecadienoic acid methyl ester (5.9 g) was saponified in a refluxing mixture of methanol (30 mL) and 2N NaOH (30 mL). After 3 hours the reaction was worked up in the usual way and the crude acid was crystallized from hexane to give 3.27 g of (E,E)-5-(4-methoxyphenyl)-2,4-undecadienoic acid, mp 88°-89.5° C.

Anal. Calcd for $C_{18}H_{24}O_3$: C, 74.97; H, 8.39. Found: C, 75.01; H, 8.34.

EXAMPLE 245

Preparation of (E,E)-5-(4-methoxyphenyl)-2,4-tridecadlenoic acid methyl ester and (2E,4Z)-5-(4-methoxyphenyl)-2,4-tridecadienoic acid methyl ester As described in Example 99, a mixture (3:2) of (E)- and (Z)-3-(4-methoxyphenyl)-2-undecenal (26 g) was treated with (carbomethoxymethylene)triphenylphosphorane (37 g) in carbon tetrachloride (150 mL) and dichloromethane (10 mL) for 4 days at room temperature. The crude product, isolated in the normal manner, was separated by HPLC (ether-hexane; 1:7.5; 1 recycle) to furnish 11.3 g of the less polar isomer. (E,E)-5-(4-methoxyphenyl)-2,4-tridecadienoic acid methyl ester as an oil as well as 9.1 of (2E,4Z)-5-(4-methoxyphenyl)-2,4-tridecadienoic acid methyl ester as an oil.

EXAMPLE 246

Preparation of (E,E)-5-(4-methoxyphenyl)-2,4-tridecadienoic acid

As described in Example 99, (E,E)-5-(4-methoxyphenyl)-2,4-tridecadienoic acid methyl ester (11 g) was saponified in a refluxing mixture of methanol (40 mL) and 2N NaOH (40 mL). After 2.5 hours the reaction was worked up in the usual way and the crude acid was crystallized from hexane to give 3.27 g of (E,E)-5-(4-methoxyphenyl)-2,4-tridecadienoic acid, mp 109°–110° C.

Anal. Calcd for $C_{20}H_{28}O_3$: C, 75.91; H, 8.92. Found: C, 75.78: H, 8.900.

EXAMPLE 247

Preparation of (E,E)-5-(4-methoxyphenyl)-2,4-heptadecadienoic acid methyl ester and (2E,4Z)-5-(4-methoxyphenyl)-2,4-heptadecadienoic acid methyl ester.

As described in Example 99, a mixture (1:1) of (E)- and (Z)-3-(4-methoxyphenyl)-2-Pentadecenal (32 g), was treated with (carbomethoxymethylene)triphenylphosphorane (37.5 g) in dichloromethane (150 mL) for 4 days at room temperature. The crude esters, isolated in the normal way, was separated by HPLC (ether-hexane; 1:9; 3 recycles) to yield 12,4 g of the less polar material, (E,E)-5-(4-methoxyphenyl)-2,4-heptadecadienoic acid methyl ester as an oil and 14.5 g of the isomeric (2E,4Z)-5-(4- methoxyphenyl)-2,4-heptadecadienoic acid methyl ester as an oil.

EXAMPLE 248

Preparation of (E,E)-5-(4-methoxyphenyl)-2,4-heptadecadienoic acid.

As described in Example 99, (E,E)-5-(4-methoxyphenyl)-2,4heptadecadienoic acid methyl ester (11.9 g) was saponified in a refluxing mixture of methanol (30 mL) and 2N NaOH (30 mL). After 2,5 hours the crude acid was isolated in the usual way and was crystallized from hexane to give 7.86 g of (E,E)-5-(4-methoxyphenyl)-2,4-heptadecadienoic acid. A sample was recrystallized from the same solvent to afford the analytical specimen mp 85°–88° C.

Anal. Calcd for $C_{24}H_{36}O_3$: C, 77.38; H, 9.74. Found: C, 77.15; H. 9.89.

Example 249

Preparation of 5-pentyl-2,4-decadienoic acid.

As described in Example 99, 3-pentyl-2-octenal (7.85 g) was treated with (carbomethoxymethylene)triphenylphosphorane (15.3 g) in carbon tetrachloride (100 mL) containing dichloromethane (50 mL) for 3 days at room temperature. The usual work up furnished 10.1 g of 5-pentyl-2,4-decadienoic acid methyl ester which was then saponified in a refluxing mixture of methanol (40 mL) and 2N NaOH (30 mL). After 1 hour the acid was isolated in the usual way to give 8.15 g of 5-pentyl-2,4-decadienoic acid as an oil.

EXAMPLE 250

Preparation of (E,E)-5-(4-methoxypheny)-5-phenyl-2,4-pentadienoic acid 4-nitrophenyl ester.

As in Example 115, (E,E)-5-(4-methoxyphenyl)-5-phenyl-2,4-pentadienoic acid (5.2 g) and 4-nitrophenol (3.14 g) in 30 mL of carbon tetrachloride and 10 mL of dichloromethane was treated with 1.3-dicyclohexylcarbodiimide (3.8 g). The mixture was stirred at room temperature for 2 days. After the usual work up. the ester was crystallized from ether-hexane to yield 4.14 g of (E,E)-5-(4-methoxyphenyl)-5-phenyl-2,4-pentadienoic acid 4-nitrophenyl ester, mP 113°–115° C.

Anal Calcd for : $C_{24}H_{19}NO_5$: C, 71.81; H, 4.77; N, 3.49. Found: C, 71.91; H. 5.05; N, 3.52.

EXAMPLE 251

Preparation of (2E,4Z)-5-(4-methoxyphenyl)-5-phenyl-2,4-pentadienoic acid 4-nitrophenyl ester.

As in Example 115, (2E,4Z)-5-(4-methoxyphenyl)-5-phenyl-2,4-pentadienoic acid (0.85 g) and 4-nitrophenol (0.5 g) in 5 mL of carbon tetrachloride and 5 mL of dichloromethane was treated with 1,3-dicyclohexylcarbodiimide (0.62 g). The mixture was stirred at room temperature for 18 hours and the usual work up furnished 1.0 g of (2E,4Z)-5-(4-methoxyphenyl)-5-phenyl-2,4-pentadienoic acid 4-nitrophenyl ester as an oil.

EXAMPLE 252

Preparation of (E,E)-5-(2-methoxypheny)-5-(4-methoxyohenvl)-2,4-pentadienoic acid 4-nitrophenyl ester.

As in Example 115, (E,E)-5-(2-methoxyphenyl)-5-(4-methoxyphenyl)-2,4-pentadienoic acid (3.4 g) and 4-nitrophenol (1.8 g) in 25 mL of dichloromethane was treated with 1,3-dicyclohexylcarbodiimide (2.27 g). The mixture was stirred at room temperature for 2 hours. After the usual work up, the ester was crystallized from 2-propanol to yield 3.0 g of (E,E)-5-(2-methoxyphenyl)-5-(4-methoxyphenyl)-2,4-pentadienoic acid 4-nitrophenyl ester, mp 149°–150° C.

Anal. Calcd for $C_{25}C_{21}NO_6$: C, 69.60; H, 4.91; N, 3.25. Found: C, 69.20; H. 5.09; N, 3.22.

EXAMPLE 253

Preparation of (2E,4Z)-5-(2-methoxyphenyl)-5-(4-methoxyphenyl)-2,4-pentadienoic acid 4-nitrophenyl ester.

As in Example 115. (2E,4Z)-5-(2-methoxyphenyl)-5-(4-methoxyphenyl)-2,4-pentadienoic acid (1 g) and 4-nitrophenol (0.54 g) in 7 mL of dichloromethane was treated with 1,3-dicyclohexylcarbodiimide (0.67 g). The mixture was stirred at room temperature for 2 hours. After the usual work up. the crude ester was crystallized from 2-propanol to give 0.825 g of (2E,4Z)-5-(2-methoxyphenyl)-5-(4-methoxyphenyl)-2,4-pentadienoic acid 4-nitrophenyl ester, mp 133.5°–135° C.

Anal. Calcd for $C_{25}H_{21}NO_6$: C, 69.60: H, 4.91; N, 3.25. Found: C, 69.15; H, 5.12; N, 3.21.

EXAMPLE 254

Preparation of
(E)-5.5-bis(4-methylphenYl)-2,4-pentadienoic acid
4-nitrophenyl ester.

As in Example 115, (E)-5,5-bis(4-methylphenyl)-2,4-pentadienoic acid (7.25 g) and 4-nitrophenol (4.4 g) in dichloromethane (60 mL) was treated with 1.3-dicyclohexylcarbodiimide (5.36 g). The mixture was stirred at 0°-5° C. for 30 minutes and then at room temperature for 18 hours. After the usual work up. the ester was crystallized from 2-propanol to yield 8.9 g of (E)-5,5-bis(4-methylphenyl)-2,4-pentadienoic acid 4-nitrophenyl ester, mp 153.5°-154.5° C.

Anal. Calcd for $C_{25}H_{21}NO_4$: C, 75.17; H, 5.30; N, 3.51. Found: C, 74.82; H, 5.48; N, 3.62.

EXAMPLE 255

Preparation of
(E)-5.5-bis(2-methoxypheny)-2,4-pentadienoic acid
4-nitrophenyl ester.

As in Example 115. (E)-5.5-bis(2-methoxyphenyl)-2,4-pentadienoic acid (5 g) and 4-nitrophenol (2.7 g) in dichloromethane (35 mL) was treated with 1,3-dicyclohexylcarbodiimide (3.34 g). The mixture was stirred at 0°-5° C. for 30 minutes and then at room temperature for 18 hours. After the usual work up. the crude Product was crystallized from 2-propanol to give 6.1 g of (E)-5,5-bis(2-methoxyphenyl)2,4-pentadienoic acid 4-nitrophenyl ester. mp 141.5°-143° C. A portion from the 2-propanol to yield the analytical sample, mp 142°-143° C.

Anal. Calcd for $C_{25}H_{21}NO_6$: C. 69.60; H, 4.91; N, 3.25. Found: C, 69.17; H, 4.90; N, 3.25.

EXAMPLE 258

Preparation of
(2E,4Z)-5-(4-methoxyphenyl)-5-(2-thienyl)-2,4-pentadienoic acid 4-nitrophenyl ester.

As in Example 115. (2E,4Z)-5-(4-methoxyphenyl)-5-(2-thienyl)-2 4-pentadienoic acid (1.76 g) and 4-nitrophenol (1 g) in 20 mL of dichloromethane was treated with 1.3-dicyclohexylcarbodiimide (1.24 g). The mixture was stirred at room temperature for 18 hours then, after the usual work up, the ester was crystallized from 2-propanol to yield 1.45 g of (2E,4Z)-5-(4-methoxyphenyl)-5-(2-thienyl)-2,4-pentadienoic acid 4-nitrophenyl ester, mp 113°-115° C. A sample was recrystallized from 2-propanol to give the analytical specimen. mp 114.5°-115.5° C.

Anal. Calcd for $C_{22}H_{17}NO_5S$: C, 64.85; H, 4.21; N, 3.44; S, 7.87. Found: C, 64.15; H, 4.07; N, 3.64; S, 7.79.

EXAMPLE 259

Preparation of
(2E,4Z)-5-cyclopropyl-5-(4-methoxyphenyl)-2,4-pentadienoic acid 4-nitrophenyl ester.

As in Example 115, (2E,4Z)-5-cyclopropyl-5-(4-methoxyphenyl)-2,4-pentadienoic acid (1.95 g) and 4-nitrophenol (1.33 g) in 15mL of dichloromethane was reacted with 1,3-dicyclohexylcarbodiimide (1.66 g) and the mixture was stirred at room temperature for 18 hours. After the work up. the crude ester was crystallized from 2-propanol to furnish 1.9 g of (2E,4Z)-5-cyclopropyl-5-(4-methoxyphenyl)-2,4-pentadienoic acid 4-nitrophenyl ester, mp 115.5°-116.5° C.

Anal Calcd for $C_{21}H_{19}NO_5$: C, 69.03; H, 5.24; N, 3.83. Found: C, 68.84; H, 5.24; N. 3.89.

EXAMPLE 256

Preparation of
(E,E)-5,4-methoxypheny)-5-(3-pyridinyl)-2,4-pentadienoic acid 4-nitrophenyl ester.

As in Example 115, (E,E)-5-(4-methoxyphenyl)-5-(3-pyridinyl)-2,4-pentadienoic acid (2.6 g) and 4-nitrophenol (1.42 g) in 35 mL of dichloromethane was treated with 1,3-dicyclohexylcarbodiimide (1.91 g). The mixture was stirred at room temperature for 18 hours, and after the usual work up. the ester was crystallized from ether to give 3.65 g of (E,E)-5-(4-methoxyphenyl)-5-(3-pyridinyl)-2,4-pentadienoic acid 4-nitrophenyl ester 51°-56° C. Recrystallization of a portion from ether afforded the analytical specimen, mp 54°-56° C.

Anal. Calcd for : $C_{23}H_{18}N_2O_5$: C, 68.65; H, 4.55; N, 6.96. Found: C, 68.18; H, 4.71; N, 6.94.

EXAMPLE 257

Preparation of
(2E,4Z)-5-(4-methoxyphenyl)-5-(3-pyridinyl)-2,4-pentadienoic acid 4-nitrophenyl ester.

As in Example 115, (2E,4Z)-5-(4-methoxyphenyl)-5-(3-pyridinyl) -2,4-pentadienoic acid (5.7 g) and 4-nitrophenol (3.06 g) in 80 mL of dichloromethane was treated with 1,3-dicyclohexylcarbodiimide (4.2 g) and the mixture was stirred at room temperature for 18 hours. After the usual work up. the ester was crystallized from 2-propanol to give 7.3 g of (E,E)-5-(4-methoxyphenyl)-5-(3-Pyridinyl)-2,4-pentadienoic acid 4-nitrophenyl ester 129.5°-131° C. The analytical specimen was obtained from the same solvent, mp 130°-131° C.

Anal Calcd for $C_{23}H_{18}N_2O_5$: C, 68.65; H, 4.55; N, 6.96. Found: C, 68.55 H, 4.52; N, 6.95.

EXAMPLE 260

Preparation of
(E,E)-5-cyclopropyl-5-(4-methoxyphenyl)-2,4-pentadienoic acid 4-nitrophenyl ester.

As in Example 115, (E,E)-5-cyclopropyl-5-(4-methoxyphenyl)-2,4-pentadienoic acid (2.7 g) and 4-nitrophenol (1.844 g) in 20 mL of dichloromethane was treated with 1,3-dicyclohexylcarbodiimide (2.3 g) and the mixture was stirred at room temperature overnight. After the usual work up, the ester was crystallized from 2-propanol to yield 2.8 g of (E,E)-5-cyclopropyl-5-(4-methoxyphenyl)-2,4-pentadienoic acid 4-nitrophenyl ester. mp 111°-112.5° C.

Anal. Calcd for $C_{21}H_{19}NO_5$: C, 69.03; H, 5.24; N, 3.83. Found: C, 68.78; H, 5.53; N. 3.89.

EXAMPLE 261

Preparation of
(E,E)-5-cyclohexyl-(4-methoxypheny)-2,4-pentadienoic acid 4-nitrophenyl ester.

As in Example 115. (E,E)-5-cyclohexyl-5-(4-methoxyphenyl)-2,4-pentadienoic acid (2.86 g) and 4-nitrophenol (1.67 g) in 15 mL of dichloromethane was treated with 1,3-dicyclohexylcarbodiimide (2.07 g). The mixture was stirred at room temperature for 18 hours and the usual work up furnished 3.5 g of crude ester which was crystallized from 2-propanol to furnish 3.15 g of (E,E)-5-cyclohexyl-5-(4-methoxyphenyl)-2,4-pentadienoic acid 4-nitrophenyl ester, mp 136°–137° C.

Anal. Calcd for $C_{24}H_{25}NO_5$: C, 70.75; H, 6.18; N, 3.44. Found: C, 70.55 H. 6.27; N, 3.49.

EXAMPLE 262

Preparation of (2E,4Z)-5-cyclohexyl-5-(4-methoxyphenyl)-2,4-pentadienoic acid 4-nitrophenyl ester.

As in Example 115. (2E,4Z)-5-cyclohexyl-5-(4-methoxyphenyl)-2,4-pentadienoic acid (3.5 g) and 4-nitrophenol (2.07 g) in 20mL of carbon tetrachloride and 5 mL of dichloromethane was treated with 1,3-dicyclohexylcarbodiimide (2.07 g) and the mixture was stirred at room temperature for 3 days. The usual work up yielded 4.8 g of crude ester which was crystallized from 2-propanol-hexane to give 3.8 g of (2E,4Z)-5-cyclohexyl-5-(4-methoxyphenyl)-2,4-pentadienoic acid 4-nitrophenyl ester, mp 117°–119° C.

Anal. Calcd for $C_{24}H_{25}NO_5$: C, 70.75; H, 6.18; N, 3.44. Found: C, 70.81; H, 6.04; N, 3.43.

EXAMPLE 263

Preparation of (E,E)-5-(4-methoxyphenyl)-2,4-pentadienoic acid 4-nitrophenyl ester.

As in Example 115, (E,E)-5-(4-methoxyphenyl)-2,4-pentadienoic acid (3.47 g) and 4-nitrophenol (2.83 g) in 50 mL of dichloromethane was treated with 1.3-dicyclohexylcarbodiimide (3.53 g) and the mixture was stirred at room temperature for 3 days. The usual work up gave 4.3 g of crude ester which was crystallized from tetrahydrofuran ether to give 3.7 g of (E,E)-5-(4-methoxyphenyl)-2,4-pentadienoic acid 4-nitrophenyl ester, mp 200.5°–202° C.

Anal. Calcd for $C_{18}H_{15}NO_5$: C, 66.46; H, 4.65; N, 4.31. Found: C. 66.35; H. 4.81; N, 4.35.

EXAMPLE 264

Preparation of (E,E)-5-(4-methoxypheny)-2,4-hexadienoic acid 4-nitrophenyl ester.

As in Example 115, (E,E)-5-(4-methoxyphenyl)-2,4-hexadienoic acid (3 g) and 4-nitrophenol (2.3 g) in 20 mL of dichloromethane was treated with 1,3-dicyclohexylcarbodiimide (2.85 g). The mixture was stirred at room temperature for 3 days and the usual work up gave 3.1 g of crude ester which was crystallized from dichloromethane-2-propanol to give 2.95 g of (E,E)-5-(4-methoxyphenyl)-2,4-pentadienoic acid 4-nitrophenyl ester. mp 176°–177° C.

Anal. Calcd for $C_{19}H_{17}NO_5$: C, 67.25; H, 5.05: N, 4.13. Found: C, 67.20; H, 4.96; N, 4.08.

EXAMPLE 265

Preparation of (E,E)-5-(4-methoxyphenyl)-2,4-heptadienoic acid 4-nitrophenyl ester.

As in Example 115, (E,E)-5-(4-methoxyphenyl)-2,4-heptadienoic acid (2.8 g) and 4-nitrophenol (2 g) in 20 mL of dichloromethane was reacted with 1,3-dicyclohexylcarbodiimide (2,49 g) and the mixture was stirred at room temperature overnight. The usual work up yielded 4.3 g of crude ester which was crystallized from 2-propanol to give 3.1 g of (E,E)-5-(4-methoxyphenyl)-2,4-heptadienoic acid 4-nitrophenyl ester, mp 112.5°–113.5° C.

Anal. Calcd for $C_{20}H_{19}NO_5$: C, 67.98; H. 5.42; N, 3.96. Found: C, 68.23; H, 5.48; N, 3.96.

EXAMPLE 266

Preparation of (E,E)-5-(4-methoxyphenyl)-6-methyl-2,4-heptadienoic acid 4-nitrophenyl ester.

As in Example 115, (E,E)-5-(4-methoxyphenyl)-6-methyl-2,4-heptadienoic acid (2,4 g) and 4-nitrophenol (1.63 g) in 15 mL of dichloromethane was treated with 1,3-dicyclohexylcarbodiimide (2.02 g) and the mixture was stirred at room temperature for 18 hours. Crystallization of the crude product from 2-propanol-hexane yielded 2.85 g of (E,E)-5-(4-methoxyphenyl)-6-methyl-2,4-heptadienoic acid 4-nitrophenyl ester, mp 95°–96.5° C.

Anal. Calcd for $C_{21}H_{21}NO_5$: C, 68.651H, 5.76; N, 3.81. Found: C, 68.73; H, 5.71; N, 3.98.

EXAMPLE 267

Preparation of (2E,4Z)-5-(4-methoxyphenyl)-6-methyl-2,4-heptadienoic acid 4-nitrophenyl ester.

As in Example 115, (2E,4Z)-5-(4-methoxyphenyl)-6-methyl-2,4-heptadienoic acid (3.2 g) and 4-nitrophenol (2.2 g) in 20 mL of dichloromethane was treated with 1,3-dicyclohexylcarbodiimide (2.7 g) and the mixture was stirred at room temperature for 18 hours. After the usual work up. crystallization of the crude product from 2-propanol-hexane yielded 3.55 g of (2E,4Z)-5-(4-methoxyphenyl)-6-methyl-2,4-heptadienoic acid 4-nitrophenyl ester, mp 111.5°–113° C.

Anal. Calcd for $C_{21}H_{21}NO_5$ C. 68.65; H, 5.76; N, 3.81. Found C. 68.67; H, 5.79; N, 3.86.

EXAMPLE 268

Preparation of (E E)-5-(4-methoxyphenyl)-2,4-octadienoic acid 4-nitrophenyl ester.

As in Example 115, (E,E)-5-(4-methoxyphenyl)-2,4-octadienoic acid 2,47 g) and 4-nitrophenol (1.5 g) in 15 mL of dichloromethane was treated with 1,3-dicyclohexylcarbodiimide (1.86 g). The mixture was stirred at room temperature for 3 days. Crystallization of the crude product from 2-propanol furnished 2,5 g of (E,E)-5-(4-methoxyphenyl)-2,4-octadienoic acid 4-nitrophenyl ester, mp 90°–92° C.

Anal. Calcd for $C_{21}H_{21}NO_5$: C, 68.65; H, 5.76; N, 3.81. Found: C, 68.93; H, 5.82; N, 3.79.

EXAMPLE 269

Preparation of (E,E)-5-(4-methoxyphenyl)-2,4-nonadienoic acid 4-nitrophenyl ester.

As in Example 11, (E,E)-5-(4-methoxyphenyl)-2,4-nonadienoic acid (3.12 g) and 4-nitrophenol (2 g) in 20 mL of dichloromethane was treated with 1,3-dicyclohexylcarbodiimide (2,49 g) and the mix(ure was stlrred at room temperature for 3 days. After the normal work up, crystallization of the crude product from 2-propanol yielded 3.55 g of (E,E)-5-(4-methoxyphenyl)-2,4-nonadienoic acid 4-nitrophenyl ester, mp 78°–80° C., resolidified and remelted at 115° C.

Anal. Calcd for $C_{21}H_{21}NO_5$: C, 69.29; H, 6.08; N, 3.67. Found: C. 69.38; H, 6.17; N, 3.70.

EXAMPLE 270

Preparation of (E,E)-5-(3-methoxyphenyl)-2,4-nonadienoic acid 4-nitrophenyl ester.

As in Example 115, (E,E)-5-(3-methoxyphenyl)-2,4-nonadienoic acid (4.48 g) and 4-nitrophenol (2.97 g) in 25 mL of dichloromethane was treated with 1,3-dicyclohexylcarbodiimide (3 59 g). The mixture was stirred at room temperature for 3 days and after the normal work up. the crude product was crystallized from 2-propanol yield 5.6 g of (E,E)-5-(3-methoxyphenyl)-2,4-nonadienoic acid 4-nitrophenyl ester, mp 81.5°–83° C. Anal. Calcd for $C_{22}H_{23}NO_5$: C, 69.29; H, 6.08; N, 3.67. Found: C, 68.89; H, 6.08; N, 3.64.

EXAMPLE 271

Preparation of (2E,4Z)-5-(3-methoxypheny)-2,4-nonadienoic acid 4-nitrophenyl ester.

As in Example 115, (2E,4Z)-5-(3-methoxyphenyl)-2,4-nonadienoic acid (7.37 g) and 4-nitrophenol (4.89 g) in 30 mL of dichloromethane was reacted with 1,3-dicyclohexylcarbodiimide (5.91 g). The mixture was stirred at room temperature for 3 days and the usual work up furnished 9.69 g of (2E,4Z)-5-(3-methoxyphenyl)-2,4-nonadienoic acid 4-nitrophenyl ester as an oil.

EXAMPLE 272

Preparation of (E,E)-5-(4-methoxyphenyl)-2,4-decadienoic acid 4-nitrophenyl ester.

As in Example 115, (E,E)-5-(4-methoxyphenyl)-2,4-decadienoic acid (4.5 g) and 4-nitrophenol (2.75 g) in 35 mL of dichloromethane was treated with 1,3-dicyclohexylcarbodiimide (3.4 g) and the mixture was stirred at room temperature for 4 hours. After the normal work up, crystallization of the crude ester from 2-propanol yielded 4.9 g of (E,E)-5-(4-methoxyphenyl)-2,4-decadienoic acid 4-nitrophenyl ester, mp 75°–76° C.

Anal. Calcd for $C_{23}H_{25}NO_5$: C, 69.86; H, 6.37; N, 3 54. Found: C, 69.96; H, 6.33; N, 3.58.

EXAMPLE 273

Preparation of (2E 4Z)-5-(4-methoxyphenyl)-2,4-decadienoic acid 4-nitrophenyl ester.

As in Example 115. (2E,4Z)-5-(4-methoxyphenyl)-2,4-decadienoic acid (2.8 g) and 4-nitrophenol (1.71 g) in 20 mL of dichloromethane was reacted with 1,3-dicyclohexylcarbodiimide (2.1 g). The mixture was stirred at room temperature for 18 hours and the usual work up furnished 4.0 g of (2E,4Z)-5-(4-methoxyphenyl)-2,4-decadienoic acid 4-nitrophenyl ester as an oil.

EXAMPLE 274

Preparation of (E,E)-5-(3,4-dimethoxyphenyl)-2 4-decadienoic acid 4-nitrophenyl ester.

As in Example 115, (E,E)-5-(3,4-dimethoxyphenyl)-2,4-decadienoic acid (3.08 g) and 4-nitrophenol (2.7 g) in 20 mL of dichloromethane was treated with 1,3-dicyclohexylcarbodiimide (2.11 g). The mixture was stirred at room temperature for 3 days and after the usual word up crystallization of the crude ester from 2-propanol-hexane gave 2.98 g of (E,E)-5-(3,4-dimethoxyphenyl)-2,4-decadienoic acid 4-nitrophenyl ester, mp 95–°96.5° C.

Anal. Calcd for $C_{24}H_{27}NO_6$: C, 67.75; H, 6.40; N. 3.29. Found: C. 67.55; H, 6.47; N, 3.15.

EXAMPLE 275

Preparation of (E,E)-5-(3-fluorophenyl)-2,4-decadienoic acid 4-nitrophenyl ester.

As in Example 115, (E,E)-5-(3-fluorophenyl)-2,4-decadienoic acid (3.55 g) and 4-nitrophenol (2.33 g) in 20 mL of dichloromethane was treated with 1,3-dicyclohexylcarbodiimide (2.81 g) and the mixture was stirred at room temperature for 3 days. After the usual work up. crystallization of the crude ester from hexane gave 3.51 g of (E,E)-5-(3-fluorophenyl)-2,4-decadienoic acid 4-nitrophenyl ester, mp 46°–47° C.

Anal Calcd for $C_{22}H_{22}FNO_4$: C, 68.92; H, 5.78; F, 4.95; N, 3.65. Found: C, 69.02; H, 5.82; F, 4.89; N, 3.60.

EXAMPLE 276

Preparation of (2E,4Z)-5-(3-fluorophenyl-2,4-decadienoic acid 4-nitrophenyl ester.

As in Example 115, (2E,4Z)-5-(3-fluorophenyl)-2,4-decadienoic acid (3.3 g) and 4-nitrophenol (2.1 g) in 20 mL of dichloromethane was treated with 1,3-dicyclohexylcarbodiimide (2.67 g) and the mixture was stirred at room temperature for 3 days. After the usual work up. crystallization of the crude material from hexane gave 3.1 g of (2E,4Z)-5-(3-fluorophenyl)-2,4-decadienoic acid 4-nitrophenyl ester, mp 50°–51° C.

Anal. Calcd for $C_{22}H_{22}FNO_4$: C, 68.92; H, 5.78; F, 4.95; N, 3.65. Found: C, 68.71; H, 6.01; F, 4.86; N, 3.66.

EXAMPLE 277

Preparation of (E,E)-5-(4-fluorophenyl)-2,4-decadienoic acid 4-nitrophenyl ester.

As in Example 115, (E,E)-5-(4-fluorophenyl)-2,4-decadienoic acid (4.78 g) and 4-nitrophenol (3.14 g) in 20 mL of dichloromethane was treated with 1,3- dicyclohexylcarbodiimide (3.8 g) and the mixture was stirred at room temperature for 3 days. After the usual work up. crystallization of the crude ester from 2-propanol-hexane gave 4.86 g of (E,E)-5-(4-fluorophenyl)-2,4-decadienoic acid 4-nitrophenyl ester, mp 71°–72,5° C.

Anal. Calcd for $C_{22}H_{22}FNO_4$: C, 68.92; H, 5.78: F, 4.95; N. 3.65. Found: C, 68.89; H, 5.89; F, 4.93; N, 3.68.

EXAMPLE 278

Preparation of (E,E)-5-(4-methoxypheny)-2,4-undecadienoic acid 4-nitrophenyl ester.

As in Example 115, (E,E)-5-(4-methoxyphenyl)-2,4-undecadienoic acid (3.75 g) and 4-nitrophenol (2.2 g) in 20 mL of dichloromethane was treated with 1,3-dicyclohexylcarbodiimide (2.7 g). The mixture was stirred at room temperature overnight to give, after the usual work up. 4.5 g of (E,E)-5-(4-methoxyphenyl)-2,4-undecadienoic acid 4-nitrophenyl ester as an oil.

EXAMPLE 279

Preparation of
(E,E)-5-(4-methoxyphenyl)-2,4-tridecadienoic acid 4-nitrophenyl ester.

As in Example 115, (E,E)-5-(4-methoxyphenyl)-2,4-tridecadienoic acid (4.75 g) and 4-nitrophenol (2,5 g) in 25 mL of dichloromethane was treated with 1,3-dicyclohexylcarbodiimide (3.1 g) and the mixture was stirred at room temperature for 18 hours. After the usual work up, 4.85 g of (E,E)-5-(4-methoxyphenyl)-2,4-tridecadienoic acid 4-nitrophenyl ester was obtained as an oil.

EXAMPLE 280

Preparation of
(E,E)-5-(4-methoxyphenyl)-2,4-heptadecadienoic acid 4-nitrophenyl ester.

As in Example 115, (E,E)-5-(4-methoxyphenyl)-2,4-heptadecadienoic acid (7.5 g) and 4-nitrophenol (3.77 g) in 30 mL of dichloromethane was treated with 1,3-dicyclohexylcarbodiimide (4.2 g). The mixture was stirred at room temperature for 3 days to give, after the usual work up, 8.5 crude ester. The material was Purified by HPLC (ether-hexane; 1:7), then was crystallized from 2-propanol to furnish 5.88 g of (E,E)-5-(4-methoxyphenyl)-2,4-decadienoic acid 4-nitrophenyl ester, mp 46°-47° C.

Anal. Calcd for $C_{30}H_{39}NO_5$: C, 72.99; H, 7.96; N, 2.84. Found: C, 73.04; H, 7.87; N, 2.97.

EXAMPLE 281

Preparation of 5-pentyl-2,4-decadienoic acid 4-nitrophenyl ester.

As in Example 115, 5-pentyl-2,4-decadienoic acid (4.0 g) and 4-nitrophenol (2.8 g) in 30 mL of dichloromethane was treated with 1,3-dicyclohexylcarbodiimide (3.48 g) and the mixture was stirred at room temperature for 18 hours. After the usual work up, the crude ester was Purified by HPLC (ether-hexane; 1:24) to furnish 2,45 g of 5-pentyl-2,4-decadienoic acid 4-nitrophenyl ester as an oil.

EXAMPLE 282

Preparation of (E)-5,5-bis(4-methoxyphenyl)-N-[5-(2-ovridinyl) pentyl]-2,4-pentadienamide As in Example 134, a solution of (E)-5.5-bis(4-methoxyphenyl) -2,4-pentadienoic acid 4-nitrophenyl ester (1.72 g) and 2-Pyridinepentanamine (0.657 g) in tetrahydrofuran (25 mL) was stirred for 17 hours at room temperature and was worked up in the usual manner. The crude product was purified by HPLC (ethyl acetate) and then was crystallized from ethyl acetate to provide 4.6 g of (E)-5,5-bis(4-methoxyphenyl)-N-[5-(2-Pyridinyl) pentyl]-2,4-pentadienamide, mp 99°-100° C.

Anal. Calcd for $C_{29}H_{32}N_2O_3$: C, 76.29; H, 7.06; N, 6.14 Found: C, 76.57; 7.06; ;N, 6.14.

EXAMPLE 283

Preparation of
(E)-5.5-bis(4-methoxyphenyl)-N-[3-(4-pyridinyl) propyl]-2,4-pentadienamide.

As in Example 134, a solution of (E)-5,5-bis(4-methoXyphenyl)-2 4-pentadienoic acid 4-nitrophenyl ester (0.647 g) and 4-Pyridinepropanamine (0.204 g) in tetrahydrofuran (5 mL) was stirred for 3 hours at room temperature. After the usual work up, the crude product was purified by HPLC (ethyl acetate) and then was crystallized from ethyl acetate to provide 0.595 g of (E)-5,5-bis(4-methoxyphenyl)-N-[3-(4-pyridinyl)-propyl]-2,4pentadienamide. mp 90°-92° C.

Anal. Calcd for $C_7H_{28}N_2O_3$: C, 75.68; H, 6.59; N. 6.54 Found: C, 75.65; H, 6.74; N, 6.58.

EXAMPLE 284

Preparation of
(E)-S,5-bis(4-methoxyphenyl)-N-[2-(3pyridinylmethyl)ethoxy]2,4-pentadienamide.

As in Example 134. a solution of (E)-5.5-bis(4-methoxyphenyl)-2,4-pentadienoic acid 4-nitrophenyl ester (1.1 g) and 2-[(3-Pyridinyl)methyloxy]ethanamine (0.43 g) in tetrahydrofuran (20 mL) was stirred for 17 hours at room temperature and was worked up in the usual manner. The crude product was purified by HPLC (ethyl acetate) and then was lyophilized from benzene to yield 0.903 g of (E)5,5-bis(4-methoxyphenyl)-N-[2-(3pyridinylmethyl)ethoxy]-2,4-pentadienamide. as an amorphous solid.

Anal Calcd. for $C_{27}H_{28}N_2O_4$: C. 72.95; H. 6.35; N, 6.30 Found: C, 72.64; H, 6.59; N, 5.99.

EXAMPLE 285

Preparation of
(E)-5.5-bis(4-methoxyphenyl)-N-[3-[(3-pyridinyl)oxy]propyl]-2,4-pentadienamide.

As described in Example 134, a solution of (E)-5,5-bis (4-methoxyphenyl)-2,4-pentadienoic acid 4-nitrophenyl ester (1.0 g) and 3-(3-pyridinyloxy)proPanamine (0.4 g) in tetrahydrofuran (10 mL) was stirred overnight at room temperature. After the usual work up, the crude product was crystallized from ethyl acetate-hexane to give 0.85 g of (E)-5.5-bis(4-methoxyphenyl)-N-[3-[(3-pyridinyl)oxy]propyl]-2,4-pentadienamide, mp 146°-147° C.

Anal. Calcd for $C_{27}H_{28}N_2O_4$: C, 72.95; H, 6.35; N, 6.39 Found; C, 72.85; H, 6.50; N, 6.35.

EXAMPLE 286

Preparation of (E)-N-[4-(4-isoquinolinyl)butyl]-5,5-bis (4-methoxypheny)-2,4-pentadienamide.

As in Example 134, a solution of (E)-5,5-bis-(4-methoxyphenyl)-2,4-pentadienoic acid 4-nitrophenyl ester (0.841 g) and 4-isoquinolinebutanamine (0.39 g) in tetrahydrofuran (8 mL) was stirred for 17 hours at room temperature and was worked up in the usual manner. The crude product was purified by HPLC (ethyl acetate-hexane; 3:1) and then was crystallized from ethyl acetate-ether to provide 0.284 g of (E)-N-[4-(4-isoquinolinyl)butyl]-5.5-bis(4-methoxyphenyl)-2,4-pentadienamide, mp 91°-93° C.

Anal. Calcd for $C_{32}H_{32}N_2O_3$ C, 78.02. H, 6.55: N, 5.69 Found: C, 78.01: H, 6.45: N, 5.97.

EXAMPLE 287

Preparation of (E)-N-[3-(8-isoquinolinyl)propyl]-5,5-bis (4-methoxyphenyl)-2,4-pentadienamide.

As in Example 134, a solution of (E)-5,5-bis(4-methoxyphenyl) -2,4-pentadienoic acid 4-nitrophenyl ester (0.24 g) and 8-isoquinolinepropanamine (0.103 g) in tetrahydrofuran (5 mL) was stirred for 17 hours at room temperature and was worked up in the usual manner. The crude amide was purified by HPLC (ethyl acetate) and then was crystallized from ethyl acetate-hexane to afford 0.181 g of (E)-N-[3-(8-isoquinolinyl)propyl]-5.5-bis(4-methoxyphenyl)-2,4-pentadienamide, mp 115°–118° C.

Anal. Calcd for $C_{31}H_{30}N_2O_3$: 77.80; H, 6.32: N, 5.85 Found: C, 77.61; H, 6.23, N, 5.76.

EXAMPLE 288

Preparation of
(E)-5,5-bis(4-methoxyphenyl)-N-[4-(3-pyridinyl)phenyl]-2,4-pentadienamide.

Oxalyl chloride (0.5 mL) was added to a suspension of (E)-5,5-bis(4-methoxyphenyl)-2,4-pentadienoic acid (0.776 g) in toluene (5 mL) and the mixture was stirred at room temperature for 30 minutes. After the solvent was removed under reduced pressure, the acid chloride was dissolved in dichloromethane (10 mL) and added dropwise to a stirred solution of 3-(4-aminophenyl)pyridine (0.426 g) and triethylamine (0.87 mL) in dichloromethane (20 mL) at 5° C. The reaction was allowed to proceed overnight at room temperature, then was washed with 0.5N NaOH solution and with brine. Evaporation of the dried ($Na_2SO_4$) organic layer gave a foam which was crystallized from acetone-ethyl acetate to yield 0.7 g of (E)-5,5-bis-(4-methoxyphenyl)-N-[4-(3-pyridinyl)phenyl]-2,4-pentadienamide, mp 210°–212° C.

Anal. Calcd for $C_{30}H_{26}N_2O_3$: C, 77.90; H 5.67; N. 6.06 Found: C, 77.85; H, 5.91, N, 5.94.

EXAMPLE 289

Preparation of
(E)-5,5-bis(4-methoxyphenyl)-N-[4-(3-pyridinylmethyl)phenyl[-2,4-pentadienamide.

As in Example 288, the acid chloride, formed by the reaction of oxalyl chloride (0.5 mL) and (E)-5,5-bis(4-methoxyphenyl)-2,4-pentadienoic acid (0.815 g), was dissolved in dichloromethane (10 mL) and added dropwise to a stirred solution of 3-(4-aminobenzyl)pyridine (0.461 g) and triethylamine (0.87 mL) in dichloromethane (20 mL) at 5° C. The reaction was allowed to proceed overnight at room temperature then was worked up in the usual manner and the crude amide was crystallized from acetone-ethyl acetate to yield 0.747 g of (E)-5,5-bis(4-methoxyphenyl)-N-[4-(3-pyridinylmethyl)phenyl]-2,4-pentadienamide, mp 185°–186° C.

Anal. Calcd for $C_{31}H_{28}N_2O_3$: C, 78.13; H, 5.92; N, 5.88 Found: C, 77,78; H, 6.13 N, 5.71.

EXAMPLE 290

Preparation of
(E)-N-(5-isocuinolinvl)-5.5-bis(4-methoxyphenyl) 2,4-pentadienamide.

As in Example 288, the acid chloride, formed by the reaction of oxalyl chloride (0.35 mL) and (E)-5,5-bis(4-methoxyphenyl)-2,4-pentadienoic acid (0.5 g). was dissolved in dichloromethane (10 mL) and added droPwise to a stirred solution of 5-aminoisoquinoline (0.22 g) and triethylamine (0.55 mL) in dichloromethane (5 mL) at 7° C. The reaction was allowed to proceed overnight at room temperature, then was worked up as before. The crude amide was purified by column chromatographhy (ethyl acetate-dichloromethane; 1:1) and then was crystallized from ethyl acetate to give 0.22 g of (E)-N-(5-isoquinolinyl)-5,5-bis(4-methoxyphenyl)-2,4-pentadienamide, mp 197°–199° C.

Anal. Calcd for $C_{28}H_{24}N_2O_3$: C. 77.04; H, 5.54; N, 6.42 Found: C, 676.24; H, 5.42; N, 6.23.

EXAMPLE 291

Preparation of
[R.S-(E)]-5,5-bis(4-methoxypheny)-N-[1-methyl-4-(6-methyl-3-pyridinyl)butyl]-2,4-pentadienamide 0.5 molar hydrate.

As in Example 134, a solution of (E)-5,5-bis-4-methoxyphenyl)-2,4-pentadienoic acid 4-nitrophenyl ester (1.93) and (R,S)-6-alpha-dimethyl-3-pyridinebutanamine (0.8 g) in tetrahydrofuran (15 mL) was stirred overnight at room temperature and was worked up in the usual manner. The crude amide was purified by HPLC (ethyl acetate) and then lyophilized from benzene to yield 1.34 g of [R,S-(E)]-5,5-bis(4-methoxyphenyl)-N-[1-methyl-4-(6-methyl-3-pyridinyl)butyl]-2,4-pentadienamide 0.5 molar hydrate as an amorphous solid.

Anal. Calcd for $C_{30}H_{34}N_2O_3 \cdot 0.5H_2O$: C, 75.13; H, 7.36; N, 5.84; $H_2O$, 1.87 Found: C, 74.81; H, 7.39; N, 5.78; $H_2O$, 2.21.

EXAMPLE 292

Preparation of
[R,S-(E)]-5,5-bis(4-methoxyphenyl)-N-[1-methyl-4-(2-methyl-3-pyridinyl)butyl]-2,4-pentadienamide.

As in Example 134, a solution of (E)-5,5-bis(4-methoxyphenyl)-2,4-pentadienoic acid 4-nitrophenyl ester (1.11 g) and (R,S)-2-alpha-dimethyl-3-pyridinebutanamine (0.46 g) in tetrahydrofuran (10 mL) was stirred overnight at room temperature. After the normal workup the crude amide was purified by HPLC (ethyl acetate) and then was lyophilized from benzene to give 1.0 g of [R,S-(E)]-5,5-bis(4-methoxyphenyl)-N-[1-methyl-4-(2-methyl-3-pyridinyl)butyl]-2,4-pentadienamide as an amorphous solid.

Anal. Calcd for $C_{30}H_{34}N_2O_3$: C, 76.57; H, 7.28; N, 5.35 Found C. 76.41; H, 7.18; N, 6.01.

EXAMPLE 293

Preparation of
[R.S-(E)]-5,5-bis(4-methoxypheny)-N-[1-methyl-4-(6-ethyl-3-pyridinyl)butyl]-2,4-pentadienamide 0.66 molar hydrate.

As in Example 134, a solution of (E)-5,5-bis(4-methoxyphenyl) -2,4-pentadienoic acid 4-nitrophenyl ester (1.88 g) and (R,S)-6-ethyl-alpha-methyl-3-pyridinebutanamine (0.84 g) in tetrahydrofuran (10 mL) was stirred overnight at room temperature and worked up in the usual way. The crude amide was purified by HPLC (ethyl acetate) and then lyophilized from benzene to give 1.1 g of [R,S-(E)]-5,5-bis-(4-methoxyphenyl)-N-[1-methyl-4-(6-ethyl-3-pyridinyl)butyl]-2,4-pentadienamide 0.66 molar hydrate as an amorphous solid.

Anal. Calcd for $C_{31}H_{36}N_2O_3 \cdot 0.66H_2O$: C, 74.99; H, 7.58; N, 5.67; $H_2O$ 2.39 Found: C, 75.19; H, 7.66; N, 5.70; $H_2O$ 2.69.

EXAMPLE 294

Preparation of
[R,S-(E)]-N-[1-ethyl-4-(3-pyridinyl)butyl]-5.5-bis(4-methoxypheny)-2,4-pentadienamide.

As before in EXample 134, a solution of (E)-5,5-bis(4-methoxyphenyl)-2,4-pentadienoic acid 4-nitrophenyl ester (2.0 g) and (R.S)-alpha-ethyl-3-pyridinebutanamine (0.83 g) in tetrahydrofuran (15 mL) was stirred for 18 hours at room temperature and was then worked up in the usual manner. The material was purified by HPLC (ethyl acetate) and then lyophilized from benzene to give 1.7 g of [R,S-(E)]-N-[1-ethyl-4 -3-pyridinyl)butyl]-5,5-bis(4-methoxyphenyl)-2,4-pentadienamide.

Anal. Calcd. for $C_{30}H_{34}N_2O_3$: C, 76.57; H, 7.28; N, 5.95 Found: C, 76.24; H, 7.38; N, 5.90.

EXAMPLE 295
Preparation of [R-(E)]-N-1-ethyl-4-(3-pyridinyl)butyl]-5,5-bis(4-methoxyphenyl)-2,4-pentadienamide.

As before in Example 134, a solution of (E)-5,5-bis-(4-methoxyphenyl)-2,4-pentadienoic acid 4-nitrophenyl ester (1.22 g) and (R)-alpha-ethyl-3-pyridinebutanamine (0.5 g) in tetrahydrofuran (15 mL) was stirred for 20 hours at 50° C. and was then worked up in the usual way. The crude amide was purified by HPLC (ethyl acetate) and was then lyophilized from benzene to give 1.05 g of [R-(E)]-N-[1-ethyl-4-(3-pyridinyl) butyl]-5,5-bis(4-methoxyphenyl)-2,4-pentadienamide as an amorphous solid.

Anal Calcd. for $C_{30}H_{34}N_2O_3$: C, 76.57; H, 7.28; N, 5.95 Found: C, 76.02; H, 7.16; N, 5.81.

EXAMPLE 296
Preparation of [S-(E)1-N-[1-ethyl-4-(3-pyridinyl)butyl]-5.5-bis(4-methoxyphenyl)-2,4-pentadienamide.

As before in Example 134, a solution of (E)-5,5-bis(4-methoxyphenyl)-2,4-pentadienoic acid 4-nitrophenyl ester (1.68 g) and (S)-alpha-ethyl-3-pyridinebutanamine (0.687 g) in tetrahydrofuran (15 mL) was stirred at 50° C. for 20 hours and was then worked up in the usual manner. The amide was purified by HPLC (ethyl acetate) and then lyophilized from benzene to give 1.655 g of [S-(E)]-N-[1-ethyl-4-(3-pyridinyl)butyl]-5,5-bis (4-methoxyphenyl)-2,4-pentadienamide as an amorphous powder.

Anal. Calcd for $C_{30}H_{24}N_2O_3$: C, 76.57, H, 7.28; N, 5.95 Found: C, 76.08; H. 7.22; N, 5.85.

EXAMPLE 297
Preparation of [R,S-(E)1-5.5-bis(4-methoxyphenyl)-N-[1-propyl-4-(3-pyridinyl)butyl]-2,4-pentadienamide.

As before in Example 134, a solution of (E)-5,5-bis(4-methoxyphenyl)-2,4-pentadienoic acid 4-nitrophenyl ester (2.16 g) and (R,S)-alpha-propyl-3-pyridinebutanamine (0.962 g) in tetrahydrofuran (20 mL) was stirred for 17 hours at 50° C. and was then worked up in the usual way. The crude material was purified by HPLC (ethyl acetate) an then was lyophilized from benzene to yield 2.1 g of [R,S-(E)]-5,5-bis(4-methoxyphenyl)-N-[1-propyl-4-(3-pyridinyl)butyl]-2,4-pentadienamide as a glass.

Anal. Calcd for $C_{31}H_{36}N_2O_3$: C, 76.83; H, 7.49; N, 5.78 Found C, 76.59; H, 7.42; N, 5.76.

EXAMPLE 298
Preparation of [R,S-(E)]-5,5-bis(4-methoxyphenyl)-N-[1-(1-methylethyl)-4-(3-pyridinyl)butyl]-2,4-pentadienamide.

As in Example 134, a solution of (E)-5,5-bis(4-methoxyphenyl)-2,4-pentadienoic acid 4-nitrophenyl ester (2.16 g) and (R,S)-alpha-(1-methylethyl)-3-pyridinebutanamine (0.962 g) in tetrahydrofuran (25 mL) was stirred at 50° C. for 20 hours and was then worked up in the normal manner. The crude was purified by HPLC (ethyl acetate) and was then lyophilized from benzene to give 2.1 g of [R,S-(E)]-5,5-bis(4-methoxyphenyl)-N-[1-(1-methylethyl)-4-(3-pyridinyl)butyl]-2,4-pentadienamide as an amorphous powder.

Anal. Calcd for $C_{31}H_{36}N_2O_3$ C, 76.83: H, 7.49; N, 5.78 Found: C, 76.72; H, 7.63; N, 5.76.

EXAMPLE 299
Preparation of [R.S-(E)]-N-[1-butyl-4-(3-pyridinyl)butyl]-5.5-bis(4-methoxychenyl)-2,4-pentadienamide.

As before in Example 134, a solution of (E)-5,5-bis(4-methoxyphenyl)-2,4-pentadienoic acid 4-nitrophenyl ester (2.16 g) and (R,S)-alpha-butyl-3-pyridinebutanamine (1.03 g) in tetrahydrofuran (20 mL) was stirred for 20 hours at 50° C. and then was worked up in the usual manner. The amide was purified by HPLC (ethyl acetate) and was then lyophilized from benzene to give 2.15 g of [R,S-(E)]-N-[1-butyl-4-(3-pyridinyl) butyl]-5,5-bis(4-methoxyphenyl)-2,4-pentadienamide as an amorphous solid.

Anal. Calcd. for $C_{32}H_{38}N_2O_3$: C, 77.08; H, 7.68; N, 5.62 Found: C, 76.88; H, 7.64; N, 5.66.

EXAMPLE 300
Preparation of [R,S-(E)]-N-[1-cyclopropyl-4-(3-pyridinyl)butyl]-5,5-bis-(4-methoxyphenyl)-2,4-pentadienamide.

As before in Example 134, a solution of (E)-5,5-bis(4-methoxyphenyl)-2,4-pentadienoic acid 4-nitrophenyl ester (2.16 g) and (R,S)-alpha-cyclopropyl-3-pyridinebutanamine (1.03 g) in tetrahydrofuran (20 mL) was stirred for 20 hours at 50° C. and then was worked up in the usual manner. The crude material was purified by HPLC (ethyl acetate) and was then lyophilized from benzene to give 2.1 g of [R,S-(E)]-N-[1-cylcopropyl-4-(3-pyridinyl)butyl]-5.5-bis(4-methoxyphenyl)-2,4-pentadienamide as an amorphous powder.

Anal. Calcd for $C_{31}H_{34}N_2O_3$: C, 77.15; H, 7.10; N, 5.80 Found: C, 76.71; H, 7.08; N, 5.76.

EXAMPLE 301
Preparation of [R,S-(E)]-N-[1-cyclopentyl-4-(3-pyridinyl)butyl]-5,5-bis-(4-methoxyphenyl)-2,4-pentadienamide As before in Example 134, a solution of (E)-5,5-bis(4-methoxyphenyl)-2,4-pentadienoic acid 4-nitrophenyl ester (1.64 g) and (R,S)-alpha-cyclopentyl-3-pyridinebutanamine (0.832 g) in tetrahydrofuran (15 mL) was stirred for 17 hours at 50° C. and then was worked up in the usual manner. The amide was purified by HPLC (ethyl acetate) and was then lyophilized from benzene to give 1.7 g of [R,S-(E)]-N-[1-cyclopentyl-4-(3-pyridinyl)butyl]-5,5-bis(4-methoxyphenyl)-2,4-pentadienamide as an amorphous solid.

Anal. Calcd. for $C_{33}H_{38}N_2O_3$: C, 77.61; H, 7.50; N, 5.49 Found: C, 77.52; H, 7.56; N, 5.46.

EXAMPLE 302

Preparation of
[R,S-(E)]-N-[1-cyclohexyl-4-(3-pyridinyl)butyl]-5,5-bis(4-methoxyphenyl)-2,4-pentadienamide As before in Example 134, a solution of (E)-5,5-bis(4-methoxyphenyl)-2,4-pentadienoic acid 4-nitrophenyl ester (2.16 g) and (R,S)-alpha-cyclohexyl-3-pyridinebutanamine (1.16 g) in tetrahydrofuran (20 mL) was stirred for 20 hours at 50° C. After the reaction was worked up in the usual manner, the crude product was purified by HPLC (ethyl acetate) and was then lyophilized from benzene to give 2.2 g of [R,S-(E)]-N-[1-cyclohexyl-4-(3-pyridinyl)butyl]-5,5-bis(4-methoxyphenyl)-2,4-pentadienamide as an amorphous powder.

Anal. Calcd for $C_{34}H_{40}N_2O_3$: C, 77.83; H, 7.68, N, 5.34 Found: C, 77.39; H, 7.65; N, 5.24.

EXAMPLE 303

Preparation of
[R,S-(E)]-N-[1-(4-bromophenyl)-4-(3-pyridinyl)butyl]-5,5-bis-(4-methoxyphenyl)-2,4-pentadienamide As before in Example 134, a solution of (E)-5,5-bis(4-methoxyphenyl)-2,4-pentadienoic acid 4-nitrophenyl ester (1.47 g) and (R,S)-alpha-(4-bromophenyl)-3-pyridinebutanamine (1.04 g) in tetrahydrofuran (20 mL) was stirred for 17 hours at 50° C. After the reaction was worked up in the usual manner, the amide was purified by HPLC (ethyl acetate) and then was crystallized from ether to provide 1.2 g of [R,S-(E)]-N-[1-(4-bromophenyl)-4-(3-pyridinyl)butyl]-5,5-bis(4-methoxyphenyl)-2,4-pentadienamide, mp 145°-146° C.

Anal. Calcd for $C_{34}H_{33}BrN_2O_3$: C, 68.34; H, 5.57; Br, 13.37; N, 4.69 Found: C, 68.44; M, 5.54; Br, 13.39; N, 4.76.

EXAMPLE 304

Preparation of
(E)-5,5-bis(4-methoxyphenyl)-N-[1-[3-(3-pyridinyl)propyl]-4-(3-pyridinyl)butyl]-2,4-pentadienamide As before in Example 134, a solution of (E)-5,5-bis(4-methoxyphenyl)-2,4-pentadienoic acid 4-nitrophenyl ester (1.94 g) and alpha-[3-(3-pyridinyl)propyl]-3-pyridinebutanamine (1.21 g) in tetrahydrofuran (25 mL) was stirred for 20 hours at 50° C. and then was worked up in the normal manner. The crude was purified by HPLC (ethyl acetate-triethylamine; 19:1) and was then lyophilized from benzene to give 1.95 g of (E)-5,5-bis(4-methoxyphenyl)-N-[1-[3-(3-pyridinyl)propyl]-4-(3-pyridinyl)butyl]-2,4-pentadienamide as a glass.

Anal Calcd for $C_{36}H_{39}N_3O_3$: C, 76.98; H, 7.00; N, 7.48 Found: C, 76.41; H, 7.17; N, 7.63.

EXAMPLE 305

Preparation of (E)-5,5-bis(2-methoxyphenyl)-N-[4-(3-pyridinyl)butyl]-2,4-pentadienamide As before in Example 134, a solution of (E)-5,5-bis(2-methoxyphenyl)-2,4-pentadienoic acid 4-nitrophenyl ester (2.1 g)and 3-pyridinebutanamine (0.9 g) in tetrahydrofuran (20 mL) was stirred overnight at room temperature and then worked up in the normal manner. The crude was purified by HPLC (ethyl acetate) and then crystallized from ether to yield 1.8 g of (E)-5,5-bis(2-methoxyphenyl)-N-[4-(3-pyridinyl)butyl]-2,4-pentadienamide, mp 103.5°-104.5° C.

Anal. Calcd. for $C_{28}H_{30}N_2O_3$: C, 75.99; H, 6.83; N, 6.33 Found: C, 76.18; H, 6.92; N, 6.40.

EXAMPLE 306

Preparation of
(E)-5,5-bis(4-methylphenyl)-N-[4-(3-pyridinyl)butyl]-2,4-pentadienamide As before in Example 134, a solution of (E)-5,5-bis(4-methylphenyl)-2,4-pentadienoic acid 4-nitrophenyl ester (2.5 g) and 3-pyridinebutanamine (1.08 g) in tetrahydrofuran (25 mL) was stirred overnight at room temperature and then worked up in the usual way. The amide was purified by HPLC (ethyl acetate) and then was crystallized two times from ether to give 1.85 g of (E)-5,5-bis(4-methylphenyl)-N-[4-(3-pyridinyl)butyl]-2,4-pentadienamide, mp 144.5°-145.5° C.

Anal. Calcd for $C_{28}H_{30}N_2O$: C, 81.91; H, 7.37; N, 6.82 Found: C, 81.65; H, 7.38; N, 6.78.

EXAMPLE 307

Preparation of
[R-(E)]-5,5-bis(4-methylphenyl)-N-[1-methyl-4-(3-pyridinyl)butyl]-2,4-pentadienamide As before in Example 134, a solution of (E)-5,5-bis(4-methylphenyl)-2,4-pentadienoic acid 4-nitrophenyl ester (2.0 g) and (R)-alpha-methyl-3-pyridinebutanamine (0.95 g) in tetrahydrofuran (20 mL) was stirred overnight at room temperature and then worked up in the normal manner. The crude was crystallized from ether and then from ethyl acetate-hexane to afford 1.4 g of [R-(E)]-5,5-bis(4-methylphenyl)-N-[1-methyl-4-(3-pyridinyl)butyl]-2,4-pentadienamide, mp 105°-108° C.

Anal. Calcd for $C_{29}H_{32}N_2O$: C, 82.04; H, 7.60; N, 6.60 Found: C, 81.73; H, 7.75; N, 6.58.

EXAMPLE 308

Preparation of
[R-(E,E)]-5-(4-methoxyphenyl)-N-[1-methyl-4-(3-pyridinyl)butyl]-5-phenyl-2,4-pentadienamide As before in Example 134, a solution of (E,E)-5-(4-methoxyphenyl)-5-phenyl-2,4-pentadienoic acid 4-nitrophenyl ester (1.8 g) and (R)-alpha-methyl-3-pyridinebutanamine (0.85 g) in tetrahydrofuran (20 mL) was stirred overnight at room temperature and then worked up in the normal manner. The crude product was purified by HPLC (ethyl acetate) and then was lyophilized from benzene to yield 1.8 g of [R-(E,E)]-5-(4-methoxyphenyl)-N-[1-methyl-4-(3-pyridinyl)butyl]-5-phenyl-2,4-pentadienamide as an amorphous solid.

Anal. Calcd for $C_{28}H_{30}N_2O_2$: C, 78.84; H, 7.09; N, 6.57 Found: C, 78.59; H, 7.27; N, 6.27.

EXAMPLE 309

Preparation of
[R-(2E,4Z)]-5-(4-methoxyphenyl)-N-[1-methyl-4-(3-pyridinyl)butyl]-5-phenyl-2,4-pentadienamide As before in Example 134, a solution of (2E,4Z)-5-(4-methoxyphenyl)-5-phenyl-2,4-pentadienoic acid 4-nitrophenyl ester (1.63 g) and (R)-alpha-methyl-3-pyridinebutanamine (0.758 g) in tetrahydrofuran (20 mL) was stirred at room temperature and then worked up in the usual way. After the crude product was purified by HPLC (ethyl acetate) it was crystallized from ether and then from ethyl acetate-hexane to provide 1.03 g of [R-(2E,4Z)]-5-(4-methoxyphenyl)-N-

[1-methyl-4-(3-pyridinyl)butyl]-5-phenyl-2,4-pentadienamide, mp 129.5°–131° C.

Anal. Calcd. for $C_{28}H_{30}N_2O_2$: C, 78.84; H, 7.09; N, 6.57 Found: C, 78.01: H, 7.30; N, 6.67.

EXAMPLE 310

Preparation of (E,E)-5-(2-methoxyphenyl)-5-(4-methoxyphenyl)-N-[4-(3-pyridinyl)butyl]-2,4-pentadienamide As before in Example 134, a solution of (E,E)-5-(2-methoxyphenyl)-5-(4-methoxyphenyl)-2,4-pentadienoic acid 4-nitrophenyl ester (1.5 g) an 3-pyridinebutanamine (0.64 g) in tetrahydrofuran (15 mL) was stirred overnight at room temperature. After the usual workup. the crude product was crystallized from ethyl acetate to furnish 1.25 g of (E,E)-5-(2-methoxyphenyl)-5-(4-methoxyphenyl)-N-[4-(3-pyridinyl)butyl]-2,4-pentadienamide, mp 164°–165° C.

Anal Calcd for $C_{28}H_{30}N_2O_3$: C, 75.99; H, 6.83; N, 6.33 Found: C, 76.21; H, 6.93; N, 6.39.

EXAMPLE 311

Preparation of (2E,4Z)-5-(2-methoxyphenyl)-5-(4-methoxyphenyl)-N-[4-(3-pyridinyl)butyl]-2,4-pentadienamide As before in Example 134, a solution of (2E,4Z)-5-(2-methoxyphenyl)-5-(4-methoxyphenyl)-2,4-pentadienoic acid 4-nitrophenyl ester (0.82 g) and 3-pyridinebutanamine (0.33 g) in tetrahydrofruan (7 mL) was stirred overnight at room temperature. After the usual work up. the crude product was purified by HPLC (ethyl acetate) and lyophilized from benzene to give 0.81 g of (2E,4Z)-5-(2-methoxyphenyl)-5-(4-methoxyphenyl)-N-[4-(3-pyridinyl)butyl]-2,4-pentadienamide as an amorphous solid.

Anal. Calcd for $C_{28}H_{30}N_2O_3$: C, 75.99, H, 6.83; N, 6.33, Found: C, 75.99; H, 6.99; N, 6.30.

EXAMPLE 312

Preparation of (E,E)-5-(4-methoxyphenyl)-5-(3-pyridinyl)-N-[4-(3-pyridinyl)butyl]-2,4-pentadienamide As before in Example 134, a solution of (E,E)-5-(4-methoxyphenyl)-5-(3-pyridinyl)-2,4-pentadienoic acid 4-nitrophenyl ester (1.61 g) and 3-pyridinebutanamine (0.61 g) in tetrahydrofuran (20 mL) was stirred overnight at room temperature. After the usual workup. the crude product was crystallized form ethyl acetate to provide 1.05 g of (E,E)-5-(4-methoxyphenyl)-5-(3-pyridinyl)-N-[4-(3-pyridinyl)butyl]-2,4-pentadienamide, mp 121°–123° C.

Anal. Calcd for $C_{26}H_{27}N_3O_2$: C, 75.52; H, 6.58; N, 10.16 Found: C, 75.48; H, 6.71; N, 10.26.

EXAMPLE 313

Preparation of (2E,4Z)-5-(4-methoxyphenyl)-5-(3-pyridinyl)-N-[4-(3-pyridinyl)butyl]-2,4-pentadienamide As before in Example 134, a solution of (2E,4Z)-5-(4-methoxyphenyl)-5-(3-pyridinyl)-2,4-pentadienoic acid 4-nitrophenyl ester (2.01 g) and 3-pyridinebutanamine (0.75 g) in tetrahydrofuran (25 mL) was stirred for 17 hours at room temperature. After the usual workup. the crude product was crystallized from ethyl acetate to yield 1.65 g of (2E,4Z)-5-(4-methoxyphenyl)-5-(3-pyridinyl)-N-[4-(3-pyridinyl)butyl]-2,4-pentadienamide mp 108°–110° C. Recrystallization of a portion from the same solvent provided the analytical sample, mp 109°–110° C.

Anal. Calcd for $C_{26}H_{27}N_3O_2$: C, 75.52; H, 6.58; N, 10.16 Found: C, 75.43; H, 6.65; N, 10.19.

EXAMPLE 314

Preparation of [R-(2E,4Z)]-5-(4-methoxyphenyl)-N-[1-methyl-4-(3-pyridinyl)butyl]-5-(2-thienyl)-2,4-pentadienamide As before in Example 134, a solution of (2E,4Z)-5-(4-methoxyphenyl)-5-(2-thienyl)-2,4-pentadienoic acid 4-nitrophenyl ester (1.02 g) and (R)-alpha-methyl-3-pyridinebutanamine (0.49 g) in tetrahydrofuran (25 mL) was stirred for 17 hours at room temperature. After the usual workup, the crude product was purified by HPLC (ethyl acetate) and lyophilized from benzene to furnish 0.9 g of [R-(2E,4Z)]-5-(4-methoxyphenyl)-N-[1-methyl-4-(3-pyridinyl)butyl]-5-(2-thienyl)-2,4-pentadienamide as an amorphous solid.

Anal. Calcd. for $C_{26}H_{28}N_2O_2S$: C, 72.19; H, 6.52; N, 6.48; S, 7.41 Found: C, 71.53; H, 6.58; N, 6.40; S, 7.02.

EXAMPLE 315

Preparation of [R-(E,E)]-5-cyclopropyl-5-(4-methoxyphenyl)-N-[1-methyl-4-(3-pyridinyl)butyl]-2,4-pentadienamide As in Example 134, a solution of (E,E)-5-cyclopropyl-5-(4-methoxyphenyl)-2,4-pentadienoic acid 4-nitrophenyl ester (1.1 g) and (R)-alpha-methyl-3-pyridinebutanamine (0.5 g) in tetrahydrofruan (15 mL) was stirred for 2 days at room temperature. After the usual workup, the amide was purified by HPLC (ethyl acetate) and then crystallized from ether to yield 0.99 g of [R-(E,E)]-5-cyclopropyl-5-(4-methoxyphenyl)-N-[1-methyl-4-(3-pyridinyl)butyl]-2,4-pentadienamide, mp 111°–113° C.

Anal. Calcd for $C_{25}H_{30}N_2O_2$: C, 76.89; H, 7.74; ;N, 7.17 Found: C, 76.84; ;H, 7.92; N, 7.18.

EXAMPLE 316

Preparation of [R-(2E,4Z)]-5-cyclopropyl-5-(4-methoxyphenyl)-N-[1-methyl-4-(3-pyridinyl)butyl]-2,4-pentadienamide As in Example 134, a solution of (2E,4Z)-5-cyclopropyl-5-(4-methoxyphenyl)-2,4-pentadienoic acid 4-nitrophenyl ester (1.1 g) and (R)-alpha-methyl-3-pyrdinebutanamine (0.5 g) in tetrahydrofuran (15 mL) was stirred for 2 days at room temperature. After the normal workup. the crude product was purified by HPLC (ethyl acetate) and then crystallized from ether to yield 1.02 g of [R-(2E,4Z)]-5-cyclopropyl-5-(4-methoxyphenyl)-N-[1-methyl-4-(3-pyridinyl)butyl]-2,4-pentadienamide, mp 99°–100° C.

Anal. Calcd. for $C_{25}H_{30}N_2O_2$: C, 76.89, H, 7.74; N, 7.17; Found: C, 76.84; H, 7.94; ;N, 7.14.

EXAMPLE 317

Preparation of [R-(E,E)]-5-cyclohexyl-5-(4-methoxyphenyl)-N-[1-methyl-4-(3-pyridinyl)butyl]-2,4-pentadienamide As in Example 134, a solution of (E,E)-5-cyclohexyl-5-(4-methoxyphenyl)-2,4-pentadienoic acid 4-nitrophenyl ester (1.22 g) and (R)-alpha-methyl-3-pyridinebutanamine (0.5 g) in tetrahydrofuran (15 mL) was stirred for 2 days at room temperature. After the usual work up, the crude amide was crystallized from ethyl acetate-hexane to furnish 0.8 g of [R-(E,E)]-5-cyclohexyl-5-(4-methoxyphenyl)-N-[1-methyl-4-(3-pyridinyl)butyl]-2,4-pentadienamide. mp 142.5°–143.5° C.

Anal. Calcd for $C_{28}H_{36}N_2O_2$: C, 77.74; H, 8.39; N, 6.48. Found: C, 77.57; H, 8.28; N, 6.54.

EXAMPLE 318

Preparation of [R-(2E,4Z)]-5-cyclohexyl-5-(4-methoxyphenyl)-N-[1-methyl-4-(3-pyridinyl)butyl]-2,4-pentadienamide As in Example 134, a solution of (2E,4Z)-5-cyclohexyl-5-(4-methoxyphenyl)-2,4-pentadienoic acid 4-nitrophenyl ester (1.83 g) and (R)-alpha-methyl-3-pyridinebutanamine (0.85 g) in tetrahydrofuran (20 mL) was stirred overnight at room temperature. After the normal work up. the crude product was crystallized from ether to yield 1.68 g of [R-(2E,4Z)]-5-cyclohexyl-5-(4-methoxyphenyl)-N-[1-methyl-4-(3-pyridinyl)butyl]-2,4-pentadienamide, mp 147°–148.5° C.

Anal. Calcd for $C_{28}H_{36}N_2O_2$: C, 77.74; H, 8.39; N, 6.48. Found: C, 77.54; H, 8.31; N, 6.51.

EXAMPLE 319

Preparation of [R-(E,E)]-5-(4-methoxyphenyl)-N-[1-methyl-4-(3-pyridinyl)butyl]-2,4-pentadienamide As before in Example 134, a solution of (E,E)-5-(4-methoxyphenyl)-2,4-pentadienoic acid 4-nitrophenyl ester (0.98 g) and (R)-alpha-methyl-3-pyridinebutanamine (0.5 g) in tetrahydrofuran (20 mL) was stirred for 8 hours at reflux. After the usual work up. the crude product was triturated with ether. Crystallized of the resulting solid from ethyl acetate provided 0.85 g of [R-(E,E)]-5-(4-methoxyphenyl)-N-[1-methyl-4-(3-pyridinyl)butyl]-2,4-pentadienamide, mp 186.5°–187.5° C.

Anal. Calcd for $C_{22}H_{26}N_2O_2$: C, 75.40; H, 7.48; N, 7.99. Found: C, 75.73; H, 7.38; N, 8.00.

EXAMPLE 320

Preparation of [R-(E,E)]-5-(4-methoxyphenyl)-N-[1-methyl-4-(3-pyridinyl)butyl]-2,4-hexadienamide As before in Example 134, a solution of (E,E)-5-(4-methoxyphenyl)-2,4-hexadienoic acid 4-nitrophenyl ester (1.02 g) and (R)-alpha-methyl-3-pyridinebutanamine (0.5 g) in tetrahydrofuran (20 mL) was stirred for 17 hours at room temperature. After the usual work up. the crude product was crystallized from ethyl acetate-hexane to afford 0.6 g of [R-(E,E)]-5-(4-methoxyphenyl)-N-[1-methyl-4-(3-pyridinyl)butyl]-2,4-hexadienamide, mp 107.5°–108.5° C.

Anal. Calcd for $C_{23}H_{28}N_2O_2$: C, 75.79; H, 7.74; N, 7.69. Found: C, 75.74; H, 7.58; N, 7.72.

EXAMPLE 321

Preparation of [R-(E,E)]-5-(4-methoxyphenyl)-6-methyl-N-[1-methyl-4-(3-pyridinyl)butyl]-2,4-heptadienamide As in Example 134, a solution of (E,E)-5-(4-methoxyphenyl)-6-methyl-2,4-heptadienoic acid 4-nitrophenyl ester (1.1 g) and (R)-alpha-methyl-3-pyridinebutanamine (0.5 g) in tetrahydrofuran (15 mL) was stirred for 2 days at room temperature. After the usual work up, the crude product was purified by HPLC (ethyl acetate) and then was lyophilized from benzene to give 0.9 g of [R-(E,E)]-5-(4-methoxyphenyl)-6-methyl-N-[1-methyl-4-(3-pyridinyl)butyl]-2,4-heptadienamide as an oil.

Anal. Calcd for $C_{25}H_{32}N_2O_2$: C, 76.50; H, 8.22; N, 7.14. Found: C, 76.76; H, 8.29; N, 7.14.

EXAMPLE 322

Preparation of [R-(2E,4Z)]-5-(4-methoxyphenyl)-6-methyl-N-[1-methyl-4-(3-pyridinyl)butyl]-2,4-heptadienamide.

As in Example 134, a solution of (2E,4Z)-5-(4-methoxyphenyl)-6-methyl-2,4-heptadienoic acid 4-nitrophenyl ester (1.65 g) and (R)-alpha-methyl-3-pyridinebutanamine (0.85 g) in tetrahydrofuran (20 mL) was stirred overnight at room temperature. After the usual work up. the crude product was purified by HPLC (ethyl acetate) and then was crystallized from ether-hexane to give 1.5 g of [R-(E,E)]-5-(4-methoxyphenyl)-6-methyl-N-[1-methyl-4-(3-pyridinyl)butyl]-2,4-heptadienamide, mp 83°–84.5° C.

Anal. Calcd for $C_{25}H_{32}N_2O_2$: C, 76.50; H, 8.22; N, 7.14. Found: C, 77.02; H, 8.33; N, 7.17.

EXAMPLE 323

Preparation of [R-(E,E)]-5-(4-methoxyphenyl)-N-[1-methyl-4-(3-pyridinyl)butyl]-2,4-heptadienamide As before in Example 134, a solution of (E,E)-5-(4-methoxyphenyl)-2,4-heptadienoic acid 4-nitrophenyl ester (1.06 g) and (R)-alpha-methyl-3-pyridinebutanamine (0.5 g) in tetrahydrofuran (15 mL) was stirred for 2 days at room temperature. After the usual work up, the crude product was crystallized from ether to afford 0.778 g of [R-(E,E)]-5-(4-methoxyphenyl)-N-[1-methyl-4-(3-pyridinyl)butyl]-2,4-heptadienamide, mp 107°–109° C.

Anal. Calcd for $C_{24}H_{30}N_2O_2$: C, 76.16; H, 7.99; N, 7.40. Found: C, 75.78; H, 8.15; N, 7.15.

EXAMPLE 324

Preparation of [R-(E,E)]-5-(4-methoxyphenyl)-N-[1-methyl-4-(3-pyridinyl)butyl]-2,4-octadienamide As before in Example 134, a solution of (E,E)-5-(4-methoxyphenyl)-2,4-octadienoic acid 4-nitrophenyl ester (1.1 g) and (R)-alpha-methyl-3-pyridinebutanamine (0.5 g) in tetrahydrofuran (15 mL) was stirred for 42 hours at room temperature. After the normal work up, the crude amide was crystallized from ether to provide 0.835 g of [R-(E,E)]-5-(4-methoxyphenyl)-N-[1-methyl-4-(3-pyridinyl)butyl]-2,4-octadienamide.

Anal. Calcd for $C_{25}H_{32}N_2O_2$: C, 75.49; H, 8.22; N, 7.14. Found: C, 75.95; H, 8.29; N, 7.00.

EXAMPLE 325

Preparation of [R-(E,E)]-5-(4-methoxyphenyl)-N-[1-methyl-4-(3-pyridinyl)butyl]-2,4-nonadienamide As before in Example 134, a solution of (E,E)-5-(3-methoxyphenyl)-2,4-nonadienoic acid 4-nitrophenyl ester (1.14 g) and (R)-alpha-methyl-3-pyridinebutanamine (0.5 g) in tetrahydrofuran (15 mL) was stirred for 42 hours at room temperature. After the usual work up, the crude product was purified by HPLC (ethyl acetate) and then crystallized from ether to afford 0.826 g of [R-(E,E)]-5-(4-methoxyphenyl)-N-[1-methyl-4-(3-pyridinyl)butyl]-2,4-nonadienamide, mp 89°-91° C.

Anal. Calcd for $C_{26}H_{34}N_2O_2$: C, 76.81; H, 8.43; N, 6.89. Found: C, 76.90; H, 9.63; N, 6.92.

EXAMPLE 326

Preparation of
[R-(E,E)]-5-(3-methoxyphenyl)-N-[1-methyl-4-(3-pyridinyl)butyl]-2,4-nonadienamide As before in Example 134, a solution of (E,E)]-5-(3-methoxyphenyl)-2,4-nonadienoic acid 4-nitrophenyl ester (1.62 g) and (R)-alpha-methyl-3-pyridinebutanamine (0.75 g) in tetrahydrofuran (15 mL) was stirred for 42 hours at room temperature. After the usual work up, the crude product was purified by HPLC (ethyl acetate) and then crystallized from ether to give 1.32 g of [R-(E,E)]-5-(4-methoxyphenyl)-N-[1-methyl-4-(3-pyridinyl)butyl]-2,4-nonadienamide, mp 72°-73.5° C.

Anal. Calcd for $C_{26}H_{34}N_2O_2$: C, 76.81; H, 8.43; N, 6.89. Found: C, 76.66; H, 8.57; N, 6.82.

EXAMPLE 327

Preparation of
[R-(2E,4Z)]-5-(3-methoxyphenyl)-N-[1-methyl-4-(3-pyridinyl)butyl]-2,4-nonadienamide As before in Example 134, a solution of (2E,4Z)]-5-(4-methoxyphenyl)-2,4-nonadienoic acid 4-nitrophenyl ester (1.62 g) and (R)-alpha-methyl-3-pyridinebutanamine (0.75 g) in tetrahydrofuran (15 mL) was stirred for 2 days at room temperature. After the usual work up, the crude product was purified by HPLC (ethyl acetate) and then was lyophilized from benzene to give 1.45 g of [R-(2E,4Z)]-5-(4-methoxyphenyl)-N-[1-methyl-4-(3-pyridinyl)butyl]-2,4-nonadienamide as an oil.

EXAMPLE 328

Preparation of
[R-(E,E)]-5-(4-methoxyphenyl)-N-[4-(3-pyridinyl)butyl]-2,4-decadienamide As in Example 134, a solution of (E,E)]-5-(4-methoxyphenyl)-2,4-decadienoic acid 4-nitrophenyl ester (2.5 g) and (R)-alpha-methyl-3-pyridinebutanamine (1.12 g) in tetrahydrofuran (25 mL) was stirred overnight at room temperature. After the usual work up. the crude product was purified by HPLC (ethyl acetate) and then was crystallized from ether-hexane to provide 1.3 g of [R-(E,E)]-5-(4-methoxyphenyl)-N-[4-(3-pyridinyl)butyl]-2,4-decadienamide, mp 83.5°-84.5° C.

Anal. Calcd for $C_{26}H_{34}N_2O_2$: C, 76.81; H, 8.43; N, 6.89. Found: C, 77.05; H, 8.52; N, 6.87.

EXAMPLE 329

Preparation of
[R-(2E,4Z)]-5-(4-methoxyphenyl)-N-[4-(3-pyridinyl)butyl]-2,4-decadienamide As in Example 134, a solution of (2E,4Z)-5-(4-methoxyphenyl)-2,4-decadienoic acid 4-nitrophenyl ester (2 g) and (R)-alpha-methyl-3-pyridinebutanamine (0.9 g) in tetrahydrofuran (20 mL) was stirred overnight at room temperature. After the usual work up, the crude product was purified by HPLC (ethyl acetate) and the resulting solid was triturated with ether to give 1.45 g of [R-(E,E)]-5-(4-methoxyphenyl)-N-[4-(3-pyridinyl)butyl]-2,4-decadienamide. A portion was recrystallized from ethyl acetate-hexane to furnish the analytical sample, mp 81.5°-82.5° C.

Anal. Calcd for $C_{26}H_{34}N_2O_2$: C, 76.81; H, 8.43; N, 6.89. Found: C, 77.76; H, 8.56; N, 6.74.

EXAMPLE 330

Preparation of
[R-(E,E)]-5-(4-methoxyphenyl)-N-[1-methyl-4-(3-pyridinyl)butyl]-2,4-decadienamide As before in Example 134, a solution of (E,E)]-5-(4-methoxyphenyl)-2,4-decadienoic acid 4-nitrophenyl ester (13.2 g) and (R)-alpha-methyl-3-pyridinebutanamine (5.6 g) in tetrahydrofuran (100 mL) was stirred for 2 days at room temperature. After the usual work up, the amide was purified by HPLC (ethyl acetate) and then recrystallized from ethyl acetate-hexane to give 12.5 g of [R-(E,E)]-5-(4-methoxyphenyl)-N-[1-methyl-4-(3-pyridinyl)butyl]-2,4-decadienamide. mp 88°-89° C.; $[\alpha]_D^{RT} -28.65°$ (c, 1.0, MeOH).

Anal. Calcd for $C_{27}H_{36}N_2O_2$: C, 77.10; H, 8.63; N, 6.66. Found: C, 77.21; H, 8.72; N, 6.65.

EXAMPLE 331

Preparation of
[S-(E,E)]-5-(4-methoxyphenyl)-N-[1-methyl-4-(3-pyridinyl)butyl]-2,4-decadienamide As before in Example 134, a solution of (E,E)-5-(4-methoxyphenyl)-2,4-decadienoic acid 4-nitrophenyl ester (7.9 g) and (S)-alpha-methyl-3-pyridinebutanamine (3.35 g) in tetrahydrofuran (75 mL) was stirred for 17 hours at room temperature and then at reflux for 3 hours. After the usual work up, the crude was recrystallized from ethyl acetate-hexane to give 7.19 g of [S-(E,E)]-5-(4-methoxyphenyl)-N-[1-methyl-4-(3-pyridinyl)butyl]-2,4-decadienamide, mp 88°-89° C.; $[\alpha]_D^{RT} +28.6°$ (c, 1.0, MeOH).

Anal. Calcd for $C_{27}H_{36}N_2O_2$: C, 77.10; H, 8.63; N, 6.66. Found: C, 77.31; H, 8.67; N, 6.70.

EXAMPLE 332

Preparation of
[R-(2E,4Z)]-5-(4-methoxyphenyl)-N-[1-methyl-4-(3-pyridinyl)butyl]-2,4-decadienamide As before in Example 134, a solution of (2E,4Z)-5-(4-methoxyphenyl)-2,4-decadienoic acid 4-nitrophenyl ester (1.8 g) and (R)-alpha-methyl-3-pyridinebutanamine (0.94 g) in tetrahydrofuran (20 mL) was stirred overnight at room temperature. After the usual work up, the crude product was purified by HPLC (ethyl acetate) and then was lyophilized from benzene to give 1.8 g of [R-(2E,4Z)]-5-(4-methoxyphenyl)-N-[1-methyl-4-(3-pyridinyl)butyl]-2,4-decadienamide as a semi-solid.

Anal. Calcd for $C_{27}H_{36}N_2O_2$: C, 77.10; H, 8.63; N, 6 66. Found: C, 76.62; H, 8.60; N, 6.64.

EXAMPLE 333

Preparation of
[R-(E,E)]-5-(3-fluorophenyl)-N-[1-methyl-4-(3-pyridinyl)butyl]-2,4-decadienamide As before in Example 134, a solution of (E,E)-5-(3-fluorophenyl)-2,4-decadienoic acid 4-nitrophenyl ester (1.53 g) and (R)-alpha-methyl-3-pyridinebutanamine (0.75 g) in tetrahydrofuran (100 mL) was stirred for 2 days at room temperature. After the usual work up, the amide was purified by HPLC (ethyl acetate) and then crystallized from ether to yield 1.2 g of [R-(E,E)]-5-(3- fluorophenyl)-N-[1-methyl-4-(3-pyridinyl)butyl]-2,4-decadienamide, mp 87°–88° C.

Anal. Calcd for C$_{26}$H$_{33}$FN$_2$O: C, 76.42; H, 8.14; F, 4.65; N, 6.86. Found: C, 76.46; H, 8.45; F, 4.48; N, 6.86.

EXAMPLE 334

Preparation of
[R-(2E,4Z)]-5-(3-fluorophenyl)-N-[1-methyl-4-(3-pyridinyl)butyl]-2,4-decadienamide As in Example 134, a solution of (2E,4Z)-5-(3-fluorophenyl)-2,4-decadienoic acid 4-nitrophenyl ester (1.53 g) and (R)-alpha-methyl-3-pyridinebutanamine (0.75 g) in tetrahydrofuran (20 mL) was stirred for 2 days at room temperature. After the usual work up, the crude product was purified by HPLC (ethyl acetate) and then was crystallized from ether-hexane to give 1.1 g of [R-(2E,4Z)]-5-(3-fluorophenyl)-N-[1-methyl-4-(3-pyridinyl)butyl]-2,4-decadienamide, mp 71°–73° C.

Anal. Calcd for C$_{26}$H$_{33}$FN$_2$O: C, 76.43; H, 8.14; F, 4.65; N, 6.86. Found: C, 76.71; H, 8.14; F, 4.57; N, 6.89.

EXAMPLE 335

Preparation of
[R-(E,E)]-5-(4-fluorophenyl)-N-[1-methyl-4-(3-pyridinyl)butyl]-2,4-decadienamide As before in Example 134, a solution of (E,E)-5-(4-fluorophenyl)-2,4-decadienoic acid 4-nitrophenyl ester (1.53 g) and (R)-alpha-methyl-3-pyridinebutanamine (0.75 g) in tetrahydrofuran (20 mL) was stirred for 2 days at room temperature. After the usual work up, the amide was purified by HPLC (ethyl acetate) and then crystallized from ether to give 1.34 g of [R-(E,E)]-5-(4-fluorophenyl)-N-[1-methyl-4-(3-pyridinyl)butyl]-2,4-decadienamide, mp 76°–77° C.

Anal. Calcd for C$_{26}$H$_{33}$FN$_2$O: C, 76.43; H, 8.14; F, 4.65; N, 6.86. Found: C, 76.53; H, 8.33; F, 4.33; N, 6.92.

EXAMPLE 336

Preparation of
[R-(E,E)]-5-(3,4-dimethoxyphenyl)-N-[1-methyl-4-(3-pyridinyl)butyl]-2,4-decadienamide As before in Example 134, a solution of (E,E)-5-(3,4-dimethoxyphenyl)-4-decadienoic acid 4-nitrophenyl ester (1.7 g) and (R)-alpha-methyl-3-pyridinebutanamine (0.75 g) in tetrahydrofuran (20 mL) was stirred for 2 days at room temperature. After the usual work up, the crude product was first purified by HPLC (ethyl acetate) and then was crystallized from ether to give 1.52 g of [R-(E,E)]-5-(3,4-dimethoxyphenyl)-N-[1-methyl-4-(3-pyridinyl)butyl]-2,4-decadienamide. mp 67°–69° C.

Anal. Calcd for C$_{28}$H$_{38}$N$_2$C$_{28}$H$_{38}$N$_2$O$_3$O: C, 74.63; H, 8.50; N, 6.22. Found: C, 74.68; H, 8.64; N, 6.26.

EXAMPLE 337

Preparation of
[R,S-(E,E)]-5-(4-methoxyphenyl)-N-[1-methyl-4-(2-methyl-3-pyridinyl)butyl]-2,4-decadienamide 0.5 molar hydrate As before in Example 134, a solution of (E,E)-5-(4-methoxyphenyl)-2,4-decadienoic acid 4-nitrophenyl ester (1.1 g) and (R,S)-2-alpha-dimethyl-3-pyridinebutanamine (0.5 g) in tetrahydrofuran (12 mL) was stirred overnight at room temperature. After the usual work up, the amide was purified by chromatography over silica gel (ethyl acetate) and then was lyophilized from benzene to give 0.95 g of [R,S-(E,E)]-5-(4-methoxyphenyl)-N-[1-methyl-4-(2-methyl-3-pyridinyl)butyl]-2,4-decadienamide 0.5 molar hydrate as a glass.

Anal. Calcd for C$_{28}$H$_{38}$N$_2$O$_2$.0.5H$_2$O: C, 75.81; H, 8.86; N, 6.31. Found: C, 75.59; H, 8.75; N, 6.42.

EXAMPLE 338

Preparation of
[R,S-(E,E)]-5-(4-methoxyphenyl)-N-[(Z)-1-methyl-4-(3-pyridinyl)-3-butenyl]-2,4-decadienamide As in Example 134, a solution of (E,E)-5-(4-methoxyphenyl)-2,4-decadienoic acid 4-nitrophenyl ester (1.72 g) and [(R,S)-(Z)]-5-(3-pyridinyl)-4-penten-2-amine (0.811 g) in tetrahydrofuran (20 mL) was stirred for 2 days at room temperature. After the usual work up. the crude product was first purified by HPLC (ethyl acetate) and then was crystallized from ether to yield 1.32 g of [R,S-(E,E)]-5-(4-methoxyphenyl)-N-[(Z)-1-methyl-4-(3-pyridinyl)-3-butenyl]-2,4-decadienamide. mp 79°–81° C.

Anal. Calcd for C$_{27}$H$_{34}$N$_2$O$_2$: C, 77.47; H, 8.19; N, 6.69. Found: C, 77.67; H, 8.20; N, 6.80.

EXAMPLE 339

Preparation of
[R-(E,E)]-5-(4-methoxyphenyl)-N-[1-methyl-4-(3-pyridinyl)butyl]-2,4-undecadienamide As in Example 134, a solution of (E,E)-5-(4-methoxyphenyl)-2,4-undecadienoic acid 4-nitrophenyl ester (1.78 g) and (R)-alpha-methyl-3-pyridinebutanamine (0.85 g) in tetrahydrofuran (20 mL) was stirred overnight at room temperature. After the usual work up, the crude product was purified by HPLC (ethyl acetate:hexane; 9:1) and then was crystallized from ether-hexane to give 0.84 g of [R-(E,E)]-5-(4-methoxyphenyl)-N-[1-methyl-4-(3-pyridinyl)butyl]-2,4-undecadienamide, mp 71.5°–73° C.

Anal. Calcd for C$_{28}$H$_{38}$N$_2$O$_2$: C, 77.38; H, 8.81; N, 6.44. Found: C, 77.69; H, 9.06; N, 6.56.

EXAMPLE 340

Preparation of
[R-(E,E)]-5-(4-methoxyphenyl)-N-[1-methyl-4-(3-pyridinyl)butyl]-2,4-tridecadienamide As in Example 134, a solution of (E,E)-5-(4-methoxyphenyl)-2,4-tridecadienoic acid 4-nitrophenyl ester (1.92 g) and (R)-alpha-methyl-3-pyridinebutanamine (0.85 g) in tetrahydrofuran (20 mL) was stirred overnight at room temperature. After the usual work up, the amide was purified by HPLC (ethyl acetate:hexane; 9:1) and then was crystallized from ether to provide 1.63 g of [R-(E,E)]-5-(4-methoxyphenyl)-N-[1-methyl-4-(3-pyridinyl)butyl]-2,4-tridecadienamide. mp 92.5°–94° C.

Anal. Calcd for C$_{30}$H$_{42}$N$_2$O$_2$: C, 77.88; H, 9.15; N, 6.05. Found: C, 78.10; H, 9.19; N, 6.19.

EXAMPLE 341

Preparation of
[R-(E,E)]-5-[4-methoxyphenyl)-N-[1-methyl-4-(3-pyridinyl)butyl]-2,4-heptadecadienamide As in Example 134, a solution of (E,E)-5-(4-methoxyphenyl)-2,4-heptadecadienoic acid 4-nitrophenyl ester (1.97 g) and (R)-alpha-methyl-3-pyridinebutanamine (0.75 g) in tetrahydrofuran (20 mL) was stirred for 2 days at room temperature. After the usual work up, the crude product was first purified by HPLC (ethyl acetate) and then crystallized from ether-hexane to give 1.6 g of [R-(E,E)]-5-(4-methoxyphenyl)-N-[1-methyl-4-(3-pyridinyl)butyl]-2,4-heptadecadienamide, mp 60°-62° C.

Anal. Calcd for $C_{34}H_{50}N_2O_2$: C, 78.72; H, 9.71; N, 5.40. Found: C, 78.58; H, 9.76; N, 5.28.

EXAMPLE 342

Preparation of
[R-(E)]-N-[1-methyl-4-(3-pyridinyl)butyl]-5-pentyl-2,4-decadienamide As in Example 134, a solution of (E)-5-pentyl-2,4-decadienoic acid 4-nitrophenyl ester (1.08 g) and (R)-alpha-methyl-3-pyridinebutanamine (0.5 g) in tetrahydrofuran (15 mL) was stirred overnight at room temperature. After the usual work up, the crude product was purified by HPLC (ethyl acetate:hexane; 7:3) to give 0.9 g of [R-(E)]-N-[1-methyl-4-(3-pyridinyl)butyl]-5-pentyl-2,4-decadienamide as an oil.

EXAMPLE 343

Preparation of
[S-(R*,R*)]-alpha-hydroxy-N-[1-methyl-4-(2-methyl-3-pyridinyl)butyl]benzeneacetamide Using the procedure described in Example 14a and starting with (S)-mandelic acid and (R,S)-alpha-2-dimethyl-3-pyridinebutanamine, [S-(R*,R*)]-alpha-hydroxy-N-[1-methyl-4-(2-methyl-3-pyridinyl)-butyl]benzeneacetamide was obtained after recrystallization from isopropanol, mp 133°-134° C. $[\alpha]_D$ +30.50° (c, 0.986, EtOH).

EXAMPLE 344

Preparation of
[R-(R*,S*)]-alpha-hydroxy-N-[1-methyl-4-(2-methyl-3-pyridinyl)butyl]benzeneacetamide Using the procedure described in Example 14a and starting with (R)-mandelic acid and (R,S)-alpha-2-dimethyl-3-pyridinebutamamine, [R-(R*,S*)]-alpha-hydroxy-N-[1-methyl-4-(2-methyl-3-pyridinyl)butyl]-benzeneacetamide was obtained after recrystallization from isopropanol, mp 133°-134° C., $[\alpha]_D$ −30.24° (c, 1.068, EtOH).

EXAMPLE 345

Preparation of
(S)-alpha-2-dimethyl-3-pyridinebutanamine

Using the procedure described in Example 16 and starting with [R-(R*,S*)]-alpha-hydroxy-N-[1-methyl-4-(2-methyl-3-pyridinyl)-butyl]benzeneacetamide, (S)-alpha-2-dimethyl-3-pyridinebutanamine was obtained as a 0.1 molar hydrate after bulb to bulb distillation, bp (air bath temperature) 105°-110° C./0.1 mm, $[\alpha]_D$ +3.18° (c, 1.4125, EtOH).

EXAMPLE 346

Preparation of
(R)-alpha-2-dimethyl-3-pyridinebutanamine

Using the procedure described in Example 16 and starting with [S-(R*,R*)]-alpha-hydroxy-N-[1-methyl-4-(2-methyl-3-pyridinyl)butyl]benzeneacetamide. (R)-alpha-2-dimethyl-3-pyridinebutanamine, was obtained as a 0.1 molar hydrate after bulb to bulb distillation, bp (air bath temperature) 105°-110° C./0.15 mm, $[\alpha]_D$ −4.18° (c, 1.0265, EtOH).

EXAMPLE 347

Preparation of
[S-(E,E)]-5-(4-methoxyphenyl)-N-[1-methyl-4-(2-methyl-3-pyridinyl)butyl]-2,4-decadienamide Using the procedure described in Example 134 and starting with (E,E)-5-(4-methoxyphenyl)-2,4-decadienamide 4-nitrophenyl ester and (S)-alpha-2-dimethyl-3-pyridinebutanamine, [S-(E,E)]-5-(4-methoxyphenyl)-N-[1-methyl-4-(2-methyl-3-pyridinyl)butyl]-2,4-decadienamide was obtained, mp 87°-89° C. (ethyl acetate-hexane), $[\alpha]_D$ +29.07° (c, 0.9734, EtOH).

EXAMPLE 348

Preparation of
[R-(E,E)]-5-(4-methoxyphenyl)-N-[1-methyl-4-(2-methyl-3-pyridinyl)butyl]-2,4-decadienamide Using the procedure described in Example 134 and starting with (E,E)-5-(4-methoxyphenyl)-2,4-decadienamide 4-nitrophenyl ester and (R)-alpha-2-dimethyl-3-pyridinebutanamine, [R-(E,E)]-5-(4-methoxyphenyl)-N-[1-methyl-4-(2-methyl-3-pyridinyl)-butyl]-2,4-decadienamide was obtained, mp 87°-89° C. (ethyl acetate-hexane), $[\alpha]_D$ −26.53° (c, 1.0098, EtOH).

EXAMPLE 349

Preparation of
(E,E)-5-(4-methoxyphenyl)-N-[4-(3-pyridinyl)butyl]-2,4-decadienethioamide Phosphorous pentasulfide (2.67 g) was added to a solution of (E,E)-5-(4-methoxyphenyl)-N-[4-(3-pyridinyl)butyl]-2,4-decadienamide (4.88 g) in dry tetrahydrofuran (110 mL) in an ultrasonic bath. The mixture was stirred for 1 hour and then the supernatant was decanted from the yellow solid that had formed, and the solid was triturated with 4×100 mL portions of dichloromethane. The combined extracts were washed with 1N sodium hydroxide solution (3×100 mL) and with brine, then were dried ($K_2CO_3$) and evaporated to give 2.75 g of the crude thioamide. Crystallization of the crude from ethyl acetate-hexane (2X) and then from 2-propanol-hexane yielded 1.31 g of (E,E)-5-(4-methoxyphenyl)-N-[4-(3-pyridinyl)butyl]-2,4-decadienethioamide as a yellow solid, mp 121°-122° C.

EXAMPLE 350

Preparation of
(E,E)-5-(4-methoxyphenyl)-5-phenyl-2,4-pentadienoic acid methyl ester As described in Example 99, (E)-3-(4-methoxyphenyl)-3-phenyl-2-propenal (8.7 g) was reacted with (carbomethoxymethylene)triphenylphosphorane (14.2 g) in carbon tetrachloride (50 mL) and dichloromethane (5 mL) overnight at room temperature. The crude ester was isolated in the usual manner and was purified by HPLC (ether-hexane; 3:17) to yield 8.6 g of (E,E)-5-(4-methoxyphenyl)-5-phenyl-2,4-pentadienoic acid methyl ester. Crystallization of a portion from ethyl acetate-hexane gave the analytical specimen, mp 88°-89.5° C. Anal. Calcd. for $C_{19}H_{18}O_3$: C, 77.53; H, 6.19 Found: C, 77.40; H, 6.18.

EXAMPLE 351

Preparation of
(E,E)-5-(4-methoxyphenyl)-5-phenyl-2,4-pentadienoic acid

As described in Example 99, (E,E)-5-(4-methoxyphenyl)-5-phenyl-2,4-pentadiencoic acid methyl ester (8.35 g) was saponified in a refluxing mixture of methanol (35 mL) and 2N NaOH (30 mL). After 2.5 hours, the crude acid was isolated in the usual way and was crystallized from 2-propanol to yield 5.2 g of (E,E)-5-(4-methoxyphenyl)-5-phenyl-2,4-pentadienoic acid, mp 209°–211° C. Anal. Calcd. for $C_{18}H_{16}O_3$: C, 77.12; H, 5.75 Found: C, 77.35; H, 5.85.

EXAMPLE 352

Preparation of
(2E,4Z)-5-(3-methoxyphenyl)-5-phenyl-N-[4-(3-pyridinyl)butyl]-2,4-pentadienamide As described in Example 134, (E,E)-5-(4-methoxyphenyl)-5-phenyl-2,4-pentadienoic acid 4-nitrophenyl ester (3.3 g) and 3-pyridinebutanamine (1.24 g) in tetrahydrofuran (20 mL) was stirred for 1 hour at room temperature. After the usual work up, the crude amide was purified by HPLC (ethyl acetate) and crystallized from ethyl acetate to furnish 2.7 g of (2E,4Z)-5-(3-methoxyphenyl)-5-phenyl-N-[4-(3-pyridinyl)butyl]-2,4-pentadienamide, mp 89°–91° C. A portion was recrystallized from the same solvent to provide the pure amide, mp 90°–92° C. Anal. Calcd for $C_{27}H_{28}N_2O_2$: C, 78.61; H, 6.84; N, 6.79 Found: C, 78.88; H, 6.87; N, 6.66.

EXAMPLE 353

Preparation of
(2E,4Z)-5-(3-fluorophenyl)-5-(3-methoxyphenyl)-N-[4-(3-pyridinyl)butyl]-2,4-pentadienamide As described in Example 134, (2E,4Z)-5-(3-fluorophenyl)-5-(4-methoxyphenyl)-2,4-pentadienoic acid 4-nitrophenyl ester (3.4 g) and 3-pyridinebutanamine (1.23 g) in tetrahydrofuran (20 mL) was stirred overnight at room temperature and was worked up in the usual manner. The crude amide was purified by HPLC (ethyl acetate) and crystallized from ethyl acetate-hexane to provide 2.6 g of (2E,4Z)-5-(3-fluorophenyl)-5-(3-methoxyphenyl)-N-[4-(3-pyridinyl)butyl]-2,4-pentadienamide, mp 96°–98° C. A portion was recrystallized from ethyl acetate-hexane to yield the analytical specimen, mp 98°–100° C. Anal. Calcd for $C_{27}H_{27}FN_2O_2$: C, 75.33; H, 6.32; F, 4.41; N, 6.51 Found: C, 75.05; H, 6.28; F, 4.42; N, 6.41.

EXAMPLE 354

| INHALATION AEROSOL FORMULATION (SOLUTION) | | |
| --- | --- | --- |
| Item | Ingredients | % w/w |
| 1. | [R-(E,E)]-5-(4-Methoxyphenyl)-N-[1-methyl-4-(3-pyridinyl)-butyl]-2,4-decadienamide | 1.0 |
| 2. | Ethyl Alcohol | 30.0 |
| 3. | Ascorbic Acid | 0.5 |
| 4. | Freon 12 | 54.8 |
| 5. | Freon 114 | 13.7 |
| | TOTAL | 100% |

Manufacturing Procedure:

(1) Dissolve Items 1 and 3 in Item 2.
(2) Fill solution from Step 1 into a suitable glass bottle.
(3) Pressure-fill a 80:20 mixture of Items 4 and 5 into the container.

NOTE: A suitable valve may be used to deliver 25–100 microliters in volume.

EXAMPLE 355

| INHALATION AEROSOL FORMULATION (SUSPENSION) | | |
| --- | --- | --- |
| Item | Ingredients | % w/w |
| 1. | [R-(E,E)]-5-(4-Methoxyphenyl)-N-[1-methyl-4-(3-pyridinyl)butyl]-2,4-decadienamide | 1.0 |
| 2. | Sorbitan Trioleate | 0.5 |
| 3. | Freon 12 | 64.0 |
| 4. | Freon 11 | 18.5 |
| 5. | Freon 114 | 16.0 |
| | TOTAL | 100% |

Manufacturing Procedure:

(1) Mix Items 1 and 2 into 4 and homogenize.
(2) Fill the concentrate suspension from Step 1 into a suitable can and place in valve and crimp to seal container.
(3) Pressure-fill a 80:20 mixture of Items 3 and 5.

NOTE: A suitable valve may be used to deliver 25–100 microliters in volume.

EXAMPLE 356

| TABLET FORMULATION (Wet Granulation) | | | |
| --- | --- | --- | --- |
| | | mg/tablet | |
| Item | Ingredients | 100 mg | 500 mg |
| 1. | [R-(E,E)]-5-(4-Methoxyphenyl)-N-[1-methyl-4-(3-pyridinyl)butyl]-2,4-decadienamide | 100 | 500 |
| 2. | Lactose | 30 | 150 |
| 3. | Pregelatinized Starch | 6 | 30 |
| 4. | Microcrystalline Cellulose | 30 | 150 |
| 5. | Magnesium Stearate | 1 | 6 |
| | TOTAL | 167 | 836 |

Manufacturing Procedure:

(1) Mix Items 1, 2, 3 and 4 and granulate with water.
(2) Dry the granulation at 50° C.
(3) Pass the granulation through suitable milling equipment.
(4) Add Item 5 and mix for three minutes; compress on a suitable press.

EXAMPLE 357

| CAPSULE FORMULATION | | | |
| --- | --- | --- | --- |
| | | mg/tablet | |
| Item | Ingredients | 100 mg | 500 mg |
| 1. | [R-(E,E)]-5-(4-Methoxyphenyl)-N-[1-methyl-4-(3-pyridinyl)butyl]-2,4-decadienamide | 100 | 500 |
| 2. | Corn Starch | 8 | 40 |
| 3. | Modified Starch | 4 | 20 |
| 4. | Talc | 4 | 20 |
| 5. | Magnesium Stearate | 1 | 2 |
| | TOTAL | 117 | 582 |

Manufacturing Procedure:

(1) Mix Items 1, 2, and 3 and wet granulate with water. Dry at 45° C. overnight.

(2) Mill through suitable screen using appropriate milling equipment.

(3) Add Items 4 and 5 and mix for five minutes.

EXAMPLE 358

CAPSULE FORMULATION

| Item | Ingredients | mg/capsule | | | |
|---|---|---|---|---|---|
| 1. | [R-(E,E)]-5-(4-Methoxyphenyl)-N-[1-methyl-4-(3-pyridinyl)butyl]-2,4-decadienamide | 0.01 | 0.5 | 5.0 | 25.0 |
| 2. | Lactose Hydrous | 168.99 | 168.5 | 159.0 | 123.0 |
| 3. | Corn Starch | 20.0 | 20.0 | 25.0 | 35.0 |
| 4. | Talc | 10.0 | 10.0 | 10.0 | 15.0 |
| 5. | Magnesium Stearate | 1.0 | 1.0 | 1.0 | 2.0 |
| | TOTAL | 200.0 | 200.0 | 200.0 | 200.0 |

Manufacturing Procedure:

(1) Mix Items 1, 2 and 3 in a suitable mixer for 30 minutes.

(2) Add Items 4 and 5 and mix for 3 minutes.

(3) Fill into suitable capsule.

EXAMPLE 359

WET GRANULATION FORMULATION

| Item | Ingredients | mg/tablet | | | |
|---|---|---|---|---|---|
| 1. | [R-(E,E)]-5-(4-Methoxyphenyl)-N-[1-methyl-4-(3-pyridinyl)butyl]-2,4-decadienamide | 0.01 | 0.5 | 5.0 | 25.0 |
| 2. | Lactose Anhydrous DTG | 106.99 | 106.5 | 102.0 | 118.0 |
| 3. | Avicel PH 102 | 15.0 | 15.0 | 15.0 | 25.0 |
| 4. | Modified Starch | 7.0 | 7.0 | 7.0 | 10.0 |
| 5. | Magnesium Stearate | 1.0 | 1.0 | 1.0 | 2.0 |
| | TOTAL | 130.0 | 130.0 | 130.0 | 180.0 |

Manufacturing Procedure:

(1) Dissolve Item 1 in a suitable solvent such as alcohol.

(2) Spread the solution in Step 1 over Item 2, dry.

(3) Add Items 3 and 4 and mix for 10 minutes.

(4) Add magnesium stearate and mix for 3 minutes and compress.

EXAMPLE 360

Cream 0.5%

The following is the quantitative composition of drug:

| Ingredients | g/kg | Reasonable Variations |
|---|---|---|
| [R-(E,E)]-5-(4-Methoxyphenyl)-N-[1-methyl-4-(3-pyridinyl)butyl]-2,4-decadienamide | 5.150* | — |
| Glyceryl Monostearate S.E.[1] | 100.00 | 80–120 |
| Polysorbate 60[2] | 20.00 | 15–25 |
| Cetyl Alcohol | 50.00 | 40–60 |
| Petrolatum | 70.00 | 50–90 |
| Methylparaben | 1.50 | 1.25–1.75 |
| Propylparaben | 0.50 | 0.4–0.6 |

-continued

| Ingredients | g/kg | Reasonable Variations |
|---|---|---|
| Propylene Glycol | 200.00 | 150–250 |
| Purified Water | 568.05 | 475–575 |
| TOTAL | 1,015.20 | |

*3% excess
[1]Arlacel 165
[2]Tween 60

We claim:

1. A compound of the formula

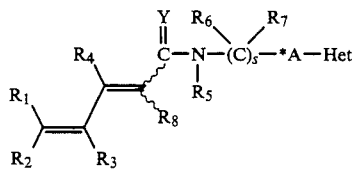

Y is O or S, *A is paraphenylene or *—(CH$_2$)$_n$—(X—)$_m$—(CH$_2$)$_r$—, X is O, S or —CH═CH—, n or r, independently, are integers from 0 to 3, s is an integer from 0 to 1, m is an integer from 0 to 1, provided that when m is 1, n+s must be at least 2, R$_1$ and R$_2$, independently, are hydrogen, lower alkyl, cycloalkyl, lower alkenyl, Het, naphthalenyl, phenyl or phenyl or naphthalenyl mono-, di- or trisubstituted by halogen, trifluoromethyl, lower alkyl, phenyl, lower alkoxy or nitro, R$_3$, R$_4$ and R$_8$, independently, are hydrogen, lower alkyl, naphthalenyl, phenyl or phenyl or naphthalenyl mono-, di- or trisubstituted by halogen, trifluoromethyl, lower alkyl, phenyl, lower alkoxy or nitro, R$_5$ and R$_6$, independently, are hydrogen or lower alkyl, R$_7$ is hydrogen, lower alkyl, cycloalkyl, Het-lower alkyl, naphthalenyl, phenyl or phenyl or naphthalenyl mono-, di-or trisubstituted by halogen, trifluoromethyl, lower alkyl, phenyl, lower alkoxy or nitro, Het is isoquinolinyl unsubstituted or substituted by lower alkyl, halogen, naphthalenyl, phenyl or phenyl or naphthalenyl mono-, di-or trisubstituted by halogen, trifluoromethyl, lower alkyl, phenyl, lower alkoxy or nitro, and the asterisk denotes the point of attachment, and when R$_6$ and R$_7$ are different, an enantiomer or racemic mixture thereof, when R$_1$ and R$_2$ are different, a geometric isomer, or a pharmaceutically acceptable acid addition salt thereof.

2. A compound according to claim 1, of the formula

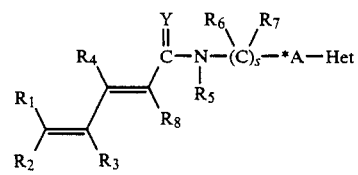

(E) or trans isomer.

3. A compound according to claim 1, of the formula

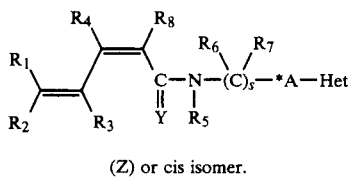

(Z) or cis isomer.

4. A compound according to claim 1, of the formula

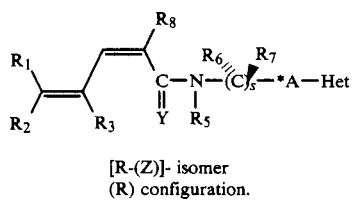

[R-(Z)]- isomer
(R) configuration.

5. A compound according to claim 1, of the formula

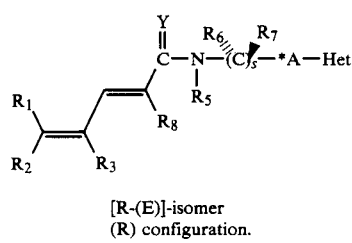

[R-(E)]-isomer
(R) configuration.

6. A compound according to claim 1, of the formula

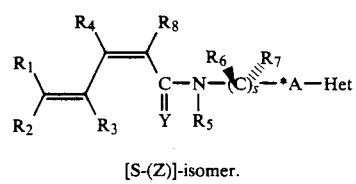

[S-(Z)]-isomer.

7. A compound according to claim 1,

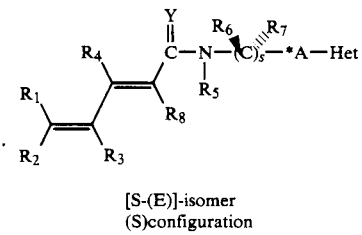

[S-(E)]-isomer
(S)configuration wherein $R_1$, $R_2$, $R_3$, $R_4$, $R_5$, $R_6$, $R_7$, $R_8$, s *A and Het are as described in claim 1.

8. A compound in accordance with claim 1, wherein $R_1$ and $R_2$, independently, are lower alkyl, naphthalenyl, phenyl or phenyl or naphthalenyl mono-, di- or trisubstituted by halogen, trifluoromethyl, lower alkyl, phenyl, lower alkoxy or nitro, $R_3$, $R_4$ and $R_8$ independently are hydrogen or lower alkyl, $R_5$ and $R_7$ are hydrogen, $R_6$ is hydrogen, lower alkyl or cycloalkyl, *A is $-(CH_2)_n-(X)_m-(CH_2)_r$ wherein n+2=2 to 6, m=0, Het is isoquinolinyl unsubstituted or substituted by lower alkyl, halogen, naphthalenyl, phenyl or phenyl or naphthalenyl mono-, di- or trisubstituted by halogen, trifluoromethyl, lower alkyl, phenyl, lower alkoxy or nitro, Y is oxygen or sulfur, and s is 1.

9. A compound in accordance with claim 1, wherein $R_1$ is lower alkyl, naphthalenyl, phenyl or phenyl or naphthalenyl mono-, di- or trisubstituted by halogen, trifluoromethyl, lower alkyl, phenyl, lower alkoxy or nitro, $R_2$ is naphthalenyl, phenyl or phenyl or naphthalenyl mono-, di- or trisubstituted by halogen, trifluoromethyl, lower alkyl, phenyl, lower alkoxy or nitro, $R_3$, $R_4$ and $R_8$ are independently hydrogen or lower alkyl, *A is $-(CH_2)_n-X_m-(CH_2)_r-$ wherein n+r=3, m=0, Het is isoquinolinyl substituted with lower alkyl, $R_5$ and $R_7$ are hydrogen, $R_6$ is hydrogen, lower alkyl or cyclopropyl, Y is oxygen, s is 1.

10. A pharmaceutical composition comprising an effective amount of a compound of the formula

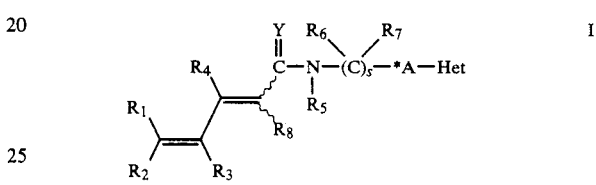

Y is O or S, *A is a paraphenylene or *$-(CH_2)_n-(X-)_m-(CH_2)_r-$, X is O, S or $-CH=CH-$, n or r, independently, are integers from 0 to 3, s is an integer from 0 to 1, m is an integer from 0 to 1, provided that when m is 1, n+s must be at least 2, $R_1$ and $R_2$, independently, are hydrogen, lower alkyl, cycloalkyl, lower alkenyl, Het, naphthalenyl, phenyl or phenyl or naphthalenyl mono-, di- or trisubstituted by halogen, trifluoromethyl, lower alkyl, phenyl, lower alkoxy or nitro, $R_3$, $R_4$ and $R_8$, independently, are hydrogen, lower alkyl, naphthalenyl, phenyl or phenyl or naphthalenyl mono-, di- or trisubstituted by halogen, trifluoromethyl, lower alkyl, phenyl, lower alkoxy or nitro, $R_5$ and $R_6$, independently, are hydrogen or lower alkyl, $R_7$ is hydrogen, lower alkyl, cycloalkyl, Het-lower alkyl, naphthalenyl, phenyl or phenyl or naphthalenyl mono-, di- or trisubstituted by halogen, trifluoromethyl, lower alkyl, phenyl, lower alkoxy or nitro, Het is isoquinolinyl unsubstituted or substituted by lower alkyl, halogen, naphthalenyl, phenyl or phenyl or naphthalenyl mono-, di- or trisubstituted by halogen, trifluoromethyl, lower alkyl, phenyl, lower alkoxy or nitro, and the asterisk denotes the point of attachment, and when $R_6$ and $R_7$ are different, an enantiomer or racemic mixture thereof, when $R_1$ and $R_2$ are different, a geometric isomer, or a pharmaceutically acceptable acid addition salt thereof, and an inert carrier.

11. A method of treating a disease state characterized by an excess of platelet activating factor which comprises administering to a host requiring such treatment an effective amount of a compound of the formula,

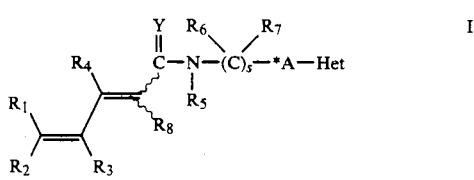

Y is O or S, *A is paraphenylene or *—(CH$_2$)$_n$—(X—)$_m$—(CH$_2$)$_r$—, X is O, S or —CH=CH—, n or r, independently, are integers from 0 to 3, s is an integer from 0 to 1, m is an integer from 0 to 1, provided that when m is 1, n+s must be at least 2, R$_1$ and R$_2$, independently, are hydrogen, lower alkyl, cycloalkyl, lower alkenyl, Het, naphthalenyl, phenyl or phenyl or naphthalenyl mono-, di- or trisubstituted by halogen, trifluoromethyl, lower alkyl, phenyl, lower alkoxy or nitro, R$_3$, R$_4$ and R$_8$, independently, are hydrogen, lower alkyl, naphthalenyl, phenyl or phenyl or naphthenyl mono-, di- or trisubstituted by halogen, trifluoromethyl, lower alkyl, phenyl, lower alkoxy or nitro, R$_5$ and R$_6$, independently, are hydrogen or lower alkyl, R$_7$ is hydrogen, lower alkyl, cycloalkyl, Het-lower alkyl, naphthalenyl, phenyl or phenyl or naphthalenyl mono-, di- or trisubstituted by halogen, trifluoromethyl, lower alkyl, phenyl, lower alkoxy or nitro, Het is isoquinolinyl unsubstituted or substituted by lower alkyl, halogen, naphthalenyl, phenyl or phenyl or naphthalenyl mono-, di- or trisubstituted by halogen, trifluoromethyl, lower alkyl, phenyl, lower alkoxy or nitro-, and the asterisk denotes the point of attachment, and when R$_6$ and R$_7$ are different, an enantiomer or racemic mixture thereof, when R$_1$ and R$_2$ are different, a geometric isomer, or a pharmaceutically acceptable acid addition salt thereof.

12. A compound in accordance with claim 1, (E)-N-[4-(4-isoquinolinyl)butyl]-5,5-bis(4-methoxyphenyl)-2,4-pentadienamide.

13. A compound in accordance with claim 1, (E)-N-[3-(8-isoquinolinyl)propyl]-5,5-bis(4-methoxyphenyl)-2,4-pentadienamide.

14. A compound in accordance with claim 1, (E)-N-(5-isoquinolinyl)-5,5-bis (4-methoxyphenyl)-2,4-pentadienamide.

* * * * *

UNITED STATES PATENT AND TRADEMARK OFFICE
CERTIFICATE OF CORRECTION

PATENT NO. : 4,975,438

DATED : December 4, 1990

INVENTOR(S) : Robert William Guthrie, Jefferson Wright Tilley and Richard Wichtman Kierstead It is certified that error appears in the above-identified patent and that said Letters Patent is hereby corrected as shown below:

Claim 4, Column 131, Lines 12-17, in the formula

" 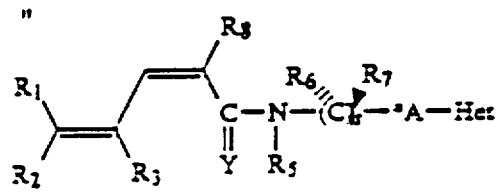 "  should be  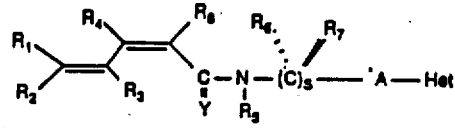

UNITED STATES PATENT AND TRADEMARK OFFICE
CERTIFICATE OF CORRECTION

PATENT NO. : 4,975,438

DATED : December 4, 1990

INVENTOR(S) : Robert William Guthrie, Jefferson Wright Tilley and Richard Wichtman Kierstead Page 2 of 2

It is certified that error appears in the above-identified patent and that said Letters Patent is hereby corrected as shown below:

Claim 5, Column 131, Lines 26-30, in the formula

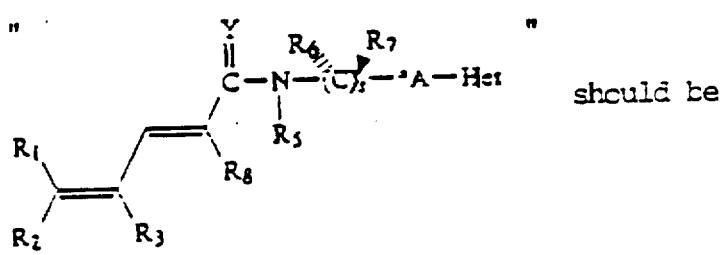 should be 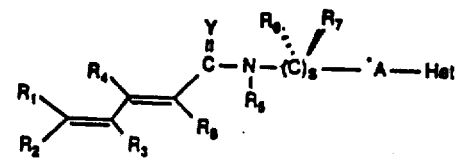

Signed and Sealed this

Sixteenth Day of March, 1993

Attest:

STEPHEN G. KUNIN

Attesting Officer

Acting Commissioner of Patents and Trademarks